US008168771B2

(12) United States Patent
Ray et al.

(10) Patent No.: US 8,168,771 B2
(45) Date of Patent: May 1, 2012

(54) USE OF CONSENSUS SEQUENCE AS VACCINE ANTIGEN TO ENHANCE RECOGNITION OF VIRULENT VIRAL VARIANTS

(75) Inventors: Stuart C. Ray, Lutherville, MD (US); Andrew L. Cox, Towson, MD (US); David L. Thomas, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 807 days.

(21) Appl. No.: 11/815,203

(22) PCT Filed: Jan. 31, 2006

(86) PCT No.: PCT/US2006/003514
§ 371 (c)(1),
(2), (4) Date: Oct. 13, 2008

(87) PCT Pub. No.: WO2006/086188
PCT Pub. Date: Aug. 17, 2006

(65) Prior Publication Data
US 2009/0186045 A1    Jul. 23, 2009

Related U.S. Application Data

(60) Provisional application No. 60/648,550, filed on Jan. 31, 2005, provisional application No. 60/648,877, filed on Feb. 2, 2005.

(51) Int. Cl.
*C07H 21/00* (2006.01)
*A61K 39/29* (2006.01)

(52) U.S. Cl. ............... 536/23.72; 424/186.1; 424/189.1; 424/228.1

(58) Field of Classification Search .......................... None
See application file for complete search history.

(56) References Cited

U.S. PATENT DOCUMENTS
5,747,241 A * 5/1998 Miyamura et al. ................ 435/5

FOREIGN PATENT DOCUMENTS
| | | |
|---|---|---|
| WO | WO 96/05315 | 2/1996 |
| WO | 01/90197 | 11/2001 |
| WO | WO 03/022880 A2 | 3/2003 |
| WO | 03/031588 | 4/2003 |
| WO | WO 2004/003141 A2 * | 1/2004 |
| WO | WO 2005/118626 A2 | 12/2005 |
| WO | WO 2006/086188 A3 | 8/2006 |

OTHER PUBLICATIONS

S. Ray et al., "Divergent and Convergent Evolution After a Common-Source Outbreak of Hepatitis C Virus," JEM, Jun. 6, 2005, pp. 1753-1759, vol. 201, No. 11.
A. Cox et al., "Cellular Immune Selection with Hepatitis C Virus Persistence in Humans," JEM, Jun. 6, 2005, pp. 1741-1752, vol. 201, No. 11.
G. Puntoriero et al., "Towards a Solution for Hepatitis C Virus Hypervariability: Mimotopes of the Hypervariable Region 1 can Induce Antibodies Cross-Reacting With a Large Number of Viral Variants," EMBO Journal, 1998, pp. 3521-3533, vol. 17, No. 13.
M. Salemi et al., "Hepatitis C Virus Evolutionary Patterns Studied Through Analysis of Full-Genome Sequences," J. Mol. Evol. (2002) 54:62-70.
M. Isaguliants et al., "Antibody Responses Against B-Cell Epitopes of the Hypervariable Region 1 of Hepatitis C Virus in Self-Limiting and Chronic Human Hepatitis C Followed-Up Using Consensus Peptides," J. of Medical Virology 66:204-217 (2002).
M. Gimenez-Barcons et al., "High Amino Acid Variability Within the NS5A of Hepatitis C Virus (HCV) is Associated With Hepatocellular Carcinoma in Patients With HCV-1b-Related Cirrhosis," Hepatology, Jul. 2001, pp. 158-167, vol. 34, No. 1.
Hua-Zhang Guo et al., "Sequence Evolution of Putative Cytotoxic T Cell Epitopes in NS3 Region of Hepatitis C Virus," World J Gastroenterol 2004;10(6):847-851.
P. Qiu et al., "Hepatitis C Virus Whole Genome Position Weight Matrix and Robust Primer Design," BMC Microbiology, Sep. 25, 2002, pp. 1-7, vol. 2, No. 1.
European Examination Report issued for corresponding European Patent Application No. 06734155.2 mailed Aug. 13, 2010.

* cited by examiner

*Primary Examiner* — Stacy B. Chen
(74) *Attorney, Agent, or Firm* — Banner & Witcoff, Ltd

(57) ABSTRACT

The invention provides consensus sequences for hepatitis C virus 1a and 1b. Also provided are non-synonymous changes for each residue of the consensus sequences. These sequences are useful as compositions or vaccines for prophylactic use or treating HCV-infected individuals. Also provided are methods for lessening the chances for a HCV-infected individual to enter a chronic phase of infection and methods of diagnosing an individual with HCV 1a or HCV 1b infection.

2 Claims, 13 Drawing Sheets

Fig. 8

```
              10         20         30         40         50         60         70         80         90        100
         ....|....|  ....|....|  ....|....|  ....|....|  ....|....|  ....|....|  ....|....|  ....|....|  ....|....|  ....|....|
Cons1a   MSTNPKPQRK  TKRNTNRRPQ  DVKFPGGGQI  VGGVYLLPRR  GPRLGVRATR  KTSERSQPRG  RRQPIPKARR  PEGRTWAQPG  YPWPLYGNEG  CGWAGWLLSP 110        120        130        140        150        160        170        180        190        200
         ....|....|  ....|....|  ....|....|  ....|....|  ....|....|  ....|....|  ....|....|  ....|....|  ....|....|  ....|....|
Cons1a   RGSRPSWGPT  DPRRRSRNLG  KVIDTLTCGF  ADLMGYIPLV  GAPLGGAARA  LAHGVRVLED  GVNYATGNLP  GCSFSIPLLA  LLSCLTVPAS  AYQVRNSSGL 210        220        230        240        250        260        270        280        290        300
         ....|....|  ....|....|  ....|....|  ....|....|  ....|....|  ....|....|  ....|....|  ....|....|  ....|....|  ....|....|
Cons1a   YHVTNDCPNS  SIVYEAADAI  LHTPGCVPCV  REGNASRCWV  AVTPTVATRD  GKLPTTQLRR  HIDLLVGSAT  LCSALYVGDL  CGSVFLVGQL  FTFSPRRHWT 310        320        330        340        350        360        370        380        390        400
         ....|....|  ....|....|  ....|....|  ....|....|  ....|....|  ....|....|  ....|....|  ....|....|  ....|....|  ....|....|
Cons1a   TQDCNCSIYP  GHITGHRMAW  DMMMNMSPTT  ALVVAQLLRI  PQAILDMIAG  AHWGVLAGIA  YFSMVGNWAK  VLVVLLLFAG  VDAETHVTGG  SAARTTSGLA 410        420        430        440        450        460        470        480        490        500
         ....|....|  ....|....|  ....|....|  ....|....|  ....|....|  ....|....|  ....|....|  ....|....|  ....|....|  ....|....|
Cons1a   GLFSPGAKQN  IQLINTNGSW  HINRTALNCN  DSLNTGWIAG  LFYYHKFNSS  GCPERLASCR  PLTDFDQGWG  PISYANGSGP  DQRPYCWHYP  PKPCGIVPAK 510        520        530        540        550        560        570        580        590        600
         ....|....|  ....|....|  ....|....|  ....|....|  ....|....|  ....|....|  ....|....|  ....|....|  ....|....|  ....|....|
Cons1a   SVCGPVYCPT  PSPVVVGTTD  RSGAPTYNWG  ENDTDVFVLN  NTRPPLGNWF  GCTWMNSTGF  TKVCGAPPCV  IGGVGNNTLH  CPTDCFRKHP  EATYSRCGSG 610        620        630        640        650        660        670        680        690        700
         ....|....|  ....|....|  ....|....|  ....|....|  ....|....|  ....|....|  ....|....|  ....|....|  ....|....|  ....|....|
Cons1a   PWITPRCLVH  YPYRLWHYPC  TINYTIFKVR  MYVGGVEHRL  EAACNWTRGE  RCDLEDRDRS  ELSPLLLSTT  QWQVLPCSFT  TLPALSTGLI  HLHQNIVDVQ 710        720        730        740        750        760        770        780        790        800
         ....|....|  ....|....|  ....|....|  ....|....|  ....|....|  ....|....|  ....|....|  ....|....|  ....|....|  ....|....|
Cons1a   YLYGVGSSIA  SWAIKWEYVV  LLFLLLADAR  VCSCLWMMLL  ISQAEAALEN  LVVLNAASLA  GTHGLVSFLV  FFCFAWYLKG  RWVPGAAYAL  YGMWPLLLLL 810        820        830        840        850        860        870        880        890        900
         ....|....|  ....|....|  ....|....|  ....|....|  ....|....|  ....|....|  ....|....|  ....|....|  ....|....|  ....|....|
Cons1a   LALPQRAYAL  DIEVAASCGG  VVLVGLMALT  LSPYYKRYIS  WCLWWLQYFL  TRVEAQLHVW  VPPLNVRGGR  DAVILLMCAV  HPTLVFDITK  LLLAIFGPLW 910        920        930        940        950        960        970        980        990       1000
         ....|....|  ....|....|  ....|....|  ....|....|  ....|....|  ....|....|  ....|....|  ....|....|  ....|....|  ....|....|
Cons1a   ILQASLLKVP  YFVRVQGLLR  ICALARKMAG  GHYVQMAIIK  LGALTGTYVY  NHLTPLRDWA  HNGLRDLAVA  VEPVVFSQME  TKLITWGADT  AACGDIINGL 1010       1020       1030       1040       1050       1060       1070       1080       1090       1100
         ....|....|  ....|....|  ....|....|  ....|....|  ....|....|  ....|....|  ....|....|  ....|....|  ....|....|  ....|....|
Cons1a   PVSARRGREI  LLGPADGMVS  KGWRLLAPIT  AYAQQTRGLL  GCIITSLTGR  DKNQVEGEVQ  IVSTAAQTFL  ATCINGVCWT  VYHGAGTRTI  ASSKGPVIQM 1110       1120       1130       1140       1150       1160       1170       1180       1190       1200
         ....|....|  ....|....|  ....|....|  ....|....|  ....|....|  ....|....|  ....|....|  ....|....|  ....|....|  ....|....|
Cons1a   YTNVDQDLVG  WPAPQGARSL  TPCTCGSSDL  YLVTRHADVI  PVRRRGDSRG  SLLSPRPISY  LKGSSGGPLL  CPAGHAVGIF  RAAVCTRGVA  KAVDFIPVEN 1210       1220       1230       1240       1250       1260       1270       1280       1290       1300
         ....|....|  ....|....|  ....|....|  ....|....|  ....|....|  ....|....|  ....|....|  ....|....|  ....|....|  ....|....|
Cons1a   LETTMRSPVF  TDNSSPPAVP  QSFQVAHLHA  PTGSGKSTKV  PAAYAAQGYK  VLVLNPSVAA  TLGFGAYMSK  AHGIDPNIRT  GVRTITTGSP  ITYSTYGKFL 1310       1320       1330       1340       1350       1360       1370       1380       1390       1400
         ....|....|  ....|....|  ....|....|  ....|....|  ....|....|  ....|....|  ....|....|  ....|....|  ....|....|  ....|....|
Cons1a   ADGGCSGGAY  DIIICDECHS  TDATSILGIG  TVLDQAETAG  ARLVVLATAT  PPGSVTVPHP  NIEEVALSTT  GEIPFYGKAI  PLEVIKGGRH  LIFCHSKKKC 1410       1420       1430       1440       1450       1460       1470       1480       1490       1500
         ....|....|  ....|....|  ....|....|  ....|....|  ....|....|  ....|....|  ....|....|  ....|....|  ....|....|  ....|....|
Cons1a   DELAAKLVAL  GINAVAYYRG  LDVSVIPTSG  DVVVVATDAL  MTGYTGDFDS  VIDCNTCVTQ  TVDFSLDPTF  TIETTTLPQD  AVSRTQRRGR  TGRGKPGIYR 1510       1520       1530       1540       1550       1560       1570       1580       1590       1600
         ....|....|  ....|....|  ....|....|  ....|....|  ....|....|  ....|....|  ....|....|  ....|....|  ....|....|  ....|....|
Cons1a   FVAPGERPSG  MFDSSVLCEC  YDAGCAWYEL  TPAETTVRLR  AYMNTPGLPV  CQDHLEFWEG  VFTGLTHIDA  HFLSQTKQSG  ENFPYLVAYQ  ATVCARAQAP 1610       1620       1630       1640       1650       1660       1670       1680       1690       1700
         ....|....|  ....|....|  ....|....|  ....|....|  ....|....|  ....|....|  ....|....|  ....|....|  ....|....|  ....|....|
Cons1a   PPSWDQMWKC  LIRLKPTLHG  PTPLLYRLGA  VQNHVTLTHP  VTKYIMTCMS  ADLEVVTSTW  VLVGGVLAAL  AAYCLSTGCV  VIVGRIVLSG  KPAIIPDREV 1710       1720       1730       1740       1750       1760       1770       1780       1790       1800
         ....|....|  ....|....|  ....|....|  ....|....|  ....|....|  ....|....|  ....|....|  ....|....|  ....|....|  ....|....|
Cons1a   LYREFDEMEE  CSQHLPYIEQ  GMMLAEQFKQ  KALGLLQTAS  RQAEVIAPAV  QTNWQKLEAF  WAKHMWNFIS  GIQYLAGLST  LPGNPAIASL  MAFTAAVTSP 1810       1820       1830       1840       1850       1860       1870       1880       1890       1900
         ....|....|  ....|....|  ....|....|  ....|....|  ....|....|  ....|....|  ....|....|  ....|....|  ....|....|  ....|....|
Cons1a   LTTSQTLLFN  ILGGWVAAQL  AAPGAATAFV  GAGLAGAAIG  SVGLGKVLVD  ILAGYGAGVA  GALVAFKIMS  GEVPSTEDLV  NLLPAILSPG  ALVVGVVCAA 1910       1920       1930       1940       1950       1960       1970       1980       1990       2000
         ....|....|  ....|....|  ....|....|  ....|....|  ....|....|  ....|....|  ....|....|  ....|....|  ....|....|  ....|....|
Cons1a   ILRRHVGPGE  GAVQWMNRLI  AFASRGNHVS  PTHYVPESDA  AARVTAILSS  LTVTQLLRRL  HQWISSECTS  MGSGSWLRDI  WDWICEVLSD  FKTWLKAKLM 2010       2020       2030       2040       2050       2060       2070       2080       2090       2100
         ....|....|  ....|....|  ....|....|  ....|....|  ....|....|  ....|....|  ....|....|  ....|....|  ....|....|  ....|....|
Cons1a   PQLPGIPFVS  CQRGYRGVWR  GDGIMHTRCH  CGAEITGHVK  NGTMRIVGPR  TCRNMWSGTF  PINAYTTGPC  TPLPAPNYTF  ALNRVSAEEY  VEIRQVGDFH 2110       2120       2130       2140       2150       2160       2170       2180       2190       2200
         ....|....|  ....|....|  ....|....|  ....|....|  ....|....|  ....|....|  ....|....|  ....|....|  ....|....|  ....|....|
Cons1a   YVTGMTTDNL  KCPCQVPSPE  FFTELDGVRL  HRFAPPCKPL  LREEVSFRVG  LHEYPVGSQL  PCEPEPDVAV  LTSMLTDPSH  ITAEAAGRRL  ARGSPPSVAS
```

Fig. 9

```
              2210       2220       2230       2240       2250       2260       2270       2280       2290       2300
          ....|....|  ....|....|  ....|....|  ....|....|  ....|....|  ....|....|  ....|....|  ....|....|  ....|....|  ....|....|
Consla    SSASQLSAPS  LKATCTANHD  SPDAELIEAN  LLWRQEMGGN  ITRVESENKV  VILDSFDPLV  AEEDEREISV  PAEILRKSRR  FAPALPVWAR  PDYNPPLLET
              2310       2320       2330       2340       2350       2360       2370       2380       2390       2400
          ....|....|  ....|....|  ....|....|  ....|....|  ....|....|  ....|....|  ....|....|  ....|....|  ....|....|  ....|....|
Consla    WKKPDYEPPV  VHGCPLPPPQ  SPPVPPPRKK  RTVVLTESTV  STALAELATK  SFGSSSTSGI  TGDNTTTSSE  PAPSGCPPDS  DAESYSSMPP  LEGEPGDPDL
              2410       2420       2430       2440       2450       2460       2470       2480       2490       2500
          ....|....|  ....|....|  ....|....|  ....|....|  ....|....|  ....|....|  ....|....|  ....|....|  ....|....|  ....|....|
Consla    SDGSWSTVSS  EAGTEDVVCG  SHSYSWTGAL  VTPCAABEQK  LPINALSNSL  LRHHNLVYST  TSRSACQRQK  KVTPDRLQVL  DSHYQDVLKE  VKAAASKVKA
              2510       2520       2530       2540       2550       2560       2570       2580       2590       2600
          ....|....|  ....|....|  ....|....|  ....|....|  ....|....|  ....|....|  ....|....|  ....|....|  ....|....|  ....|....|
Consla    NLLSVEEACG  LTPPHSAKSK  FGYGAKDVRC  HARKAVNHIN  SVWKDLLEDS  VTPIDTTIKA  KNEVFCVQPE  KGGRKPARLI  VFPDLGVRVC  EKMALYDVVS
              2610       2620       2630       2640       2650       2660       2670       2680       2690       2700
          ....|....|  ....|....|  ....|....|  ....|....|  ....|....|  ....|....|  ....|....|  ....|....|  ....|....|  ....|....|
Consla    KLPLAVMGSS  YGFQYSPGQR  VEFLVQAWKS  KKTPNGFSYD  TRCFDSTVTS  SDIRTEEAIY  QCCDLDPQAR  VAIKSLTERL  YVGGPLTNSR  GENCGYRRCR
              2710       2720       2730       2740       2750       2760       2770       2780       2790       2800
          ....|....|  ....|....|  ....|....|  ....|....|  ....|....|  ....|....|  ....|....|  ....|....|  ....|....|  ....|....|
Consla    ASGVLTTSCG  NTLTCYIKAQ  AACRAAGLRD  CTMLVCGDDL  VVICESAGVQ  EDAASLRAFT  EAMTRYSAPP  GDPPQPEYDL  ELITSCSSNV  SVAHDGAGKR
              2810       2820       2830       2840       2850       2860       2870       2880       2890       2900
          ....|....|  ....|....|  ....|....|  ....|....|  ....|....|  ....|....|  ....|....|  ....|....|  ....|....|  ....|....|
Consla    VYYLTRDFTT  PLARAAWETA  RHTPVNSWLG  NIIMPAPTLW  ARMILMTHFF  SVLIARDQLE  QALDCEIYGA  CYSIEPLDLP  PIIQRLHGLS  AFSLHSYSPG
              2910       2920       2930       2940       2950       2960       2970       2980       2990       3000
          ....|....|  ....|....|  ....|....|  ....|....|  ....|....|  ....|....|  ....|....|  ....|....|  ....|....|  ....|....|
Consla    EINRVAACLR  KLGVPPLRAW  RHRARSVRAR  LLSRGGRAAI  CGKYLFNWAV  RTKLKLTPIA  AAGQLDLSGW  FTAGYSGGDI  YHSVSRARPR  WFWFCLLLLA
              3010
          ....|....|
Consla    AGVGIYLLPN  R          (SEQ ID NO:1)
```

Fig. 9 (continued)

```
              10         20         30         40         50         60         70         80         90        10
         ....|....|  ....|....|  ....|....|  ....|....|  ....|....|  ....|....|  ....|....|  ....|....|  ....|....|  ....|....|
Cons1b   MSTNPKPQRK  TKRNTNRRPQ  DVKFPGGGQI  VGGVYLLPRR  GFRLGVRATR  KTSERSQPKG  RRQPIPKARR  PEGRAHAQPG  YPHPLYGNEG  MGWAGWLLSP 110        120        130        140        150        160        170        180        190        20
         ....|....|  ....|....|  ....|....|  ....|....|  ....|....|  ....|....|  ....|....|  ....|....|  ....|....|  ....|....|
Cons1b   RGSRPSWGPT  DPRRRSRNLG  KVIDTLTCGF  ADLMGYIPLV  GAPLGGAARA  LAHGVRVLED  GVNYATGNLF  GCSFSIFLLA  LLSCLTIPAS  AYEVRNVSGV 210        220        230        240        250        260        270        280        290        30
         ....|....|  ....|....|  ....|....|  ....|....|  ....|....|  ....|....|  ....|....|  ....|....|  ....|....|  ....|....|
Cons1b   YHVTNDCSNS  STVYEAADMI  MHTPGCVPCV  RENNSSRCWV  ALTPTLAARN  SSVPTTTIRR  HVDLLVGAAA  FCSAMYVGDL  CGSVFLVSQL  PTFSPRRHET 310        320        330        340        350        360        370        380        390        40
         ....|....|  ....|....|  ....|....|  ....|....|  ....|....|  ....|....|  ....|....|  ....|....|  ....|....|  ....|....|
Cons1b   VQDCNCSIYP  GHVSGHRMAW  DMHMNWSPTT  ALVVSQLLRI  PQAVVDMVAG  AHWGVLAGLA  YYSMVGNWAK  VLIVMLLFAG  VDGSTHVTGG  AAARTTRGLT 410        420        430        440        450        460        470        480        490        50
         ....|....|  ....|....|  ....|....|  ....|....|  ....|....|  ....|....|  ....|....|  ....|....|  ....|....|  ....|....|
Cons1b   SLFSPGPSQK  IQLVNTNGSW  HINRTALNCN  DSLQTGFLAA  LFYTHKFNAS  GCPERMASCR  PIDKFAQGWG  PITYAEPDSS  DQRPYGWHYA  PRPCGIVPAS 510        520        530        540        550        560        570        580        590        60
         ....|....|  ....|....|  ....|....|  ....|....|  ....|....|  ....|....|  ....|....|  ....|....|  ....|....|  ....|....|
Cons1b   QVCGPVYCFT  PSPVVVGTTD  RFGVPTYSWG  ENETDVLDLN  NTRPPQGNWF  GCTWMNSTGF  TKTCGGPPCN  IGGVGNNTLT  CPTDCFRKHP  NATYTKCGSG 610        620        630        640        650        660        670        680        690        70
         ....|....|  ....|....|  ....|....|  ....|....|  ....|....|  ....|....|  ....|....|  ....|....|  ....|....|  ....|....|
Cons1b   PWLTPRCMVD  YPYRLWHYPC  TVNFTIFKVR  MYVGGVEHRL  NAACNWTRGE  RCDLEDRDRS  ELSPLLLSTT  EWQILPCSFT  TLPALSTGLI  HLHQNIVDVQ 710        720        730        740        750        760        770        780        790        80
         ....|....|  ....|....|  ....|....|  ....|....|  ....|....|  ....|....|  ....|....|  ....|....|  ....|....|  ....|....|
Cons1b   YLYGIGSAVV  SFAIKWEYVL  LLFLLLADAR  VCACLWMMLL  IAQAEAALEN  LVVLNAASVA  GAHGILSFLV  FFCAAWYIKG  RLVPGAAYAP  YGVWPLLLLL 810        820        830        840        850        860        870        880        890        90
         ....|....|  ....|....|  ....|....|  ....|....|  ....|....|  ....|....|  ....|....|  ....|....|  ....|....|  ....|....|
Cons1b   LALPPRAYAM  DREMAASCGG  AVFVGLALLT  LSPHYKVFLA  RLIWWLQYFI  TRAEAHLQVW  IPPINVRGGR  DAIILLTCAV  HPELIFDITK  ILLAILGPLM 910        920        930        940        950        960        970        980        990       100
         ....|....|  ....|....|  ....|....|  ....|....|  ....|....|  ....|....|  ....|....|  ....|....|  ....|....|  ....|....|
Cons1b   VLQAGITRVP  YFVRAQGLIR  ACMLVRKVAG  GHYVQMAFMK  LAALTGTYFY  DHLTPLRDWA  HAGLRDLAVA  VEPVVFSDME  TKIITWGADT  AACGDIILGL 1010       1020       1030       1040       1050       1060       1070       1080       1090       1100
         ....|....|  ....|....|  ....|....|  ....|....|  ....|....|  ....|....|  ....|....|  ....|....|  ....|....|  ....|....|
Cons1b   PVSARRGREI  LLGPADSLEG  QGWRLLAPIT  AYSQQTRGLL  GCIITSLTGR  DKNQVEGEVQ  VVSTATQSFL  ATCGVNGVCWT  VYHGAGSKTL  AGPKGPITQM 1110       1120       1130       1140       1150       1160       1170       1180       1190       1200
         ....|....|  ....|....|  ....|....|  ....|....|  ....|....|  ....|....|  ....|....|  ....|....|  ....|....|  ....|....|
Cons1b   YTNVDQDIVG  WQAFPGARSL  TPCTCGSSDL  YLVTRHADVI  PVRRRGDSRG  SLLSPRPVSY  LKGSSGGPLL  CPSGHAVGIF  RAAVCTRGVA  KAVDFVPVES 1210       1220       1230       1240       1250       1260       1270       1280       1290       1300
         ....|....|  ....|....|  ....|....|  ....|....|  ....|....|  ....|....|  ....|....|  ....|....|  ....|....|  ....|....|
Cons1b   METTMRSPVF  TDNSSPPAVP  QTFQVAHLHA  PTGSGKSTKV  FAAYAAQGYK  VLVLNPSVAA  TLGFGAYMSK  AHGVDPNIRT  GVRTITTGAP  ITYSTYGKFL 1310       1320       1330       1340       1350       1360       1370       1380       1390       1400
         ....|....|  ....|....|  ....|....|  ....|....|  ....|....|  ....|....|  ....|....|  ....|....|  ....|....|  ....|....|
Cons1b   ADGGCSGGAY  DIIICDECHS  TDSTTILGIG  TVLDQAETAG  ARLVVLATAT  PPGSVTVPHP  NIEEVALSNT  GEIPFYGKAI  PIETIKGGRH  LIFCHSKKKC 1410       1420       1430       1440       1450       1460       1470       1480       1490       1500
         ....|....|  ....|....|  ....|....|  ....|....|  ....|....|  ....|....|  ....|....|  ....|....|  ....|....|  ....|....|
Cons1b   DELAAKLSGL  GLNAVAYYRG  LDVSVIPTSG  DVVVVATDAL  MTGFTGDFDS  VIDCNTCVTQ  TVDFSLDPTF  TIETTTVPQD  AVGRSQRRGR  TGRGRRGIYR 1510       1520       1530       1540       1550       1560       1570       1580       1590       1600
         ....|....|  ....|....|  ....|....|  ....|....|  ....|....|  ....|....|  ....|....|  ....|....|  ....|....|  ....|....|
Cons1b   FVTPGERPSG  MFDSSVLCEC  YDAGCAWYEL  TPAETSVRLR  AYLNTPGLPV  CQDHLEFWSS  VFTGLTHIDA  HFLSQTKQAG  DNFPYLVAYQ  ATVCARAQAP 1610       1620       1630       1640       1650       1660       1670       1680       1690       1700
         ....|....|  ....|....|  ....|....|  ....|....|  ....|....|  ....|....|  ....|....|  ....|....|  ....|....|  ....|....|
Cons1b   PPSWDQMWKC  LIRLKPTLHG  PTPLLYRLGA  VQNEVTLTHP  ITKYIMACMS  ADLEVVTSTW  VLVGGVLAAL  AAYCLTTGSV  VIVGRIILSG  KPAVIPDREV 1710       1720       1730       1740       1750       1760       1770       1780       1790       1800
         ....|....|  ....|....|  ....|....|  ....|....|  ....|....|  ....|....|  ....|....|  ....|....|  ....|....|  ....|....|
Cons1b   LYQEFDEMEE  CASHLPYIEQ  GKQLAEQFKQ  KALGLLQTAT  KQAEAAAPVV  ESKWRALETF  WAKHMWNFIS  GIQYLAGLST  LPGNPAIASL  MAFTASITSP 1810       1820       1830       1840       1850       1860       1870       1880       1890       1900
         ....|....|  ....|....|  ....|....|  ....|....|  ....|....|  ....|....|  ....|....|  ....|....|  ....|....|  ....|....|
Cons1b   LTTQHTLLFN  ILGGWVAAQL  APPSAASAFV  GAGIAGAAVG  SIGLGKVLVD  ILAGYGAGVA  GALVAFKVMS  GEMPSTEDLV  NLLPAILSPG  ALVVGVVCAA 1910       1920       1930       1940       1950       1960       1970       1980       1990       2000
         ....|....|  ....|....|  ....|....|  ....|....|  ....|....|  ....|....|  ....|....|  ....|....|  ....|....|  ....|....|
Cons1b   ILRRHVGPGE  GAVQWMNRLI  AFASRGNHVS  PTHYVPESDA  AARVTQILSS  LTITQLLKRL  HQWINEDCST  PCSGSWLRDV  WDWICTVLTD  FKTWLQSKLL 2010       2020       2030       2040       2050       2060       2070       2080       2090       2100
         ....|....|  ....|....|  ....|....|  ....|....|  ....|....|  ....|....|  ....|....|  ....|....|  ....|....|  ....|....|
Cons1b   PRLPGVPFFS  CQRGYKGVWR  GDGIMQTTCP  CGAQITGHVK  NGSMRIVGPK  TCSNTWHGTF  PINAYTTGPC  TPSEAPNYSR  ALWRVAABEY  VEVTRVGDFH 2110       2120       2130       2140       2150       2160       2170       2180       2190       2200
         ....|....|  ....|....|  ....|....|  ....|....|  ....|....|  ....|....|  ....|....|  ....|....|  ....|....|  ....|....|
Cons1b   YVTGMTTDNV  KCPCQVPAPE  FFTEVDGVRL  HRYAPACKPL  LREEVTFQVG  LNQYLVGSQL  PCEPEPDVAV  LTSMLTDPSH  ITAETAKRRL  ARGSPPSLAS
```

Fig. 10

```
            2210       2220       2230       2240       2250       2260       2270       2280       2290       2300
        ....|....|  ....|....|  ....|....|  ....|....|  ....|....|  ....|....|  ....|....|  ....|....|  ....|....|  ....|....|
Cons1b  SSASQLSAPS  LKATCTTRHD  SPDADLIEAN  LLWRQEWGGN  ITRVESENKV  VILDSPDPLR  ABSDEREVSV  PAEILRKSRK  FPPAMPIWAR  PDYNPPLLES 2310       2320       2330       2340       2350       2360       2370       2380       2390       2400
        ....|....|  ....|....|  ....|....|  ....|....|  ....|....|  ....|....|  ....|....|  ....|....|  ....|....|  ....|....|
Cons1b  WKDPDYVPPV  VHGCPLPPTK  APPIPPPRRK  RTVVLTESTV  SSALAELATK  TFGSSESSAV  DSGTATAPPD  QPSDDGDAGS  DVESYSSMPF  LEGSPGDPDL 2410       2420       2430       2440       2450       2460       2470       2480       2490       2500
        ....|....|  ....|....|  ....|....|  ....|....|  ....|....|  ....|....|  ....|....|  ....|....|  ....|....|  ....|....|
Cons1b  SDGSWSTVSE  EASEDVVCCS  MSYTWTGALI  TPCAAEESKL  PINALSNSLL  RHHDMVYATT  SRSASQRQKK  VTFDRLQVLD  DHYRDVLKEK  KAKASTVKAK 2510       2520       2530       2540       2550       2560       2570       2580       2590       2600
        ....|....|  ....|....|  ....|....|  ....|....|  ....|....|  ....|....|  ....|....|  ....|....|  ....|....|  ....|....|
Cons1b  LLSVEEACKL  TPPHSAKSKF  GYGAKDVRNL  SSKAVNHIRS  VNKDLLEDTE  TPIDTTIMAK  NEVFCVQPEK  GGRKPARLIV  FPDLGVRVCE  KMALYDVVST 2610       2620       2630       2640       2650       2660       2670       2680       2690       2700
        ....|....|  ....|....|  ....|....|  ....|....|  ....|....|  ....|....|  ....|....|  ....|....|  ....|....|  ....|....|
Cons1b  LPQAVMGSSY  GPQYSPGQRV  EPLVNAWKSK  KNPHGFAYDT  RCPDSTVTEN  DIRVEESIYQ  CCDLAPEARQ  AIRSLTERLY  IGGPLTNSKG  QNCGYRRCRA 2710       2720       2730       2740       2750       2760       2770       2780       2790       2800
        ....|....|  ....|....|  ....|....|  ....|....|  ....|....|  ....|....|  ....|....|  ....|....|  ....|....|  ....|....|
Cons1b  SGVLTTSCGN  TLTCYLKASA  ACRAAKLQDC  TMLVCGDDLV  VICESAGTQE  DAASLRVFTE  AMTRYSAPPG  DPPQPEYDLE  LITSCSSNVS  VAHDASGKRV 2810       2820       2830       2840       2850       2860       2870       2880       2890       2900
        ....|....|  ....|....|  ....|....|  ....|....|  ....|....|  ....|....|  ....|....|  ....|....|  ....|....|  ....|....|
Cons1b  YYLTRDPTTP  LARAAWETAR  RTPVNSWLGN  IIMYAPTLWA  RMILMTHFFS  ILLAQEQLEK  ALDCQIYGAC  YSIEPLDLPQ  IIQRLHGLSA  FSLHSYSPGE 2910       2920       2930       2940       2950       2960       2970       2980       2990       3000
        ....|....|  ....|....|  ....|....|  ....|....|  ....|....|  ....|....|  ....|....|  ....|....|  ....|....|  ....|....|
Cons1b  INRVASCLRK  LGVPPLRVWR  HRARSVRAKL  LSQGGRAAIC  GKYLFNWAVR  TKLKLTPIPA  ASQLDLSGWF  VAGTSGGDIY  HSLSRARPRW  FMLCLLLLSV 3020
        ....|....|
Cons1b  GVGIYLLPNR        (SEQ ID NO:2)
```

Fig. 10 (continued)

SEQUENCE LISTING

<160> NUMBER OF SEQ ID NOS: 22

<210> SEQ ID NO 1
<211> LENGTH: 3011
<212> TYPE: PRT
<213> ORGANISM: Hepatitis C Virus
<220> FEATURE:
<221> NAME/KEY: VARIANT
<222> LOCATION: 618, 1765, 2268, 2653, 2885
<223> OTHER INFORMATION: Xaa = Any Amino Acid

<400> SEQUENCE: 1

```
Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
                35                  40                  45

Thr Arg Lys Thr Ser Glu Arg Ser Gln Pro Arg Gly Arg Arg Gln Pro
            50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
            130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
```

-continued

```
                180                 185                 190
Gln Val Arg Asn Ser Ser Gly Leu Tyr His Val Thr Asn Asp Cys Pro
            195                 200                 205
Asn Ser Ser Ile Val Tyr Glu Ala Ala Asp Ala Ile Leu His Thr Pro
        210                 215                 220
Gly Cys Val Pro Cys Val Arg Glu Gly Asn Ala Ser Arg Cys Trp Val
225                 230                 235                 240
Ala Val Thr Pro Thr Val Ala Thr Arg Asp Gly Lys Leu Pro Thr Thr
                245                 250                 255
Gln Leu Arg Arg His Ile Asp Leu Leu Val Gly Ser Ala Thr Leu Cys
            260                 265                 270
Ser Ala Leu Tyr Val Gly Asp Leu Cys Gly Ser Val Phe Leu Val Gly
        275                 280                 285
Gln Leu Phe Thr Phe Ser Pro Arg Arg His Trp Thr Thr Gln Asp Cys
        290                 295                 300
Asn Cys Ser Ile Tyr Pro Gly His Ile Thr Gly His Arg Met Ala Trp
305                 310                 315                 320
Asp Met Met Met Asn Trp Ser Pro Thr Thr Ala Leu Val Val Ala Gln
                325                 330                 335
Leu Leu Arg Ile Pro Gln Ala Ile Leu Asp Met Ile Ala Gly Ala His
            340                 345                 350
Trp Gly Val Leu Ala Gly Ile Ala Tyr Phe Ser Met Val Gly Asn Trp
        355                 360                 365
Ala Lys Val Leu Val Val Leu Leu Phe Ala Gly Val Asp Ala Glu
        370                 375                 380
Thr His Val Thr Gly Gly Ser Ala Ala Arg Thr Thr Ser Gly Leu Ala
385                 390                 395                 400
Gly Leu Phe Ser Pro Gly Ala Lys Gln Asn Ile Gln Leu Ile Asn Thr
                405                 410                 415
Asn Gly Ser Trp His Ile Asn Arg Thr Ala Leu Asn Cys Asn Asp Ser
            420                 425                 430
Leu Asn Thr Gly Trp Ile Ala Gly Leu Phe Tyr Tyr His Lys Phe Asn
        435                 440                 445
Ser Ser Gly Cys Pro Glu Arg Leu Ala Ser Cys Arg Pro Leu Thr Asp
450                 455                 460
Phe Asp Gln Gly Trp Gly Pro Ile Ser Tyr Ala Asn Gly Ser Gly Pro
465                 470                 475                 480
Asp Gln Arg Pro Tyr Cys Trp His Tyr Pro Pro Lys Pro Cys Gly Ile
                485                 490                 495
Val Pro Ala Lys Ser Val Cys Gly Pro Val Tyr Cys Phe Thr Pro Ser
            500                 505                 510
Pro Val Val Val Gly Thr Thr Asp Arg Ser Gly Ala Pro Thr Tyr Asn
        515                 520                 525
Trp Gly Glu Asn Asp Thr Asp Val Phe Val Leu Asn Asn Thr Arg Pro
        530                 535                 540
Pro Leu Gly Asn Trp Phe Gly Cys Thr Trp Met Asn Ser Thr Gly Phe
545                 550                 555                 560
Thr Lys Val Cys Gly Ala Pro Pro Cys Val Ile Gly Val Gly Asn
                565                 570                 575
Asn Thr Leu His Cys Pro Thr Asp Cys Phe Arg Lys His Pro Glu Ala
            580                 585                 590
Thr Tyr Ser Arg Cys Gly Ser Gly Pro Trp Ile Thr Pro Arg Cys Leu
        595                 600                 605
```

-continued

```
Val His Tyr Pro Tyr Arg Leu Trp His Xaa Pro Cys Thr Ile Asn Tyr
610                 615                 620

Thr Ile Phe Lys Val Arg Met Tyr Val Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Val Leu Asn Ala Ala Ser Leu Ala Gly Thr His Gly Leu Val Ser Phe
        755                 760                 765

Leu Val Phe Phe Cys Phe Ala Trp Tyr Leu Lys Gly Arg Trp Val Pro
770                 775                 780

Gly Ala Ala Tyr Ala Leu Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Leu Trp Trp Leu Gln Tyr
        835                 840                 845

Phe Leu Thr Arg Val Glu Ala Gln Leu His Val Trp Val Pro Pro Leu
850                 855                 860

Asn Val Arg Gly Gly Arg Asp Ala Val Ile Leu Leu Met Cys Ala Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Ile Cys Ala Leu Ala Arg Lys Met
        915                 920                 925

Ala Gly Gly His Tyr Val Gln Met Ala Ile Ile Lys Leu Gly Ala Leu
930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Gln Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Arg
        995                 1000                1005

Glu Ile Leu Leu Gly Pro Ala Asp Gly Met Val Ser Lys Gly Trp Arg
1010                1015                1020

Leu Leu Ala Pro Ile Thr Ala Tyr Ala Gln Gln Thr Arg Gly Leu Leu
1025                1030                1035                1040
```

-continued

Gly Cys Ile Ile Thr Ser Leu Thr Gly Arg Asp Lys Asn Gln Val Glu
            1045                1050                1055

Gly Glu Val Gln Ile Val Ser Thr Ala Ala Gln Thr Phe Leu Ala Thr
            1060                1065                1070

Cys Ile Asn Gly Val Cys Trp Thr Val Tyr His Gly Ala Gly Thr Arg
            1075                1080                1085

Thr Ile Ala Ser Ser Lys Gly Pro Val Ile Gln Met Tyr Thr Asn Val
            1090                1095                1100

Asp Gln Asp Leu Val Gly Trp Pro Ala Pro Gln Gly Ala Arg Ser Leu
1105                1110                1115                1120

Thr Pro Cys Thr Cys Gly Ser Ser Asp Leu Tyr Leu Val Thr Arg His
            1125                1130                1135

Ala Asp Val Ile Pro Val Arg Arg Arg Gly Asp Ser Arg Gly Ser Leu
            1140                1145                1150

Leu Ser Pro Arg Pro Ile Ser Tyr Leu Lys Gly Ser Ser Gly Gly Pro
            1155                1160                1165

Leu Leu Cys Pro Ala Gly His Ala Val Gly Ile Phe Arg Ala Ala Val
            1170                1175                1180

Cys Thr Arg Gly Val Ala Lys Ala Val Asp Phe Ile Pro Val Glu Asn
1185                1190                1195                1200

Leu Glu Thr Thr Met Arg Ser Pro Val Phe Thr Asp Asn Ser Ser Pro
            1205                1210                1215

Pro Ala Val Pro Gln Ser Phe Gln Val Ala His Leu His Ala Pro Thr
            1220                1225                1230

Gly Ser Gly Lys Ser Thr Lys Val Pro Ala Ala Tyr Ala Ala Gln Gly
            1235                1240                1245

Tyr Lys Val Leu Val Leu Asn Pro Ser Val Ala Ala Thr Leu Gly Phe
            1250                1255                1260

Gly Ala Tyr Met Ser Lys Ala His Gly Ile Asp Pro Asn Ile Arg Thr
1265                1270                1275                1280

Gly Val Arg Thr Ile Thr Thr Gly Ser Pro Ile Thr Tyr Ser Thr Tyr
            1285                1290                1295

Gly Lys Phe Leu Ala Asp Gly Gly Cys Ser Gly Gly Ala Tyr Asp Ile
            1300                1305                1310

Ile Ile Cys Asp Glu Cys His Ser Thr Asp Ala Thr Ser Ile Leu Gly
            1315                1320                1325

Ile Gly Thr Val Leu Asp Gln Ala Glu Thr Ala Gly Ala Arg Leu Val
            1330                1335                1340

Val Leu Ala Thr Ala Thr Pro Pro Gly Ser Val Thr Val Pro His Pro
1345                1350                1355                1360

Asn Ile Glu Glu Val Ala Leu Ser Thr Thr Gly Glu Ile Pro Phe Tyr
            1365                1370                1375

Gly Lys Ala Ile Pro Leu Glu Val Ile Lys Gly Gly Arg His Leu Ile
            1380                1385                1390

Phe Cys His Ser Lys Lys Lys Cys Asp Glu Leu Ala Ala Lys Leu Val
            1395                1400                1405

Ala Leu Gly Ile Asn Ala Val Ala Tyr Tyr Arg Gly Leu Asp Val Ser
            1410                1415                1420

Val Ile Pro Thr Ser Gly Asp Val Val Val Ala Thr Asp Ala Leu
1425                1430                1435                1440

Met Thr Gly Tyr Thr Gly Asp Phe Asp Ser Val Ile Asp Cys Asn Thr
            1445                1450                1455

Cys Val Thr Gln Thr Val Asp Phe Ser Leu Asp Pro Thr Phe Thr Ile

-continued

```
                1460                1465                1470
Glu Thr Thr Thr Leu Pro Gln Asp Ala Val Ser Arg Thr Gln Arg Arg
            1475                1480                1485
Gly Arg Thr Gly Arg Gly Lys Pro Gly Ile Tyr Arg Phe Val Ala Pro
            1490                1495                1500
Gly Glu Arg Pro Ser Gly Met Phe Asp Ser Ser Val Leu Cys Glu Cys
1505                1510                1515                1520
Tyr Asp Ala Gly Cys Ala Trp Tyr Glu Leu Thr Pro Ala Glu Thr Thr
            1525                1530                1535
Val Arg Leu Arg Ala Tyr Met Asn Thr Pro Gly Leu Pro Val Cys Gln
            1540                1545                1550
Asp His Leu Glu Phe Trp Glu Gly Val Phe Thr Gly Leu Thr His Ile
            1555                1560                1565
Asp Ala His Phe Leu Ser Gln Thr Lys Gln Ser Gly Glu Asn Phe Pro
            1570                1575                1580
Tyr Leu Val Ala Tyr Gln Ala Thr Val Cys Ala Arg Ala Gln Ala Pro
1585                1590                1595                1600
Pro Pro Ser Trp Asp Gln Met Trp Lys Cys Leu Ile Arg Leu Lys Pro
            1605                1610                1615
Thr Leu His Gly Pro Thr Pro Leu Leu Tyr Arg Leu Gly Ala Val Gln
            1620                1625                1630
Asn Glu Val Thr Leu Thr His Pro Val Thr Lys Tyr Ile Met Thr Cys
            1635                1640                1645
Met Ser Ala Asp Leu Glu Val Val Thr Ser Thr Trp Val Leu Val Gly
            1650                1655                1660
Gly Val Leu Ala Ala Leu Ala Ala Tyr Cys Leu Ser Thr Gly Cys Val
1665                1670                1675                1680
Val Ile Val Gly Arg Ile Val Leu Ser Gly Lys Pro Ala Ile Ile Pro
            1685                1690                1695
Asp Arg Glu Val Leu Tyr Arg Glu Phe Asp Glu Met Glu Glu Cys Ser
            1700                1705                1710
Gln His Leu Pro Tyr Ile Glu Gln Gly Met Met Leu Ala Glu Gln Phe
            1715                1720                1725
Lys Gln Lys Ala Leu Gly Leu Leu Gln Thr Ala Ser Arg Gln Ala Glu
            1730                1735                1740
Val Ile Ala Pro Ala Val Gln Thr Asn Trp Gln Lys Leu Glu Ala Phe
1745                1750                1755                1760
Trp Ala Lys His Xaa Trp Asn Phe Ile Ser Gly Ile Gln Tyr Leu Ala
            1765                1770                1775
Gly Leu Ser Thr Leu Pro Gly Asn Pro Ala Ile Ala Ser Leu Met Ala
            1780                1785                1790
Phe Thr Ala Ala Val Thr Ser Pro Leu Thr Thr Ser Gln Thr Leu Leu
            1795                1800                1805
Phe Asn Ile Leu Gly Gly Trp Val Ala Ala Gln Leu Ala Ala Pro Gly
            1810                1815                1820
Ala Ala Thr Ala Phe Val Gly Ala Gly Leu Ala Gly Ala Ala Ile Gly
1825                1830                1835                1840
Ser Val Gly Leu Gly Lys Val Leu Val Asp Ile Leu Ala Gly Tyr Gly
            1845                1850                1855
Ala Gly Val Ala Gly Ala Leu Val Ala Phe Lys Ile Met Ser Gly Glu
            1860                1865                1870
Val Pro Ser Thr Glu Asp Leu Val Asn Leu Leu Pro Ala Ile Leu Ser
            1875                1880                1885
```

```
Pro Gly Ala Leu Val Val Gly Val Cys Ala Ala Ile Leu Arg Arg
        1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
            1925                1930                1935

Glu Ser Asp Ala Ala Ala Arg Val Thr Ala Ile Leu Ser Ser Leu Thr
        1940                1945                1950

Val Thr Gln Leu Leu Arg Arg Leu His Gln Trp Ile Ser Ser Glu Cys
        1955                1960                1965

Thr Ser Met Gly Ser Gly Ser Trp Leu Arg Asp Ile Trp Asp Trp Ile
        1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Arg
            2005                2010                2015

Gly Val Trp Arg Gly Asp Gly Ile Met His Thr Arg Cys His Cys Gly
        2020                2025                2030

Ala Glu Ile Thr Gly His Val Lys Asn Gly Thr Met Arg Ile Val Gly
        2035                2040                2045

Pro Arg Thr Cys Arg Asn Met Trp Ser Gly Thr Phe Pro Ile Asn Ala
        2050                2055                2060

Tyr Thr Thr Gly Pro Cys Thr Pro Leu Pro Ala Pro Asn Tyr Thr Phe
2065                2070                2075                2080

Ala Leu Trp Arg Val Ser Ala Glu Glu Tyr Val Glu Ile Arg Gln Val
            2085                2090                2095

Gly Asp Phe His Tyr Val Thr Gly Met Thr Thr Asp Asn Leu Lys Cys
        2100                2105                2110

Pro Cys Gln Val Pro Ser Pro Glu Phe Phe Thr Glu Leu Asp Gly Val
        2115                2120                2125

Arg Leu His Arg Phe Ala Pro Pro Cys Lys Pro Leu Leu Arg Glu Glu
        2130                2135                2140

Val Ser Phe Arg Val Gly Leu His Glu Tyr Pro Val Gly Ser Gln Leu
2145                2150                2155                2160

Pro Cys Glu Pro Glu Pro Asp Val Ala Val Leu Thr Ser Met Leu Thr
            2165                2170                2175

Asp Pro Ser His Ile Thr Ala Glu Ala Ala Gly Arg Arg Leu Ala Arg
        2180                2185                2190

Gly Ser Pro Pro Ser Val Ala Ser Ser Ser Ala Ser Gln Leu Ser Ala
        2195                2200                2205

Pro Ser Leu Lys Ala Thr Cys Thr Ala Asn His Asp Ser Pro Asp Ala
        2210                2215                2220

Glu Leu Ile Glu Ala Asn Leu Leu Trp Arg Gln Glu Met Gly Gly Asn
2225                2230                2235                2240

Ile Thr Arg Val Glu Ser Glu Asn Lys Val Val Ile Leu Asp Ser Phe
            2245                2250                2255

Asp Pro Leu Val Ala Glu Glu Asp Glu Arg Glu Xaa Ser Val Pro Ala
        2260                2265                2270

Glu Ile Leu Arg Lys Ser Arg Arg Phe Ala Pro Ala Leu Pro Val Trp
        2275                2280                2285

Ala Arg Pro Asp Tyr Asn Pro Pro Leu Leu Glu Thr Trp Lys Lys Pro
        2290                2295                2300

Asp Tyr Glu Pro Pro Val Val His Gly Cys Pro Leu Pro Pro Pro Gln
2305                2310                2315                2320
```

```
Ser Pro Pro Val Pro Pro Arg Lys Lys Arg Thr Val Leu Thr
            2325                2330                2335

Glu Ser Thr Val Ser Thr Ala Leu Ala Glu Leu Ala Thr Lys Ser Phe
            2340                2345                2350

Gly Ser Ser Thr Ser Gly Ile Thr Gly Asp Asn Thr Thr Thr Ser
            2355                2360                2365

Ser Glu Pro Ala Pro Ser Gly Cys Pro Pro Asp Ser Asp Ala Glu Ser
            2370                2375                2380

Tyr Ser Ser Met Pro Pro Leu Glu Gly Glu Pro Gly Asp Pro Asp Leu
2385                2390                2395                2400

Ser Asp Gly Ser Trp Ser Thr Val Ser Ser Glu Ala Gly Thr Glu Asp
                2405                2410                2415

Val Val Cys Cys Ser Met Ser Tyr Ser Trp Thr Gly Ala Leu Val Thr
                2420                2425                2430

Pro Cys Ala Ala Glu Glu Gln Lys Leu Pro Ile Asn Ala Leu Ser Asn
                2435                2440                2445

Ser Leu Leu Arg His His Asn Leu Val Tyr Ser Thr Thr Ser Arg Ser
                2450                2455                2460

Ala Cys Gln Arg Gln Lys Lys Val Thr Phe Asp Arg Leu Gln Val Leu
2465                2470                2475                2480

Asp Ser His Tyr Gln Asp Val Leu Lys Glu Val Lys Ala Ala Ser
                2485                2490                2495

Lys Val Lys Ala Asn Leu Leu Ser Val Glu Glu Ala Cys Ser Leu Thr
                2500                2505                2510

Pro Pro His Ser Ala Lys Ser Lys Phe Gly Tyr Gly Ala Lys Asp Val
                2515                2520                2525

Arg Cys His Ala Arg Lys Ala Val Asn His Ile Asn Ser Val Trp Lys
                2530                2535                2540

Asp Leu Leu Glu Asp Ser Val Thr Pro Ile Asp Thr Thr Ile Met Ala
2545                2550                2555                2560

Lys Asn Glu Val Phe Cys Val Gln Pro Glu Lys Gly Gly Arg Lys Pro
                2565                2570                2575

Ala Arg Leu Ile Val Phe Pro Asp Leu Gly Val Arg Val Cys Glu Lys
                2580                2585                2590

Met Ala Leu Tyr Asp Val Val Ser Lys Leu Pro Leu Ala Val Met Gly
                2595                2600                2605

Ser Ser Tyr Gly Phe Gln Tyr Ser Pro Gly Gln Arg Val Glu Phe Leu
                2610                2615                2620

Val Gln Ala Trp Lys Ser Lys Lys Thr Pro Met Gly Phe Ser Tyr Asp
2625                2630                2635                2640

Thr Arg Cys Phe Asp Ser Thr Val Thr Glu Ser Asp Xaa Arg Thr Glu
                2645                2650                2655

Glu Ala Ile Tyr Gln Cys Cys Asp Leu Asp Pro Gln Ala Arg Val Ala
                2660                2665                2670

Ile Lys Ser Leu Thr Glu Arg Leu Tyr Val Gly Gly Pro Leu Thr Asn
                2675                2680                2685

Ser Arg Gly Glu Asn Cys Gly Tyr Arg Arg Cys Arg Ala Ser Gly Val
                2690                2695                2700

Leu Thr Thr Ser Cys Gly Asn Thr Leu Thr Cys Tyr Ile Lys Ala Gln
2705                2710                2715                2720

Ala Ala Cys Arg Ala Ala Gly Leu Arg Asp Cys Thr Met Leu Val Cys
                2725                2730                2735

Gly Asp Asp Leu Val Val Ile Cys Glu Ser Ala Gly Val Gln Glu Asp
```

```
                        2740                2745                2750
Ala Ala Ser Leu Arg Ala Phe Thr Glu Ala Met Thr Arg Tyr Ser Ala
                2755                2760                2765

Pro Pro Gly Asp Pro Pro Gln Pro Glu Tyr Asp Leu Glu Leu Ile Thr
            2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
                2805                2810                2815

Trp Glu Thr Ala Arg His Thr Pro Val Asn Ser Trp Leu Gly Asn Ile
            2820                2825                2830

Ile Met Phe Ala Pro Thr Leu Trp Ala Arg Met Ile Leu Met Thr His
                2835                2840                2845

Phe Phe Ser Val Leu Ile Ala Arg Asp Gln Leu Glu Gln Ala Leu Asp
            2850                2855                2860

Cys Glu Ile Tyr Gly Ala Cys Tyr Ser Ile Glu Pro Leu Asp Leu Pro
2865                2870                2875                2880

Pro Ile Ile Gln Xaa Leu His Gly Leu Ser Ala Phe Ser Leu His Ser
                2885                2890                2895

Tyr Ser Pro Gly Glu Ile Asn Arg Val Ala Ala Cys Leu Arg Lys Leu
            2900                2905                2910

Gly Val Pro Pro Leu Arg Ala Trp Arg His Arg Ala Arg Ser Val Arg
                2915                2920                2925

Ala Arg Leu Leu Ser Arg Gly Gly Arg Ala Ala Ile Cys Gly Lys Tyr
            2930                2935                2940

Leu Phe Asn Trp Ala Val Arg Thr Lys Leu Lys Leu Thr Pro Ile Ala
2945                2950                2955                2960

Ala Ala Gly Gln Leu Asp Leu Ser Gly Trp Phe Thr Ala Gly Tyr Ser
            2965                2970                2975

Gly Gly Asp Ile Tyr His Ser Val Ser Arg Ala Arg Pro Arg Trp Phe
                2980                2985                2990

Trp Phe Cys Leu Leu Leu Leu Ala Ala Gly Val Gly Ile Tyr Leu Leu
            2995                3000                3005

Pro Asn Arg
    3010

<210> SEQ ID NO 2
<211> LENGTH: 3010
<212> TYPE: PRT
<213> ORGANISM: Hepatitis C Virus

<400> SEQUENCE: 2

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
```

```
              100                 105                 110
Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Val Tyr His Val Thr Asn Asp Cys Ser
            195                 200                 205

Asn Ser Ser Ile Val Tyr Glu Ala Ala Asp Met Ile Met His Thr Pro
210                 215                 220

Gly Cys Val Pro Cys Val Arg Glu Asn Ser Ser Arg Cys Trp Val
225                 230                 235                 240

Ala Leu Thr Pro Thr Leu Ala Ala Arg Asn Ser Ser Val Pro Thr Thr
                245                 250                 255

Thr Ile Arg Arg His Val Asp Leu Leu Val Gly Ala Ala Ala Phe Cys
                260                 265                 270

Ser Ala Met Tyr Val Gly Asp Leu Cys Gly Ser Val Phe Leu Val Ser
            275                 280                 285

Gln Leu Phe Thr Phe Ser Pro Arg Arg His Glu Thr Val Gln Asp Cys
            290                 295                 300

Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Ala Gly Ala His
                340                 345                 350

Trp Gly Val Leu Ala Gly Leu Ala Tyr Tyr Ser Met Val Gly Asn Trp
            355                 360                 365

Ala Lys Val Leu Ile Val Met Leu Leu Phe Ala Gly Val Asp Gly Ser
            370                 375                 380

Thr His Val Thr Gly Gly Ala Ala Ala Arg Thr Thr Arg Gly Leu Thr
385                 390                 395                 400

Ser Leu Phe Ser Pro Gly Pro Ser Gln Lys Ile Gln Leu Val Asn Thr
                405                 410                 415

Asn Gly Ser Trp His Ile Asn Arg Thr Ala Leu Asn Cys Asn Asp Ser
                420                 425                 430

Leu Gln Thr Gly Phe Leu Ala Ala Leu Phe Tyr Thr His Lys Phe Asn
            435                 440                 445

Ala Ser Gly Cys Pro Glu Arg Met Ala Ser Cys Arg Pro Ile Asp Lys
            450                 455                 460

Phe Ala Gln Gly Trp Gly Pro Ile Thr Tyr Ala Glu Pro Asp Ser Ser
465                 470                 475                 480

Asp Gln Arg Pro Tyr Cys Trp His Tyr Ala Pro Arg Pro Cys Gly Ile
                485                 490                 495

Val Pro Ala Ser Gln Val Cys Gly Pro Val Tyr Cys Phe Thr Pro Ser
            500                 505                 510

Pro Val Val Val Gly Thr Thr Asp Arg Phe Gly Val Pro Thr Tyr Ser
            515                 520                 525
```

```
Trp Gly Glu Asn Glu Thr Asp Val Leu Leu Leu Asn Asn Thr Arg Pro
            530                 535                 540

Pro Gln Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Gly Val Gly Asn
                565                 570                 575

Asn Thr Leu Thr Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Met
                595                 600                 605

Val Asp Tyr Pro Tyr Arg Leu Trp His Tyr Pro Cys Thr Val Asn Phe
610                 615                 620

Thr Ile Phe Lys Val Arg Met Tyr Val Gly Gly Val Glu His Arg Leu
625                 630                 635                 640

Asn Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Glu Trp
                660                 665                 670

Gln Ile Leu Pro Cys Ser Phe Thr Thr Leu Pro Ala Leu Ser Thr Gly
                675                 680                 685

Leu Ile His Leu His Gln Asn Ile Val Asp Val Gln Tyr Leu Tyr Gly
            690                 695                 700

Ile Gly Ser Ala Val Val Ser Phe Ala Ile Lys Trp Glu Tyr Val Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala Ala Leu Glu Asn Leu Val
            740                 745                 750

Val Leu Asn Ala Ala Ser Val Ala Gly Ala His Gly Ile Leu Ser Phe
            755                 760                 765

Leu Val Phe Phe Cys Ala Ala Trp Tyr Ile Lys Gly Arg Leu Val Pro
            770                 775                 780

Gly Ala Ala Tyr Ala Phe Tyr Gly Val Trp Pro Leu Leu Leu Leu Leu
785                 790                 795                 800

Leu Ala Leu Pro Pro Arg Ala Tyr Ala Met Asp Arg Glu Met Ala Ala
                805                 810                 815

Ser Cys Gly Gly Ala Val Phe Val Gly Leu Ala Leu Leu Thr Leu Ser
                820                 825                 830

Pro His Tyr Lys Val Phe Leu Ala Arg Leu Ile Trp Trp Leu Gln Tyr
            835                 840                 845

Phe Ile Thr Arg Ala Glu Ala His Leu Gln Val Trp Ile Pro Pro Leu
850                 855                 860

Asn Val Arg Gly Gly Arg Asp Ala Ile Ile Leu Leu Thr Cys Ala Val
865                 870                 875                 880

His Pro Glu Leu Ile Phe Asp Ile Thr Lys Ile Leu Leu Ala Ile Leu
                885                 890                 895

Gly Pro Leu Met Val Leu Gln Ala Gly Ile Thr Arg Val Pro Tyr Phe
                900                 905                 910

Val Arg Ala Gln Gly Leu Ile Arg Ala Cys Met Leu Val Arg Lys Val
            915                 920                 925

Ala Gly Gly His Tyr Val Gln Met Ala Phe Met Lys Leu Ala Ala Leu
            930                 935                 940

Thr Gly Thr Tyr Val Tyr Asp His Leu Thr Pro Leu Arg Asp Trp Ala
945                 950                 955                 960
```

```
His Ala Gly Leu Arg Asp Leu Ala Val Ala Val Glu Pro Val Phe
            965                 970                 975

Ser Asp Met Glu Thr Lys Ile Ile Thr Trp Gly Ala Asp Thr Ala Ala
            980                 985                 990

Cys Gly Asp Ile Ile Leu Gly Leu Pro Val Ser Ala Arg Arg Gly Arg
            995                1000                1005

Glu Ile Leu Leu Gly Pro Ala Asp Ser Leu Glu Gly Gln Gly Trp Arg
           1010                1015                1020

Leu Leu Ala Pro Ile Thr Ala Tyr Ser Gln Gln Thr Arg Gly Leu Leu
1025                1030                1035                1040

Gly Cys Ile Ile Thr Ser Leu Thr Gly Arg Asp Lys Asn Gln Val Glu
            1045                1050                1055

Gly Glu Val Gln Val Val Ser Thr Ala Thr Gln Ser Phe Leu Ala Thr
            1060                1065                1070

Cys Val Asn Gly Val Cys Trp Thr Val Tyr His Gly Ala Gly Ser Lys
            1075                1080                1085

Thr Leu Ala Gly Pro Lys Gly Pro Ile Thr Gln Met Tyr Thr Asn Val
            1090                1095                1100

Asp Gln Asp Leu Val Gly Trp Gln Ala Pro Gly Ala Arg Ser Leu
1105                1110                1115                1120

Thr Pro Cys Thr Cys Gly Ser Ser Asp Leu Tyr Leu Val Thr Arg His
            1125                1130                1135

Ala Asp Val Ile Pro Val Arg Arg Arg Gly Asp Ser Arg Gly Ser Leu
            1140                1145                1150

Leu Ser Pro Arg Pro Val Ser Tyr Leu Lys Gly Ser Ser Gly Gly Pro
            1155                1160                1165

Leu Leu Cys Pro Ser Gly His Ala Val Gly Ile Phe Arg Ala Ala Val
            1170                1175                1180

Cys Thr Arg Gly Val Ala Lys Ala Val Asp Phe Val Pro Val Glu Ser
1185                1190                1195                1200

Met Glu Thr Thr Met Arg Ser Pro Val Phe Thr Asp Asn Ser Ser Pro
            1205                1210                1215

Pro Ala Val Pro Gln Thr Phe Gln Val Ala His Leu His Ala Pro Thr
            1220                1225                1230

Gly Ser Gly Lys Ser Thr Lys Val Pro Ala Ala Tyr Ala Ala Gln Gly
            1235                1240                1245

Tyr Lys Val Leu Val Leu Asn Pro Ser Val Ala Ala Thr Leu Gly Phe
            1250                1255                1260

Gly Ala Tyr Met Ser Lys Ala His Gly Val Asp Pro Asn Ile Arg Thr
1265                1270                1275                1280

Gly Val Arg Thr Ile Thr Thr Gly Ala Pro Ile Thr Tyr Ser Thr Tyr
            1285                1290                1295

Gly Lys Phe Leu Ala Asp Gly Gly Cys Ser Gly Gly Ala Tyr Asp Ile
            1300                1305                1310

Ile Ile Cys Asp Glu Cys His Ser Thr Asp Ser Thr Thr Ile Leu Gly
            1315                1320                1325

Ile Gly Thr Val Leu Asp Gln Ala Glu Thr Ala Gly Ala Arg Leu Val
            1330                1335                1340

Val Leu Ala Thr Ala Thr Pro Pro Gly Ser Val Thr Val Pro His Pro
1345                1350                1355                1360

Asn Ile Glu Glu Val Ala Leu Ser Asn Thr Gly Glu Ile Pro Phe Tyr
            1365                1370                1375

Gly Lys Ala Ile Pro Ile Glu Thr Ile Lys Gly Gly Arg His Leu Ile
```

```
                    1380              1385              1390
Phe Cys His Ser Lys Lys Cys Asp Glu Leu Ala Ala Lys Leu Ser
            1395              1400              1405
Gly Leu Gly Leu Asn Ala Val Ala Tyr Tyr Arg Gly Leu Asp Val Ser
            1410              1415              1420
Val Ile Pro Thr Ser Gly Asp Val Val Val Ala Thr Asp Ala Leu
1425              1430              1435              1440
Met Thr Gly Phe Thr Gly Asp Phe Asp Ser Val Ile Asp Cys Asn Thr
                    1445              1450              1455
Cys Val Thr Gln Thr Val Asp Phe Ser Leu Asp Pro Thr Phe Thr Ile
                    1460              1465              1470
Glu Thr Thr Thr Val Pro Gln Asp Ala Val Ser Arg Ser Gln Arg Arg
            1475              1480              1485
Gly Arg Thr Gly Arg Gly Arg Arg Gly Ile Tyr Arg Phe Val Thr Pro
            1490              1495              1500
Gly Glu Arg Pro Ser Gly Met Phe Asp Ser Ser Val Leu Cys Glu Cys
1505              1510              1515              1520
Tyr Asp Ala Gly Cys Ala Trp Tyr Glu Leu Thr Pro Ala Glu Thr Ser
                    1525              1530              1535
Val Arg Leu Arg Ala Tyr Leu Asn Thr Pro Gly Leu Pro Val Cys Gln
                    1540              1545              1550
Asp His Leu Glu Phe Trp Glu Ser Val Phe Thr Gly Leu Thr His Ile
            1555              1560              1565
Asp Ala His Phe Leu Ser Gln Thr Lys Gln Ala Gly Asp Asn Phe Pro
            1570              1575              1580
Tyr Leu Val Ala Tyr Gln Ala Thr Val Cys Ala Arg Ala Gln Ala Pro
1585              1590              1595              1600
Pro Pro Ser Trp Asp Gln Met Trp Lys Cys Leu Ile Arg Leu Lys Pro
            1605              1610              1615
Thr Leu His Gly Pro Thr Pro Leu Leu Tyr Arg Leu Gly Ala Val Gln
            1620              1625              1630
Asn Glu Val Thr Leu Thr His Pro Ile Thr Lys Tyr Ile Met Ala Cys
            1635              1640              1645
Met Ser Ala Asp Leu Glu Val Val Thr Ser Thr Trp Val Leu Val Gly
            1650              1655              1660
Gly Val Leu Ala Ala Leu Ala Ala Tyr Cys Leu Thr Thr Gly Ser Val
1665              1670              1675              1680
Val Ile Val Gly Arg Ile Ile Leu Ser Gly Lys Pro Ala Val Ile Pro
            1685              1690              1695
Asp Arg Glu Val Leu Tyr Gln Glu Phe Asp Glu Met Glu Glu Cys Ala
            1700              1705              1710
Ser His Leu Pro Tyr Ile Glu Gln Gly Met Gln Leu Ala Glu Gln Phe
            1715              1720              1725
Lys Gln Lys Ala Leu Gly Leu Leu Gln Thr Ala Thr Lys Gln Ala Glu
            1730              1735              1740
Ala Ala Ala Pro Val Val Glu Ser Lys Trp Arg Ala Leu Glu Thr Phe
1745              1750              1755              1760
Trp Ala Lys His Met Trp Asn Phe Ile Ser Gly Ile Gln Tyr Leu Ala
                    1765              1770              1775
Gly Leu Ser Thr Leu Pro Gly Asn Pro Ala Ile Ala Ser Leu Met Ala
            1780              1785              1790
Phe Thr Ala Ser Ile Thr Ser Pro Leu Thr Thr Gln His Thr Leu Leu
            1795              1800              1805
```

-continued

Phe Asn Ile Leu Gly Gly Trp Val Ala Ala Gln Leu Ala Pro Pro Ser
     1810                1815                1820

Ala Ala Ser Ala Phe Val Gly Ala Gly Ile Ala Gly Ala Ala Val Gly
1825            1830                1835                1840

Ser Ile Gly Leu Gly Lys Val Leu Val Asp Ile Leu Ala Gly Tyr Gly
         1845                1850                1855

Ala Gly Val Ala Gly Ala Leu Val Ala Phe Lys Val Met Ser Gly Glu
1860                1865                1870

Met Pro Ser Thr Glu Asp Leu Val Asn Leu Leu Pro Ala Ile Leu Ser
         1875                1880                1885

Pro Gly Ala Leu Val Val Gly Val Val Cys Ala Ala Ile Leu Arg Arg
         1890                1895                1900

His Val Gly Pro Gly Glu Gly Ala Val Gln Trp Met Asn Arg Leu Ile
1905            1910                1915                1920

Ala Phe Ala Ser Arg Gly Asn His Val Ser Pro Thr His Tyr Val Pro
             1925                1930                1935

Glu Ser Asp Ala Ala Arg Val Thr Gln Ile Leu Ser Ser Leu Thr
         1940                1945                1950

Ile Thr Gln Leu Leu Lys Arg Leu His Gln Trp Ile Asn Glu Asp Cys
         1955                1960                1965

Ser Thr Pro Cys Ser Gly Ser Trp Leu Arg Asp Val Trp Asp Trp Ile
         1970                1975                1980

Cys Thr Val Leu Thr Asp Phe Lys Thr Trp Leu Gln Ser Lys Leu Leu
1985            1990                1995                2000

Pro Arg Leu Pro Gly Val Pro Phe Phe Ser Cys Gln Arg Gly Tyr Lys
             2005                2010                2015

Gly Val Trp Arg Gly Asp Gly Ile Met Gln Thr Thr Cys Pro Cys Gly
         2020                2025                2030

Ala Gln Ile Thr Gly His Val Lys Asn Gly Ser Met Arg Ile Val Gly
         2035                2040                2045

Pro Lys Thr Cys Ser Asn Thr Trp His Gly Thr Phe Pro Ile Asn Ala
         2050                2055                2060

Tyr Thr Thr Gly Pro Cys Thr Pro Ser Pro Ala Pro Asn Tyr Ser Arg
2065            2070                2075                2080

Ala Leu Trp Arg Val Ala Ala Glu Glu Tyr Val Glu Val Thr Arg Val
             2085                2090                2095

Gly Asp Phe His Tyr Val Thr Gly Met Thr Thr Asp Asn Val Lys Cys
         2100                2105                2110

Pro Cys Gln Val Pro Ala Pro Glu Phe Phe Thr Glu Val Asp Gly Val
         2115                2120                2125

Arg Leu His Arg Tyr Ala Pro Ala Cys Lys Pro Leu Leu Arg Glu Glu
         2130                2135                2140

Val Thr Phe Gln Val Gly Leu Asn Gln Tyr Leu Val Gly Ser Gln Leu
2145            2150                2155                2160

Pro Cys Glu Pro Glu Pro Asp Val Ala Val Leu Thr Ser Met Leu Thr
             2165                2170                2175

Asp Pro Ser His Ile Thr Ala Glu Thr Ala Lys Arg Arg Leu Ala Arg
         2180                2185                2190

Gly Ser Pro Pro Ser Leu Ala Ser Ser Ala Ser Gln Leu Ser Ala
         2195                2200                2205

Pro Ser Leu Lys Ala Thr Cys Thr Thr Arg His Asp Ser Pro Asp Ala
         2210                2215                2220

Asp Leu Ile Glu Ala Asn Leu Leu Trp Arg Gln Glu Met Gly Gly Asn
2225            2230                2235                2240

```
Ile Thr Arg Val Glu Ser Glu Asn Lys Val Val Ile Leu Asp Ser Phe
            2245                2250                2255
Asp Pro Leu Arg Ala Glu Asp Glu Arg Glu Val Ser Val Pro Ala
            2260                2265                2270
Glu Ile Leu Arg Lys Ser Arg Lys Phe Pro Pro Ala Met Pro Ile Trp
            2275                2280                2285
Ala Arg Pro Asp Tyr Asn Pro Pro Leu Leu Glu Ser Trp Lys Asp Pro
            2290                2295                2300
Asp Tyr Val Pro Pro Val Val His Gly Cys Pro Leu Pro Pro Thr Lys
2305                2310                2315                2320
Ala Pro Pro Ile Pro Pro Pro Arg Arg Lys Arg Thr Val Val Leu Thr
                2325                2330                2335
Glu Ser Thr Val Ser Ser Ala Leu Ala Glu Leu Ala Thr Lys Thr Phe
            2340                2345                2350
Gly Ser Ser Glu Ser Ser Ala Val Asp Ser Gly Thr Ala Thr Ala Pro
            2355                2360                2365
Pro Asp Gln Pro Ser Asp Asp Gly Asp Ala Gly Ser Asp Val Glu Ser
            2370                2375                2380
Tyr Ser Ser Met Pro Pro Leu Glu Gly Glu Pro Gly Asp Pro Asp Leu
2385                2390                2395                2400
Ser Asp Gly Ser Trp Ser Thr Val Ser Glu Glu Ala Ser Glu Asp Val
                2405                2410                2415
Val Cys Cys Ser Met Ser Tyr Thr Trp Thr Gly Ala Leu Ile Thr Pro
            2420                2425                2430
Cys Ala Ala Glu Glu Ser Lys Leu Pro Ile Asn Ala Leu Ser Asn Ser
            2435                2440                2445
Leu Leu Arg His His Asn Met Val Tyr Ala Thr Thr Ser Arg Ser Ala
            2450                2455                2460
Ser Gln Arg Gln Lys Lys Val Thr Phe Asp Arg Leu Gln Val Leu Asp
2465                2470                2475                2480
Asp His Tyr Arg Asp Val Leu Lys Glu Met Lys Ala Lys Ala Ser Thr
            2485                2490                2495
Val Lys Ala Lys Leu Leu Ser Val Glu Glu Ala Cys Lys Leu Thr Pro
            2500                2505                2510
Pro His Ser Ala Lys Ser Lys Phe Gly Tyr Gly Ala Lys Asp Val Arg
            2515                2520                2525
Asn Leu Ser Ser Lys Ala Val Asn His Ile Arg Ser Val Trp Lys Asp
            2530                2535                2540
Leu Leu Glu Asp Thr Glu Thr Pro Ile Asp Thr Thr Ile Met Ala Lys
2545                2550                2555                2560
Asn Glu Val Phe Cys Val Gln Pro Glu Lys Gly Gly Arg Lys Pro Ala
                2565                2570                2575
Arg Leu Ile Val Phe Pro Asp Leu Gly Val Arg Val Cys Glu Lys Met
            2580                2585                2590
Ala Leu Tyr Asp Val Val Ser Thr Leu Pro Gln Ala Val Met Gly Ser
            2595                2600                2605
Ser Tyr Gly Phe Gln Tyr Ser Pro Gly Gln Arg Val Glu Phe Leu Val
            2610                2615                2620
Asn Ala Trp Lys Ser Lys Lys Asn Pro Met Gly Phe Ala Tyr Asp Thr
2625                2630                2635                2640
Arg Cys Phe Asp Ser Thr Val Thr Glu Asn Asp Ile Arg Val Glu Glu
                2645                2650                2655
Ser Ile Tyr Gln Cys Cys Asp Leu Ala Pro Glu Ala Arg Gln Ala Ile
```

```
                   2660              2665              2670
Arg Ser Leu Thr Glu Arg Leu Tyr Ile Gly Gly Pro Leu Thr Asn Ser
            2675              2680              2685

Lys Gly Gln Asn Cys Gly Tyr Arg Arg Cys Arg Ala Ser Gly Val Leu
        2690              2695              2700

Thr Thr Ser Cys Gly Asn Thr Leu Thr Cys Tyr Leu Lys Ala Ser Ala
2705              2710              2715              2720

Ala Cys Arg Ala Ala Lys Leu Gln Asp Cys Thr Met Leu Val Cys Gly
            2725              2730              2735

Asp Asp Leu Val Val Ile Cys Glu Ser Ala Gly Thr Gln Glu Asp Ala
                2740              2745              2750

Ala Ser Leu Arg Val Phe Thr Glu Ala Met Thr Arg Tyr Ser Ala Pro
            2755              2760              2765

Pro Gly Asp Pro Pro Gln Pro Glu Tyr Asp Leu Glu Leu Ile Thr Ser
            2770              2775              2780

Cys Ser Ser Asn Val Ser Val Ala His Asp Ala Ser Gly Lys Arg Val
2785              2790              2795              2800

Tyr Tyr Leu Thr Arg Asp Pro Thr Thr Pro Leu Ala Arg Ala Ala Trp
            2805              2810              2815

Glu Thr Ala Arg His Thr Pro Val Asn Ser Trp Leu Gly Asn Ile Ile
            2820              2825              2830

Met Tyr Ala Pro Thr Leu Trp Ala Arg Met Ile Leu Met Thr His Phe
            2835              2840              2845

Phe Ser Ile Leu Leu Ala Gln Glu Gln Leu Glu Lys Ala Leu Asp Cys
        2850              2855              2860

Gln Ile Tyr Gly Ala Cys Tyr Ser Ile Glu Pro Leu Asp Leu Pro Gln
2865              2870              2875              2880

Ile Ile Gln Arg Leu His Gly Leu Ser Ala Phe Ser Leu His Ser Tyr
            2885              2890              2895

Ser Pro Gly Glu Ile Asn Arg Val Ala Ser Cys Leu Arg Lys Leu Gly
            2900              2905              2910

Val Pro Pro Leu Arg Val Trp Arg His Arg Ala Arg Ser Val Arg Ala
            2915              2920              2925

Lys Leu Leu Ser Gln Gly Gly Arg Ala Ala Thr Cys Gly Lys Tyr Leu
            2930              2935              2940

Phe Asn Trp Ala Val Arg Thr Lys Leu Lys Leu Thr Pro Ile Pro Ala
2945              2950              2955              2960

Ala Ser Gln Leu Asp Leu Ser Gly Trp Phe Val Ala Gly Tyr Ser Gly
            2965              2970              2975

Gly Asp Ile Tyr His Ser Leu Ser Arg Ala Arg Pro Arg Trp Phe Met
            2980              2985              2990

Leu Cys Leu Leu Leu Leu Ser Val Gly Val Gly Ile Tyr Leu Leu Pro
            2995              3000              3005

Asn Arg
    3010

<210> SEQ ID NO 3
<211> LENGTH: 10
<212> TYPE: PRT
<213> ORGANISM: Hepatitis C Virus

<400> SEQUENCE: 3

Lys Leu Val Ala Leu Gly Ile Asn Ala Val
1               5                   10
```

```
<210> SEQ ID NO 4
<211> LENGTH: 10
<212> TYPE: PRT
<213> ORGANISM: Hepatitis C Virus

<400> SEQUENCE: 4

Lys Leu Val Ala Met Gly Ile Asn Ala Val
1               5                   10

<210> SEQ ID NO 5
<211> LENGTH: 9
<212> TYPE: PRT
<213> ORGANISM: Hepatits C Virus

<400> SEQUENCE: 5

Ala Thr Asp Ala Leu Met Thr Gly Tyr
1               5

<210> SEQ ID NO 6
<211> LENGTH: 9
<212> TYPE: PRT
<213> ORGANISM: Hepatitis C Virus

<400> SEQUENCE: 6

Ala Thr Asp Ala Leu Met Thr Gly Phe
1               5

<210> SEQ ID NO 7
<211> LENGTH: 9
<212> TYPE: PRT
<213> ORGANISM: Hepatitis C Virus

<400> SEQUENCE: 7

Arg Leu Trp His Tyr Pro Cys Thr Val
1               5

<210> SEQ ID NO 8
<211> LENGTH: 9
<212> TYPE: PRT
<213> ORGANISM: Hepatitis C Virus

<400> SEQUENCE: 8

Cys Ile Asn Gly Val Cys Trp Thr Val
1               5

<210> SEQ ID NO 9
<211> LENGTH: 10
<212> TYPE: PRT
<213> ORGANISM: Hepatitis C Virus
<220> FEATURE:
<221> NAME/KEY: VARIANT
<222> LOCATION: 4
<223> OTHER INFORMATION: or Leu

<400> SEQUENCE: 9

Ser Ile Tyr Pro Gly His Ile Thr Gly His
1               5                   10

<210> SEQ ID NO 10
<211> LENGTH: 10
<212> TYPE: PRT
<213> ORGANISM: Hepatitis C Virus
<220> FEATURE:
<221> NAME/KEY: VARIANT
<222> LOCATION: 1
<223> OTHER INFORMATION: or Arg

<400> SEQUENCE: 10
```

```
His Pro Ala Leu Val Phe Asp Ile Thr Lys
1               5                   10
```

<210> SEQ ID NO 11
<211> LENGTH: 9
<212> TYPE: PRT
<213> ORGANISM: Hepatitis C Virus
<220> FEATURE:
<221> NAME/KEY: VARIANT
<222> LOCATION: 2
<223> OTHER INFORMATION: or Ser

<400> SEQUENCE: 11

```
His Pro Asn Ile Glu Glu Val Ala Leu
1               5
```

<210> SEQ ID NO 12
<211> LENGTH: 10
<212> TYPE: PRT
<213> ORGANISM: Hepatitis C Virus

<400> SEQUENCE: 12

```
Gly Glu Ile Pro Phe Tyr Gly Lys Ala Ile
1               5                   10
```

<210> SEQ ID NO 13
<211> LENGTH: 15
<212> TYPE: PRT
<213> ORGANISM: Hepatitis C Virus

<400> SEQUENCE: 13

```
Pro Leu Tyr Gly Asn Glu Gly Cys Gly Trp Ala Gly Trp Leu Leu
1               5                   10                  15
```

<210> SEQ ID NO 14
<211> LENGTH: 14
<212> TYPE: PRT
<213> ORGANISM: Hepatitis C Virus
<220> FEATURE:
<221> NAME/KEY: VARIANT
<222> LOCATION: 10
<223> OTHER INFORMATION: or His

<400> SEQUENCE: 14

```
Thr Thr Asp Lys Ser Gly Ala Pro Thr Tyr Ser Trp Gly Glu
1               5                   10
```

<210> SEQ ID NO 15
<211> LENGTH: 8
<212> TYPE: PRT
<213> ORGANISM: Hepatitis C Virus
<220> FEATURE:
<221> NAME/KEY: VARIANT
<222> LOCATION: 2
<223> OTHER INFORMATION: or Asn
<221> NAME/KEY: VARIANT
<222> LOCATION: 6
<223> OTHER INFORMATION: or Ser

<400> SEQUENCE: 15

```
Arg Asp Trp Ala His Asn Ser Leu
1               5
```

<210> SEQ ID NO 16
<211> LENGTH: 16
<212> TYPE: PRT
<213> ORGANISM: Hepatitis C Virus
<220> FEATURE:

```
<221> NAME/KEY: VARIANT
<222> LOCATION: 12
<223> OTHER INFORMATION: or Arg

<400> SEQUENCE: 16

Ile Asn Gly Leu Pro Val Ser Ala Arg Arg Gly Gln Glu Ile Leu Leu
1               5                   10                  15

<210> SEQ ID NO 17
<211> LENGTH: 9
<212> TYPE: PRT
<213> ORGANISM: Hepatitis C Virus

<400> SEQUENCE: 17

Cys Ile Asn Gly Val Cys Trp Thr Val
1               5

<210> SEQ ID NO 18
<211> LENGTH: 9
<212> TYPE: PRT
<213> ORGANISM: Hepatitis C Virus
<220> FEATURE:
<221> NAME/KEY: VARIANT
<222> LOCATION: 8
<223> OTHER INFORMATION: or Asp

<400> SEQUENCE: 18

His Ser Lys Lys Lys Cys Asp Glu Leu
1               5

<210> SEQ ID NO 19
<211> LENGTH: 9
<212> TYPE: PRT
<213> ORGANISM: Hepatitis C Virus
<220> FEATURE:
<221> NAME/KEY: VARIANT
<222> LOCATION: 9
<223> OTHER INFORMATION: or Phe

<400> SEQUENCE: 19

Ala Thr Asp Ala Leu Met Thr Gly Tyr
1               5

<210> SEQ ID NO 20
<211> LENGTH: 10
<212> TYPE: PRT
<213> ORGANISM: Hepatitis C Virus
<220> FEATURE:
<221> NAME/KEY: VARIANT
<222> LOCATION: 5
<223> OTHER INFORMATION: or Arg

<400> SEQUENCE: 20

Gly Thr Thr Asp Lys Ser Gly Ala Pro Thr
1               5                   10

<210> SEQ ID NO 21
<211> LENGTH: 9
<212> TYPE: PRT
<213> ORGANISM: Hepatitis C Virus
<220> FEATURE:
<221> NAME/KEY: VARIANT
<222> LOCATION: 4
<223> OTHER INFORMATION: or Lys

<400> SEQUENCE: 21

His Ser Lys Arg Lys Cys Asp Glu Leu
1               5
```

```
<210> SEQ ID NO 22
<211> LENGTH: 16
<212> TYPE: PRT
<213> ORGANISM: Hepatitis C Virus
<220> FEATURE:
<221> NAME/KEY: VARIANT
<222> LOCATION: 10
<223> OTHER INFORMATION: or Arg

<400> SEQUENCE: 22

Ser Pro Val Val Val Gly Thr Thr Asp Lys Ser Gly Ala Pro Thr Tyr
 1               5                  10                  15
```

USE OF CONSENSUS SEQUENCE AS VACCINE ANTIGEN TO ENHANCE RECOGNITION OF VIRULENT VIRAL VARIANTS

CROSS-REFERENCE TO RELATED APPLICATIONS

This application claims the benefit and priority of U.S. Provisional Application Ser. No. 60/648,550, filed Jan. 31, 2005, and Provisional Application Ser. No. 60/648,877, filed Feb. 2, 2005, both of which are herein incorporated by reference for all purposes.

STATEMENT REGARDING FEDERALLY SPONSORED RESEARCH OR DEVELOPMENT

This invention was made with Government support under DA-11880, DK-57998 and AI-40035 awarded by the PHS. The Government has certain rights in the invention.

FIELD OF THE INVENTION

The invention relates to consensus sequences for hepatitis C virus and uses thereof. The invention also relates to immunogenic epitopes of hepatitis C virus and uses thereof. The invention also relates to methods of prophylaxis, treating, and diagnosing individuals infected with or exposed to hepatitis C virus.

BACKGROUND OF THE INVENTION

Currently, it is estimated there are about 270 to 300 million people worldwide who are infected with hepatitis C virus (HCV), 2.7 to 4 million of those are in the United States. In industrialized countries, HCV accounts for 20% of cases of acute hepatitis, 70% of cases of chronic hepatitis, 40% of cases of end-stage cirrhosis, 60% of cases of hepatocellular carcinoma and 30-40% of liver transplants. The incidence of new symptomatic infections of HCV has been estimated to be 13 cases/100,000 persons annually. For every one person that is infected with the AIDS virus, there are more than four infected with HCV. Currently, 8,000 to 10,000 deaths each year are a result of Hepatitis C (updated Jan. 31, 2006). The CDC (Center For Disease Control) estimates that there are up to 30,000 new HCV infections in the U.S. every year.

About 80% of HCV-infected individuals have no signs or symptoms. In others, the symptom include: jaundice, fatigue, dark urine, abdominal pain, loss of appetite, and nausea. For 55-85% of infected individuals, over the long term, HCV infection persists and become a chronic infection. Of the chronically infected individuals, about 30% develop liver disease.

Hepatitis C virus has six different genotypes. The most prevalent types circulating in the Western countries are subgenotypes 1a and 1b. In a person with chronic infection, hepatitis C virus reproduces up to $10^{12}$ virion each day. Neumann, et al. *Science* 282:103-107 (1998). This rate of reproduction exceeds the rate of reproduction for human immunodeficiency virus (HIV) by an order of magnitude. The reproduction rate of HCV coupled with the lack of proofreading function by the HCV RNA polymerase results many mutations in HCV sequences.

Treatments for hepatitis C include interferon and ribavirin, both of which are licensed for the treatment of persons with chronic hepatitis C. Interferon can be taken alone or in combination with ribavirin. Combination therapy, using pegylated interferon and ribavirin, is currently the treatment of choice. Combination therapy can get rid of the virus in up to 5 out of 10 persons for genotype 1 and in up to 8 out of 10 persons for genotype 2 and 3.

There are no known vaccines for the prevention of hepatitis C virus infection. Until the present inventors made their discovery herein, the reason as to why individuals with chronic stage HCV infection had weak and ineffective immune responses was poorly understood. The inventors and others have demonstrated that most, if not all of the HCV sequences obtained from persons with HCV infection contain epitope escape variants. As such, the inventors have made a novel and useful discovery that describes, inter alia, the reasons for the observed genetic changes taking place during infection of a human host. These include the tendency of the virus to mutate towards a consensus sequence that is optimal for viral replication and fitness, and the competing tendency of the virus to mutate away from sequences that induce effective immunological responses in particular human hosts. This discovery has important implications for vaccine design.

Several computational alternatives to isolate-based vaccine design exist. One approach is reconstruction of the most recent common ancestor (MRCA) sequence. In this type of analysis, the ancestral state is an estimate of the actual sequence that existed in the past (i.e., it comes directly from the reconstructed history). See *Science,* 299:1515-1518 (2003). Another type of computational analysis is a center of the tree (COT) approach. The COT approach identifies a point on the unrooted phylogeny, where the average evolutionary distance from that point to each tip on the phylogeny is minimized. Advocates of this approach state that because the COT is a point on the phylogeny, the estimated COT sequence will have the same advantages as the estimated ancestral sequence. See, for example, U.S. Application 2005/0137387 A1. However, this COT approach is sufficiently complex that reducing it to practice for a large and heterologous data set is not practical with technology; specifically, the phylogenetic methods cannot address a sparse data set like the one for HCV, wherein most of the data for any individual sequence are missing. In addition, the premise of the COT approach is that when the phylogenetic tree is unbalanced (dominated by a particular lineage), the COT approach proposed therein provides a more representative sequence than the ancestral sequence. However, the HCV tree has been shown, by the inventors and others, to be balanced and star-like (see Ray S C et al, *J Exp Med* 2005 Jun. 6; 201(11):1753-9 and Salemi M and Vandamme A, *J Mol Evol* 2002; 54:62-70). Overall, the MRCA and COT approaches are impractical for application to the HCV sequence database, and their primary justification does not apply.

A third type of computational analysis is the consensus sequence approach. Because the consensus sequence is composed of the amino acid most commonly observed at each position, it likely represents the most fit state of the virus. Thus, effective evasion of the immune response by selection of a sequence divergent from consensus may result in a less fit virus from a replicative standpoint. The consensus sequence approach favors heavily sampled sublineages and deemphasizes outliers. The consideration of an unbalanced phylogenetic tree is not important for HCV, because the phylogeny is balanced (star-like). As such, the approaches disclosed herein are far more straightforward than the other types of computational analysis. Furthermore, these approaches can use the entire data set for HCV. One advantage of the consensus sequence is that it minimizes the genetic differences between vaccine strains and contemporary isolates, effectively reducing the extent of diversity by half, and thus it may have enhanced potential for eliciting cross-reactive responses.

A computational method is therefore needed to generate a sequence for use in vaccines that more broadly represents circulating strains, and also restores the immunogenic forms of HCV epitopes. Currently, there is a need for a method to effectively treat individuals who are infected with HCV or exposed to HCV. With the decline in an infected individual's immune system as he/she enters chronic phase, it would be highly desirable to lessen that individual's chances of progressing to the chronic phase by administering a form of treatment during the acute phase of infection. Most chronically infected people are ineligible for the currently available therapies. A vaccine could be used to enhance responses to currently available or future therapies. Further, there is a need for a prophylaxis of HCV infection. The invention disclosed herein meets all these needs and provides even more beneficial uses.

All references, patent, and patent applications cited in this patent application are herein incorporated by reference, each in its respective entirety for all purposes.

BRIEF SUMMARY OF THE INVENTION

The invention provides for an isolated nucleic acid encoding an HCV polyprotein or a fragment thereof wherein the HCV polyprotein comprises the consensus sequence 1a (SEQ ID NO: 1). In one embodiment, the invention is a nucleic acid wherein the encoded HCV polyprotein or fragment thereof comprises one or more of the non-synonymous changes shown in Table 5.

In one aspect, the invention is an isolated nucleic acid encoding an HCV polyprotein or a fragment thereof wherein the HCV polyprotein comprises the consensus sequence 1b (SEQ ID NO: 2). In one embodiment, the invention is a nucleic acid wherein the encoded HCV polyprotein or fragment thereof comprises one or more of the non-synonymous changes shown in Table 6.

In another aspect, the invention is an isolated HCV protein having the amino acid sequence comprising the consensus sequence 1a (SEQ ID NO:1) or a fragment thereof. In another aspect, the invention is an isolated HCV protein having the amino acid sequence comprising the consensus sequence 1b (SEQ ID NO:2) or a fragment thereof. In another aspect, the invention is an isolated HCV 1a core protein sequence or fragments thereof comprising the consensus sequence or non-synonymous changes as shown in Table 5. In another aspect, the invention is an isolated HCV 1a E1 protein sequence or fragments thereof comprising the consensus sequence or non-synonymous changes as shown in Table 5. In another aspect, the invention is an isolated HCV 1a E2 protein sequence or fragments thereof comprising the consensus sequence or non-synonymous changes as shown in Table 5. In another aspect, the invention is an isolated HCV 1a p7 protein sequence or fragments thereof comprising the consensus sequence or non-synonymous changes as shown in Table 5. In another aspect, the invention is an isolated HCV 1a NS2 protein sequence or fragments thereof comprising the consensus sequence or non-synonymous changes as shown in Table 5. In another aspect, the invention is an isolated HCV 1a NS3 protein sequence or fragments thereof comprising the consensus sequence or non-synonymous changes as shown in Table 5. In another aspect, the invention is an isolated HCV 1a NS4a protein sequence or fragments thereof comprising the consensus sequence or non-synonymous changes as shown in Table 5. In another aspect, the invention is an isolated HCV 1a NS4b protein sequence or fragments thereof comprising the consensus sequence or non-synonymous changes as shown in Table 5. In another aspect, the invention is an isolated HCV 1a NS5a protein sequence or fragments thereof comprising the consensus sequence or non-synonymous changes as shown in Table 5. In another aspect, the invention is an isolated HCV 1a NS5b protein sequence or fragments thereof comprising the consensus sequence or non-synonymous changes as shown in Table 5.

In yet another aspect, the invention is an isolated HCV 1b core protein sequence or fragments thereof comprising the consensus sequence or non-synonymous changes as shown in Table 6. In another aspect, the invention is an HCV 1b E1 protein sequence or fragments thereof comprising the consensus sequence or non-synonymous changes as shown in Table 6. In another aspect, the invention is an HCV 1b E2 protein sequence or fragments thereof comprising the consensus sequence or non-synonymous changes as shown in Table 6. In another aspect, the invention is an HCV 1b p7 protein sequence or fragments thereof comprising the consensus sequence or non-synonymous changes as shown in Table 6. In another aspect, the invention is an HCV 1b NS2 protein sequence or fragments thereof comprising the consensus sequence or non-synonymous changes as shown in Table 6. In another aspect, the invention is an HCV 1b NS3 protein sequence or fragments thereof comprising the consensus sequence or non-synonymous changes as shown in Table 6. In another aspect, the invention is an HCV 1b NS4a protein sequence or fragments thereof comprising the consensus sequence or non-synonymous changes as shown in Table 6. In another aspect, the invention is an HCV 1b NS4b protein sequence or fragments thereof comprising the consensus sequence or non-synonymous changes as shown in Table 6. In another aspect, the invention is an HCV 1b NS5a protein sequence or fragments thereof comprising the consensus sequence or non-synonymous changes as shown in Table 6. In another aspect, the invention is an HCV 1b NS5b protein sequence or fragments thereof comprising the consensus sequence or non-synonymous changes as shown in Table 6. In another aspect, the invention is an consensus protein which comprises at least 5 contiguous amino acids of a hepatitis C 1a virus.

The invention also provides for an isolated expression construct comprising the following operably linked elements: transcription promoter and a nucleic acid encoding an HCV consensus protein or a fragment thereof. In another aspect, the invention is an isolated consensus protein or fragment thereof from Hepatitis C 1a virus which is immunogenic. In another aspect, the invention is an isolated consensus protein which comprises at least 5 contiguous amino acids of a hepatitis C 1b virus. In another aspect, the invention is an isolated expression construct comprising the following operably linked elements: transcription promoter and a nucleic acid encoding the consensus protein of claim 30 or a fragment thereof. In another aspect, the invention is an isolated consensus protein or fragment thereof from Hepatitis C 1b virus which is immunogenic. In another aspect, the invention is an isolated nucleic acid encoding an HCV epitope capable of eliciting an immunogenic response in an individual wherein the sequence of the epitope is selected from any of the epitopes listed in Table 7. In another aspect, the invention is an isolated HCV epitope capable of eliciting an immunogenic response in an individual wherein the sequence of the epitope is selected from any of the epitopes listed in Table 7.

The invention also provides for composition comprising at least one HCV protein or a fragment thereof encoded by a polynucleotide. In another aspect, the invention is a composition comprising at least one HCV protein or a fragment thereof encoded by a polynucleotide. In another aspect, the invention is a composition comprising at least one HCV protein or a fragment thereof. In another aspect, the invention is a composition comprising at least one nucleic acid sequence for HCV consensus sequence. In another aspect, the invention is a composition comprising at least one nucleic acid sequence for HCV consensus sequence. In another aspect, the invention is a composition comprising at least one nucleic acid sequence which codes for an HCV protein or a fragment thereof.

The invention also provides for a vaccine comprising all or a portion of consensus sequence 1a (SEQ ID NO:1). In one embodiment, the vaccine comprises a non-synonymous change at a modal consensus sequence. In another aspect, the invention is a vaccine comprising all or a portion of consensus sequence 1b (SEQ ID NO:2). In one embodiment, the vaccine comprises wherein there is a non-synonymous change at a modal consensus sequence.

The invention also provides for a method of identifying an immunogen for use as a vaccine comprising: a) Obtaining a sequence of HCV that is derived from a subject and is longer than 500 nucleotides; b) Obtaining the primary open reading frame of the sequence; c) Removing sequences that contain more than 1% ambiguous sites or more than 1 frameshift; d) Converting terminal "gap" characters to "missing"; e) Removing sequences that are redundant by identifying identical sequences and checking related publications and removing linked sequences; f) Generating predicted polyprotein sequences by using standard eukaryotic genetic code; and g) Identifying majority-rule consensus sequence for each subtype to identify modal amino acid residue at each site.

The invention also provides for a method of inducing or augmenting an immune response against hepatitis C virus comprising administering an effective amount of any one of the vaccines recited disclosed herein. The invention also provides for a method for protecting an individual from hepatitis C virus infection comprising administering an effective amount of any one of the vaccines disclosed herein. The invention also provides for a method of lessening the probability that a HCV-infected individual will enter a chronic phase of hepatitis C infection comprising administering an effective amount of any one of the vaccine disclosed herein.

The invention also provides for a method for diagnosing an individual infected with hepatitis C virus 1a comprising: a. obtaining a biological sample from the individual and b. using PCR primers to consensus sequences of HCV 1a to amplify nucleic acids in the biological sample to determine if the individual has been infected with hepatitis C virus 1a. The invention also provides for a method for diagnosing an individual infected with hepatitis C virus 1b comprising: a. obtaining a biological sample from the individual and b. using PCR primers to consensus sequences of HCV 1b to amplify nucleic acids in the biological sample to determine if the individual has been infected with hepatitis C virus 1b. The invention also provides for a kit comprising a HCV vaccine and instructions for the administration thereof.

BRIEF DESCRIPTION OF THE DRAWINGS

Figure 8:
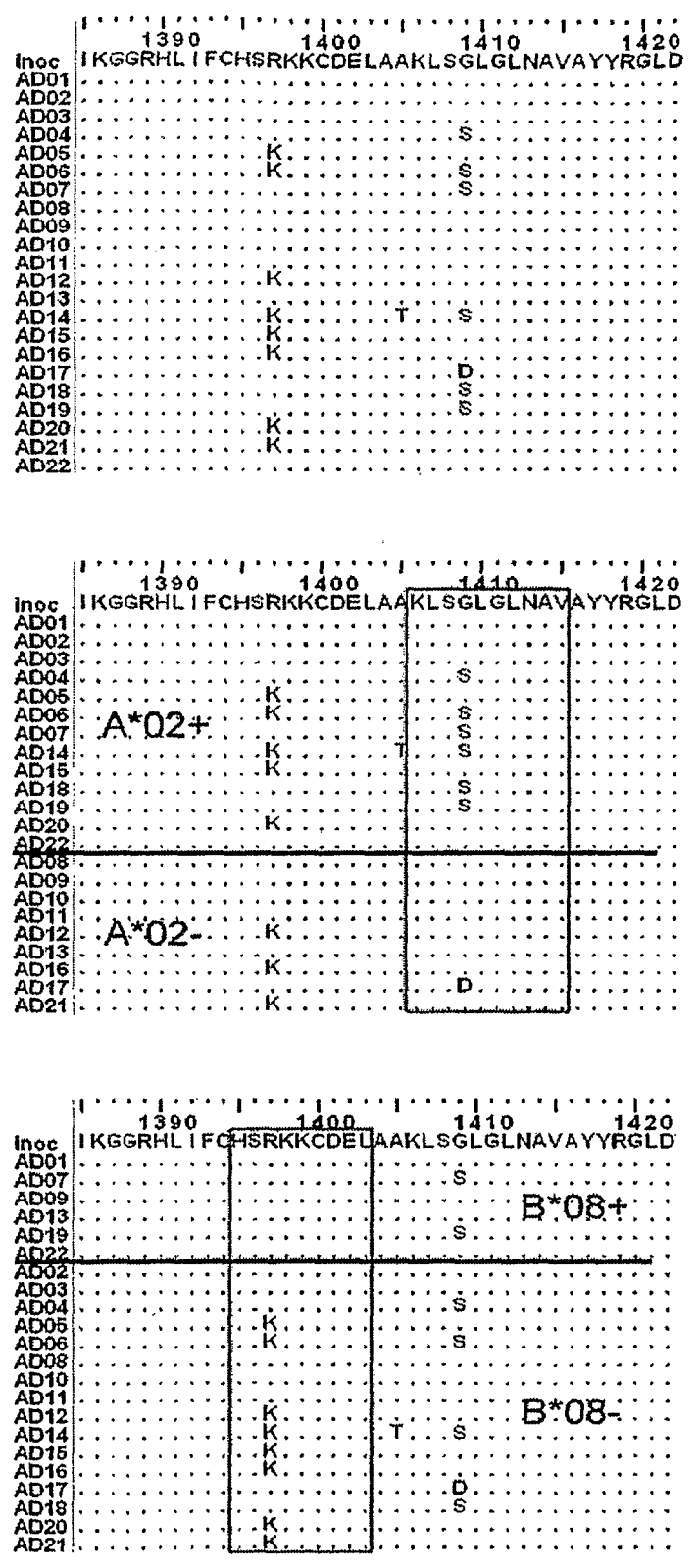

FIG. 8 shows escape versus reversion in the presence versus absence of the restricting HLA allele. (A) Amino acid alignment of a region in NS3 (positions 1388 to 1431 relative to strain H, GenBank entry AF009606; SEQ ID NO: 1 or 2) showing sites with polymorphism. Study subjects are listed in arbitrary order. Identity to the inoculum sequence ("inoc") is indicated by ".". (B) Sorting the subjects by the presence of HLA A*02, G14095 substitution in the 4th position of a frequently-recognized HLA A*02-restricted epitope at 1406-1415 is limited to subjects having the HLA A*02 allele. The subtype 1b consensus sequence for this epitope is shown above the alignment, and has been shown to be recognized as readily as the prototype (subtype 1a) KLVALGINAV sequence (23; SEQ ID NO: 3). Subject AD17 (HLA A*01, A*11) had G1409D substitution, the impact of which on recognition is unknown. (C) Variation resulting in reversion to a HLA B*08-restricted epitope. Sorting the subjects by presence of HLA B*08, R1397K substitution in the 3rd position of a frequently-recognized HLA B*08-restricted epitope at 1395-1403 is limited to subjects lacking the HLA B*08 allele. The inoculum sequence differs from the prototypical epitope (HSKKKCDEL; SEQ ID NO: 18) at the 3rd position. Reversion to consensus (and the prototype epitope) occurred only in study subjects lacking the HLA B*08 allele.

FIG. 9 shows HCV consensus sequence 1a (SEQ ID NO:1).

FIG. 10 shows HCV consensus sequence 1b (SEQ ID NO:2).

DETAILED DESCRIPTION OF THE INVENTION

Figure 1:
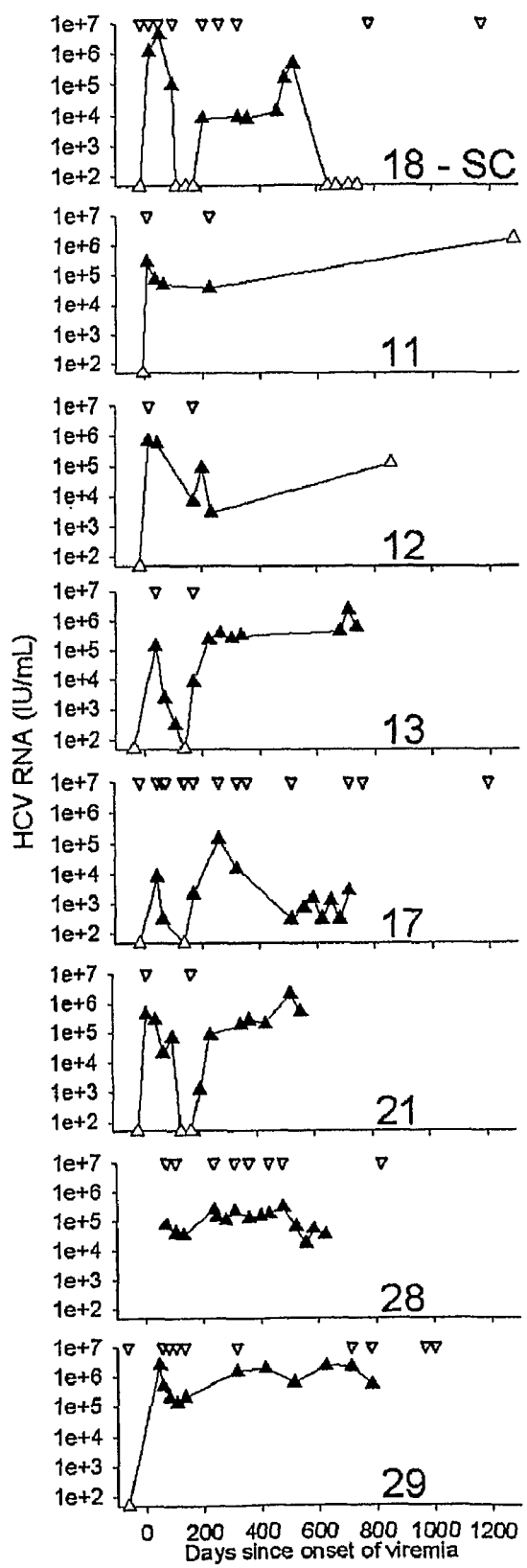
FIG. 1 shows fluctuating HCV RNA level during acute infection. Spontaneous clearance (SC) occurred in one subject, and persistence developed in seven others. A solid triangle (▲) indicates detectable HCV RNA. An open triangle (∆) indicates an HCV RNA level of less than 50 IU/ml. The number in the bottom right corner of each panel is the subject number. A gray inverted triangle (▼) indicates that IFN-γ ELISPOT analysis of T cell responses was performed at that time point. Subject 28 entered the study antibody negative and HCV RNA positive so that the time of infection is estimated using the average time from infection to seroconversion.

The invention provides consensus sequences for HCV 1a sub-genotype (or subtype) and HCV 1b subtype. The invention further provides details on which residues of the consensus sequence have known amino acids substitutions. In addition, the invention further provides epitopes useful for inducing immune responses to HCV. The consensus sequence, its variants, and epitopes provides for vaccines for prophylaxis against and treatment of chronic HCV infection. The vaccines further provide a method for inducing an immune response against HCV. Further, the invention provides methods for preventing an individual's entrance into a chronic phase of HCV. The invention also provides methods of diagnosis of HCV 1a and 1b. The invention further provides for kits for use in prophylaxis and treatment of HCV.

DEFINITIONS

All scientific and technical terms used in this application have meanings commonly used in the art unless otherwise specified. As used in this application, the following words or phrases have the meanings specified.

An "B cell epitope" is a term well-understood in the art and means any chemical moiety which exhibits specific binding to an antibody. An "epitope" can also comprise an antigen, which is a moiety or molecule that contains an epitope, and, as such, also specifically binds to antibody.

A "T cell epitope" means a component or portion thereof for which a T cell has an antigen-specific specific binding site, the result of binding to which activates the T cell.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases.

An "individual" is a vertebrate, preferably a mammal, more preferably a human. Mammals include, but are not limited to, farm animals, sport animals, pets, primates, mice and rats.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

As used herein, the singular form "a", "an", and "the" includes plural references unless indicated otherwise. For example, "an" epitope includes one or more epitopes.

Consensus Sequences

Hepatitis C virus mutates rapidly and has two to three times more genetic variability than HIV. Hepatitis C reproduces more than 100 billion times a day, about 100 times faster than HIV. The inventors have discovered that instead of random changes, as conventional wisdom surmised, the HCV changes in a "Darwinian" manner. That is, the viral genome changes in a way to make the virus more reproductively fit in the face of each individual immune system it encounters. The inventors have discovered that the HCV genome changed in a manner to evade the individual's immune system in regions subject to effective T cell immune responses; and in regions where there was no effective T cell response due to lack of HLA epitopes, the HCV genome naturally mutated toward a consensus sequence which was the viruses' most replicatively fit state.

The HCV polyprotein is expressed as a single open reading frame, and is then processed by host (structural genes through the p7/NS2 junction) and viral (remainder) proteases. The structure and numbering of the positions in the HCV genome and polyprotein are based by convention on the subtype 1a genome, as described at the Los Alamos National Laboratory HCV sequence database web site (URL:http://hcv.lanl.gov/content/hcv-db/MAP/landmark.html) and in a recent publication (see Simmonds P, et al. Hepatology 2005; 42:962-73). HCV 1a core protein spans residues 1 to 191. E1 protein spans residues 192 to 383. E2 protein spans residues 384 to 746. p7 protein spans residues 747 to 809. NS2 protein spans residues 810 to 1026. NS3 protein spans residues 1027 to 1657. NS4a protein spans residues 1658 to 1711. NS4b protein spans residues 1712 to 1972. NS5a spans residues 1973 to 2420. NS5b protein spans residues 2421 to 3011. For HCV 1b subtype, there is an insertion at residue 2413 of an additional residue relative to the consensus 1a sequence.

Determination of a Consensus Sequence

To determine a consensus sequence from any genotype of HCV, or other viruses, one method that can be used is as follows: a) Obtain a sequence of HCV or the virus of interest that is derived from a subject (e.g., a human) and is longer than 500 nucleotides; b) Obtain the primary open reading frame of the sequence; c) Remove sequences that contain more than 1% ambiguous sites or more than 1 frameshift; d) Convert terminal "gap" characters to "missing"; e) Remove sequences that are redundant by identifying identical sequences and checking related publications and removing linked sequences; f) Generate predicted polyprotein sequences by using standard eukaryotic genetic code; and g) Identify majority-rule consensus sequence for each subtype to identify modal amino acid residue at each site.

The methodology disclosed herein is for obtaining consensus sequences and is not the same methodology used for obtaining ancestral sequences or center of tree (COT) sequences. However, for balanced (i.e., star-like) phylogeny like that seen for HCV, all three methodologies could yield the same end result. For commentary on general consensus and ancestral states as applied to HIV, see *Science* Vol. 29, pp. 1515-1518 (2003). However, the methodology disclosed herein provides advantages in that it is far more straightforward to use than previously disclosed methods and can be used with the entire data set for HCV, which has never been done before.

As detailed in the Examples, by using the methodology disclosed herein consensus sequence 1a (SEQ ID NO: 1) (FIG. 9) and consensus sequence 1b (SEQ ID NO:2) (FIG. 10) were obtained. Furthermore, the invention not only discloses the consensus sequence, but also details precisely which residues have non-synonmyous (amino acid changing) changes and precisely what those changes are at a certain frequency. The consensus sequence and its amino acid substitutions (or variants) are displayed in Tables 5 and 6. The first column indicates the residue position of each consensus sequence and the remaining columns indicate the residue-frequency displayed as a pair. The frequency is displayed as a subscript of the residue in this table. Residues indicated with an "X" means that that one or more sequences in the database have errors or ambiguity at that site, resulting in a codon that does not map to the genetic code. Common reasons for this include single base deletions and multistate characters (e.g., IUPAC R for A or G; Y for C or T, etc). BioEdit translates these as "X" to indicate that an amino acid could not be assigned. Using this information, one of skill in the art can predict what substitutions, if any, can be expected at a particular residue position and if a substitution is expected, then the information provided herein allows one to know which amino acids will be expected and at what frequency. For each of the 3011 residues for HCV 1a and 3010 residues for HCV1b, there are 19 other amino acids possible for substitution. It creates an overwhelming number of possible sequences for one of skill in the art to experiment with if there were not the kind of explicit teaching provided herein. It would be impossible for one of skill in the art to predict, a priori, what the consensus sequence would be for HCV 1a and HCV 1b and which amino acids are found as possible substitutes at each of the 6021 positions possible and at what frequency these non-synonymous changes are found.

Polypeptides of HCV Consensus Sequences

The invention also provides for consensus sequences for the entire HCV polyprotein as well as for each HCV protein that has been processed by host or viral proteases. These HCV proteins include: core, E1, E2, p7, NS2, NS3, NS4a, NS4b, NS5a, and NS5b. One aspect of the invention contemplates the entire HCV polyprotein while other aspects of the invention contemplate the HCV proteins post-processing. The invention encompasses HCV proteins with non-synonymous changes as well as heterologous polypeptides.

The invention further provides a number of epitopes that have been found to be immunogenic (i.e., capable of inducing an immune response). These epitopes are disclosed in Table 7. As detailed in the Examples, some of these epitopes have been mapped systemically and found to be immunogenic. HCV has been found to mutate more frequently in the areas which comprise T cell epitopes than in areas which are not within T cell epitopes. Individuals who self-recovered from HCV infection had no changes in the sequences in the T cell epitope areas while those who progressed to chronic infection had one or more changes within the T cell epitopes. Further, in those chronically infected individuals with changes outside the T cell epitopes, many of the substitutions resulted in an amino acid that matched the consensus sequence. B cell epitopes are contained within the consensus sequences disclosed herein. Accordingly, the invention encompasses T cell epitopes as well as B cells epitopes. Accordingly, the invention encompasses polypeptides comprising these epitopes and heterologous polypeptides comprising these epitopes.

The invention also encompasses polypeptides which are fusion proteins. A fusion protein is a single polypeptide comprising regions from two or more different proteins. The regions normally exist in separate proteins and are brought together in the fusion protein. They may be linked together so that the amino acid sequence of one begins where the amino acid sequence of the other ends, or they may be linked via linker amino acids which are not normally a part of the constituent proteins. A fusion protein may contain more than one copy of any of its constituent proteins. The constituent proteins may include the entire amino acid sequences of the proteins or portions of the amino acid sequences. In one embodiment, the fusion protein of this invention are two or more HCV proteins (e.g., core, E1, E2, p7, NS2, NS3, NS4a, NS4b, NS5a, and NS5b) or fragments thereof brought together as a fusion protein. The HCV proteins can contain substitutions at various residue positions as disclosed in Tables 5 and 6. In another embodiment, a fusion protein is made from two or more epitopes disclosed herein. The epitopes can be a combination of different T cell epitopes or a combination of B cell epitopes or a combination of both T cell and B cell epitopes.

A vector can include nucleic acid coding for the fusion protein of the invention in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein.

The recombinant expression vectors of the invention can be designed for expression of the fusion proteins of the invention in prokaryotic or eukaryotic cells. For example, polypeptides of the invention can be expressed in *E. coli*, insect cells (e.g., using baculovirus expression vectors), yeast cells, mammalian cells in culture, or in transgenic animals. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

A way to maximize recombinant protein expression in *E. coli* is to express the protein in host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The fusion protein expression vector can also be a yeast expression vector, a vector for expression in insect cells, e.g., a baculovirus expression vector or a vector suitable for expression in mammalian cells in culture, or in transgenic animals. When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and iimmunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

A "host cell" includes an individual cell or cell culture which can be or has been a recipient for vector(s) or for incorporation of polynucleotide molecules and/or proteins. A host cell can be any prokaryotic or eukaryotic cell. For example, fusion proteins of the invention can be expressed in bacterial cells such as *E. coli*, insect cells, yeast or mammalian cells (such as Chinese hamster ovary cells (CHO) or COS cells). Other suitable host cells are known to those skilled in the art. Host cells include progeny of a single host cell, and the progeny may not necessarily be completely identical (in morphology or in genomic of total DNA complement) to the original parent cell due to natural, accidental, or deliberate mutation. A host cell includes cells transfected in vivo with a polynucleotide(s) of this invention.

Polynucleotides Encoding the HCV Consensus Sequences

The invention also encompasses polynucleotides encoding the HCV consensus sequences or fragments thereof. Polynucleotides coding for the epitopes disclosed herein are also encompassed by the invention. Polynucleotides coding for heterologous polypeptides and for fusion proteins are also encompassed by this invention.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989) Cold Spring Harbor Press; *Oligonucleotide Synthesis* (M. J. Gait, ed., 1984); *Animal Cell Culture* (R. I. Freshney), ed., 1987); *Methods in Enzymology* (Academic Press, Inc.); *Handbook* of Experimental Immunology (D. M. Weir & C. C. Blackwell, eds.); Gene *Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991) and *Short Protocols in Molecular Biology* (Wiley and Sons, 1999).

The invention further provides isolated polynucleotides that encode a HCV consensus sequence or fragments thereof, as well as vectors comprising the polynucleotide and a host cell containing the vector. Such expression systems can be used in a method of producing an HCV consensus sequence polypeptide or fragments thereof, wherein the host cell is cultured and the polypeptide produced by the cultured host cell is recovered. Polynucleotides encoding consensus sequences of the invention can also be delivered to a host subject for expression of the consensus sequence by cells of the host subject.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise the consensus sequence (or a fragment thereof) or may comprise a variant of such a sequence. Polynucleotide variants contain one or more substitutions, additions, deletions and/or insertions such that the immunoreactivity of the encoded polypeptide is not diminished, relative to the original immunoreactive molecule. The effect on the immunoreactivity of the encoded polypeptide may generally be assessed as described herein. Polynucleotide variants preferably exhibit at least about 70% identity, more preferably at least about 80% identity and most preferably at least about 90% identity to a polynucleotide sequence that encodes the HCV consensus sequences disclosed herein or a fragment thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 5 contiguous positions, at least about 10 contiguous positions, at least about 15 contiguous positions, or at least about 20 contiguous positions in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) *A model of evolutionary change in proteins—Matrices for detecting distant relationships*. In Dayhoff, M. O. (ed.) *Atlas of protein Sequence and Structure, National Biomedical Research Foundation*, Washington D.C. Vol. 5, Suppl. 3, pp. 345-358; Hein J., 1990, *Unified Approach to Alignment and Phylogenes pp.* 626-645 *Methods in Enzymology* vol. 183, Academic Press, Inc., San Diego, Calif.; Higgins, D. G. and Sharp, P. M., 1989, *CABIOS* 5:151-153; Myers, E. W. and Muller W., 1988, *CABIOS* 4:11-17; Robinson, E. D., 1971, *Comb. Theor.* 11:105; Santou, N., Nes, M., 1987, *Mol. Biol. Evol.* 4:406-425; Sneath, P. H. A. and Sokal, R. R., 1973, *Numerical Taxonomy the Principles and Practice of Numerical Taxonomy*, Freeman Press, San Francisco, Calif.; Wilbur, W. J. and Lipman, D. J., 1983, *Proc. Natl. Acad. Sci. USA* 80:726-730.

Preferably, the "percentage of sequence identity" is determined by comparing two optimally aligned sequences over a window of comparison of at least 5 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Polynucleotides may be prepared using any of a variety of techniques known in the art. The nucleic acid sequence that encodes for the HCV consensus sequences disclosed herein may be obtained from publicly available databases (e.g., GenBank) or from reverse translation from the amino acid sequence of the HCV consensus sequence. Although hepatitis C virus is a RNA virus, DNA sequences (including cDNA) that code for the HCV consensus sequences are also encompassed by this invention. Such nucleic acid sequences can also be obtained as part of a genomic library or a cDNA library. Screening the cDNA or genomic library with the selected probe may be conducted using standard procedures, such as those described in Sambrook et al., *Molecular Cloning: A Laboratory Manual*, New York: Cold Spring Harbor Laboratory Press, 1989.

Polynucleotides, polynucleotide variants, and whole viruses may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding an antibody, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to an individual such that the encoded polypeptide is generated in vivo (e.g., by transfecting antigen-presenting cells, such as dendritic cells, with a cDNA construct encoding the polypeptide, and administering the transfected cells to the individual).

Any polynucleotide may be further modified to increase stability in vivo. Possible modifications include, but are not limited to, the addition of flanking sequences at the 5' and/or 3' ends; the use of phosphorothioate or 2'O-methyl rather than phosphodiesterase linkages in the backbone; and/or the inclusion of nontraditional bases such as inosine, queosine and wybutosine, as well as acetyl-, methyl-, thio- and other modified forms of adenine, cytidine, guanine, thymine and uridine.

Nucleotide sequences can be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and to permit expression therein. Such formulations can be particularly useful for therapeutic purposes, for example for treating HCV infection or as a prophylaxis. In one embodiment, the invention encompasses an expression construct for expressing any portion of the consensus sequence will contain the following operably linked elements: a transcription promoter, a nucleic acid encoding all or some fragment of the consensus sequences and its possible variants disclosed herein, and a transcription terminator. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Additional methods of expression for vaccine purposes are disclosed below. Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Uses for Consensus Sequences

The invention provides for many uses for the consensus sequences disclosed herein. In one aspect, an isolated consensus protein with the sequences disclosed herein is used as a vaccine for prophylactic and treatment purposes. In another aspect, the invention provides for the uses of HCV epitopes disclosed herein to induce or augment an immune response in an individual. In another aspect, the invention is a composition comprising at least one HCV 1a or 1b consensus protein or a fragment thereof. In yet another aspect, the invention is a pharmaceutical composition comprising at least one HCV 1a or 1b consensus protein or a fragment thereof and a suitable carrier. It is understood that this invention not only encompasses polypeptides comprising the consensus sequences but also polynucleotides coding for the polypeptides.

The consensus sequences disclosed herein can be used in its entirety or as fragments. In one embodiment, the consensus sequence comprises at least one HCV protein (e.g., core, E1, E2, p7, NS2, NS3, NS4a, NS4b, NS5a, or NS5b) or a fragment thereof. In another embodiment, the consensus protein fragment has at least 5 contiguous amino acids of either HCV 1a or HCV1b virus. In another embodiment, the consensus protein fragment has least 8 contiguous amino acids of either HCV 1a or HCV1b virus. In other embodiments, the consensus protein fragment has least 11, at least 14, at least 17, at least 20, at least 23, at least 27, at least 30, at least 33, at least 36, at least 39, at least 42, at least 45, at least 48, or at least 51 contiguous amino acids of either HCV 1a or HCV1b virus.

As the HCV mutates, the invention provided herein teaches one of skill in the art how to predict changes in the sequence. Since some of the residues have several variants, the teachings herein on the precise amino acid and the frequency with which was observed allows one of skill in the art to practice the invention without undue experimentation.

Pharmaceutical Compositions

The invention encompasses pharmaceutical compositions comprising HCV consensus sequence proteins or fragments thereof and polynucleotides encoding the same. In addition to the HCV consensus protein (or polynucleotide), the pharmaceutical composition includes a pharmaceutically acceptable excipient. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in *Remington's Pharmaceutical Sciences* 19th Ed. Mack Publishing (1995). Generally, these compositions are formulated for administration by injection (e.g., intraperitoneally, intravenously, subcutaneously, intramuscularly, etc.). Accordingly, these compositions are preferably combined with pharmaceutically acceptable vehicles such as saline, Ringer's solution, dextrose solution, and the like.

Vaccines Using HCV Consensus Sequences

Several general approaches exist for making a vaccine against a virus that mutates rapidly and has multiple subtypes around the world. From an efficiency perspective, it would be ideal to be able to make one vaccine that could be effective against the same virus, even if it has mutated as it is transmitted from person to person. One general approach is to use isolates of a particular subtype to make the vaccine. However, because it is likely that each geographical area will have mutations that are clustered and make the virus phylogenetically a different clade, the isolate approach is not economically viable because country-specific vaccine efforts would be needed. Another approach, using the consensus sequence instead of the actual sequence isolated from within the infected population, has the advantages of being central and having the potential to induce or augment cross-reactive responses in infected individuals. Other considerations when making a vaccine also include whether the protein should be polyvalent or to target specific types of valencies, for example, in HIV, designing modified envelopes to enhance exposure of epitopes known to be capable of inducing broadly neutralizing antibodies. See, for example, Gaschen at el. *Science* 296: 2354-2360 (2002).

Use of a consensus sequence as a vaccine for HCV should take into account considerations that would stimulate responses that drive the virus to mutate to a less fit state, thereby rendering it less able to replicate, and easier to eradicate. Such considerations include co-receptor usage (if any), protein folding, and exposure of antigenic or immunogenic domains. Selection of a consensus sequence for use as a vaccine against HCV would elicit both T cell and/or B cell responses in such way to engage the immune system to eradicate the existing HCV in the infected individual.

The vaccines of the invention comprise HCV consensus sequence or a fragment thereof or a polynucleotide encoding HCV consensus sequence or a fragment thereof. For instance, the vaccine may comprise or encode the HCV polyprotein, the primary translation product, or the full-length translation product of the HCV consensus sequence. In another embodiment, the vaccine comprises the processed HCV proteins or fragments thereof. In addition to the use of consensus sequence proteins (or polynucleotides encoding those proteins), polypeptides comprising fragments of HCV consensus sequence, or polynucleotides encoding fragments of HCV consensus sequence may be used in the vaccines. The polypeptides in the vaccines or encoded by polynucleotides of the vaccines are optionally at least about 99%, at least about 95%, at least about 90%, at least about 85%, at least about 80%, at least about 75%, at least about 70%, at least about 65%, at least about 60%, at least about 55%, or at least about 50% identical to the HCV consensus sequence disclosed herein.

In addition, the polynucleotides of the vaccines are optionally at least about 99%, at least about 95%, at least about 90%, at least about 85%, at least about 80%, at least about 75%, at least about 70%, at least about 65%, at least about 60%, at least about 55%, or at least about 50% identical to the polynucleotides encoding the HCV consensus sequence disclosed herein.

Delivery/Expression Systems

The HCV consensus sequence vaccines can be delivered to the individual using various expression systems. A few of the possible systems are described below.

1. Mammalian Cell-Based Delivery Systems

In one embodiment of the invention, the immunogenic composition comprises a cell. The cell of the immunogenic composition comprises a consensus sequence or epitope-containing polypeptide described herein or a polynucleotide encoding an epitope-containing polypeptide described herein. Prior to delivery of the cell to a host, the cell optionally comprises an epitope from the consensus sequence on its surface (for instance, as an HLA-bound peptide). In an alternative embodiment, the cell comprises an epitope-containing polypeptide described herein and/or a polynucleotide encoding a consensus sequence or epitope-containing polypeptide described herein in the interior of the cell. In one embodiment, the immunogenic composition comprising the consensus sequence or polynucleotide encoding the consensus sequence is an eukaryotic cell, such as a mammalian cell.

In another embodiment, the immunogenic composition comprises a mammalian cell which is an antigen-presenting cell. Antigen presenting cells, as referred to herein, express at least one class I or class II MHC determinant and may include those cells which are known as professional antigen-presenting cells such as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen-presenting cells include astrocytes, follicular cells, endothelium and fibroblasts. In one embodiment, the immunogenic composition comprises an antigen-presenting cell that affords MHC class I antigen presentation.

The polypeptides or polynucleotides of the invention may be delivered to cells in vivo or ex vivo. The loading of antigen onto antigen-presenting cells such as dendritic cells has been achieved by different methods, including peptide pulsing (see Melero et al., *Gene Therapy* 7:1167 (2000). This method for administering polypeptide vaccine is accomplished by pulsing the polypeptide onto an APC or dendritic cell in vitro. The polypeptide binds to MHC molecules on the surface of the APC or dendritic cell. Prior treatment of the APCs or dendritic cells with interferon-γ can be used to increase the number of MHC molecules on the APCs or dendritic cells. The pulsed cells can then be administered as a carrier for the polypeptide.

2. Yeast-Based Delivery Systems

In another embodiment of the invention, a consensus sequence or epitope-containing polypeptide described herein, or a polynucleotide encoding the consensus sequence or epitope-containing polypeptide, is delivered to a host organism in a vaccine comprising yeast. The use of live yeast DNA vaccine vectors for antigen delivery has been reviewed recently and reported to be efficacious in a mouse model using whole recombinant *Saccharomyces cerevisiae* yeast expressing tumor or HIV-1 antigens (see Stubbs et al. (2001) *Nature Medicine* 7: 625-29).

The use of live yeast vaccine vectors is known in the art. Furthermore, U.S. Pat. No. 5,830,463 describes particularly useful vectors and systems for use in the instant invention. The use of yeast delivery systems may be particularly effective for use in the viral vaccine methods and formulations of the invention as yeast appear to trigger cell-mediated immunity without the need for an adjuvant. Possible yeast vaccine delivery systems are nonpathogenic yeast carrying at least one recombinant expression system capable of modulating an immune response. In an alternative, heat killed yeast may also be used to express the protein antigen of interest as part of a yeast-based delivery system (e.g., GlobeImmune products).

3. Bacterial Systems

In another embodiment, the cell that comprises the consensus sequence or epitope-containing polypeptide, or polynucleotide encoding the consensus sequence or epitope-containing polypeptide, is a microbial cell. In one embodiment, the microbial cell is a bacterium, typically a mutant or recombinant bacterium. The bacterium is optionally attenuated. For instance, a number of bacterial species have been studied for their potential use as vaccines and can be used in the present invention, including, but not limited to, *Shigella flexneri, E. Coli, Listeria monocytogenes, Yersinia enterocolitica, Salmonella typhimurium, Salmonella typhi* or *mycobacterium*. In one embodiment, the bacterial vector used in the immunogenic composition is a facultative, intracellular bacteria vector. In one embodiment, the bacterium is used to deliver an epitope-containing polypeptide to antigen-presenting cells in the host organism.

The use of live bacterial vaccine vectors for antigen delivery has been reviewed (Medina and Guzman (2001) *Vaccine* 19: 1573-1580; and Darji et al. (2000) *FEMS Immunol and Medical Microbiology* 27: 341-9). Furthermore, U.S. Pat. Nos. 6,261,568 and 6,488,926 describe particularly useful systems for use in this HCV vaccine invention.

The use of live bacterial vaccine vectors can be particularly advantageous. Bacteria-mediated gene transfer finds particular advantage in genetic vaccination by intramuscular, intradermal or oral administration of plasmids which leads to antigen expression in the mammalian host-thereby offering the possibility of both antigen modification as well as immune modulation. Furthermore, the bacterial-mediated DNA vaccine provides adjuvant effects and the ability to target inductive sites of the immune system. In preferred embodiments, *S. typhimurium, S. typhi, S. flexneri* or *L. monocytogenes* are used as vehicles for trans-kingdom DNA vaccine delivery.

Furthermore, many live bacterial vaccine vectors make use of the almost unlimited coding capacity of bacterial plasmids, and broad availability of bacterial expression vectors, to express virtually any target tumor antigen of interest. The use of bacterial carriers is often associated with still other significant benefits, such as the availability of convenient direct mucosal or oral delivery. Other direct mucosal delivery systems (besides live viral or bacterial vaccine carriers) include mucosal adjuvants, viral particles, ISCOMs, liposomes, microparticles and transgenic plants. Other advantages of this technology are: low batch preparation costs, facilitated technology transfer following development of the prototype, increased shelf-life and stability in the field respect to other formulations (e.g., subunit vaccines), easy administration and low delivery costs. Taken together, these advantages make this strategy particularly suitable for vaccine programs including HCV vaccines. The carrier operationally becomes an equivalent of a subunit recombinant vaccine.

Both attenuated and commensal microorganisms have been successfully used as carriers for vaccine antigens. Attenuated mucosal pathogens which may be used in the invention include: *L. monocyotgenes, Salmonella* spp., *V. cholorae, Shigella* spp., *mycobacterium, Y. enterocolitica,* and *B. anthracis*. Commensal strains for use in the invention include: *S. gordonii, Lactobacillus* spp., and *Staphylococcus* ssp. The background of the carrier strain used in the formulation, the type of mutation selected to achieve attenuation, and the intrinsic properties of the immunogen can be used in optimizing the extent and quality of the immune response elicited. The general factors to be considered to optimize the immune response stimulated by the bacterial carrier include carrier-related factors including: selection of the carrier; the specific background strain, the attenuating mutation and the level of attenuation; the stabilization of the attenuated phenotype and the establishment of the optimal dosage. Other considerations include antigen-related factors such as: instrinsic properties of the antigen; the expression system, antigen-display form and stabilization of the recombinant phenotype; co-expression of modulating molecules and vaccination schedules.

Descriptions of exemplary bacterial vaccine vectors follows, including references which demonstrate the availability in the art of the knowledge required to generate recombinant bacterial vaccine vectors that express the antigen of choice and can be used in immunogenic compositions. Each of the following references in incorporated herein in its entirety.

For instance, *Salmonella typhimurium* could be used as a bacterial vector in the immunogenic compositions of the invention. Use of this type of bacteria as an effective vector for a vaccine has been demonstrated in the art. For instance, the use of *S. typhimurium* as an attenuated vector for oral somatic transgene vaccination has been described (see Darji et al. (1997) *Cell* 91: 765-775; and Darji et al. (2000) *FEMS Immun and Medical Microbiology* 27:341-9). Indeed most knowledge on bacteria-mediated gene transfer has been acquired using attenuated *S. typhimurium* as carrier. Two metabolically attenuated strains that have been used include *S. typhimurium* aroA, which is unable to synthesize aromatic amino acids, and *S. typhimurium* 22-11, which is defective in purine metabolism. Several antigens have been expressed using these carriers: originally, listeriolysin and actA (two virulence factors of *L. monocytogenes*) and beta-galactosidase (beta-gal) of *E. coli* were successfully tested. Cytotoxic and helper T cells as well as specific antibodies could be detected against these antigens following oral application of a single dose of the recombinant *salmonella*. In addition, immunization with *salmonella* carrying a listeriolysin-encoding expression plasmid elicited a protective response against a lethal challenge with *L. monocytogenes*. Interestingly, this protection was observed in the lung although the vaccine was administered orally. Oral transgene vaccination methodology has now been extended to include protective responses in herpes simplex virus 2 and hepatitis B infection models, with cell-mediated immune responses detected at the mucosal level.

In another embodiment, the immunogenic compositions of the present invention optionally comprise *Shigella flexneri* as a delivery vehicle. *S. flexneri* represents the prototype of a bacterial DNA transfer vehicle as it escapes from the vacuole into the cytosol of the host cell. Several attenuated mutants have been used successfully to transfer DNA to cell lines in vitro. Auxotrophic strains were defective in cell-wall synthesis (see Sizemore et al. (1995) *Science* 270:299-302; and dapB (see Courvalin et al. (1995) *C R Acad Sci Ser III,* 318:1207-12), synthesis of aromatic amino acids (aroA (see Powell et al. (1996) *Vaccines* 96: Molecular Approaches to the Control of Infectious Disease; Cold Spring Harbor Laboratory Press) or synthesis of guanine nucleotides (guaBA (see Anderson et al. (2000) *Vaccine* 18: 2193-2202).

In still another embodiment, the immunogenic compositions of the present invention comprise *Listeria monocytogenes* (Portnoy et al, Journal of Cell Biology, 158:409-414 (2002); Glomski et al., *Journal of Cell Biology,* 156:1029-1038 (2002)). Strains of *Listeria monocytogenes* have recently been developed as effective intracellular delivery vehicles of heterologous proteins providing delivery of antigens to the immune system to induce an immune response to clinical conditions that do not permit injection of the disease-causing agent, such as cancer (U.S. Pat. No. 6,051,237 Paterson; Gunn et al., *J. Immun.* 167:6471-6479 (2001); Liau, et al., *Cancer Research,* 62: 2287-2293 (2002)) and HIV (U.S. Pat. No. 5,830,702 Portnoy & Paterson). A recombinant *L. monocytogenes* vaccine expressing a lymphocytic choriomeningitis virus (LCMV) antigen has also been shown to induce protective cell-mediated immunity to the antigen (Shen et al., *PNAS,* 92: 3987-3991 (1995). The ability of *L. monocytogenes* to serve as a vaccine vector has been reviewed (Wesikirch, et al., *Immunol. Rev.* 158:159-169 (1997)).

As a facultative intracellular bacterium, *L. monocytogenes* elicits both humoral and cell-mediated immune responses. Following entry of the *Listeria* into a cell of the host organism, the *Listeria* produces *Listeria*-specific proteins that enable it to escape from the phagolysosome of the engulfing host cell into the cytosol of that cell. Here, *L. monocytogenes* proliferates, expressing proteins necessary for survival, but also expressing heterologous genes operably linked to *Listeria* promoters. Presentation of peptides of these heterologous proteins on the surface of the engulfing cell by MHC proteins permits the development of a T cell response. Two integration vectors which are particularly useful for introducing heterologous genes into the bacteria for use as vaccines include pPL1 and pPL2 as described in Lauer et al., *Journal of Bacteriology,* 184: 4177-4186 (2002).

Attenuated forms of *L. monocytogenes* have been produced. The ActA protein of *L. monocytogenes* is sufficient to promote the actin recruitment and polymerization events responsible for intracellular movement. A human safety study has reported that administration of an actA/plcB-deleted attenuated form of *Listeria monocytogenes* caused no serious sequelae in adults (Angelakopoulos et al., *Infection and Immunity,* 70:3592-3601 (2002)).

Another possible delivery system is based on killed but metabolically active (KBMA) bacteria, that simultaneously takes advantage of the potency of live vaccines and the safety of killed vaccines. In these microbes, for example *L. monocytogenes*, genes required for nucleotide excision repair (uvrAB) are removed, rendering microbial-based vaccines exquisitely sensitive to photochemical inactivation with psoralen and long-wavelength ultraviolet light. Colony formation of the nucleotide excision repair mutants can be blocked by infrequent, randomly distributed psoralen crosslinks, but the bacterial population is still able to express its genes, synthesize and secrete proteins. See Brockstedt et al *Nat. Med.* 2005 August; 11(8):853-60 and US 2004/0197343 A1. Other systems that can be used include those taught in US 2004/0228877 A1, US 2005/0281783 A1, and US 2005/0249748 A1.

4. Viral-Based Delivery Systems

In another embodiment of the invention, the immunogenic composition comprising the consensus sequence or epitope-containing polypeptide and/or the polynucleotide encoding the consensus sequence or epitope-containing further comprises a viral vector. The viral vector will typically comprise a highly attenuated, non-replicative virus. Vaccinia variants, avipoxviruses, adenoviruses, polio viruses, influenza viruses, and herpes viruses can all be used as delivery vectors in conjunction with the present invention.

Formulations

Compositions comprising any of the consensus sequences described herein are also provided. In some embodiments, the compositions are pharmaceutical compositions. In some embodiments, the compositions are immunogenic compositions. The pharmaceutical compositions optionally comprise a pharmaceutically acceptable carrier or adjuvant. In some embodiments, the compositions are vaccine compositions (i.e., vaccines). The vaccine compositions optionally comprise a pharmaceutically acceptable carrier or adjuvant.

The vaccine compositions of the present invention can be used to stimulate an immune response in an individual. The formulations can be administered to an individual by a variety of administration routes. Methods of administration of such a vaccine composition are known in the art, and include oral, nasal, intravenous, intradermal, intraperitoneal, intramuscular, intralymphatic, percutaneous, scarification, and subcutaneous routes of administration, as well as intradermally by gene gun wherein gold particles coated with DNA may be used in the gene gun and any other route that is relevant for an infectious disease.

The vaccine compositions may further comprise additional components known in the art to improve the immune response to a vaccine, such as adjuvants, T cell co-stimulatory molecules, or antibodies, such as anti-CTLA4. The invention also includes medicaments comprising the pharmaceutical compositions of the invention. An individual to be treated with such vaccines, is any vertebrate, preferably a mammal, including domestic animals, sport animals, and primates, including humans. The vaccine can be administered as a prophylactic or for treatment purposes.

Vaccine formulations are known in the art. Known vaccine formulations can include one or more possible additives, such as carriers, preservatives, stabilizers, adjuvants, antibiotics, and other substances. Preservatives, such as thimerosal or 2-phenoxy ethanol, can be added to slow or stop the growth of bacteria or fungi resulting from inadvertent contamination, especially as might occur with vaccine vials intended for multiple uses or doses. Stabilizers, such as lactose or monosodium glutamate (MSG), can be added to stabilize the vaccine formulation against a variety of conditions, such as temperature variations or a freeze-drying process. Adjuvants, such as aluminum hydroxide or aluminum phosphate, are optionally added to increase the ability of the vaccine to trigger, enhance, or prolong an immune response. Additional materials, such as cytokines, chemokines, and bacterial nucleic acid sequences, like CpG, are also potential vaccine adjuvants. Antibiotics, such as neomycin and streptomycin, are optionally added to prevent the potentially harmful growth of germs. Vaccines may also include a suspending fluid such as sterile water or saline. Vaccines may also contain small amounts of residual materials from the manufacturing process, such as cell or bacterial proteins, egg proteins (from vaccines that are produced in eggs), DNA or RNA, or formaldehyde from a toxoiding process. Formulations may be re-suspended or diluted in a suitable diluent such as sterile water, saline, isotonic buffered saline (e.g. phosphate buffered to physiological pH), or other suitable diluent.

The consensus sequence vaccine is optionally administered to a host in a physiologically acceptable carrier. Optionally, the vaccine formulation further comprises an adjuvant. Useful carriers known to those of ordinary skill in the art include, e.g., citrate-bicarbonate buffer, buffered water, 0.4% saline, and the like. In some embodiments, the vaccine compositions are prepared as liquid suspensions. In other embodiments, the vaccine compositions comprising the consensus sequence strains are lyophilized (i.e., freeze-dried). The lyophilized preparation can then be combined with a sterile solution (e.g., citrate-bicarbonate buffer, buffered water, 0.4% saline, or the like) prior to administration.

Viral vectors can be used to administer polynucleotides encoding a polypeptide comprising one or more HCV consensus sequences or polynucleotides encoding a HCV epitope or any fragment thereof. Such viral vectors include vaccinia virus and avian viruses, such as Newcastle disease virus. Others may be used as are known in the art.

Naked DNA can be injected directly into the host to produce an immune response. Such naked DNA vaccines may be injected intramuscularly into human muscle tissue, or through transdermal or intradermal delivery of the vaccine DNA, typically using biolistic-mediate gene transfer (i.e., gene gun). Recent reviews describing the gene gun and muscle injection delivery strategies for DNA immunization include Tuting, *Curr. Opin. Mol. Ther.* (1999) 1: 216-25, Robinson, *Int. J. Mol. Med.* (1999) 4: 549-55, and Mumper and Ledbur, *Mol. Biotechnol.* (2001) 19: 79-95. Other possible methods for delivering plasmid DNA include electroporation and iontophoreses.

Another possible gene delivery system comprises ionic complexes formed between DNA and polycationic liposomes (see, e.g., Caplen et al. (1995) Nature Med. 1: 39). Held together by electrostatic interaction, these complexes may dissociate because of the charge screening effect of the polyelectrolytes in the biological fluid. A strongly basic lipid composition can stabilize the complex, but such lipids may be cytotoxic. Other possible methods for delivering DNA include electroporation and iontophoreses.

The use of intracellular and intercellular targeting strategies in DNA vaccines may further enhance the effect of HCV vaccine compositions. Previously, intracellular targeting strategies and intercellular spreading strategies have been used to enhance MHC class I or MHC class II presentation of antigen, resulting in potent CD8+ or CD4+ T cell-mediated antitumor immunity, respectively. For example, MHC class I presentation of a model antigen, HPV-16 E7, was enhanced using linkage of *Mycobacterium tuberculosis* heat shock protein 70 (HSP70) (Chen, et al., (2000), *Cancer Research,* 60: 1035-1042), calreticulin (Cheng, et al., (2001) *J Clin Invest,* 108:669-678) or the translocation domain (domain II) of *Pseudomonas aeruginosa* exotoxin A (ETA(dII)) (Hung, et al., (2001) *Cancer Research,* 61: 3698-3703) to E7 in the context of a DNA vaccine. To enhance MHC class II antigen processing, the sorting signals of the lysosome associated membrane protein (LAMP-1) have been linked to the E7 antigen, creating the Sig/E7/LAMP-1 chimera (Ji, et al, (1999), *Human Gene Therapy*, 10: 2727-2740).

To enhance further the potency of naked DNA vaccines, an intercellular strategy that facilitates the spread of antigen between cells can be used. This improves the potency of DNA vaccines as has been shown using herpes simplex virus (HSV-1) VP22, an HSV-1 tegument protein that has demonstrated the remarkable property of intercellular transport and is capable of distributing protein to many surrounding cells (Elliot, et al., (1997) *Cell*, 88: 223-233). Such enhanced intercellular spreading of linked protein, results in enhancement of HCV-specific CD8+ T cell-mediated immune responses and anti-HCV effect. Any such methods can be used to enhance DNA vaccine potency against HCV in an infected individual.

Prophylactic Vaccines Using HCV Consensus Sequences

The HCV consensus sequence taught herein can also be used as a vaccine prophylactically, i.e., lessening the symptoms associated with HCV in an individual who is infected with HCV. In one embodiment, an individual is preventing from contracting HCV. The vaccine compositions of the invention are administered to an individual who is not infected with HCV. By its ability to induce or augment an effective immune response, the vaccine mollifies the dangers of becoming infected with HCV. The individual should be given an amount effective to induce or augment effective immune responses, which can be measured using the assays detailed in the Examples section. The invention discloses epitopes which are immunogenic in individuals with certain MHC haplotypes. Thus, depending on the MHC haplotype of the individual, a customized vaccine may also be made if desired. Even if the individual does not have matching MHC haplotype, the advantage of using consensus sequence as a vaccine is that it has the potential for cross reactivity. In another embodiment, the individual has been exposed to ACV experiences a lessening of the symptoms associated with HCV. In this case, the individual is monitored by a physician or another individual suitably trained to monitor the progression of HCV infection. As disclosed above, symptoms associated with HCV include jaundice, fatigue, dark urine, abdominal pain, loss of appetite, and nausea, liver disease, and hepatocellular carcinoma. Physicians can monitor the individuals for the presence and level of HCV (e.g., by RNA levels) to assess the individual's responses to vaccination.

Methods of Treating HCV-Infected Individuals

The invention provides methods for treating individuals infected with HCV. Using the compositions comprising HCV consensus sequences disclosed herein, individuals who are infected with HCV can be treated by administering an effective amount of the composition. An effective amount is an amount that is sufficient to stimulate an immune response. The immune response can be monitored by using the assays disclosed in the Examples or any other standard measure of immune response (e.g., measuring antibodies, cytokine levels, activation markers on immune cells, etc.) Optionally, the levels of HCV can be measured by standard assays known to one of ordinary skill in the art. In one embodiment, the administration of a composition comprising HCV consensus sequences (e.g., a vaccine) will stimulate T cell and/or B cell response. The stimulation of an immune response will serve to eradicate circulating HCV in the individual.

In some embodiments, the administration of one or more HCV consensus sequence proteins or a fragment thereof is capable of inducing an immune response in a host animal. In one embodiment, the immune response is a cell-mediated immune response. In one embodiment, the effective immune response induced or augmented by the one or more HCV consensus sequence proteins or a fragment thereof comprises a T cell response, such as a CD4+ T cell response or a CD8+ T cell response, or both.

These immune cell responses can be measured by both in vitro and in vivo methods to determine if the immune response involved in the present invention is effective. Efficacy can be determined by comparing these measurements for those to whom have received treatment to those who have received no treatment. Another alternative to compare the measurements of an individual before treatment with his/her measurements after treatment. One possibility is to measure the presentation of the HCV consensus protein or consensus epitope of interest by an antigen-presenting cell. The HCV consensus protein or consensus epitope of interest may be mixed with a suitable antigen presenting cell or cell line, for example a dendritic cell, and the antigen presentation by the dendritic cell to a T cell that recognizes the protein or antigen can be measured. If the HCV consensus protein or consensus epitope of interest is being recognized by the immune system at a sufficient level, it will be processed into peptide fragments by the dendritic cells and presented in the context of MHC class I or class II to T cells. For the purpose of detecting the presented protein or antigen, a T cell clone or T cell line responsive to the particular protein or antigen may be used. The T cell may also be a T cell hybridoma, where the T cell is immortalized by fusion with a cancer cell line. Such T cell hybridomas, T cell clones, or T cell lines can comprise either CD8+ or CD4+ T cells. The dendritic cell can present to either CD8+ or CD4+ T cells, depending on the pathway by which the antigens are processed. CD8+ T cells recognize antigens in the context of MHC class I molecules while CD4+ recognize antigens in the context of MHC class II molecules. The T cell will be stimulated by the presented antigen through specific recognition by its T cell receptor, resulting in the production of certain proteins, such as IL-2, tumor necrosis factor-α (TNF-α), or interferon-γ (IFN-γ), that can be quantitatively measured (for example, using an ELISA assay, ELISPOT assay, or Intracellular Cytokine Staining (ICS)).

In another aspect, the invention provides methods for preventing an already infected individual from entering a chronic phase of infection. As the infection moves into the chronic phase, an infected individual's immune system is weakened and less effective against the HCV. By utilizing the precise genetic changes disclosed herein, methods of treatment are possible to prevent the chronic phase of infection. An effective amount of a composition comprising HCV consensus sequences (e.g., a vaccine) is administered to the infected individual. The progress of the infection is monitored afterwards. Optionally, prior to the administration of a vaccine, the full or partial sequence of the HCV infecting the individual is determined and the consensus sequence for administration can be customized if desired.

Methods of Diagnosis

The invention also provides for methods of diagnosing an individual with HCV. By using the consensus sequences disclosed herein, one of skill in the art can obtain a biological sample from an individual to be tested and then use PCR primers (or any comparable molecular biological technique) to the consensus sequence to amplify nucleic acids in the biological sample to determine if the individual has been infected with a particular strain of HCV (e.g., HCV 1a or HCV 1b).

In another embodiment, the nucleic acid sequence of portions of the HCV consensus sequence can be used as probes for purposes of diagnosis. The oligonucleotide sequences selected as probes should be sufficiently long and sufficiently unambiguous that false positives are minimized. The oligonucleotide can be labeled such that it can be detected upon hybridization to the nucleic acid (e.g., DNA) being screened. Methods of labeling are well known in the art, and include the use of radiolabels, such as $^{32}$P-labeled ATP, biotinylation or enzyme labeling. Hybridization conditions, including moderate stringency and high stringency, are provided in Sambrook et al., supra.

Kits

The invention further provides kits (or articles of manufacture) comprising the HCV consensus sequences of the present invention.

In one aspect, the invention provides a kit comprising both (a) a composition comprising a HCV consensus sequence described herein, and (b) instructions for the use of the composition in the prevention or treatment of HCV in a host. In some embodiments, the instructions are on a label. In other embodiments, the instructions are on an insert contained within the kit.

In another aspect, the invention provides a kit comprising both (a) a composition comprising a HCV consensus sequence described herein; and (b) instructions for the administration of the composition to a host. In some embodiments, the instructions are on a label. In other embodiments, the instructions are on an insert contained within the kit.

In another aspect, the invention provides a kit comprising both (a) a composition comprising a HCV consensus sequence described herein; and (b) instructions for selecting a host to which the composition is to be administered. In some embodiments, the instructions are on a label. In other embodiments, the instructions are on an insert contained within the kit.

In another aspect, the invention provides a kit comprising both (a) a composition comprising a HCV consensus sequence described herein; and (b) instructions for selecting one or more consensus sequence(s) to administer to an individual. In some embodiments, the instructions are on a label. In other embodiments, the instructions are on an insert contained within the kit In some embodiments of each of the aforementioned aspects, the composition is a vaccine. In some embodiments of each of the aforementioned aspects, the vaccine comprises the entire consensus sequence 1a or a fragment thereof. In other embodiments, the vaccine comprises the entire consensus sequence 1b or a fragment thereof. In other embodiments, the vaccine comprises one or more HCV proteins or a fragment thereof. It is understood that these composition include non-synonymous changes as well.

The following are provided to illustrate, but not to limit, the invention.

EXAMPLES

Example 1

Obtaining HCV Consensus Sequence 1a and 1b

Using HCV Sequence Database at Los Alamos National Laboratories at the website: http://hcv.lanl.gov, all available non-redundant human sequences greater than 500 nucleotides were obtained. Then, the options were set as default except for: "Genotype" was set to "1", "Subtype" to "a or b", "Include recombinants" set to "off", "Include fragments longer than" was set to "on, 500" and "Exclude Non-human hosts" was set to "on." Once the preliminary query result was displayed, "Exclude related" was chosen. Then the sequences were downloaded with default options. The rationale behind these series of steps is that size restriction reduces the number of unidirectional (poor quality) sequences.

Next, the alignments were neatened by performing any number of commands, such as restoring codon boundaries, closing gaps and removing non-translated termini. The rationale behind this step is that only the primary open reading frame is desired. Next, sequences that contain >1% ambiguous sites or >1 frameshift were removed. The rationale for this step is to remove low-quality sequences. Next, the terminal "gap" characters were converted to "missing." The rationale behind this step is to distinguish true gaps from missing data for subsequent analysis. Using the CleanCollapse program, which was written by Stuart Ray and publicly available at <http://sray.med.som.jhmi.edu/SCRoftware/CleanCollapse>, identical sequences were identified. The CleanCollapse program has also been disclosed in Kieffer T L, et al. *J Infect Dis.* 2004; 189(8):1452-65. For identical sequences, related publications were checked and any linked sequences were removed. The rationale behind this approach is that oversampling individuals could skew sequence distributions. Despite use of "Exclude related" option above, the returned data set can still include many redundant/related sequences. Thus, these were removed to prevent skewing of sequence distributions.

Predicted polyprotein sequences were generated by automated translation in BioEdit (Tom Hall, URL: <http://www.mbio.ncsu.edu/RNaseP/info/programs/BIOEDIT/bioedit.html>) using standard eukaryotic genetic code. The majority-rule consensus sequence were identified for each subtype by using the MargFreq program written by Stuart Ray and publicly available at <http://sray.med.som.jhmi.edu/SCRoftware/MargFreq> to identify modal aa residue at each site. The MargFreq program has also been disclosed in Ray S C, et al. *J. Virol.* 1999 April; 73(4):2938-46. Where there is a near-tie at a site, the nearest neighbor (the other subtype) distribution for likely ancestor/shared state was examined and then used. The rationale behind this is that it reduces likelihood of escape mutant for common HLA allele being used. The result was consensus sequence1a (SEQ ID NO:1) and consensus sequence1b (SEQ ID NO:2).

Example 2

Cellular Immune Selection with Hepatitis C Persistence in Humans

Hepatitis C virus (HCV) infection frequently persists despite substantial virus-specific cellular immune responses. To determine if immunologically-driven sequence variation occurs with HCV persistence, we coordinately analyzed sequence evolution and CD8+ T cell responses to epitopes covering the entire HCV polyprotein in subjects followed prospectively from prior to infection to beyond the first year. There were no substitutions in T-cell epitopes for a year following infection in a subject who cleared viremia. In contrast, in subjects with persistent viremia and detectable T cell responses, we observed substitutions in 69% of T cell epitopes, and every subject had a substitution in at least one epitope. In addition, amino acid substitutions occurred 13-fold more often within than outside T cell epitopes (p<0.001, range 5-38). T lymphocyte recognition of eight of ten mutant peptides was markedly reduced compared to the initial sequence, indicating viral escape. Of 16 non-envelope substitutions that occurred outside of known T cell epitopes, eight represented conversion to consensus (p=0.015). These findings reveal two distinct mechanisms of sequence evolution involved in HCV persistence: viral escape from CD8+ T cell responses and optimization of replicative capacity.

The World Health Organization estimates there are 170 million persons with HCV infection worldwide, and an estimated 4 million persons are infected with hepatitis C virus (HCV) in the United States.(1,2) In most countries, HCV infection is found in 1-2% of the general population and may cause cirrhosis or hepatocellular cancer, but only when infection persists.(3-7)

Patients in the acute phase of HCV infection are much more likely to respond to therapy designed to eradicate the virus than are patients after progression to chronicity.(8-10) The features unique to acute infection that allow increased responsiveness to interferon therapy remain unknown. Spontaneous clearance of HCV infection occurs in about 20% of acutely infected individuals and is associated with a broadly specific and vigorous cellular immune response.(11-14) Although the cellular immune response is often less vigorous and more narrowly directed in those who fail to clear the infection, a cellular immune response is nonetheless often present in early infection and may even persist into chronic infection. Why the early response fails to control viremia in those who progress to chronic infection is not clear, but responses generated in acute infection have been shown to decline in some subjects who remained persistently infected and chronic infection is characterized by low frequencies of CD8+ T cells in peripheral blood.(13, 15-20) Although the liver has the potential to delete antigen-specific T cell responses, HCV-specific CD8+ CTL lines have been generated from the liver of both chronically infected humans and chimpanzees, suggesting that elimination of HCV specific lymphocytes from the liver is neither universal nor necessary for HCV persistence.(21-24) Survival of HCV despite virus-specific CD8+ CTL might be explained by impaired cellular effector functions (proliferation, cytokine secretion, or cytolytic activity), T cell exhaustion, or dendritic cell dysfunction.(16, 25-27) A final possibility is that persistence is facilitated by viral evolution over the course of infection, enabling escape by mutation of key epitopes targeted by T-lymphocytes. Mutational escape from T cell responses has indeed been noted in HIV, which uses an error prone RNA polymerase similar to HCV.(28)

Mathematical models of viral kinetics suggest that up to $10^{12}$ virions are produced each day in a human with chronic hepatitis C.(29) This rate exceeds comparable estimates of the production of HIV by more than an order of magnitude, and, coupled with the absence of proofreading by the HCV NS5B RNA polymerase, results in frequent mutations within the HCV genome. Mutation of class I or II MHC restricted T cell epitopes could alter the outcome of infection by preventing or delaying clearance of infected hepatocytes.(30) In the face of a vigorous multispecific CTL response, mutation of several epitopes, perhaps simultaneously, would be required for survival of the virus. In HCV infection, a strong association between viral persistence and the development of escape mutations has been demonstrated in the chimpanzee model (31) and one group examined viral evolution in a single human histocompatibility leukocyte antigen (HLA)-B8-restricted NS3 epitope,(32) but evidence of evasion of a multispecific CTL response in humans is lacking. Although mutations in class I MHC restricted HCV epitopes have been observed in humans with chronic HCV infection, it is uncertain that these mutations result from CD8+ T cell selection pressure or that they occur during the acute phase of infection, when clearance or persistence is determined.(33-35)

Studies of the cellular immune response to acute HCV infection have been challenging because acute hepatitis C is usually clinically silent, making early virus isolates and CTL difficult to obtain. In addition, no consistent pattern of HCV epitope dominance has emerged in humans so large numbers of PBMC are needed for the broad screening required to identify CTL responses. We have overcome these challenges to test the hypothesis that cytotoxic T lymphocyte (CTL)-driven sequence variation occurs with progression to persistent HCV in humans. We prospectively studied HCV antibody negative injection drug users at risk for HCV infection and compared the viral sequences at initial viremia to sequences obtained at multiple time points in acute HCV infection. In parallel, a genome wide analysis of T cell responsiveness was performed. As evidence of immune selection pressure, we determined the percentage of T cell epitopes that underwent substitution, assessed the likelihood of amino acid changing substitutions to occur within versus outside T cell epitopes, and examined the effects of observed amino acid sequence changes in epitopes on T cell recognition and MHC class I binding. For amino acid substitutions outside T cell epitopes, we investigated explanations other than T cell pressure. Our results provide strong evidence in humans that both immune and fitness selection occur during the acute phase of HCV infection.

Materials and Methods

Participants. The Risk Evaluation Assessment of Community Health (REACH) prospective study of young IDUs in Baltimore, Md. examined the incidence and risk factors for HCV infection, as described previously. (47) Participants eligible for the study were anti-HCV antibody negative, between 15 to 30 years of age, and acknowledged use of injection drugs. Participants were invited to co-enroll in a substudy of acute hepatitis C and those who consented had blood drawn for isolation of serum, plasma, and peripheral blood mononuclear cells in a protocol designed for monthly follow up. At each visit, participants were provided counseling to reduce the risks of drug use. The REACH protocol and the HCV substudy protocols were approved by the institutional review boards of the Johns Hopkins Schools of Medicine and Hygiene and Public Health.

From 1997 to 2002, 179 participants were enrolled and 62 (34.6%) developed anti-HCV antibodies (seroconverted). Beginning in November 2001, acutely infected persons were assessed for donation of ~$10^8$-$10^{10}$ PBMC by blood donation or apheresis. HCV-specific lymphocyte responses and sequences were studied in detail in 5 acutely infected persons who were assessed frequently during the six-month period following infection and from whom large volumes of PBMC were obtained. HCV sequencing and limited analysis of the cellular response were performed using an additional 3 subjects for whom smaller numbers of cells were available, as described below.

HCV testing protocol. Serum or plasma, stored at −80° C., from monthly follow-up visits was tested for the presence of HCV specific antibodies using the commercially available Ortho version 3.0 enzyme-linked immunosorbent assay (ELISA) (Ortho Clinical Diagnostics, Raritan, N.J.) according to manufacturer's instructions. Specimens in which antibodies were detected were retested in duplicate along with the participant's previous seronegative sample to identify seroconverters. HCV RNA testing was performed on sera or plasma separated from blood within two hours of collection and stored at −80° C. For HCV seroconverters, HCV RNA testing was done on samples collected before seroconversion until a negative result was obtained and after seroconversion to evaluate the outcome of infection (viral persistence versus clearance) by using quantitative, and if undetectable, qualitative HCV RNA tests that are described below.

HCV RNA Assays—Qualitative. For detecting HCV RNA, we used the COBAS AMPLICOR™ Hepatitis C Virus Test version 2.0 (Roche Molecular Systems, Branchburg, N.J.). A limit of detection of 1.7 $\log_{10}$ International Units (IU)/mL at >95% detection is reported for this assay. Quantitative. To determine concentration of HCV RNA in serum, we used a quantitative RT-PCR assay (COBAS AMPLICOR™ HCV Monitor version 2.0, Roche Molecular Systems). This assay has a lower limit of quantitation of 2.8 $\log_{10}$ IU/mL. When HCV RNA was not detected by using this assay, the sample was retested using the Roche qualitative test.

HCV Genotyping. Genotype was determined by performing phylogenetic analysis on Core-E1 region sequences of HCV obtained from the first viremic specimen. For most specimens, sequences were obtained from cDNA clones generated with a long amplicon RT-PCR method that has been described previously.(48) For other specimens, genotype was determined by direct sequencing of RT-PCR products from the same Core-E1 region as previously described.(49) Sequences were aligned using ClustalX,(50) trimmed to equal length using BioEdit.(51) The GTR+I+G analytical model (parameters available on request from the authors) was selected using the AIC criterion as implemented in ModelTest version 3.06(52) and PAUP* version 4b10 (Sinauer Associates, Sunderland, Mass.). Phylogenetic trees were estimated using the neighbor-joining algorithm implemented in PAUP*, and robustness of clustering was tested using by bootstrap analysis.(53)

Viral recovery. HCV clearance was defined as the presence of anti-HCV with HCV RNA undetectable by the COBAS AMPLICOR™ qualitative assay in serum or plasma specimens from ≧2 consecutive visits obtained at least 300 days after initial detection of viremia. Persistence was defined as the persistent presence of anti-HCV with HCV RNA detectable by the qualitative or quantitative COBAS AMPLICOR assay in serum or plasma specimens obtained at least 300 days after initial viremia.(54)

Hemigenomic HCV sequencing and analysis. From 140-280 uL of serum or plasma, the 5.2 kb region from the 5'UTR to the NS3/NS4A junction was cloned as previously described.(48) For each specimen, thirty-three clones were assigned to clonotypes by using a previously-described gel shift assay,(55) and 2 clones representing the modal clonotype were sequenced, with a third clone used as needed to resolve discrepancies. Sequences were assembled into contigs using Aligner (CodonCode). Sequence data were obtained at the point of initial viremia and approximately six months later.

Reference sequence analysis. Reference sequence data were obtained from the HCV Sequence Database (http://hcv.lanl.gov). For table 1, amino acid sequence was inferred from cDNA sequences, which were obtained using the HCV Sequence Database's Search Interface. Default search parameters were used, except that (i) only subtype 1a sequences were included, (ii) recombinant sequences were excluded, (iii) non-human sequences were excluded, and (iv) the search was performed for the codon of interest based on position in the HCV polyprotein. When multiple sequences with the same "patient ID" were obtained, only the first occurrence was retained.

Cellular immunology. IFN-γ ELISPOT assay to assess HCV-specific T-cell responses. HCV-specific CD8+ T-cell responses were quantified by ELISPOT assay as previously described(56) with the following modifications. For Subjects 17, 18, 21, 28, and 29, enough PBMC were acquired to test for T cell recognition of 523 overlapping peptides (16-22mer peptides overlapping by 10 amino acids) spanning the entire expressed HCV-H77 genome (genotype 1a) as well as 83 peptides corresponding to optimal described CTL epitopes (57) in a matrix format. The peptides recognized in the matrix were subsequently tested individually and in at least duplicate to confirm recognition and to measure the number of spot forming colonies (SFC) produced. For three additional subjects where the number of cells was limited, responses to peptides spanning regions of sequence variation detected during sequencing, but not to the entire collection of 523 overlapping peptides, were assessed. Ninety-six well polyvinylidene plates (Millipore, Billerica, Mass.) were coated with 2.5 µg/ml recombinant human anti-IFN-gamma antibody (Endogen, Pierce Biotechnology, Rockford, Ill.) in PBS at 4° C. overnight. Fresh or previously frozen PBMC were added at 200,000 cells/well in 140 µl R10 media (RPMI 1640 (Sigma-Aldrich Corp., St. Louis, Mo.), 10% FCS (Sigma-Aldrich), and 10 mM Hepes buffer(Sigma-Aldrich) with 2 mM glutamine and antibiotics (50 U/ml penicillin-streptomycin)). Peptides were added directly to the wells at a final concentration of 10 µg/ml. The plates were incubated for 20 hours at 37° C., 5% $CO_2$. Plates were then washed, labelled with 0.25 µg/ml biotin-labelled anti-IFN-γ (Endogen), and developed by incubation with streptavidin-alkaline phophatase (Bio-Rad Lab., Hercules, Calif.) followed by incubation with BCIP/NBT (Bio-Rad) in Tris-buffer (pH 9.5). The reaction was stopped by washing with tap water and the plates were dried, prior to counting on an ELISPOT reader (Cellular Technology Ltd, Cleveland, Ohio). For quantitation of ex-vivo responses, the assay was performed at least in duplicate and background was not more than 15 SFC per million PBMC. Responses were considered positive if the number of spots per well minus the background was at least 25 SFC per million PBMC.(56) A control of pooled cytomegalovirus, Epstein-Barr virus, and influenza antigens (CEF control peptide pool) and phytohemmaglutinin (PHA) were used as positive controls.(58) Responses to the CEF control peptide pool were quantifiable and remained relatively constant over time. Responses to PHA were uniformly positive.

Intracellular cytokine staining (ICS). To determine whether the lines generated for each epitope were CD4+ or CD8+ T cell lines, intracellular cytokine staining (ICS) for IFN-γ was performed as previously described.(56) Briefly, $1\times10^6$ PBMC were incubated with 4 µg/ml peptide at 37° C. and 5% $CO_2$ for 1 h before the addition of Monensin (1 µl/ml; Sigma-Aldrich). The cells were incubated for an additional 5 h at 37° C. and 5% CO2. PBMC were then washed and stained with surface antibodies, fluorescein isothiocyanate (FITC)-conjugated anti-CD8 or FITC-conjugated anti-CD4 (Becton Dickinson, BD, Franklin Lakes, N.J.) at 4° C. for 20 min. Following the washing, the PBMC were fixed and permeabilized (Caltag, Burlingame, Calif.), and the phycoerythrin (PE)-conjugated anti-IFN-γ MAb (Becton Dickinson) was added. Cells were then washed and analyzed on a FACS-Calibur flow cytometer using CellQuest software (Becton Dickinson).

Magnetic bead separation of CD8+ and CD4+ T cells. To determine if the responding T cells in PBMC were CD4+ or CD8+ T cells, between 3 and $10\times10^7$ PBMC were labeled with magnetic beads bearing anti-CD8 or anti-CD4 antibodies (Miltenyi Biotec, Auburn, Calif.) according to the manufacturer's instructions and cells were positively selected using an Auto MACS (Miltenyi Biotec) to isolate either CD8+ or CD4+ cells. The ELISPOT assay was repeated using the isolated CD8+ or CD4+ T cells to determine if recognition of an epitope were mediated by CD8+ or CD4+ T cells.

Bulk stimulation of peripheral blood mononuclear cells. To establish CD8+ T cell lines, cryopreserved or fresh PBMC (4–10×10⁶) were stimulated with 10 μg/ml of synthetic HCV peptide and 0.5 μg/ml of the costimulatory antibodies anti-CD28 and anti-CD49d (Becton Dickinson) in R10 media. Recombinant interleukin-2 (IL-2, 25 IU/ml) was added on day 2 and every other day thereafter. Cells were restimulated with 25×10⁶ irradiated allogeneic PBMC and 10 μg/ml of synthetic HCV peptide after ten days.

Testing impact of amino acid substitutions on T cell recognition. To assess the impact of amino acid substitutions on T cell recognition, HCV peptide-specific T cell lines generated from PBMC obtained six months after initial viremia were tested for IFN-γ production in response to serial dilutions of synthetic peptides representing the viral sequences present at initial viremia ($t_0$) or at six months following initial viremia ($t_6$). In five cases where the frequency of T cells specific for the HCV epitope was high, bulk PBMC obtained six months following initial viremia were also tested in this way. Comparison of initial and variant epitopes was performed using $\log_{10}$ dilutions of the $t_0$ and $t_6$ peptides from 10 μM to 0.001 μM in the IFN-γ ELSIPOT assay described above for PBMC, but using 30,000 T cells when T cell lines were tested. Ten peptide pairs from subjects with chronic viremia were tested, and three patterns were observed. Loss of recognition was defined as either no recognition at the highest concentration of the $t_6$ peptide or at least 20 fold greater recognition of the to peptide than the $t_6$ peptide at all concentrations. Decreased recognition was defined as greater than 2 and less than 20 fold fewer spot forming colonies (SFC) produced at two or more concentrations of the $t_6$ peptide. Comparable recognition was defined as no more than a two fold difference in SFC between the $t_0$ and $t_6$ peptides at two or more concentrations tested.

MHC-peptide binding assays. EBV transformed cell lines were used as the primary sources of HLA molecules. Cells were maintained in vitro and HLA molecules purified by affinity chromatography as previously described.(59) Quantitative assays to measure the binding of peptides to purified class I molecules are based on the inhibition of binding of a radiolabeled standard peptide.(59) Briefly, 1-10 nM of radiolabeled peptide was co-incubated at room temperature with 1 μM to 1 nM of purified MHC in the presence of 1 μM human, β2-microglubulin (Scripps Laboratories, San Diego, Calif.) and a cocktail of protease inhibitors. After a two-day incubation, binding of the radiolabeled peptide to the corresponding MHC class I molecule was determined by capturing MHC/peptide complexes on Greiner Lumitrac 600 microplates (Greiner Bio-one, Longwood, Fla.) coated with the W6/32 antibody, and measuring bound cpm using the TopCount microscintillation counter (Packard Instrument Co. Meriden, Conn.).

Statistical analysis. Statistical analysis was done with the aid of SigmaStat software version 3.10 (Systat software, Inc.). For comparing proportions, Fisher's exact (small sample size) and Chi squared (large sample size) tests were used. Differences were considered significant if p-values were <0.05.

Results—We assessed T cell responses and sequenced half the HCV genome in eight subjects, seven of whom progressed to chronic infection (FIG. 1). T cell and viral analyses were done for all eight at initial detection of viremia and then six months later. Additional assessment of T cell responses was done at the time points designated by arrows in FIG. 1. No T cell responses were detectable at initial viremia, but all of the subsequently detected T cell responses were present by 6 months following infection.

Figure 2:
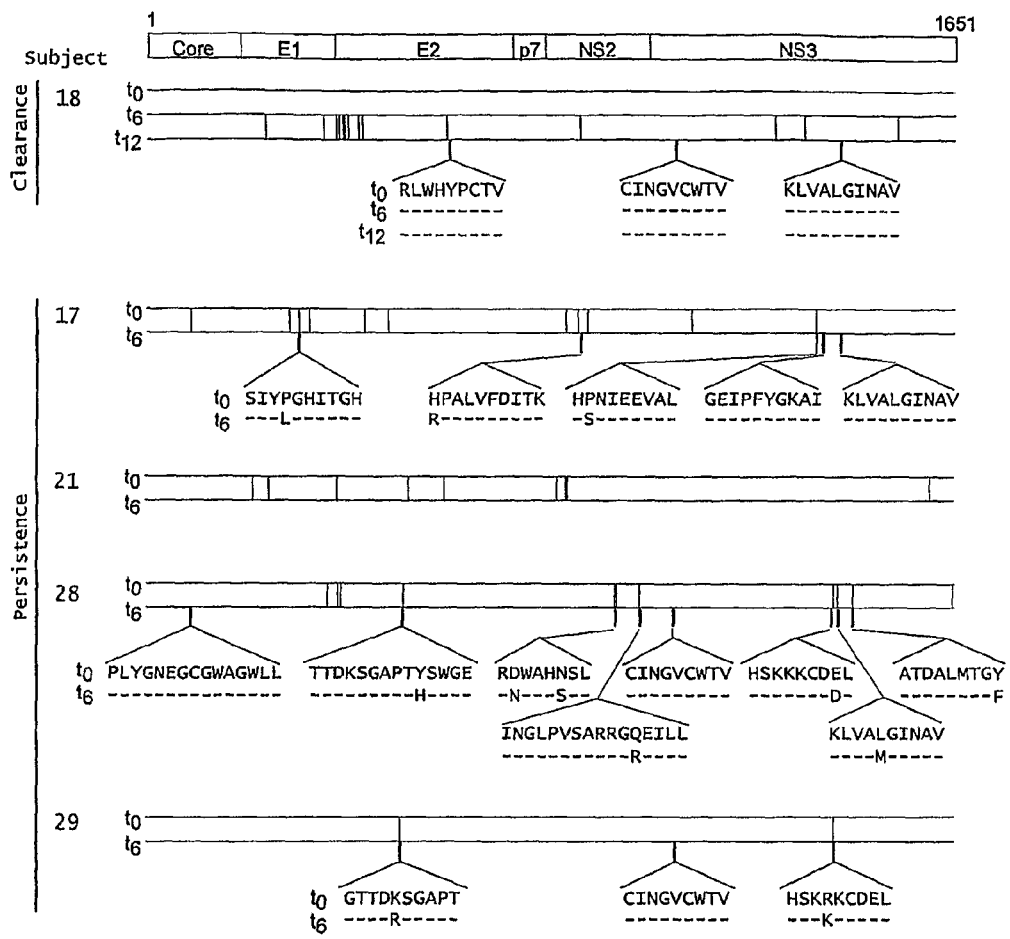
FIG. 2 shows amino acid substitutions and epitopes recognized during the first 6 months of HCV infection for five subjects. The map at the top of the figure indicates the region of the HCV polyprotein sequenced. For each study subject, horizontal lines represent the sequences obtained at initial viremia ($t_0$), six months after viremia was first detected ($t_6$), and 12 months after viremia was first detected ($t_{12}$). Thin vertical lines represent amino acid substitutions. Shorter, thicker vertical lines indicate recognized epitopes, below which the $t_0$ and $t_6$ sequences of the epitope are shown. The sequences shown for subject 18 are from left to right: SEQ ID NOs: 7, 8, and 3. The sequences shown for subject 17 are from left to right SEQ ID NOs: 9, 10, 11, 12, and 3. The sequences shown for subject 28 are from left to right: SEQ ID NOs: 13, 14, 15, 16, 17, 18, 4, and (5 and 6). The sequences shown for subject 29 are from left to right: SEQ ID NOs: 20, 17, and 21.

Persistence versus Loss of T cell Epitopes with Sequence Evolution—The locations of amino acid substitutions and recognized CD8+ T cell epitopes are shown for subjects 17, 18, 21, 28, and 29 in FIG. 2. Subject 21 was the only subject with no detectable T cells responses. The only subject who cleared HCV spontaneously (18) was also the only individual whose HCV genome had no substitutions within any recognized T cell epitope at 6 or 12 months following initial viremia. Subjects 17, 28, and 29 remain persistently infected and had substitutions at six months in ⅗, ⅝, and ⅔ of recognized CD8+ T cell epitopes, respectively. In summary, the subject who cleared infection had no substitutions in 3 recognized T-cell epitopes at 6 or at 12 months after infection, whereas the three subjects with chronic viremia and T cell responses had substitutions in 60-75% of CD8+ T cell epitopes by six months following infection.

Figure 3:
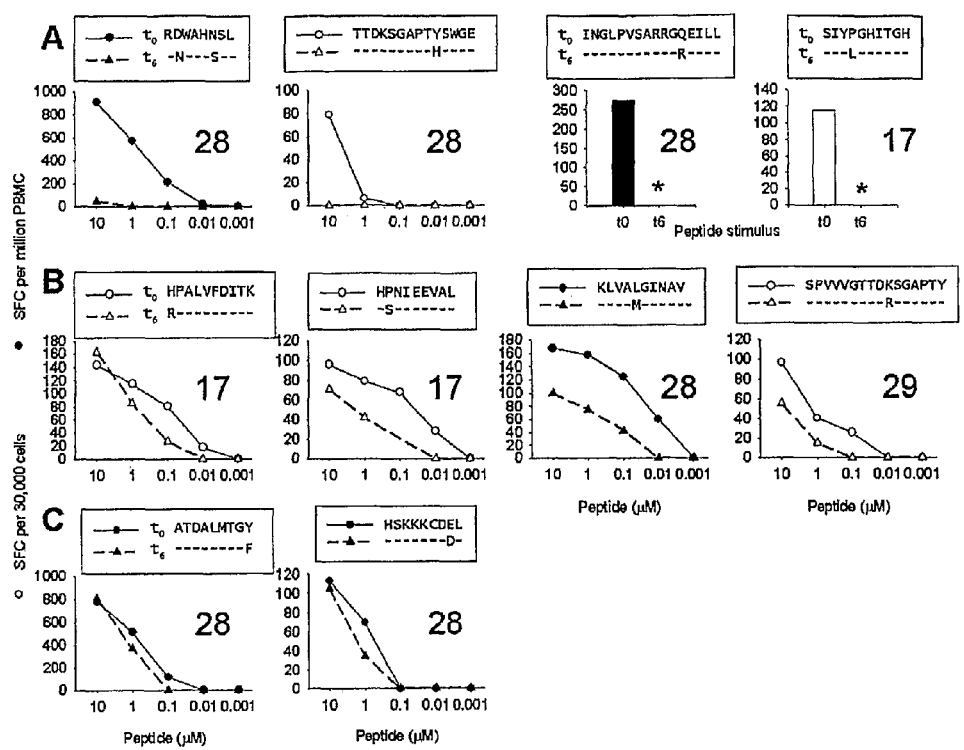
FIG. 3 shows amino acid substitutions in epitopes and the effect on T cell responses. Peptide sequences observed to vary between to (circle, initial viremia) and $t_6$ (triangle, 6 months after onset of viremia) were used as antigens in IFN-.gamma. ELISPOT, using PBMC (filled symbols) or T cell lines generated from PBMC (open symbols) obtained at $t_6$ as effectors. (A) Loss of recognition: For 4 of 10 peptide pairs, recognition of the $t_6$ variant peptide was dramatically reduced. Sequences shown are from left to right: SEQ ID NOs: 15, 14, 16, and 9. (B) Decreased recognition: For 4 of 10 peptide pairs, recognition of the $t_6$ variant peptide was reduced more than 2-fold but less than 20-fold at least two concentrations of peptide. Sequences shown are from left to right: SEQ ID NOs: 10, 11, 4, and 22 (C) Comparable recognition: For 2 of 10 pairs of peptides, recognition of the $t_6$ variant was not reduced more than 2-fold relative to the to peptide at more than one concentration tested. Sequences shown are from left to right: SEQ ID NOs: 19 and 18.
Figure 4:
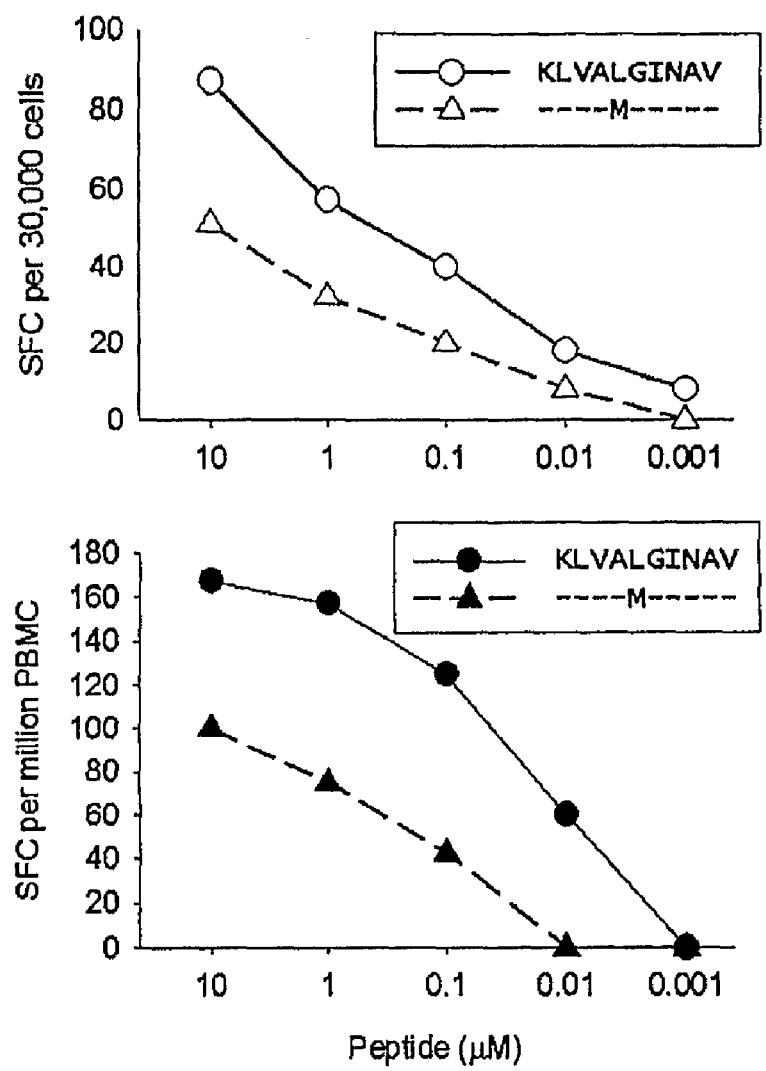
FIG. 4 shows similar recognition patterns using lines and PBMC. IFN-γ ELISPOT responses for both a T cell line (open symbols) and for PBMC (closed symbols) from which the line was generated using the peptide KLVALGINAV are shown using the same antigens. The peptide representing the to sequence is KLVALGINAV (circles; SEQ ID NO: 3) and the peptide representing the $t_6$ sequence is KLVAMGINAV (triangles; SEQ ID NO: 4)). As shown for this peptide pair, responses for PBMC and T cell lines using five distinct peptide $t.sub.0/t_6$ pairs were consistently similar aside from the expected differences in the proportion of responding cells (note difference in axes).
Figure 5:
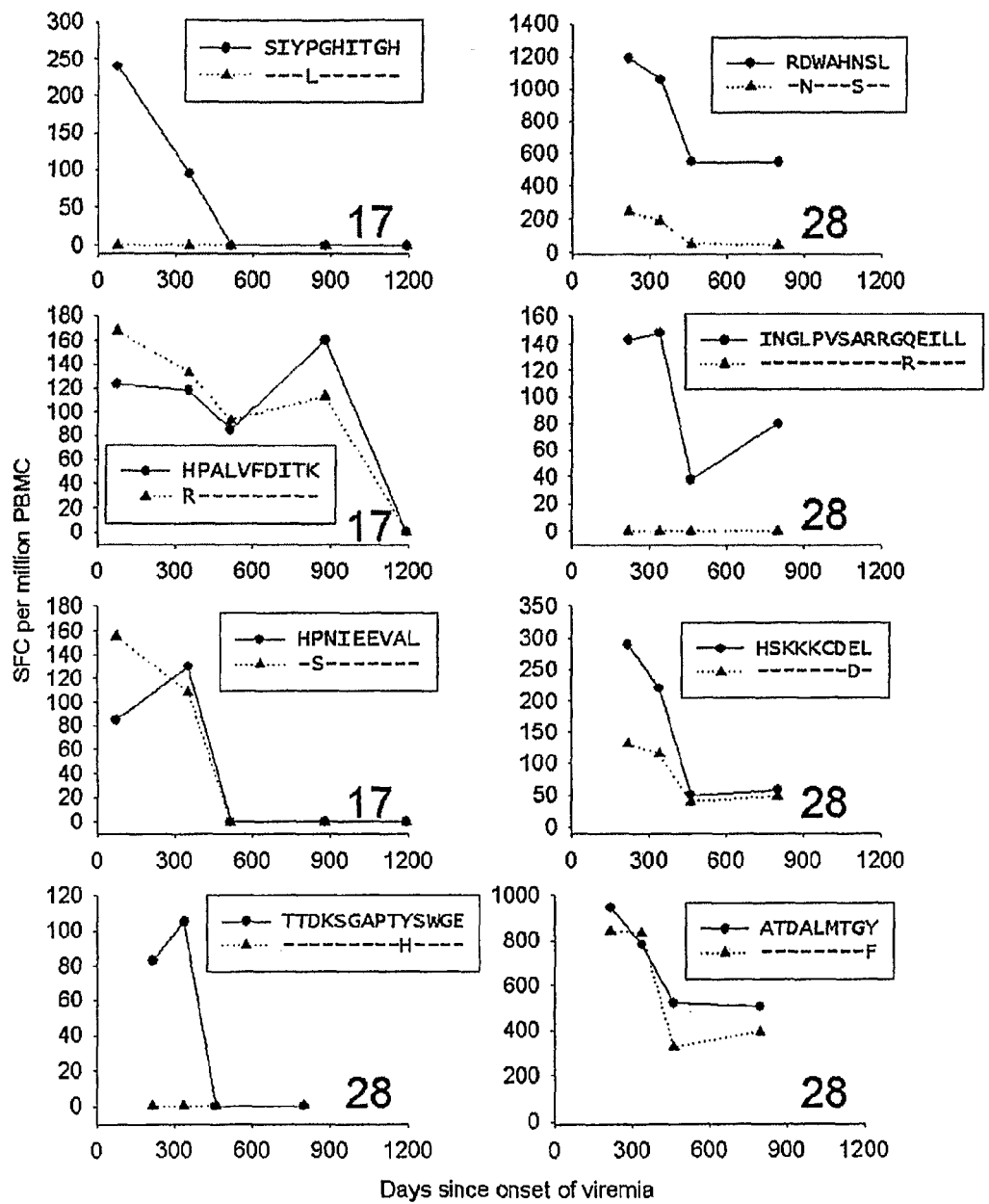
FIG. 5 shows results that show recognition patterns persist with time. To rule out the subsequent development of T cell responses to the $t_6$ HCV sequence, IFN-γ ELISPOT testing for recognition of the $t_6$ peptides demonstrating escape was also performed for subjects 17 and 28 using PBMC obtained approximately 12, 18, 24, and, for subject 17, 36 months following initial infection. The number in the bottom right corner of each panel is the subject number. Patterns of recognition persisted over time and recognition of the $t_6$ peptides (▲) declined in parallel with the decline in recognition of the to peptides (●) that occurred with prolonged infection. From top row to bottom row of panels, going from left to right in each row, the sequences shown are SEQ ID NOs: 9, 15, 10, 16, 11, 18, 14, and 19.

Impact of Amino Acid Substitutions on T cell Recognition—T cell lines were generated from PBMC using synthetic peptides representing the viral sequences present at initial viremia ($t_0$). To assess the impact of amino acid substitutions on T cell recognition, those T cell lines and bulk PBMC obtained approximately 6 months after initial viremia were tested for IFN-γ production in response to serial dilutions of the to peptide or a synthetic peptide representing the viral sequence present at six months following initial viremia ($t_6$). Ten $t_0/t_6$ peptide pairs from subjects with persistent viremia were tested using T cell lines, and three patterns were observed (FIG. 3). For the ten $t_6$ peptides tested, we noted loss of recognition of four (FIG. 3a), decreased recognition of four others, (FIG. 3b), and comparable recognition of two (FIG. 3c). Therefore, for 8 of the 10 mutations in recognized epitopes tested, recognition by T lymphocytes was lost or significantly reduced compared to recognition of the sequence present at initial viremia, indicating escape. In no case was the $t_6$ variant peptide recognized better than the to peptide. For five $t_0/t_6$ peptide pairs also tested with bulk PBMC, the patterns of recognition were the same as those observed using T cell lines, as shown for one peptide pair in FIG. 4. That PBMC as well as T-cell lines generated against the to peptides failed to recognize the $t_6$ peptides suggests that not only did the substitution allow escape from the T-cells specific for the original sequence, but also that no new T-cell responses were generated against the $t_6$ sequence. To rule out transient suppression or problems with specimen handling and the subsequent development of T cell responses to the $t_6$ HCV sequence, IFN-γ ELISPOT testing for recognition of the $t_6$ peptides demonstrating escape was also performed in subjects 17 and 28 using PBMC obtained approximately 12, 18, 24, and in subject 17, 36 months following initial infection. The patterns of recognition persisted over time and recognition of the $t_6$ peptides declined in parallel with the decline in recognition of the to peptides that occurred with prolonged infection (FIG. 5). Despite months of persistent exposure to the $t_6$ peptides that escaped recognition at six months following infection, in no case did a new T cell response specific for a $t_6$ peptide arise in the following 6 to 36 months.

Mechanisms of Loss of T cell Recognition with Amino Acid Substitutions—Amino acid substitutions may result in decreased recognition through reduced HLA binding capacity, abrogation of T cell recognition, or altered processing with failure to generate the correct sequence for presentation on the surface. We did observe marked reduction in HLA biding capacity as one mechanism for reduced recognition in our subjects. For example, the HLA A*0101-restricted ATDALMTGY epitope recognized at to by Subject 28 had an A*0101 binding capacity ($IC_{50}$) of 0.24 nM while the ATDALMTGF peptide recognized at $t_6$ had a binding capacity of 64 nM. A five fold difference in binding capacity is considered significant, thus the variant peptide is less well bound to the HLA. However, the HLA A*0201-restricted KLVALGINAV epitope recognized at to by Subject 28 had an A0201 binding capacity of 5.0 nM while the KLVAMGINAV peptide recognized at $t_6$ had a binding capacity of 2.3 nM, an insignificant difference that if anything favors the less well recognized peptide, $t_6$. This $t_6$ peptide may stimulate less IFN-γ production in the ELISPOT assay because of decreased T cell recognition rather than reduced HLA binding capacity. Although two of the ten $t_0$/$t_6$ peptide pairs were recognized comparably, we can not rule out that they represent escape mutations as well since substitutions have been shown by others to result in altered processing such that the peptide is no longer presented on the cell surface.(32,36,37) This mode of escape is circumvented when peptides are loaded onto the surface of the cell, as is the case in an ELISPOT assay.

Driving Forces for Sequence Evolution—We next evaluated the proportion of substitutions occurring in observed T cell epitopes and investigated explanations for substitutions outside of T cell epitopes. Of 69 substitution observed in the eight subjects, 17 (25%) occurred within detected CD8+ T-cell epitopes, 36 (52%) in envelope proteins (likely antibody targets), and 16 (23%) outside envelope regions and T cell epitopes. Of the eight subjects, five subjects had persistent viremia and T cell responses, and amino acid substitutions were a median of 13 fold more likely to occur within T cell epitopes than outside epitopes ($p<0.001$, range 5-38) in those subjects. Even though at a population level the envelope proteins are highly diverse, amino acid substitutions in T cell epitopes exceeded those in E1 and E2 by 7 fold ($p<0.001$, range 4-14). Of the 16 amino acid substitutions observed outside of the envelope proteins or recognized T cell epitopes (Table 1), 8 represented conversion to the most commonly-observed residue in reference sequences (i.e., convergence to the consensus sequence). Because each change has 19 alternative amino acids, and each site has only one modal (most frequently-observed) state, the convergence on modal residues at 50% of sites is highly unexpected if substitution is random ($p=0.015$, Table 2). In addition, the convergent changes were not consistently conservative changes, arguing against strict structural or functional constraint. These data are consistent with an accompanying study of chronically infected individuals for whom the inoculum sequence was known. That study showed that substitutions occurring in known epitopes for which the infected individual lacked the presenting HLA allele were consistently reversions toward the worldwide consensus sequence for subtype 1b.

Discussion—In this investigation of sequence variation in T cell epitopes as a potential mechanism for viral persistence, we show that amino acid substitutions during acute HCV infection are nonrandom and may be explained in part by escape from CD8+ T cell recognition and convergence, possibly because of replicatively unfit substitutions selected in a previous host. Significantly, there is early fixation of the T cell repertoire since we observed no instances of de novo development of T cells that recognized mutant t6 epitopes better than the original t0 epitope using lines or PBMC.

Using the chimpanzee model of HCV infection, mutation of multiple class I MHC restricted epitopes early in the course of chronic HCV infection has been demonstrated.(31) The role of CD8+ CTL in control of HCV replication was further reinforced by a statistically significant increase in the number of mutations resulting in amino acid changes in class I MHC restricted epitopes but not unrestricted epitopes or flanking sequences of the viral genome. These data indicate that in chimpanzees, amino acid substitutions in class I MHC restricted epitopes are selected and possibly maintained by HCV-specific CD8+ CTL populations that exert positive Darwinian selection pressure.

We also observed a statistically significant increase in the number of mutations resulting in amino acid changes in class I MHC restricted epitopes versus portions of the viral genome outside T cell epitopes and that amino acid substitutions in class I MHC restricted epitopes resulted in escape from CD8+ T cell recognition in acutely HCV-infected humans who progressed to chronic infection. New T cells specific for the sequences detected six months after initial viremia were not detected despite follow-up for as long as three years following infection. Thus, selection of HCV variants that evade CD8+ T cell recognition may represent a mechanism for persistence of HCV infection in humans. Supporting this, we observed no substitutions within recognized CD8+ T cell epitopes in the subject who cleared infection and substitution in 60-75% of CD8+ T cell epitopes in subjects with persistent infection. The number of CTL epitopes with substitutions has previously been shown to correlate with control of HIV viremia,(28) but a relationship between HCV control and maintenance of T cell epitopes had not been shown previously.

Although the observed substitutions were disproportionately contained within the portion of the HCV polyprotein in T-cell epitopes, many were found outside detectable T cell epitopes. It is possible that we missed CD8+ T cell epitopes and that some of the substitutions observed outside of T cell epitopes actually represented substitutions within T cell epitopes. We took several steps to minimize the chances of this occurring. Where there were substitutions and the H77 sequence used to make overlapping peptides as potential antigens differed from that of the subject, we tested for recognition of overlapping peptides representing autologous sequence. Where the subject's sequence matched H77 in areas of amino acid substitution, but there were no responses detected, we tested for recognition of additional overlapping peptides with different termini to minimize the possibility that we cut within a region containing an epitope. We detected no additional epitopes via ELISPOT analysis with either method of antigen modification (data not shown).

Since there is no clinical indication for liver biopsy in acute infection, we could only assess responses in the periphery. It is therefore possible that some of the substitutions may represent pressure for T cell responses present in the liver but not detectable in the periphery, We do not favor this explanation since previous studies have shown that the majority of T cell responses in the liver are also detectable in the peripheral blood.(38,39) There are several possible alternative mechanisms for selection of these substitutions occurring outside of observed CD8+ T cell epitopes. The first is that they represent substitutions in CD4+ T cell epitopes. Although we detect a few CD4+ T cell epitopes using our ELISPOT assay, the conditions of the assay preferentially detect CD8+ T cell epitopes and we may fail to detect all the possible CD4+ T cell epitopes. The second possible explanation is that they represent substitutions in B cell epitopes. Mutations in dominant antibody epitope(s) located in the hypervariable region 1 (HVR-1) of envelope glycoprotein 2 (E2) have been linked to persistence of HCV infection.(40) B cell epitopes are predicted to occur within the envelope regions of the polyprotein and the majority of mutations outside T cell epitopes were found in the envelope proteins for most subjects. Another possible explanation is that the mutations outside of T cell epitopes are selected because they confer a viral replication advantage. Some mutations may represent epitopes recognized by the previous host that revert to a more stable sequence when the new host fails to mount similar immune pressure. This may occur when the new host lacks the MHC allele required to present that epitope. Loss of escape mutations upon passage of SIV to new animals (41), and HIV to humans (42), that do not exert immune pressure on that region has been described recently, with the inference that escape from CTL responses may reduce viral fitness.

The relevance of those studies to human infection with HCV is supported by a recent study of one epitope in an acutely HCV infected patient (32), and our accompanying study of chronically infected individuals. The latter study shows that HCV amino acid sequence tends to revert to consensus in areas outside of T cell epitopes in subjects who are persistently infected. The consensus sequence likely represents a more replicatively fit state than the initial infecting strains, which have presumably adapted to the immune response of the previous host. Taken together, these results reveal at least two types of sequence variation occurring simultaneously in progression of acute HCV to persistence: immune pressure that selects T cell escape variants, and reversion to consensus sequence that is likely to result in enhanced replicative fitness.

Despite viral mutation resulting in the production of new potential antigens, no new T cell responses developed in response to mutant peptides that escaped initial recognition over months and in some cases years following the appearance of the mutation. This phenomenon has also been observed with HIV sequence evolution and there the failure to prime new responses may be due to impaired CD4+ T cell function. Although overall CD4+ T cell function is intact in HCV infection, chronic HCV infection has been linked to loss of HCV specific CD4+ T cell responses.(43) In addition, HCV has been linked to impaired DC function, decreased IRF3 signaling, and PKR inhibition, which may inhibit priming of an immune response to the mutated peptides.(26,27, 44,45) However, the failure to prime responses to the newly generated sequences is observed even in HIV infected individuals with relatively high CD4 counts and there is no evidence in those with HCV infection of impaired priming of immune responses to other antigens, as would be evident by global immunosuppression. An alternative explanation is that original antigenic sin (the higher threshold required for stimulation of an immune response to an epitope resembling a previously recognized epitope (46)) may be responsible for the lack of response to mutant sequences seen in HIV and HCV, though this phenomenon has not been demonstrated in humans. Lastly, since the selective pressures of the immune system favor the emergence of a viral sequence that fails to elicit a productive response, we may be observing sequences that cannot be processed effectively for presentation or that resemble self antigens and are therefore incapable of stimulating an immune response.

Although the features of acute infection responsible for increased responsiveness to interferon therapy are unknown, this study suggests a mechanistic linkage between viral sequence variation and progression to chronicity. The arrested development of new T cell responses despite ongoing viremia with sequence evolution distinguishes the acute and chronic phases of HCV infection. Enhanced understanding of cellular immune failure leading to chronic HCV infection could accelerate development of vaccines to prevent the development of chronic infection, and agents that could increase responsiveness to interferon-based therapy for chronic HCV infection.

REFERENCES

1. World Health Organization. 1997. Hepatitis C: global prevalence. Weekly Epidemiological Record 341-348.
2. Alter, M. J. 1997. Epidemiology of hepatitis C. Hepatology 26:62 S-65S.
3. Alter, M. J. 1995. Epidemiology of hepatitis C in the West. Semin Liver Dis 15:5-14.
4. Centers for Disease Control and Prevention. 1998. Recommendations for prevention and control of hepatitis C virus (HCV) infection and HCV-related chronic disease. MMWR 47(No. RR-19):1-39.
5. Villano, S. A., D. Vlahov, K. E. Nelson, S. Cohn, and D. L. Thomas. 1999. Persistence of viremia and the importance of long-term follow-up after acute hepatitis C infection. Hepatology 29:908-914.
6. Cao, J., N. Sullivan, E. Desjardin, C. Parolin, J. Robinson, R. Wyatt, and J. Sodroski. 1997. Replication and neutralization of human immunodeficiency virus type 1 lacking the V1 and V2 variable loops of the gp120 envelope glycoprotein. J. Virol. 71:9808-9812.
7. Tong, M. J., N. S. El-Farra, A. R. Reikes, and R. L. Co. 1995. Clinical outcomes after transfusion-associated hepatitis C. N. Engl. J. Med. 332:1463-1466.
8. Jaeckel, E., M. Comberg, J. Mayer, J. N. Koerbel, H. Wedemeyer, A. Z. M. Schueler, C. Trautwein, and M. P. Manns. 2000. Early treatment of acute hepatitis C infection with interferon-alfa 2B monotherapy prevents development of chronic HCV infection. Hepatology Abstract 634: 318A. (Abstr.)
9. Jaeckel, E., M. Cornberg, H. Wedemeyer, T. Santantonio, J. Mayer, M. Zankel, G. Pastore, M. Dietrich, C. Trautwein, and M. P. Manns. 2001. Treatment of acute hepatitis C with interferon alfa-2b. N. Engl. J. Med. 345:1452-1457.
10. Nomura, H., S. Sou, H. Tanimoto, T. Nagahama, Y. Kimura, J. Hayashi, H. Ishibashi, and S. Kashiwagi. 2004. Short-term interferon-alfa therapy for acute hepatitis C: a randomized controlled trial. Hepatology 39:1213-1219.
11. Cooper, S., A. L. Erickson, E. J. Adams, J. Kansopon, A. J. Weiner, D. Y. Chien, M. Houghton, P. Parham, and C. M. Walker. 1999. Analysis of a successful immune response against hepatitis C virus. Immunity. 10:439-449.
12. Gruner, N. H., T. J. Gerlach, M. C. Jung, H. M. Diepolder, C. A. Schirren, W. W. Schraut, R. Hoffmann, R. Zachoval, T. Santantonio, M. Cucchiarini, A. Cerny, and G. R. Pape. 2000. Association of hepatitis C virus-specific CD8+ T cells with viral clearance in acute hepatitis C. J. Infect. Dis. 181:1528-1536.
13. Lechner, F., D. K. Wong, P. R. Dunbar, R. Chapman, R. T. Chung, P. Dohrenwend, G. Robbins, R. Phillips, P. Klenerman, and B. D. Walker. 2000. Analysis of successful immune responses in persons infected with hepatitis C virus. J. Exp. Med 191:1499-1512.
14. Takaki, A., M. Wiese, G. Maertens, E. Depla, U. Seifert, A. Liebetrau, J. L. Miller, M. P. Manns, and B. Rehermann. 2000. Cellular immune responses persist and humoral responses decrease two decades after recovery from a single-source outbreak of hepatitis C. Nat. Med. 6:578-582.
15. Gruener, N. H., F. Lechner, M. C. Jung, H. Diepolder, T. Gerlach, G. Lauer, B. Walker, J. Sullivan, R. Phillips, G. R. Pape, and P. Klenerman. 2001. Sustained dysfunction of antiviral CD8+ T lymphocytes after infection with hepatitis C virus. J. Virol. 75:5550-5558.
16. Thimme, R., D. Oldach, K. M. Chang, C. Steiger, S. C. Ray, and F. V. Chisari. 2001. Determinants of viral clearance and persistence during acute hepatitis C virus infection. J. Exp. Med. 194:1395-1406.

17. Battegay, M., J. Fikes, A. M. Di Bisceglie, P. A. Wentworth, A. Sette, E. Celis, W.-M. Ching, A. Grakoui, C. M. Rice, K. Kurokohchi, J. A. Berzofsky, J. H. Hoofnagle, S. M. Feinstone, and T. Akatsuka. 1995. Patients with chronic hepatitis C have circulating cytotoxic T cells which recognize hepatitis C virus-encoded peptides binding to HLA-A2.1 molecules. J. Virol. 69:2462-2470.

18. Hiroishi, K., H. Kita, M. Kojima, H. Okamoto, T. Moriyama, T. Kaneko, T. Ishikawa, S. Ohnishi, T. Aikawa, N. Tanaka, Y. Yazaki, K. Mitamura, and M. Imawari. 1997. Cytotoxic T lymphocyte response and viral load in hepatitis C virus infection. Hepatology 25:705-712.

19. Shirai, M., H. Okada, M. Nishioka, T. Akatsuka, C. Wychowski, R. Houghten, C. D. Pendleton, S. M. Feinstone, and J. A. Berzofsky. 1994. An epitope in hepatitis C virus core region recognized by cytotoxic T cells in mice and humans. J. Virol. 68:3334-3342.

20. Rehermann, B., K. M. Chang, J. G. McHutchison, R. Kokka, M. Houghton, and F. V. Chisari. 1996. Quantitative analysis of the peripheral blood cytotoxic T lymphocyte response in patients with chronic hepatitis C virus infection. J. Clin. Invest. 98:1432-1440.

21. Crispe, I. N. 2003. Hepatic T cells and liver tolerance. Nat. Rev. Immunol. 3:51-62.

22. Erickson, A. L., M. Houghton, Q. L. Choo, A. J. Weiner, R. Ralston, E. Muchmore, and C. M. Walker. 1993. Hepatitis C virus-specific CTL responses in the liver of chimpanzees with acute and chronic hepatitis C. J. Immunol. 151:4189-4199.

23. Koziel, M. J., D. Dudley, J. T. Wong, J. Dienstag, M. Houghton, R. Ralston, and B. D. Walker. 1992. Intrahepatic cytotoxic T lymphocytes specific for hepatitis C virus in persons with chronic hepatitis [published erratum appears in J Immunol 1993 Mar. 15; 150(6):2563]. J. Immunol. 149:3339-3344.

24. Wong, D. K., D. D. Dudley, N. H. Afdhal, J. Dienstag, C. M. Rice, L. P. Wang, M. Houghton, B. D. Walker, and M. J. Koziel. 1998. Liver-derived CTL in hepatitis C virus infection: Breadth and specificity of responses in a cohort of persons with chronic infection. J. Immunol. 160:1479-1488.

25. Wedemeyer, H., X. S. He, M. Nascimbeni, A. R. Davis, H. B. Greenberg, J. H. Hoofnagle, T. J. Liang, H. Alter, and B. Rehermann. 2002. Impaired effector function of hepatitis C virus-specific CD8+ T cells in chronic hepatitis C virus infection. J. Immunol. 169:3447-3458.

26. Bain, C., A. Fatmi, F. Zoulim, J. P. Zarski, C. Trepo, and G. Inchauspe. 2001. Impaired allostimulatory function of dendritic cells in chronic hepatitis C infection. Gastroenterology 120:512-524.

27. Kanto, T., N. Hayashi, T. Takehara, T. Tatsumi, N. Kuzushita, A. Ito, Y. Sasaki, A. Kasahara, and M. Hori. 1999. Impaired allostimulatory capacity of peripheral blood dendritic cells recovered from hepatitis C virus-infected individuals. J. Immunol. 162:5584-5591.

28. Jones, N. A., X. Wei, D. R. Flower, M. Wong, F. Michor, M. S. Saag, B. H. Hahn, M. A. Nowak, G. M. Shaw, and P. Borrow. 2004. Determinants of human immunodeficiency virus type 1 escape from the primary CD8+ cytotoxic T lymphocyte response. J. Exp. Med. 200:1243-1256.

29. Neumann, A. U., N. P. Lam, H. Dahari, D. R. Gretch, T. E. Wiley, T. J. Layden, and A. S. Perelson. 1998. Hepatitis C viral dynamics in vivo and the antiviral efficacy of interferon-alpha therapy. Science 282:103-107.

30. Eckels, D. D., H. Wang, T. H. Bian, N. Tabatabai, and J. C. Gill. 2000. Immunobiology of hepatitis C virus (HCV) infection: the role of CD4 T cells in HCV infection. Immunol. Rev. 174:90-97.

31. Erickson, A. L., Y. Kimura, S. Igarashi, J. Eichelberger, M. Houghton, J. Sidney, D. McKinney, A. Sette, A. L. Hughes, and C. M. Walker. 2001. The outcome of hepatitis C virus infection is predicted by escape mutations in epitopes targeted by cytotoxic T lymphocytes. Immunity. 15:883-895.

32. Timm, J., G. M. Lauer, D. G. Kavanagh, I. Sheridan, A. Y. Kim, M. Lucas, T. Pillay, K. Ouchi, L. L. Reyor, J. S. Zur Wiesch, R. T. Gandhi, R. T. Chung, N. Bhardwaj, P. Klenerman, B. D. Walker, and T. M. Allen. 2004. CD8 epitope escape and reversion in acute HCV infection. J. Exp. Med. 200:1593-1604.

33. Chang, K. M., B. Rehermann, J. G. McHutchison, C. Pasquinelli, S. Southwood, A. Sette, and F. V. Chisari. 1997. Immunological significance of cytotoxic T lymphocyte epitope variants in patients chronically infected by the hepatitis C virus. J. Clin. Invest. 100:2376-2385.

34. Kaneko, T., I. Nakamura, H. Kita, K. Hiroishi, T. Moriyama, and M. Imawari. 1996. Three new cytotoxic T cell epitopes identified within the hepatitis C virus nucleoprotein. J. Gen. Virol. 77:1305-1309.

35. Tsai, S. L., Y. M. Chen, M. H. Chen, C. Y. Huang, I. S. Sheen, C. T. Yeh, J. H. Huang, G. C. Kuo, and Y. F. Liaw. 1998. Hepatitis c virus variants circumventing cytotoxic T lymphocyte activity as a mechanism of chronicity. Gastroenterology 115:954-966.

36. Mizukoshi, E., C. Eisenbach, B. Edlin, C. Weiler, M. Carrington, T. O'Brien, and B. Rehermann. 2003. HCV-specific cellular immune responses in subjects who are anti-HCV-negative, HCV RNA-negative despite long term (>15 years) injection drug use (AASLD Annual Meeting 2003 abstract #111). Hepatology 38:210A.

37. Walker, C. M., D. J. Moody, D. P. Stites, and J. A. Levy. 1986. CD8+ lymphocytes can control HIV infection in vitro by suppressing virus replication. Science 234:1563-1566.

38. He, X. S., B. Rehermann, F. X. Lopez-Labrador, J. Boisvert, R. Cheung, J. Mumm, H. Wedemeyer, M. Berenguer, T. L. Wright, M. M. Davis, and H. B. Greenberg. 1999. Quantitative analysis of hepatitis C virus-specific CD8(+) T cells in peripheral blood and liver using peptide-MHC tetramers. Proc. Natl. Acad. Sci. USA 96:5692-5697.

39. Wong, D. K., D. D. Dudley, P. B. Dohrenwend, G. M. Lauer, R. T. Chung, D. L. Thomas, and B. D. Walker. 2001. Detection of diverse hepatitis C virus (HCV)-specific cytotoxic T lymphocytes in peripheral blood of infected persons by screening for responses to all translated proteins of HCV. J. Virol. 75:1229-1235.

40. Farci, P., A. Shimoda, A. Coiana, G. Diaz, G. Peddis, J. C. Melpolder, A. Strazzera, D. Y. Chien, S. J. Munoz, A. Balestrieri, R. H. Purcell, and H. J. Alter. 2000. The outcome of acute hepatitis C predicted by the evolution of the viral quasispecies. Science 288:339-344, 41. Friedrich, T. C., E. J. Dodds, L. J. Yant, L. Vojnov, R. Rudersdorf, C. Cullen, D. T. Evans, R. C. Desrosiers, B. R. Mothe, J. Sidney, A. Sette, K. Kunstman, S. Wolinsky, M. Piatak, J. Lifson, A. L. Hughes, N. Wilson, D. H. O'Connor, and D. I. Watkins. 2004. Reversion of CTL escape-variant immunodeficiency viruses in vivo. Nat. Med. 10:275-281.

42. Allen, T. M., M. Altfeld, X. G. Yu, K. M. O'Sullivan, M. Lichterfeld, S. Le Gall, M. John, B. R. Mothe, P. K. Lee, E. T. Kalife, D. E. Cohen, K. A. Freedberg, D. A. Strick, M. N. Johnston, A. Sette, E. S. Rosenberg, S. A. Mallal, P. J.

Goulder, C. Brander, and B. D. Walker. 2004. Selection, transmission, and reversion of an antigen-processing cytotoxic T-lymphocyte escape mutation in human immunodeficiency virus type 1 infection. J. Virol. 78:7069-7078.
43. Grakoui, A., N. H. Shoukry, D. J. Woollard, J. H. Han, H. L. Hanson, J. Ghrayeb, K. K. Murthy, C. M. Rice, and C. M. Walker. 2003. HCV persistence and immune evasion in the absence of memory T cell help. Science 302:659-662.
44. Foy, E., K. Li, C. Wang, R. Sumpter, Jr., M. Ikeda, S. M. Lemon, and M. Gale, Jr. 2003; Regulation of interferon regulatory factor-3 by the hepatitis C virus serine protease. Science 300:1145-1148.
45. Gale, M. J., C. M. Blakely, B. Kwieciszewski, S. L. Tan, M. Dossett, N. M. Tang, M. J. Korth, S. J. Polyak, D. R. Gretch, and M. G. Katze. 1998. Control of PKR protein kinase by hepatitis C virus nonstructural 5A protein: molecular mechanisms of kinase regulation. Mol Cell Biol 18:5208-5218.
46. Klenerman, P. and R. M. Zinkernagel. 1998. Original antigenic sin impairs cytotoxic T lymphocyte responses to viruses bearing variant epitopes. Nature 394:482-485.
47. Garfein, R. S., M. C. Doherty, E. R. Monterroso, D. L. Thomas, K. E. Nelson, and D. Vlahov. 1998. Prevalence and incidence of hepatitis C virus infection among young adult injection drug users. J. Acquir. Immune. Defic. Syndr. Hum. Retrovirol. 18 Suppl 1: S11-S19.
48. Liu, Z., D. M. Netski, Q. Mao, O. Laeyendecker, J. R. Ticehurst, X. H. Wang, D. L. Thomas, and S. C. Ray. 2004. Accurate representation of the hepatitis C virus quasispecies in 5.2-kilobase amplicons. J. Clin. Microbiol. 42:4223-4229.
49. Ray, S. C., R. R. Arthur, A. Carella, J. Bukh, and D. L. Thomas. 2000. Genetic Epidemiology of Hepatitis C Virus throughout Egypt. J. Infect. Dis. 182:698-707.
50. Jeanmougin, F., J. D. Thompson, M. Gouy, D. G. Higgins, and T. J. Gibson. 1998. Multiple sequence alignment with Clustal X. Trends Biochem. Sci. 23:403-405.
51. Hall, T. A. 2001. BioEdit: Biological sequence alignment editor for Windows 95/98/NT version 5.0.7. software. Distributed by author: http://www.mbio.ncsu.edu/RNaseP/info/programs/BIOEDIT/bioedit.html.
52. Posada, D. and K. A. Crandall. 1998. MODELTEST: testing the model of DNA substitution. Bioinformatics. 14:817-818.
53. Felsenstein, J. 1985. Confidence limits on phylogenies: an approach using the bootstrap. Evolution 39:783-791.
54. Cox, A. L., D. M. Netski, T. Mosbruger, S. G. Sherman, S. Strathdee, D. C. Ompad, D. Vlahov, D. Chien, V. Shyamala, S. C. Ray, and D. L. Thomas. 2004. Prospective evaluation of community-acquired acute Hepatitis C. Clin. Infect. Dis. (in press).
55. Wang, Y. M., S. C. Ray, O. Laeyendecker, J. R. Ticehurst, and D. L. Thomas. 1998. Assessment of hepatitis C virus sequence complexity by electrophoretic mobilities of both single- and double-stranded DNAs. J. Clin. Microbiol. 36:2982-2989.
56. Lauer, G. M., K. Ouchi, R. T. Chung, T. N. Nguyen, C. L. Day, D. R. Purkis, M. Reiser, A. Y. Kim, M. Lucas, P. Klenerman, and B. D. Walker. 2002. Comprehensive analysis of CD8(+)-T-cell responses against hepatitis C virus reveals multiple unpredicted specificities. J. Virol. 76:6104-6113.
57. Ward, S., G. Lauer, R. Isba, B. Walker, and P. Klenerman. 2002. Cellular immune responses against hepatitis C virus: the evidence base 2002. Clin. Exp. Immunol. 128:195-203.
58. Currier, J. R., E. G. Kuta, E. Turk, L. B. Earhart, L. Loomis-Price, S. Janetzki, G. Ferrari, D. L. Birx, and J. H. Cox. 2002. A panel of MHC class I restricted viral peptides for use as a quality control for vaccine trial ELISPOT assays. J. Immunol. Methods 260:157-172.
59. Sidney, J., S. Southwood, C. Oseroff, J. F. Del Guercio, A. Sette, and H. Grey. 1998. Measurement of MHC/Peptide Interactions by Gel Filtration. In Current Protocols in Immunology. B. Bierer, J. E. Coligan, D. H. Margulies, E. M. Shevach, W. Strober, and A. Kruisbeek, editors. John Wiley & Sons, Inc., 18.3.1-18.3.19.

Example 3

Divergent and Convergent Evolution Following a Common-Source Outbreak of Hepatitis C The genomic sequences of viruses that are highly mutable and cause chronic infection tend to diverge over time. We report that these changes represent both immune driven selection and, in the absence of immune pressure, reversion toward a more "fit" ancestral consensus. Sequence changes in hepatitis C virus (HCV) structural and nonstructural genes were studied in a cohort of women accidentally infected with HCV in a rare common-source outbreak. We compared sequences present in serum obtained 18-22 years after infection to sequences present in the shared inoculum and found that HCV had evolved along a distinct path in each woman. Amino acid substitutions in known epitopes were directed away from consensus in persons having the HLA allele associated with that epitope (immune selection), and toward consensus in those lacking the allele (reversion). Vaccines for genetically-diverse viruses may be more effective if they represent consensus sequence, rather than a human isolate.

A virus capable of genetic variation and of causing chronic infection will evolve to optimize its fitness in each host, which is the net sum of immune recognition (positive selection) and functional constraint on replication (negative selection). Because an estimated $10^{12}$ virions are produced each day through an error-prone, non-proofreading NS5B RNA polymerase, hepatitis C virus (HCV) is especially capable of viral evolution (1,2) (These numbers in Example 3 refer to the list of references listed after Example 3). However, we previously showed that evolution is not driven by replication alone. In the acute phase of infection before adaptive immune responses (but after weeks of replication supporting a viral RNA level of more than 105 IU/mL), the same major viral variant was detected in each of a serial passage of eight chimpanzees (3). In contrast, the sequence of envelope genes, particularly HVR1, changes in virtually all humans who have been persistently infected (including the source of the inoculum passaged through this chimpanzee lineage (4)), a notable exception being persons with agammaglobulinemia, who have been shown to have reduced variability in HVR1 (5). Longitudinal studies of chimpanzees experimentally infected with HCV have revealed that amino acid replacements in immunodominant CD8+ T cell epitopes presented on MHC class I in an allele-restricted manner contribute to viral persistence (6). Thus, we hypothesized that the net evolution of HCV would demonstrate functional constraint (reversion of sequences toward consensus) as well as positive pressure (and thus reveal immunodominant epitopes).

Although it required that persons be infected with the same inoculum, it was possible to test this hypothesis because between May 1977 and November 1978 over 500 women were inadvertently infected with HCV from a single acutely-infected source, as a result of treatment with contaminated anti-D immune globulin (7). In a single amplicon, a 5.2 kb cDNA spanning 5'UTR through the NS3/NS4A junction was cloned from serum collected from 22 women 18-23 years after infection, as well as in 2 specimens of frozen plasma from the inoculum donor.

Methods and Materials

Study subjects. Twenty-two women from this outbreak were studied because they provided consent and had at least one of the 3 most common alleles at the HLA A locus (A*01, A*02, or A*03) (16).

Hemigenomic cDNA cloning. The region encoding Core, E1, E2, p7, NS2, and NS3 was amplified and cloned as previously described (17), and 40 clones per specimen were stored. For each specimen, envelope sequences from 10 random randomly-selected clones were determined using primer H77-1868a21 (17) on a PRISM version 3100 sequencer (ABI, Foster City, Calif.).

Estimation of Consensus Sequence. An alignment of full-length HCV subtype 1b sequences was obtained from the Los Alamos National Laboratories HCV database (http://hcv.lanl.gov). The alignment was edited by hand to remove gaps introduced for alignment to other genotypes, and to remove duplicate sequences from the same human source and those obtained from non-human sources. The resulting alignment included 83 sequences. A majority-rule consensus sequence was formed, with residues occurring in less than 42 sequences flagged as non-consensus. Changes in the anti-D recipients were then classified as "toward" (change results in a residue matching the consensus) or "away" (change results in a residue not matching the consensus, or residue is non-consensus).

Estimation of the likelihood of convergence. The expected frequency of co-variation assuming independence was calculated as the product of the marginal frequencies, and compared to the observed value using the Chi-squared distribution with 3 degrees of freedom. If we assume that all amino acid replacements are equally likely over a time period that is very long with respect to the rate of mutation, then sharing of amino acids at 4 variable sites in just 2 study subjects would be expected to occur at a frequency of $1/20^4$ or 0.00000625. Of course, all amino acid replacements are not equally likely, even in the highly variable HVR1 (8); therefore, the likelihood of sharing of 4 variable sites by 2 subjects would be higher, e.g. $1/3^4$ or 0.012 if each site is equally likely to have one of 3 residues. Because the likelihood of shared residues at variable sites in multiple study subjects is the product of such probabilities, the observed findings in this study are clearly incompatible with random substitution and most consistent with convergent evolution.

Phylogenetic Analysis. Sequences were aligned using ClustalX (18), codon boundaries were restored by hand in BioEdit (19), and phylogenetic analysis was performed using PAUP* version 4b10 (Sinauer Associates, Sunderland, Mass.) using a HKY85+G model and parameters (Ti/Tv 2.78, gamma=0.37) selected with the aid of ModelTest (20). Initial results from one specimen were consistent with subtype 1a, and that specimen was not examined further. Reference sequences included 3 from subtype 1a, 83 from subtype 1b (including AF313916), 2 from subtype 1c, 6 from subtype 2a, 8 from subtype 2b, 1 each from subtypes 2c and 2k, 4 from subtype 3a, and 1 each from subtypes 3b, 3k, 4a, 5a, 6a, 6b, 6d, 6g, 6h, and 6k (obtained from http://hcv.lanl.gov). VarPlot was used to calculate nonsynonymous and synonymous distances using the method of Nei and Gojobori, in a sliding window 20 codons wide, moving in 1 codon steps, as previously described (21).

Sequence logos. The sequence logos in FIG. 7 were generated using a novel software program, V is SPA (Visual Sequence Pattern Analysis, available on request from the author S. C. R.). The algorithm is identical to that described for type 2 logos by Gorodkin et al (22), except that the a priori distributions for the logo are calculated empirically from input sequences, and missing values in the a priori distribution are assigned the lowest frequency of residues at that site (if more than one state is represented) or $1/20$ if the a priori distribution has only one residue at that site.

Results and Discussion

Figure 6A:
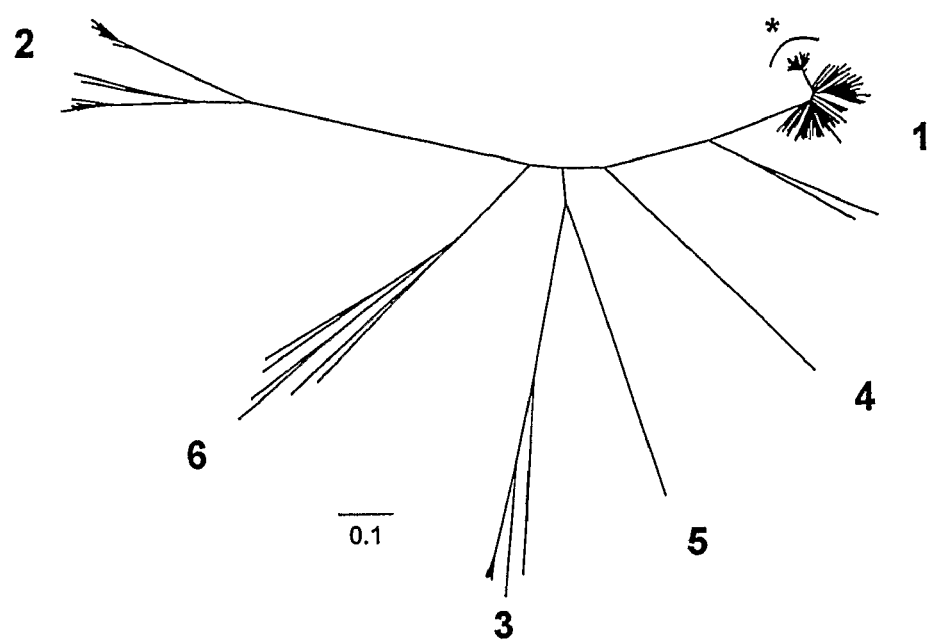
FIG. 6 shows a phylogenetic analysis of HCV 18-22 years after common-source outbreak. (A) Phylogenetic tree of 5.2 kb sequence alignment placing outbreak clade (*) in context with reference sequences for all major subtypes. (B) Detailed analysis of the outbreak clade, using 10 cDNA clones from each study subject to obtain the sequence of a 698 nt region spanning the E1/E2 junction. The label "inoculum" indicates twenty clones from inoculum source plasma (10 each from 2 specimens), and a full-length clone (Genbank Accession No. AF313916) obtained in an independent study of this material using smaller amplicons. For both trees, numbers at nodes are bootstrap values, indicating the percentage of 1000 permuted trees that supported the presence of that node. Bootstrap support was 100% for each of the major clades in panel A; in panel B, only bootstrap values greater than 80% are shown, and values for nodes within a study subject's clade were omitted for clarity. Boxes highlight 2 subjects whose sequences were segregated into two separate clades.
Figure 6B:
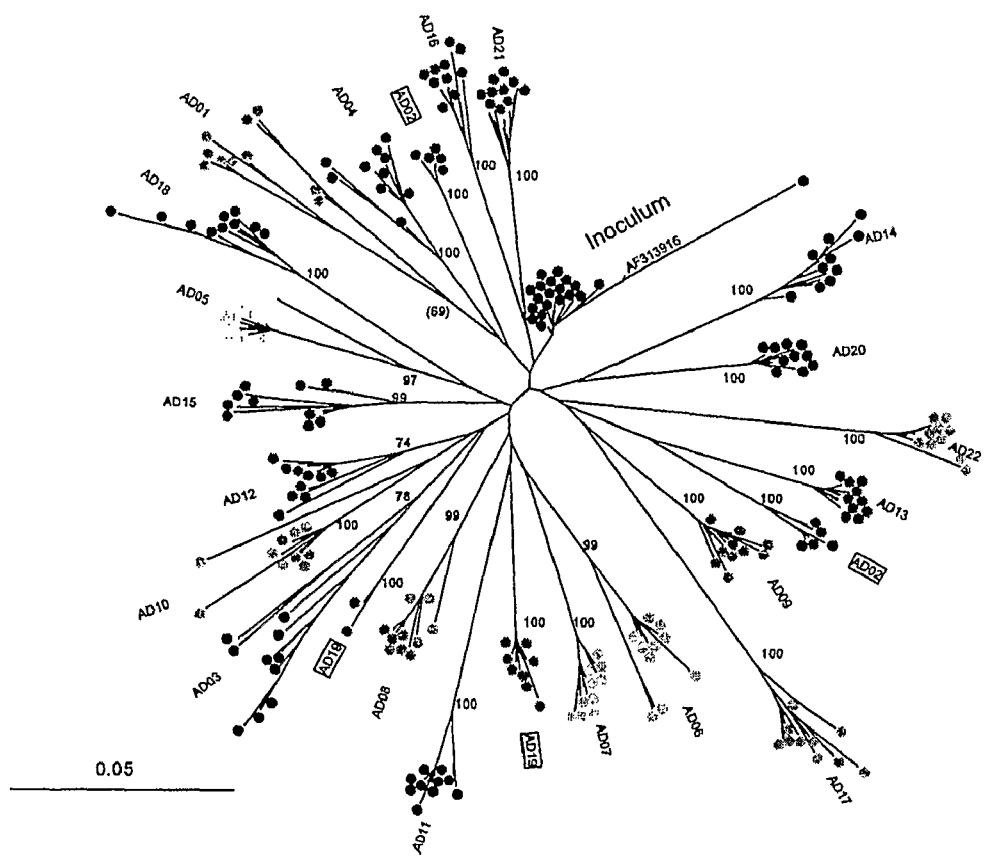

HCV envelope sequence from the inoculum clustered near the base of the clade formed by sequences from the chronically-infected women (FIG. 6), and the entire anti-D cohort clade was clearly distinct from all other sequences in available databases (excluding those from this outbreak), consistent with the previously-reported clinical history of common-source infection from an acutely infected donor (7). Nonetheless, HCV sequences in each woman diverged along distinct paths.

Figure 7:
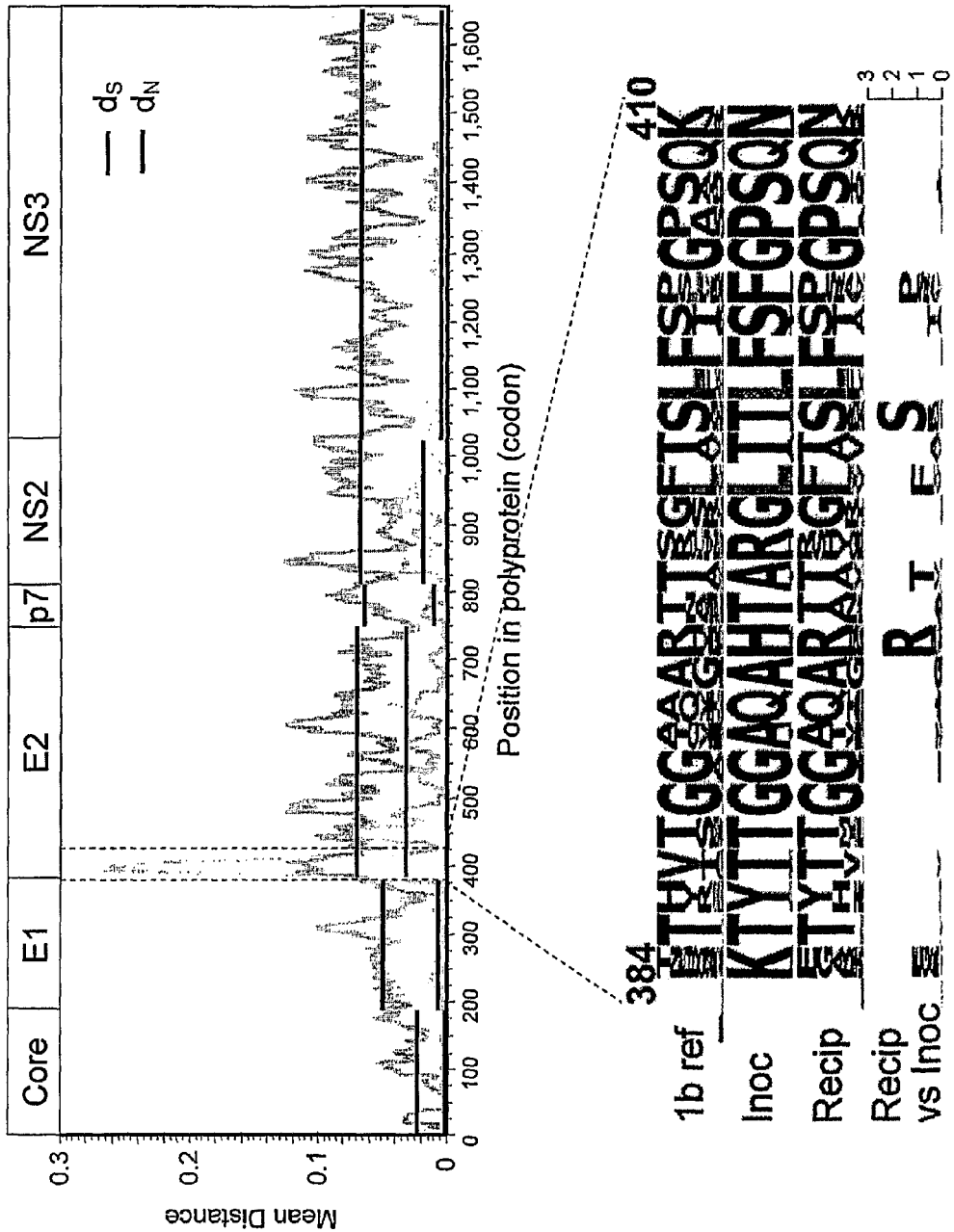
FIG. 7 shows HCV divergence and convergence following a common-source outbreak. The upper panel shows a sliding-window analysis of nonsynonymous (lighter curve, with lower mean variability) and synonymous (darker curve, with higher mean variability) variation, calculated by comparing the mean pairwise distance between the inoculum (2 cDNA clones obtained from two inoculum source plasma specimens obtained one week apart in 1977) to 44 clones (2 per study subject) obtained from chronically-infected women 18-22 years after exposure, in a sliding window 20 codons wide, moving in 1-codon increments, generated using VarPlot. Horizontal bars indicate average distance for each gene region. The lower panel shows detail of variability in HVR1 (the region indicated by dashed lines in the upper panel), indicating position relative to the H77 polyprotein (residues 384 to 410 in SEQ ID NO: 1 and 2). The first three rows show the subtype 1b reference sequences, inoculum sequences (20 clones from 2 plasma specimens obtained one week apart), and 220 recipient sequences (10 per study subject) respectively, with the height of each single-letter amino acid code proportional to its frequency. The fourth row shows differences between the amino acid frequencies in the recipient sequences versus the inoculum sequences as a type 2 logo, in which the height of each amino acid is determined by the $\log_2$ relative risk of observing it, with the scale indicated. Empty spaces indicate a distribution highly similar to the inoculum distribution, because the logarithm of a relative risk of one is zero.

There was strong evidence of negative selection in both the regional differences in genetic divergence, as well as by comparison of the rates of nonsynonymous (amino acid-changing) and synonymous (silent) change (FIG. 7). Overall, the highest rate of non-synonymous change was observed in the E2 gene, followed by NS2, p7, E1, NS3, and Core. Synonymous substitution rates were consistently higher than nonsynonymous rates for all genes, suggesting strong negative selection is a consistent feature of chronic HCV infection. HVR1 sequences were highly divergent at many sites, but constrained at others (8,9).

The HVR1 sequences illustrated two distinct patterns of sequence change. When the amino acid of the inoculum matched the consensus for that viral subtype, residues either did not change or changed in an apparently 'sporadic' fashion (risk of finding the residue in recipients was not different than finding the residue in the inoculum, indicated by near-zero height of the sequence logo in FIG. 7. In contrast, when the amino acid in the inoculum differed from the consensus, there was convergent evolution toward consensus (residue was found >2 times more often in the recipients than in the inoculum, FIG. 7). For example, 16 of the 22 women had replaced H in the inoculum with R at position 394, 12 replaced A with T at 396, 11 replaced L with F at 399, and 16 replaced T with S at 401. Four women had all 4 of these changes, not significantly different from the expected frequency of 3.2, indicating that these changes occurred independently. Since there is an infinitesimal likelihood that these same amino acid substitutions occurred by chance in each of the women, these data indicate that the sequences converged to a more fit state, implying that prior evolution of the inoculum sequence to optimize its fitness in the original host resulted in changes that diminished its fitness in the subsequent hosts.

Rather than convergent evolution, these results might have been due to shared selection and then divergence (at other sites) from a rare variant that we did not detect in the inoculum. We did detect one clone (clone #5) among 20 in the inoculum material that carried the RxTxxFxS motif at positions 394-401, but it was highly divergent from all other sequences described here, as; evident from its position in the phylogenetic tree (FIG. 6B), and therefore less likely than the other 19 sequences to represent the founder strain for these women. While it is possible that a less divergent RxTxxFxS clone was present in the inoculum at very low frequency, shared selection of such a rare variant would support the same conclusion.

Because HVR1 is a potential target of both humoral and cellular immunity and the precise recognition motifs remain difficult to identify due to the extreme variability, further examination of immune selection and convergence was focused on other genes, and in particular, on known MHC class I-restricted epitopes. Consistent with immune selection hypothesis, the number of changes in epitopes associated with specific class I alleles was significantly greater than the number of changes in other sites and greater than what was found in that same site for persons who did not possess the allele (Table 3). For HLA B*35 and B*37, sequence changes were 7.0 and 8.5 times as likely to occur in an epitope associated with an allele in women having the allele as compared with those that lacked it (P<0.001). An example of such an epitope is shown in a 38 amino acid region that spans an HLA A2 motif (FIG. 7). Mutations from R to K were noted outside the A2 epitope, and mutations from G to S were noted within the epitope in 8 and 6 of 22 women, respectively. However, while R to K mutation was noted in a similar percentage of A2 positive and A2 negative women (41.7% versus 30:0%, P>0.10), all G to S mutations were observed in A2 positive women (P=0.015), consistent with immune escape as has been observed in the SIV macaque model (10) and chimpanzees infected with HCV (6).

As seen with envelope sequences, the opposite effect was observed in other alleles. For alleles A*01 and B*08, sequence changes were 0.2 and 0.4 times as likely to occur in an epitope restricted by an allele in women having the allele as compared with those who lack it (Table 3). In fact, the R to K mutation that was described above in both A2 positive and negative women, only occurred in women who were not HLA B*08 positive, while the apparently A2-restricted G1409S substitution occurred in both B*08 positive and negative women (FIG. 7).

Collectively, these findings indicate that HCV sequence change is a non-random process that reflects negative selection (change is disadvantageous) as well as positive selection. Moreover, we find evidence that positive selection represents both the direct effect of pressure applied by immune responses in the current host (in this case, HLA class I restricted CD8+ cytotoxic T lymphocytes) as well as reversion of sequence to a more fit consensus, as we saw with envelope sequences.

To independently evaluate this paradigm, we compared the amino acid sequences of these women with a HCV 1b consensus sequence. For the epitopes that showed evidence of HLA class I restricted positive selection (a significantly increased risk of mutations from the inoculum occurred when the restricting allele was present), there was also an increased number of changes away from the 1b prototype consensus in women with one of these alleles, but not those without (Table 4). In addition, for epitopes that showed the converse effect, i.e., evidence of positive selection when the allele was absent (a significantly lower risk of mutations from the inoculum when the restricting allele was present), there was also an increased number of changes toward consensus in those who lacked the allele versus those who had the allele, suggesting reversion (Table 4). These findings are supported in an accompanying report (Cox, et al. *J Exp Med.* 2005 Jun. 6; 201(11):1741-52 and Example 2), which shows that amino acid substitutions in CD8+ T cell epitopes are associated with a loss of T cell recognition during acute infection, whereas non-epitope changes revert toward consensus at a rate much higher than expected by chance.

Prior studies have demonstrated reversion of CTL-escape variant sequences in macaques experimentally infected with SIV (11), reversion of an HIV-1 epitope in humans (12), and evidence of HIV-1 adaptation to common HLA alleles (13). This is the first report of viral adaptation to multiple HLA alleles across multiple genes, and provides additional support for the suggestion, based on minimizing differences between vaccine and circulating strains, that vaccine effectiveness may be enhanced by using a consensus (14) or ancestral (15) sequence. The ability of viruses to restrict adaptive immune responses and evade those that are formed contributes to persistence and is a major barrier to vaccine development. These data demonstrate that although immune responses diminish the fitness of viral variants, viral divergence occurs in persistently infected hosts. Nonetheless, this divergence actually reduces the fitness of the virus in the population (that is, in other hosts). From an evolutionary perspective, these forces maintain the virus as a distinct pathogen. However, the data also suggest that immune responses to consensus sequences (rather than a product based on the sequence in a given host) would establish the highest barrier to viral escape and consequently the most effective protection against chronic infection.

REFERENCES

1. Neumann, A. U., N. P. Lam, H. Dahari, D. R. Gretch, T. E. Wiley, T. J. Layden, and A. S. Perelson. 1998. Hepatitis C viral dynamics in vivo and the antiviral efficacy of interferon-alpha therapy. Science 282:103-107.
2. Martell, M., J. I. Esteban, J. Quer, J. Genesca, A. Weiner, R. Esteban, Guardia, and J. Gomez. 1992. Hepatitis C virus (HCV) circulates as a population of different but closely related genomes: quasispecies nature of HCV genome distribution. J. Virol. 66:3225-3229.
3. Ray, S. C., Q. Mao, R. E. Lanford, S. Bassett, O. Laeyendecker, Y. M. Wang, and D. L. Thomas. 2000. Hypervariable region 1 sequence stability during hepatitis C virus replication in chimpanzees. J. Virol. 74:3058-3066.
4. Ogata, N., H. J. Alter, R. H. Miller, and R. H. Purcell. 1991. Nucleotide sequence and mutation rate of the H strain of hepatitis C virus. Proc. Natl. Acad. Sci. USA 88:3392-3396.
5. Gaud, U., B. Langer, T. Petropoulou, H. C. Thomas, and P. Karayiannis. 2003. Changes in hypervariable region 1 of the envelope 2 glycoprotein of hepatitis C virus in children and adults with humoral immune defects. J. Med. Virol. 69:350-356.
6. Erickson, A. L., Y. Kimura, S. Igarashi, J. Eichelberger, M. Houghton, J. Sidney, D. McKinney, A. Sette, A. L. Hughes, and C. M. Walker. 2001. The outcome of hepatitis C virus infection is predicted by escape mutations in epitopes targeted by cytotoxic T lymphocytes. Immunity. 15:883-895.
7. Kenny-Walsh, E. 1999. Clinical outcomes after hepatitis C infection from contaminated anti-D immune globulin. Irish Hepatology Research Group. N. Engl. J. Med. 340:1228-1233.
8. McAllister, J., C. Casino, F. Davidson, J. Power, E. Lawlor, P. L. Yap, P. Simmonds, and D. B. Smith. 1998. Long-term evolution of the hypervariable region of hepatitis C virus in a common-source-infected cohort. J. Virol. 72:4893-4905.
9. Penin, F., C. Combet, G. Germanidis, P. O. Frainais, G. Deleage, and J. M. Pawlotsky. 2001. Conservation of the conformation and positive charges of hepatitis C virus E2 envelope glycoprotein hypervariable region 1 points to a role in cell attachment. J. Virol. 75:5703-5710.
10. Allen, T. M., D. H. O'Connor, P. Jing, J. L. Dzuris, B; R. Mothe, T. U. Vogel, E. Dunphy, M. E. Liebl, C. Emerson, N. Wilson, K. J. Kunstman, X. Wang, D. B. Allison, A. L. Hughes, R. C. Desrosiers, J. D. Altman, S. M. Wolinsky, A. Sette, and D. I. Watkins. 2000. Tat-specific cytotoxic T lymphocytes select for SIV escape variants during resolution of primary viraemia. Nature 407:386-390.

11. Leslie, A. J., K. J. Pfafferott, P. Chetty, R. Draenert, M. M. Addo, M. Feeney, Y. Tang, E. C. Holmes, T. Allen, J. G. Prado, M. Altfeld, C. Brander, C. Dixon, D. Ramduth, P. Jeena, S. A. Thomas, A. St John, T. A. Roach, B. Kupfer, G. Luzzi, A. Edwards, G. Taylor, H. Lyall, G. Tudor-Williams, V. Novelli, J. Martinez-Picado, P. Kiepiela, B. D. Walker, and P. J. Goulder. 2004. HIV evolution: CTL escape mutation and reversion after transmission. Nat. Med. 10:282-289.

12. Friedrich, T. C., E. J. Dodds, L. J. Yant, L. Vojnov, R. Rudersdorf, C. Cullen, D. T. Evans, R. C. Desrosiers, B. R. Mothe, J. Sidney, A. Sette, K. Kunstman, S. Wolinsky, M. Piatak, J. Lifson, A. L. Hughes, N. Wilson, D. H. O'Connor, and D. I. Watkins. 2004. Reversion of CTL escape-variant immunodeficiency viruses in vivo. Nat. Med. 10:275-281.

13. Moore, C. B., M. John, I. R. James, F. T. Christiansen, C. S. Witt, and S. A. Mallal. 2002. Evidence of HIV-1 adaptation to HLA-restricted immune responses at a population level. Science 296:1439-1443.

14. Gaschen, B., J. Taylor, K. Yusim, B. Foley, F. Gao, D. Lang, V. Novitsky, B. Haynes, B. H. Hahn, T. Bhattacharya, and B. Korber. 2002. Diversity considerations in HIV-1 vaccine selection. Science 296:2354-2360.

15. Nickle, D. C., M. A. Jensen, G. S. Gottlieb, D. Shriner, G. H. Learn, A. G. Rodrigo, and J. I. Mullins. 2003. Consensus and ancestral state HIV vaccines. Science 299:1515-1518.

16. Fanning, L. J., E. Kenny-Walsh, and F. Shanahan. 2004. Persistence of hepatitis C virus in a white population: associations with human leukocyte antigen class 1. Hum. Immunol. 65:745-751.

17. Liu, Z., D. M. Netski, Q. Mao, O. Laeyendecker, J. R. Ticehurst, X. H. Wang, D. L. Thomas, and S. C. Ray. 2004. Accurate representation of the hepatitis C virus quasispecies in 5.2-kilobase amplicons. J. Clin. Microbiol. 42:4223-4229.

18. Jearmougin, F., J. D. Thompson, M. Gouy, D. G. Higgins, and T. J. Gibson. 1998. Multiple sequence alignment with Clustal X. Trends Biochem. Sci. 23:403-405.

19. Hall, T. A. 2001. BioEdit: Biological sequence alignment editor for Windows 95/98/NT version 5.0.7. software. Distributed by author: http://www.mbio.ncsu.edu/RNaseP/info/programs/BIOEDIT/bioedit.html.

20. Posada, D. and K. A. Crandall. 1998. MODELTEST: testing the model of DNA substitution. Bioinformatics. 14:817-818.

21. Ray, S. C., Y. M. Wang, O. Laeyendecker, J. Ticehurst, S. A. Villano, and D. L. Thomas. 1998. Acute hepatitis C virus structural gene sequences as predictors of persistent viremia: hypervariable region 1 as decoy. J. Virol. 73:2938-2946.

22. Gorodkin, J., L. J. Heyer, S. Brunak, and G. D. Stormo. 1997. Displaying the information contents of structural RNA alignments: the structure logos. Comput. Appl. Biosci. 13:583-586.

23. Chang, K. M., B. Rehermann, J. G. McHutchison, C. Pasquinelli, S. Southwood, A. Sette, and F. V. Chisari. 1997. Immunological significance of cytotoxic T lymphocyte epitope variants in patients chronically infected by the hepatitis C virus. J. Clin. Invest. 100:2376-2385.

24. Ward, S., G. Lauer, R. Isba, B. Walker, and P. Klenerman. 2002. Cellular immune responses against hepatitis C virus: the evidence base 2002. Clin. Exp. Immunol. 128:195-203.

TABLE 1

Non-epitope, non-envelope changes[a] frequently result in modal residue

| Site[b] | Region | Subject | Change $t_0 \rightarrow t_6$[c] | Subtype 1a[d] | Change relative to modal residue[e] |
|---|---|---|---|---|---|
| 6 | Core | 11 | N → $\underline{K}$ | $K_{102}Y_2$ | Toward |
| 88 | Core | 17 | S → $\underline{N}$ | $N_{128}$ | Toward |
| 840 | NS2 | 21 | $\underline{S}$ → G | $S_{10}A_1$ | Away |
| 856 | NS2 | 17 | L → $\underline{Q}$ | $Q_6H_2L_1$ | Toward |
| 859 | NS2 | 21 | $\underline{V}$ → E | $V_9$ | Away |
| 861 | NS2 | 21 | $\underline{V}$ → I | $V_7I_1F_1$ | Away |
| 899 | NS2 | 17 | F → $\underline{L}$ | $L_9$ | Toward |
| 908 | NS2 | 13 | $\underline{K}$ → R | $K_9$ | Away |
| 945 | NS2 | 12 | $\underline{T}$ → A | $T_9$ | Away |
| 1021 | NS2 | 12 | $\underline{K}$ → E | $K_9$ | Away |
| 1113 | NS3 | 17 | T → $\underline{A}$ | $A_{73}T_1P_1V_1$ | Toward |
| 1278 | NS3 | 18 | $\underline{I}$ → L | $I_{78}S_1$ | Away |
| 1314 | NS3 | 12 | V → $\underline{I}$ | $I_{49}F_1$ | Toward |
| 1338 | NS3 | 18 | S → $\underline{T}$ | $T_{46}$ | Toward |
| 1600 | NS3 | 21 | $\underline{P}$ → L | $P_{50}L_1$ | Away |
| 1648 | NS3 | 28 | G → $\underline{C}$ | $C_{54}Y_1$ | Toward |

[a]Changes that were not located in demonstrated epitopes and not located in the envelope region (FIG. 2)
[b]Position in H77 polyprotein (Genbank accession AF009606)
[c]amino acids inferred from cDNA clones obtained at $t_0$ and $t_6$, respectively. Changes were only inferred when independent cDNA clone sequences were in agreement.

TABLE 2

Observed versus expected frequencies of change to modal residue at 16 sites not located in epitopes nor in envelope (E1 or E2) genes

|  | Expected | Observed |
|---|---|---|
| Change to modal residue | 16 * (1/19) = 0.8 ≈ 1 | 8* |
| Change to non-modal residue | 16 * (18/19) = 15.2 ≈ 15 | 8 |

*p = 0.015

TABLE 3

Proportion of amino acid substitutions in known epitopes located in HCV Core, p7, NS2, and NS3, according to the presence or absence of the associated HLA allele (24). Epitopes were considered in the region sequenced (corresponding to amino acid residues 1-1651 of the H77 polyprotein, GenBank AF009606). Two sequences per subject were examined. P values were calculated by comparison of proportions as implemented in SigmaStat (Systat Software, Inc., Richmond, Calif. USA). NA means not applicable due to zero cell. EpiChanges, a software program created by S.C.R. to automate this analysis, is available from the author.

| Allele | Subjects with allele (n) | Epitopes (n) | Allele present Epitope changes/sites (%) | Allele absent Epitope changes/sites | Relative Risk of change (allele present versus absent) | P value |
|---|---|---|---|---|---|---|
| A*01 | 11 | 1 | 2/198 (1.0) | 10/198 (5.1) | 0.2 | 0.019 |
| A*02 | 13 | 13 | 39/3198 (1.2) | 18/2214 (0.8) | 1.5 | >0.10 |

TABLE 3-continued

Proportion of amino acid substitutions in known epitopes located in HCV Core, p7, NS2, and NS3, according to the presence or absence of the associated HLA allele (24). Epitopes were considered in the region sequenced (corresponding to amino acid residues 1-1651 of the H77 polyprotein, GenBank AF009606). Two sequences per subject were examined. P values were calculated by comparison of proportions as implemented in SigmaStat (Systat Software, Inc., Richmond, Calif. USA). NA means not applicable due to zero cell. EpiChanges, a software program created by S.C.R. to automate this analysis, is available from the author.

| Allele | Subjects with allele (n) | Epitopes (n) | Allele present Epitope changes/ sites (%) | Allele absent Epitope changes/sites | Relative Risk of change (allele present versus absent) | P value |
|---|---|---|---|---|---|---|
| A*03 | 9 | 4 | 8/648 (1.2) | 18/936 (1.9) | 0.6 | >0.10 |
| A*11 | 3 | 3 | 6/162 (3.7) | 45/1026 (4.4) | 0.8 | >0.10 |
| A*24 | 1 | 2 | 0/36 (0.0) | 3/756 (0.4) | 0 | >0.10 |
| B*07 | 7 | 3 | 4/378 (1.1) | 0/810 (0.0) | NA | 0.003 |
| B*08 | 6 | 3 | 4/312 (1.3) | 28/832 (3.4) | 0.4 | 0.057 |
| B*35 | 3 | 3 | 11/162 (6.8) | 10/1026 (1.0) | 7.0 | <0.001 |
| B*37 | 5 | 1 | 20/80 (25.0) | 8/272 (2.9) | 8.5 | <0.001 |
| B*44 | 7 | 1 | 0/126 (0.0) | 2/270 (0.7) | 0 | >0.10 |

TABLE 4

Classification of amino acid substitutions in MHC class I restricted epitopes as being toward or away from a 1b consensus sequence in 22 women exposed to a common HCV subtype 1b inoculum. Results are stratified (in columns) by the presence or the absence of the relevant allele, and grouped (rows) according to relative risk for change shown in Table 1. Changes are per 1000 epitope sites, based on whether the resulting residue matches HCV 1b consensus.

| Effect of allele presence on likelihood of amino acid replacement | Changes in epitopes relative to 1b consensus, per 1000 sites | | | |
|---|---|---|---|---|
| | Allele present | | Allele absent | |
| | Toward consensus | Away from consensus | Toward consensus | Away from consensus |
| | 620 sites | | 2108 sites | |
| Increased relative risk (B*07, B*35, B*37) | 1.6 | 54.8* | 3.9 | 0.0 |
| | 510 sites | | 1030 sites | |
| Decreased relative risk (A*01, B*08) | 3.8 | 4.7 | 22.3* | 48 |

*P < 0.001 for comparison of Toward versus Away.

TABLE 5

| HCV 1a Consensus Sequences |
|---|

| | A | B | C | D | E | F | G | H | I | J | K | L | M | N | O | P | Q | R | S | T | U | V | W |
|---|---|---|---|---|---|---|---|---|---|---|---|---|---|---|---|---|---|---|---|---|---|---|---|
| 1 | $M_{40}$ | | | | | | | | | | | | | | | 1505 | $G_{49}$ | | | | | | |
| 2 | $S_{40}$ | | | | | | | | | | | | | | | 1506 | $E_{49}$ | | | | | | |
| 3 | $T_{39}$ | $R_1$ | | | | | | | | | | | | | | 1507 | $R_{49}$ | | | | | | |
| 4 | $N_{36}$ | $I_4$ | | | | | | | | | | | | | | 1508 | $P_{49}$ | | | | | | |
| 5 | $P_{39}$ | $L_1$ | | | | | | | | | | | | | | 1509 | $S_{47}$ | $X_2$ | | | | | |
| 6 | $K_{40}$ | | | | | | | | | | | | | | | 1510 | $G_{49}$ | | | | | | |
| 7 | $P_{39}$ | $L_1$ | | | | | | | | | | | | | | 1511 | $M_{48}$ | $X_1$ | | | | | |
| 8 | $Q_{40}$ | | | | | | | | | | | | | | | 1512 | $F_{48}$ | $X_1$ | | | | | |
| 9 | $R_{40}$ | | | | | | | | | | | | | | | 1513 | $D_{49}$ | | | | | | |
| 10 | $K_{37}$ | $Q_2$ | $R_1$ | | | | | | | | | | | | | 1514 | $S_{49}$ | | | | | | |
| 11 | $T_{40}$ | | | | | | | | | | | | | | | 1515 | $S_{48}$ | $A_1$ | | | | | |
| 12 | $K_{46}$ | | | | | | | | | | | | | | | 1516 | $V_{49}$ | | | | | | |
| 13 | $R_{46}$ | | | | | | | | | | | | | | | 1517 | $L_{49}$ | | | | | | |
| 14 | $N_{46}$ | | | | | | | | | | | | | | | 1518 | $C_{49}$ | | | | | | |
| 15 | $T_{46}$ | | | | | | | | | | | | | | | 1519 | $E_{48}$ | $X_1$ | | | | | |
| 16 | $N_{45}$ | $S_1$ | | | | | | | | | | | | | | 1520 | $C_{49}$ | | | | | | |
| 17 | $R_{46}$ | | | | | | | | | | | | | | | 1521 | $Y_{49}$ | | | | | | |
| 18 | $R_{46}$ | | | | | | | | | | | | | | | 1522 | $D_{49}$ | | | | | | |
| 19 | $P_{46}$ | | | | | | | | | | | | | | | 1523 | $A_{48}$ | $T_1$ | | | | | |
| 20 | $Q_{46}$ | | | | | | | | | | | | | | | 1524 | $G_{49}$ | | | | | | |
| 21 | $D_{46}$ | | | | | | | | | | | | | | | 1525 | $C_{48}$ | $X_1$ | | | | | |
| 22 | $V_{46}$ | | | | | | | | | | | | | | | 1526 | $A_{48}$ | $X_1$ | | | | | |
| 23 | $K_{46}$ | | | | | | | | | | | | | | | 1527 | $W_{49}$ | | | | | | |

TABLE 5-continued

HCV 1a Consensus Sequences

| | A | B | C | D | E | F | G | H | I | J | K | L | M | N | O | P | Q | R | S | T | U | V | W |
|---|---|---|---|---|---|---|---|---|---|---|---|---|---|---|---|---|---|---|---|---|---|---|---|
| 24 | $F_{46}$ | | | | | | | | | | | | | | | 1528 | $Y_{48}$ | $X_1$ | | | | | |
| 25 | $P_{46}$ | | | | | | | | | | | | | | | 1529 | $E_{49}$ | | | | | | |
| 26 | $G_{46}$ | | | | | | | | | | | | | | | 1530 | $L_{49}$ | | | | | | |
| 27 | $G_{46}$ | | | | | | | | | | | | | | | 1531 | $T_{47}$ | $X_1$ | $M_1$ | | | | |
| 28 | $P_{46}$ | | | | | | | | | | | | | | | 1532 | $P_{49}$ | | | | | | |
| 29 | $Q_{46}$ | | | | | | | | | | | | | | | 1533 | $A_{47}$ | $T_1$ | $X_1$ | | | | |
| 30 | $I_{46}$ | | | | | | | | | | | | | | | 1534 | $E_{49}$ | | | | | | |
| 31 | $V_{46}$ | | | | | | | | | | | | | | | 1535 | $T_{48}$ | $X_1$ | | | | | |
| 32 | $G_{46}$ | | | | | | | | | | | | | | | 1536 | $T_{49}$ | | | | | | |
| 33 | $G_{46}$ | $I_1$ | | | | | | | | | | | | | | 1537 | $V_{48}$ | $A_1$ | | | | | |
| 34 | $V_{45}$ | $I_1$ | | | | | | | | | | | | | | 1538 | $R_{49}$ | | | | | | |
| 35 | $Y_{46}$ | | | | | | | | | | | | | | | 1539 | $L_{49}$ | | | | | | |
| 36 | $L_{46}$ | | | | | | | | | | | | | | | 1540 | $R_{49}$ | | | | | | |
| 37 | $L_{46}$ | | | | | | | | | | | | | | | 1541 | $A_{48}$ | $X_1$ | | | | | |
| 38 | $P_{46}$ | | | | | | | | | | | | | | | 1542 | $Y_{49}$ | | | | | | |
| 39 | $R_{46}$ | | | | | | | | | | | | | | | 1543 | $M_{49}$ | | | | | | |
| 40 | $R_{45}$ | $W_1$ | | | | | | | | | | | | | | 1544 | $N_{49}$ | | | | | | |
| 41 | $G_{46}$ | | | | | | | | | | | | | | | 1545 | $T_{49}$ | | | | | | |
| 42 | $P_{46}$ | | | | | | | | | | | | | | | 1546 | $P_{49}$ | | | | | | |
| 43 | $R_{45}$ | $K_1$ | | | | | | | | | | | | | | 1547 | $G_{49}$ | | | | | | |
| 44 | $L_{46}$ | | | | | | | | | | | | | | | 1548 | $L_{49}$ | | | | | | |
| 45 | $G_{46}$ | | | | | | | | | | | | | | | 1549 | $P_{49}$ | | | | | | |
| 46 | $V_{46}$ | | | | | | | | | | | | | | | 1550 | $V_{49}$ | | | | | | |
| 47 | $R_{46}$ | | | | | | | | | | | | | | | 1551 | $C_{48}$ | $X_1$ | | | | | |
| 48 | $A_{45}$ | $T_1$ | | | | | | | | | | | | | | 1552 | $Q_{48}$ | | | | | | |
| 49 | $T_{46}$ | | | | | | | | | | | | | | | 1553 | $D_{48}$ | | | | | | |
| 50 | $R_{46}$ | | | | | | | | | | | | | | | 1554 | $H_{48}$ | | | | | | |
| 51 | $K_{46}$ | | | | | | | | | | | | | | | 1555 | $L_{48}$ | | | | | | |
| 52 | $T_{46}$ | | | | | | | | | | | | | | | 1556 | $E_{48}$ | | | | | | |
| 53 | $S_{46}$ | | | | | | | | | | | | | | | 1557 | $F_{48}$ | | | | | | |
| 54 | $E_{46}$ | | | | | | | | | | | | | | | 1558 | $W_{48}$ | | | | | | |
| 55 | $R_{46}$ | | | | | | | | | | | | | | | 1559 | $E_{48}$ | | | | | | |
| 56 | $S_{46}$ | | | | | | | | | | | | | | | 1560 | $G_{48}$ | | | | | | |
| 57 | $Q_{46}$ | | | | | | | | | | | | | | | 1561 | $V_{48}$ | | | | | | |
| 58 | $P_{46}$ | | | | | | | | | | | | | | | 1562 | $F_{48}$ | | | | | | |
| 59 | $R_{46}$ | | | | | | | | | | | | | | | 1563 | $T_{48}$ | | | | | | |
| 60 | $G_{46}$ | | | | | | | | | | | | | | | 1564 | $G_{47}$ | $X_1$ | | | | | |
| 61 | $R_{45}$ | $S_1$ | | | | | | | | | | | | | | 1565 | $L_{48}$ | | | | | | |
| 62 | $R_{46}$ | | | | | | | | | | | | | | | 1566 | $T_{48}$ | | | | | | |
| 63 | $Q_{46}$ | | | | | | | | | | | | | | | 1567 | $H_{47}$ | $Q_1$ | | | | | |
| 64 | $P_{45}$ | $L_1$ | | | | | | | | | | | | | | 1568 | $I_{48}$ | | | | | | |
| 65 | $I_{45}$ | $F_1$ | | | | | | | | | | | | | | 1569 | $D_{48}$ | | | | | | |
| 66 | $P_{45}$ | $T_1$ | | | | | | | | | | | | | | 1570 | $A_{47}$ | $X_1$ | | | | | |
| 67 | $K_{45}$ | $Q_1$ | | | | | | | | | | | | | | 1571 | $H_{47}$ | $X_1$ | | | | | |
| 68 | $A_{43}$ | $V_3$ | | | | | | | | | | | | | | 1572 | $F_{48}$ | | | | | | |
| 69 | $R_{46}$ | | | | | | | | | | | | | | | 1573 | $L_{47}$ | $I_1$ | | | | | |
| 70 | $R_{46}$ | | | | | | | | | | | | | | | 1574 | $S_{45}$ | $X_3$ | | | | | |
| 71 | $P_{43}$ | $S_2$ | $A_1$ | | | | | | | | | | | | | 1575 | $Q_{48}$ | | | | | | |
| 72 | $E_{46}$ | | | | | | | | | | | | | | | 1576 | $T_{48}$ | | | | | | |
| 73 | $G_{46}$ | | | | | | | | | | | | | | | 1577 | $K_{48}$ | | | | | | |
| 74 | $R_{46}$ | | | | | | | | | | | | | | | 1578 | $Q_{48}$ | | | | | | |
| 75 | $T_{46}$ | | | | | | | | | | | | | | | 1579 | $S_{45}$ | $X_2$ | $G_1$ | | | | |
| 76 | $W_{46}$ | | | | | | | | | | | | | | | 1580 | $G_{47}$ | $X_1$ | | | | | |
| 77 | $A_{46}$ | | | | | | | | | | | | | | | 1581 | $E_{46}$ | $X_2$ | | | | | |
| 78 | $Q_{46}$ | | | | | | | | | | | | | | | 1582 | $N_{48}$ | | | | | | |
| 79 | $P_{46}$ | | | | | | | | | | | | | | | 1583 | $F_{24}$ | $L_{23}$ | $P_1$ | | | | |
| 80 | $G_{46}$ | | | | | | | | | | | | | | | 1584 | $P_{48}$ | | | | | | |
| 81 | $Y_{46}$ | | | | | | | | | | | | | | | 1585 | $Y_{48}$ | | | | | | |
| 82 | $P_{46}$ | | | | | | | | | | | | | | | 1586 | $L_{48}$ | | | | | | |
| 83 | $W_{46}$ | | | | | | | | | | | | | | | 1587 | $V_{48}$ | | | | | | |
| 84 | $P_{46}$ | | | | | | | | | | | | | | | 1588 | $A_{48}$ | | | | | | |
| 85 | $L_{46}$ | | | | | | | | | | | | | | | 1589 | $Y_{48}$ | | | | | | |
| 86 | $Y_{46}$ | | | | | | | | | | | | | | | 1590 | $Q_{48}$ | | | | | | |
| 87 | $G_{46}$ | | | | | | | | | | | | | | | 1591 | $A_{48}$ | | | | | | |
| 88 | $N_{46}$ | | | | | | | | | | | | | | | 1592 | $T_{47}$ | $X_1$ | | | | | |
| 89 | $E_{46}$ | | | | | | | | | | | | | | | 1593 | $V_{48}$ | | | | | | |
| 90 | $G_{46}$ | | | | | | | | | | | | | | | 1594 | $C_{48}$ | | | | | | |
| 91 | $C_{46}$ | | | | | | | | | | | | | | | 1595 | $A_{48}$ | | | | | | |
| 92 | $G_{46}$ | | | | | | | | | | | | | | | 1596 | $R_{47}$ | $X_1$ | | | | | |
| 93 | $W_{46}$ | | | | | | | | | | | | | | | 1597 | $A_{47}$ | $S_1$ | | | | | |
| 94 | $A_{45}$ | $M_1$ | | | | | | | | | | | | | | 1598 | $Q_{47}$ | $R_1$ | | | | | |
| 95 | $G_{46}$ | | | | | | | | | | | | | | | 1599 | $A_{48}$ | | | | | | |
| 96 | $W_{46}$ | | | | | | | | | | | | | | | 1600 | $P_{46}$ | $L_2$ | | | | | |
| 97 | $L_{46}$ | | | | | | | | | | | | | | | 1601 | $P_{48}$ | | | | | | |
| 98 | $L_{46}$ | | | | | | | | | | | | | | | 1602 | $P_{47}$ | $X_1$ | | | | | |
| 99 | $S_{46}$ | | | | | | | | | | | | | | | 1603 | $S_{46}$ | $X_2$ | | | | | |

TABLE 5-continued

HCV 1a Consensus Sequences

| | A | B | C | D | E | F | G | H | I | J | K | L | M | N | O | P | Q | R | S | T | U | V | W |
|---|---|---|---|---|---|---|---|---|---|---|---|---|---|---|---|---|---|---|---|---|---|---|---|
| 100 | $P_{46}$ | | | | | | | | | | | | | | | 1604 | $W_{48}$ | | | | | | |
| 101 | $R_{46}$ | | | | | | | | | | | | | | | 1605 | $D_{48}$ | | | | | | |
| 102 | $G_{46}$ | | | | | | | | | | | | | | | 1606 | $Q_{48}$ | | | | | | |
| 103 | $S_{46}$ | | | | | | | | | | | | | | | 1607 | $M_{48}$ | | | | | | |
| 104 | $R_{46}$ | | | | | | | | | | | | | | | 1608 | $W_{48}$ | | | | | | |
| 105 | $P_{46}$ | | | | | | | | | | | | | | | 1609 | $K_{48}$ | | | | | | |
| 106 | $S_{44}$ | $N_2$ | | | | | | | | | | | | | | 1610 | $C_{48}$ | | | | | | |
| 107 | $W_{46}$ | | | | | | | | | | | | | | | 1611 | $L_{48}$ | | | | | | |
| 108 | $G_{46}$ | | | | | | | | | | | | | | | 1612 | $I_{36}$ | $T_8$ | $V_2$ | $X_2$ | | | |
| 109 | $P_{45}$ | $X_1$ | | | | | | | | | | | | | | 1613 | $R_{48}$ | | | | | | |
| 110 | $T_{46}$ | | | | | | | | | | | | | | | 1614 | $L_{47}$ | $X_1$ | | | | | |
| 111 | $D_{46}$ | | | | | | | | | | | | | | | 1615 | $K_{47}$ | $X_1$ | | | | | |
| 112 | $P_{45}$ | $S_1$ | | | | | | | | | | | | | | 1616 | $P_{47}$ | $X_1$ | | | | | |
| 113 | $R_{44}$ | $P_2$ | | | | | | | | | | | | | | 1617 | $T_{47}$ | | | | | | |
| 114 | $R_{46}$ | | | | | | | | | | | | | | | 1618 | $L_{46}$ | $X_2$ | | | | | |
| 115 | $R_{44}$ | $K_2$ | | | | | | | | | | | | | | 1619 | $H_{47}$ | $Y_1$ | | | | | |
| 116 | $S_{46}$ | | | | | | | | | | | | | | | 1620 | $G_{48}$ | | | | | | |
| 117 | $R_{49}$ | | | | | | | | | | | | | | | 1621 | $P_{46}$ | $S_1$ | $X_1$ | | | | |
| 118 | $N_{49}$ | | | | | | | | | | | | | | | 1622 | $T_{47}$ | $K_1$ | | | | | |
| 119 | $L_{49}$ | | | | | | | | | | | | | | | 1623 | $P_{47}$ | $X_1$ | | | | | |
| 120 | $G_{49}$ | | | | | | | | | | | | | | | 1624 | $L_{47}$ | $X_1$ | | | | | |
| 121 | $K_{49}$ | | | | | | | | | | | | | | | 1625 | $L_{47}$ | $X_1$ | | | | | |
| 122 | $V_{49}$ | | | | | | | | | | | | | | | 1626 | $Y_{48}$ | | | | | | |
| 123 | $I_{49}$ | | | | | | | | | | | | | | | 1627 | $R_{48}$ | | | | | | |
| 124 | $D_{49}$ | | | | | | | | | | | | | | | 1628 | $L_{47}$ | $X_1$ | | | | | |
| 125 | $T_{49}$ | | | | | | | | | | | | | | | 1629 | $G_{46}$ | $X_2$ | | | | | |
| 126 | $L_{48}$ | $F_1$ | | | | | | | | | | | | | | 1630 | $A_{48}$ | | | | | | |
| 127 | $T_{49}$ | | | | | | | | | | | | | | | 1631 | $V_{48}$ | | | | | | |
| 128 | $C_{49}$ | | | | | | | | | | | | | | | 1632 | $Q_{48}$ | | | | | | |
| 129 | $G_{51}$ | | | | | | | | | | | | | | | 1633 | $N_{47}$ | $H_1$ | | | | | |
| 130 | $F_{50}$ | $L_1$ | | | | | | | | | | | | | | 1634 | $E_{48}$ | | | | | | |
| 131 | $A_{51}$ | | | | | | | | | | | | | | | 1635 | $V_{40}$ | $I_7$ | $X_1$ | | | | |
| 132 | $D_{51}$ | | | | | | | | | | | | | | | 1636 | $T_{47}$ | $X_1$ | | | | | |
| 133 | $L_{50}$ | $H_1$ | | | | | | | | | | | | | | 1637 | $L_{45}$ | $M_1$ | | | | | |
| 134 | $M_{50}$ | $T_1$ | | | | | | | | | | | | | | 1638 | $T_{46}$ | | | | | | |
| 135 | $G_{51}$ | | | | | | | | | | | | | | | 1639 | $H_{46}$ | | | | | | |
| 136 | $Y_{51}$ | | | | | | | | | | | | | | | 1640 | $P_{45}$ | $X_1$ | | | | | |
| 137 | $I_{51}$ | | | | | | | | | | | | | | | 1641 | $V_{24}$ | $I_{21}$ | $X_1$ | | | | |
| 138 | $P_{51}$ | | | | | | | | | | | | | | | 1642 | $T_{46}$ | | | | | | |
| 139 | $L_{51}$ | | | | | | | | | | | | | | | 1643 | $K_{45}$ | $X_1$ | | | | | |
| 140 | $V_{51}$ | | | | | | | | | | | | | | | 1644 | $Y_{44}$ | $X_1$ | | | | | |
| 141 | $G_{51}$ | | | | | | | | | | | | | | | 1645 | $I_{45}$ | | | | | | |
| 142 | $A_{48}$ | $V_2$ | $P_1$ | | | | | | | | | | | | | 1646 | $M_{45}$ | | | | | | |
| 143 | $P_{51}$ | | | | | | | | | | | | | | | 1647 | $T_{45}$ | | | | | | |
| 144 | $L_{51}$ | | | | | | | | | | | | | | | 1648 | $C_{45}$ | | | | | | |
| 145 | $G_{50}$ | $X_1$ | | | | | | | | | | | | | | 1649 | $M_{44}$ | $X_1$ | | | | | |
| 146 | $G_{51}$ | | | | | | | | | | | | | | | 1650 | $S_{43}$ | $A_1$ | | | | | |
| 147 | $A_{50}$ | $R_1$ | | | | | | | | | | | | | | 1651 | $A_{44}$ | | | | | | |
| 148 | $A_{51}$ | | | | | | | | | | | | | | | 1652 | $D_{44}$ | | | | | | |
| 149 | $R_{49}$ | $K_2$ | | | | | | | | | | | | | | 1653 | $L_{44}$ | | | | | | |
| 150 | $A_{51}$ | | | | | | | | | | | | | | | 1654 | $E_{42}$ | $X_2$ | | | | | |
| 151 | $L_{51}$ | | | | | | | | | | | | | | | 1655 | $V_{41}$ | $I_3$ | | | | | |
| 152 | $A_{51}$ | | | | | | | | | | | | | | | 1656 | $V_{43}$ | $T_1$ | | | | | |
| 153 | $H_{51}$ | | | | | | | | | | | | | | | 1657 | $T_{43}$ | $X_1$ | | | | | |
| 154 | $G_{50}$ | $X_1$ | | | | | | | | | | | | | | 1658 | $S_{44}$ | | | | | | |
| 155 | $V_{51}$ | | | | | | | | | | | | | | | 1659 | $T_{44}$ | | | | | | |
| 156 | $R_{51}$ | | | | | | | | | | | | | | | 1660 | $W_{44}$ | | | | | | |
| 157 | $V_{51}$ | | | | | | | | | | | | | | | 1661 | $V_{44}$ | | | | | | |
| 158 | $L_{51}$ | | | | | | | | | | | | | | | 1662 | $L_{43}$ | $X_1$ | | | | | |
| 159 | $E_{51}$ | | | | | | | | | | | | | | | 1663 | $V_{44}$ | | | | | | |
| 160 | $D_{51}$ | | | | | | | | | | | | | | | 1664 | $G_{44}$ | | | | | | |
| 161 | $G_{50}$ | $S_1$ | | | | | | | | | | | | | | 1665 | $G_{44}$ | | | | | | |
| 162 | $V_{51}$ | | | | | | | | | | | | | | | 1666 | $V_{44}$ | | | | | | |
| 163 | $N_{51}$ | | | | | | | | | | | | | | | 1667 | $L_{44}$ | | | | | | |
| 164 | $Y_{51}$ | | | | | | | | | | | | | | | 1668 | $A_{44}$ | | | | | | |
| 165 | $A_{51}$ | | | | | | | | | | | | | | | 1669 | $A_{44}$ | | | | | | |
| 166 | $T_{51}$ | | | | | | | | | | | | | | | 1670 | $L_{44}$ | | | | | | |
| 167 | $G_{51}$ | | | | | | | | | | | | | | | 1671 | $A_{43}$ | $X_1$ | | | | | |
| 168 | $N_{51}$ | | | | | | | | | | | | | | | 1672 | $A_{44}$ | | | | | | |
| 169 | $L_{51}$ | | | | | | | | | | | | | | | 1673 | $Y_{44}$ | | | | | | |
| 170 | $P_{51}$ | | | | | | | | | | | | | | | 1674 | $C_{44}$ | | | | | | |
| 171 | $G_{51}$ | | | | | | | | | | | | | | | 1675 | $L_{44}$ | | | | | | |
| 172 | $C_{52}$ | | | | | | | | | | | | | | | 1676 | $S_{44}$ | | | | | | |
| 173 | $S_{52}$ | | | | | | | | | | | | | | | 1677 | $T_{43}$ | $X_1$ | | | | | |
| 174 | $F_{51}$ | $X_1$ | | | | | | | | | | | | | | 1678 | $G_{44}$ | | | | | | |
| 175 | $S_{51}$ | | | | | | | | | | | | | | | 1679 | $C_{43}$ | $S_1$ | | | | | |

TABLE 5-continued

HCV 1a Consensus Sequences

| | A | B | C | D | E | F | G | H | I | J | K | L | M | N | O | | P | Q | R | S | T | U | V | W |
|---|---|---|---|---|---|---|---|---|---|---|---|---|---|---|---|---|---|---|---|---|---|---|---|---|
| 176 | $I_{49}$ | $X_{12}$ | $M_1$ | $L_1$ | | | | | | | | | | | | 1680 | $V_{44}$ | | | | | | | |
| 177 | $F_{72}$ | | | | | | | | | | | | | | | 1681 | $V_{44}$ | | | | | | | |
| 178 | $L_{72}$ | $X_1$ | | | | | | | | | | | | | | 1682 | $I_{44}$ | | | | | | | |
| 179 | $L_{73}$ | $X_1$ | | | | | | | | | | | | | | 1683 | $V_{43}$ | $I_1$ | | | | | | |
| 180 | $A_{74}$ | $X_5$ | | | | | | | | | | | | | | 1684 | $G_{44}$ | | | | | | | |
| 181 | $L_{79}$ | | | | | | | | | | | | | | | 1685 | $R_{44}$ | | | | | | | |
| 182 | $L_{78}$ | $F_1$ | | | | | | | | | | | | | | 1686 | $I_{25}$ | $V_{18}$ | $X_1$ | | | | | |
| 183 | $S_{80}$ | | | | | | | | | | | | | | | 1687 | $V_{40}$ | $I_2$ | $D_1$ | $X_1$ | | | | |
| 184 | $C_{80}$ | | | | | | | | | | | | | | | 1688 | $L_{44}$ | | | | | | | |
| 185 | $L_{80}$ | | | | | | | | | | | | | | | 1689 | $S_{44}$ | | | | | | | |
| 186 | $T_{78}$ | $A_1$ | $I_1$ | | | | | | | | | | | | | 1690 | $G_{44}$ | | | | | | | |
| 187 | $V_{79}$ | $I_1$ | $X_1$ | | | | | | | | | | | | | 1691 | $K_{44}$ | | | | | | | |
| 188 | $P_{81}$ | | | | | | | | | | | | | | | 1692 | $P_{44}$ | | | | | | | |
| 189 | $A_{80}$ | $T_1$ | | | | | | | | | | | | | | 1693 | $A_{43}$ | $P_1$ | | | | | | |
| 190 | $S_{80}$ | $W_1$ | | | | | | | | | | | | | | 1694 | $I_{34}$ | $V_7$ | $X_3$ | | | | | |
| 191 | $A_{80}$ | $P_1$ | | | | | | | | | | | | | | 1695 | $I_{43}$ | $V_1$ | | | | | | |
| 192 | $Y_{88}$ | $H_6$ | $F_1$ | | | | | | | | | | | | | 1696 | $P_{44}$ | | | | | | | |
| 193 | $Q_{89}$ | $H_3$ | $E_3$ | | | | | | | | | | | | | 1697 | $D_{44}$ | | | | | | | |
| 194 | $V_{95}$ | | | | | | | | | | | | | | | 1698 | $R_{42}$ | $Q_1$ | $X_1$ | | | | | |
| 195 | $R_{95}$ | | | | | | | | | | | | | | | 1699 | $E_{43}$ | | | | | | | |
| 196 | $N_{93}$ | | | | | | | | | | | | | | | 1700 | $V_{43}$ | $A_1$ | | | | | | |
| 197 | $S_{91}$ | $T_1$ | $A_1$ | | | | | | | | | | | | | 1701 | $L_{44}$ | | | | | | | |
| 198 | $S_{48}$ | $T_{44}$ | $L_1$ | | | | | | | | | | | | | 1702 | $Y_{43}$ | $X_1$ | | | | | | |
| 199 | $G_{93}$ | | | | | | | | | | | | | | | 1703 | $R_{30}$ | $Q_{14}$ | | | | | | |
| 200 | $L_{87}$ | $I_4$ | $F_1$ | $S_1$ | | | | | | | | | | | | 1704 | $E_{42}$ | $G_2$ | | | | | | |
| 201 | $Y_{93}$ | | | | | | | | | | | | | | | 1705 | $F_{44}$ | | | | | | | |
| 202 | $H_{93}$ | | | | | | | | | | | | | | | 1706 | $D_{44}$ | | | | | | | |
| 203 | $V_{93}$ | $X_1$ | | | | | | | | | | | | | | 1707 | $E_{44}$ | | | | | | | |
| 204 | $T_{94}$ | | | | | | | | | | | | | | | 1708 | $M_{44}$ | | | | | | | |
| 205 | $N_{93}$ | $X_1$ | | | | | | | | | | | | | | 1709 | $E_{44}$ | | | | | | | |
| 206 | $D_{92}$ | $H_2$ | | | | | | | | | | | | | | 1710 | $E_{44}$ | | | | | | | |
| 207 | $C_{94}$ | | | | | | | | | | | | | | | 1711 | $C_{44}$ | | | | | | | |
| 208 | $P_{92}$ | $S_1$ | $L_1$ | | | | | | | | | | | | | 1712 | $S_{44}$ | | | | | | | |
| 209 | $N_{94}$ | | | | | | | | | | | | | | | 1713 | $Q_{44}$ | | | | | | | |
| 210 | $S_{94}$ | | | | | | | | | | | | | | | 1714 | $H_{44}$ | | | | | | | |
| 211 | $S_{93}$ | $G_1$ | | | | | | | | | | | | | | 1715 | $L_{44}$ | | | | | | | |
| 212 | $I_{93}$ | $V_1$ | | | | | | | | | | | | | | 1716 | $P_{43}$ | $X_1$ | | | | | | |
| 213 | $V_{94}$ | | | | | | | | | | | | | | | 1717 | $Y_{44}$ | | | | | | | |
| 214 | $Y_{92}$ | $F_2$ | | | | | | | | | | | | | | 1718 | $I_{44}$ | | | | | | | |
| 215 | $E_{94}$ | | | | | | | | | | | | | | | 1719 | $E_{44}$ | | | | | | | |
| 216 | $A_{52}$ | $T_{41}$ | $V_1$ | | | | | | | | | | | | | 1720 | $Q_{43}$ | $P_1$ | | | | | | |
| 217 | $A_{67}$ | $D_{14}$ | $T_5$ | $V_2$ | | $S_2$ | $H_1$ | $P_1$ | $N_1$ | $G_1$ | | | | | | 1721 | $G_{44}$ | | | | | | | |
| 218 | $D_{90}$ | $N_3$ | $G_1$ | | | | | | | | | | | | | 1722 | $M_{44}$ | | | | | | | |
| 219 | $A_{65}$ | $T_{27}$ | $V_1$ | $S_1$ | | | | | | | | | | | | 1723 | $M_{40}$ | $A_2$ | $V_1$ | $X_1$ | | | | |
| 220 | $I_{94}$ | | | | | | | | | | | | | | | 1724 | $L_{43}$ | $X_1$ | | | | | | |
| 221 | $L_{93}$ | $M_1$ | | | | | | | | | | | | | | 1725 | $A_{43}$ | $X_1$ | | | | | | |
| 222 | $H_{94}$ | | | | | | | | | | | | | | | 1726 | $E_{43}$ | $X_1$ | | | | | | |
| 223 | $T_{52}$ | $S_{31}$ | $A_9$ | $I_1$ | $V_1$ | | | | | | | | | | | 1727 | $Q_{44}$ | | | | | | | |
| 224 | $P_{94}$ | | | | | | | | | | | | | | | 1728 | $F_{44}$ | | | | | | | |
| 225 | $G_{94}$ | | | | | | | | | | | | | | | 1729 | $K_{44}$ | | | | | | | |
| 226 | $C_{94}$ | | | | | | | | | | | | | | | 1730 | $Q_{44}$ | | | | | | | |
| 227 | $V_{89}$ | $I_3$ | $F_1$ | $L_1$ | | | | | | | | | | | | 1731 | $K_{43}$ | $X_1$ | | | | | | |
| 228 | $P_{94}$ | | | | | | | | | | | | | | | 1732 | $A_{44}$ | | | | | | | |
| 229 | $C_{94}$ | | | | | | | | | | | | | | | 1733 | $L_{41}$ | $X_3$ | | | | | | |
| 230 | $V_{92}$ | $X_1$ | $A_1$ | | | | | | | | | | | | | 1734 | $G_{42}$ | $A_1$ | $X_1$ | | | | | |
| 231 | $R_{86}$ | $H_5$ | $C_1$ | $G_1$ | $Y_1$ | | | | | | | | | | | 1735 | $L_{44}$ | | | | | | | |
| 232 | $E_{91}$ | $K_2$ | $G_1$ | | | | | | | | | | | | | 1736 | $L_{44}$ | | | | | | | |
| 233 | $G_{90}$ | $D_3$ | $S_1$ | | | | | | | | | | | | | 1737 | $Q_{44}$ | | | | | | | |
| 234 | $N_{90}$ | $D_3$ | $S_1$ | | | | | | | | | | | | | 1738 | $T_{43}$ | $X_1$ | | | | | | |
| 235 | $A_{55}$ | $T_{15}$ | $V_{13}$ | $I_4$ | $S_2$ | $D_2$ | $L_1$ | $X_1$ | $G_1$ | | | | | | | 1739 | $A_{43}$ | $R_1$ | | | | | | |
| 236 | $S_{91}$ | $P_2$ | $A_1$ | | | | | | | | | | | | | 1740 | $S_{44}$ | | | | | | | |
| 237 | $R_{64}$ | $K_{29}$ | $T_1$ | | | | | | | | | | | | | 1741 | $R_{39}$ | $H_3$ | $X_2$ | | | | | |
| 238 | $C_{94}$ | | | | | | | | | | | | | | | 1742 | $Q_{42}$ | $H_2$ | | | | | | |
| 239 | $W_{94}$ | | | | | | | | | | | | | | | 1743 | $A_{43}$ | $X_1$ | | | | | | |
| 240 | $V_{93}$ | $A_1$ | | | | | | | | | | | | | | 1744 | $E_{44}$ | | | | | | | |
| 241 | $A_{87}$ | $P_5$ | $T_1$ | $S_1$ | | | | | | | | | | | | 1745 | $V_{37}$ | $A_3$ | $X_3$ | $T_1$ | | | | |
| 242 | $V_{54}$ | $M_{28}$ | $L_8$ | $I_4$ | | | | | | | | | | | | 1746 | $I_{41}$ | $V_1$ | $X_1$ | | | | | |
| 243 | $T_{62}$ | $A_{32}$ | | | | | | | | | | | | | | 1747 | $A_{25}$ | $T_{15}$ | $G_2$ | $X_1$ | | | | |
| 244 | $P_{93}$ | $S_1$ | | | | | | | | | | | | | | 1748 | $P_{42}$ | $X_1$ | | | | | | |
| 245 | $T_{92}$ | $S_2$ | | | | | | | | | | | | | | 1749 | $A_{38}$ | $V_3$ | $T_2$ | | | | | |
| 246 | $V_{93}$ | $L_1$ | | | | | | | | | | | | | | 1750 | $V_{43}$ | | | | | | | |
| 247 | $A_{94}$ | | | | | | | | | | | | | | | 1751 | $Q_{43}$ | | | | | | | |
| 248 | $T_{93}$ | $A_1$ | | | | | | | | | | | | | | 1752 | $T_{43}$ | | | | | | | |
| 249 | $R_{86}$ | $K_8$ | | | | | | | | | | | | | | 1753 | $N_{41}$ | $S_2$ | | | | | | |
| 250 | $D_{92}$ | $N_2$ | | | | | | | | | | | | | | 1754 | $W_{42}$ | $R_1$ | | | | | | |
| 251 | $G_{93}$ | $A_1$ | | | | | | | | | | | | | | 1755 | $Q_{42}$ | $X_1$ | | | | | | |

TABLE 5-continued

HCV 1a Consensus Sequences

| | A | B | C | D | E | F | G | H | I | J | K | L | M | N | O | | P | Q | R | S | T | U | V | W |
|---|---|---|---|---|---|---|---|---|---|---|---|---|---|---|---|---|---|---|---|---|---|---|---|---|
| 252 | $K_{75}$ | $R_{13}$ | $S_2$ | $N_2$ | $T_1$ | $X_1$ | | | | | | | | | | 1756 | $K_{34}$ | $R_7$ | $N_1$ | $X_1$ | | | | |
| 253 | $L_{92}$ | $I_1$ | $V_1$ | | | | | | | | | | | | | 1757 | $L_{42}$ | $I_1$ | | | | | | |
| 254 | $P_{93}$ | $H_1$ | | | | | | | | | | | | | | 1758 | $E_{39}$ | $V_1$ | $X_1$ | | | | | |
| 255 | $T_{77}$ | $A_{15}$ | $S_1$ | $I_1$ | | | | | | | | | | | | 1759 | $A_{21}$ | $T_{11}$ | $V_6$ | $X_2$ | $F_1$ | $S_1$ | $L_1$ |
| 256 | $T_{86}$ | $A_5$ | $K_2$ | $M_1$ | | | | | | | | | | | | 1760 | $F_{37}$ | $G_2$ | $V_1$ | $L_1$ | $I_1$ | $X_1$ | | |
| 257 | $Q_{93}$ | $T_1$ | | | | | | | | | | | | | | 1761 | $W_{37}$ | $G_6$ | $X_1$ | | | | | |
| 258 | $L_{92}$ | $I_1$ | $M_1$ | | | | | | | | | | | | | 1762 | $A_{41}$ | $G_2$ | $K_1$ | | | | | |
| 259 | $R_{94}$ | | | | | | | | | | | | | | | 1763 | $K_{43}$ | $X_2$ | $M_1$ | | | | | |
| 260 | $R_{93}$ | $Q_1$ | | | | | | | | | | | | | | 1764 | $H_{42}$ | $N_2$ | $K_2$ | | | | | |
| 261 | $H_{92}$ | $X_1$ | $Y_1$ | | | | | | | | | | | | | 1765 | $X_{27}$ | $M_{19}$ | | | | | | |
| 262 | $I_{93}$ | $V_1$ | | | | | | | | | | | | | | 1766 | $W_{18}$ | $X_1$ | | | | | | |
| 263 | $D_{94}$ | | | | | | | | | | | | | | | 1767 | $N_{18}$ | | | | | | | |
| 264 | $L_{93}$ | $X_1$ | | | | | | | | | | | | | | 1768 | $F_{17}$ | $X_1$ | | | | | | |
| 265 | $L_{93}$ | $X_1$ | | | | | | | | | | | | | | 1769 | $I_{16}$ | $X_1$ | | | | | | |
| 266 | $V_{93}$ | $G_1$ | | | | | | | | | | | | | | 1770 | $S_{17}$ | | | | | | | |
| 267 | $G_{93}$ | $R_1$ | | | | | | | | | | | | | | 1771 | $G_{17}$ | | | | | | | |
| 268 | $S_{75}$ | $G_{16}$ | $A_2$ | $X_1$ | | | | | | | | | | | | 1772 | $I_{17}$ | | | | | | | |
| 269 | $A_{94}$ | | | | | | | | | | | | | | | 1773 | $Q_{17}$ | | | | | | | |
| 270 | $T_{92}$ | $A_2$ | | | | | | | | | | | | | | 1774 | $Y_{17}$ | | | | | | | |
| 271 | $L_{91}$ | $F_2$ | $I_1$ | | | | | | | | | | | | | 1775 | $L_{17}$ | | | | | | | |
| 272 | $C_{94}$ | | | | | | | | | | | | | | | 1776 | $A_{17}$ | | | | | | | |
| 273 | $S_{94}$ | | | | | | | | | | | | | | | 1777 | $G_{17}$ | | | | | | | |
| 274 | $A_{92}$ | $T_2$ | | | | | | | | | | | | | | 1778 | $L_{17}$ | | | | | | | |
| 275 | $L_{93}$ | $M_1$ | | | | | | | | | | | | | | 1779 | $S_{17}$ | | | | | | | |
| 276 | $Y_{97}$ | | | | | | | | | | | | | | | 1780 | $T_{17}$ | | | | | | | |
| 277 | $V_{97}$ | | | | | | | | | | | | | | | 1781 | $L_{17}$ | | | | | | | |
| 278 | $G_{97}$ | | | | | | | | | | | | | | | 1782 | $P_{16}$ | $A_1$ | | | | | | |
| 279 | $D_{96}$ | $E_1$ | | | | | | | | | | | | | | 1783 | $G_{17}$ | | | | | | | |
| 280 | $L_{97}$ | | | | | | | | | | | | | | | 1784 | $N_{17}$ | | | | | | | |
| 281 | $C_{97}$ | | | | | | | | | | | | | | | 1785 | $P_{17}$ | | | | | | | |
| 282 | $G_{97}$ | | | | | | | | | | | | | | | 1786 | $A_{17}$ | | | | | | | |
| 283 | $S_{97}$ | | | | | | | | | | | | | | | 1787 | $I_{14}$ | $X_3$ | | | | | | |
| 284 | $V_{92}$ | $I_5$ | | | | | | | | | | | | | | 1788 | $A_{14}$ | | | | | | | |
| 285 | $F_{95}$ | $L_2$ | | | | | | | | | | | | | | 1789 | $S_{14}$ | | | | | | | |
| 286 | $L_{97}$ | | | | | | | | | | | | | | | 1790 | $L_{14}$ | | | | | | | |
| 287 | $V_{93}$ | $I_3$ | $L_1$ | | | | | | | | | | | | | 1791 | $M_{14}$ | | | | | | | |
| 288 | $G_{91}$ | $S_5$ | $D_1$ | | | | | | | | | | | | | 1792 | $A_{14}$ | | | | | | | |
| 289 | $Q_{97}$ | | | | | | | | | | | | | | | 1793 | $F_{14}$ | | | | | | | |
| 290 | $L_{95}$ | $M_2$ | | | | | | | | | | | | | | 1794 | $T_{14}$ | | | | | | | |
| 291 | $F_{97}$ | | | | | | | | | | | | | | | 1795 | $A_{14}$ | | | | | | | |
| 292 | $T_{96}$ | $V_1$ | | | | | | | | | | | | | | 1796 | $A_{14}$ | | | | | | | |
| 293 | $F_{92}$ | $L_4$ | $I_1$ | | | | | | | | | | | | | 1797 | $V_{13}$ | $I_1$ | | | | | | |
| 294 | $S_{97}$ | | | | | | | | | | | | | | | 1798 | $T_{14}$ | | | | | | | |
| 295 | $P_{97}$ | | | | | | | | | | | | | | | 1799 | $S_{14}$ | | | | | | | |
| 296 | $R_{95}$ | $G_1$ | $K_1$ | | | | | | | | | | | | | 1800 | $P_{14}$ | | | | | | | |
| 297 | $R_{87}$ | $H_8$ | $L_1$ | $D_1$ | | | | | | | | | | | | 1801 | $L_{14}$ | | | | | | | |
| 298 | $H_{92}$ | $Y_3$ | $R_1$ | $L_1$ | | | | | | | | | | | | 1802 | $T_{14}$ | | | | | | | |
| 299 | $W_{95}$ | $R_1$ | $E_1$ | | | | | | | | | | | | | 1803 | $T_{14}$ | | | | | | | |
| 300 | $T_{95}$ | $Q_1$ | $A_1$ | | | | | | | | | | | | | 1804 | $S_{10}$ | $G_3$ | $N_1$ | | | | | |
| 301 | $T_{94}$ | $V_2$ | $M_1$ | | | | | | | | | | | | | 1805 | $Q_{14}$ | | | | | | | |
| 302 | $Q_{97}$ | | | | | | | | | | | | | | | 1806 | $T_{14}$ | | | | | | | |
| 303 | $D_{65}$ | $G_{23}$ | $E_7$ | $S_1$ | $R_1$ | | | | | | | | | | | 1807 | $L_{14}$ | | | | | | | |
| 304 | $C_{97}$ | | | | | | | | | | | | | | | 1808 | $L_{14}$ | | | | | | | |
| 305 | $N_{97}$ | | | | | | | | | | | | | | | 1809 | $F_{14}$ | | | | | | | |
| 306 | $C_{97}$ | | | | | | | | | | | | | | | 1810 | $N_{14}$ | | | | | | | |
| 307 | $S_{96}$ | $T_1$ | | | | | | | | | | | | | | 1811 | $I_{14}$ | | | | | | | |
| 308 | $I_{83}$ | $M_{10}$ | $L_2$ | $V_2$ | | | | | | | | | | | | 1812 | $L_{14}$ | | | | | | | |
| 309 | $Y_{96}$ | | | | | | | | | | | | | | | 1813 | $G_{14}$ | | | | | | | |
| 310 | $P_{96}$ | | | | | | | | | | | | | | | 1814 | $G_{13}$ | $S_1$ | | | | | | |
| 311 | $G_{95}$ | $S_1$ | | | | | | | | | | | | | | 1815 | $W_{14}$ | | | | | | | |
| 312 | $H_{95}$ | $D_1$ | | | | | | | | | | | | | | 1816 | $V_{14}$ | | | | | | | |
| 313 | $I_{91}$ | $V_4$ | $L_1$ | | | | | | | | | | | | | 1817 | $A_{14}$ | | | | | | | |
| 314 | $T_{94}$ | $G_1$ | $S_1$ | | | | | | | | | | | | | 1818 | $A_{14}$ | | | | | | | |
| 315 | $G_{96}$ | | | | | | | | | | | | | | | 1819 | $Q_{14}$ | | | | | | | |
| 316 | $H_{96}$ | | | | | | | | | | | | | | | 1820 | $L_{14}$ | | | | | | | |
| 317 | $R_{95}$ | $G_1$ | | | | | | | | | | | | | | 1821 | $A_{14}$ | | | | | | | |
| 318 | $M_{109}$ | | | | | | | | | | | | | | | 1822 | $A_{12}$ | $N_1$ | $G_1$ | | | | | |
| 319 | $A_{109}$ | | | | | | | | | | | | | | | 1823 | $P_{14}$ | | | | | | | |
| 320 | $W_{108}$ | | | | | | | | | | | | | | | 1824 | $G_{13}$ | $R_1$ | | | | | | |
| 321 | $D_{108}$ | $X_{19}$ | $N_1$ | | | | | | | | | | | | | 1825 | $A_{14}$ | | | | | | | |
| 322 | $M_{128}$ | | | | | | | | | | | | | | | 1826 | $A_{14}$ | | | | | | | |
| 323 | $M_{133}$ | | | | | | | | | | | | | | | 1827 | $T_{14}$ | | | | | | | |
| 324 | $M_{130}$ | $V_2$ | $T_1$ | | | | | | | | | | | | | 1828 | $A_{14}$ | | | | | | | |
| 325 | $N_{132}$ | $I_1$ | | | | | | | | | | | | | | 1829 | $F_{14}$ | | | | | | | |
| 326 | $W_{134}$ | | | | | | | | | | | | | | | 1830 | $V_{14}$ | | | | | | | |
| 327 | $S_{134}$ | | | | | | | | | | | | | | | 1831 | $G_{14}$ | | | | | | | |

TABLE 5-continued

HCV 1a Consensus Sequences

| | A | B | C | D | E | F | G | H | I | J | K | L | M | N | O | | P | Q | R |
|---|---|---|---|---|---|---|---|---|---|---|---|---|---|---|---|---|---|---|---|
| 328 | P$_{134}$ | L$_2$ | X$_1$ | | | | | | | | | | | | | 1832 | A$_{14}$ | |
| 329 | T$_{136}$ | K$_1$ | | | | | | | | | | | | | | 1833 | G$_{14}$ | |
| 330 | T$_{91}$ | A$_{42}$ | I$_2$ | X$_1$ | V$_1$ | | | | | | | | | | | 1834 | L$_{14}$ | |
| 331 | A$_{138}$ | | | | | | | | | | | | | | | 1835 | A$_{13}$ | T$_1$ |
| 332 | L$_{136}$ | F$_1$ | P$_1$ | | | | | | | | | | | | | 1836 | G$_{14}$ | |
| 333 | V$_{123}$ | I$_{10}$ | L$_5$ | | | | | | | | | | | | | 1837 | A$_{14}$ | |
| 334 | V$_{100}$ | M$_{29}$ | T$_3$ | L$_3$ | A$_2$ | I$_1$ | | | | | | | | | | 1838 | A$_{13}$ | G$_1$ |
| 335 | A$_{132}$ | S$_4$ | V$_1$ | G$_1$ | | | | | | | | | | | | 1839 | I$_{13}$ | V$_1$ |
| 336 | Q$_{138}$ | | | | | | | | | | | | | | | 1840 | G$_{14}$ | |
| 337 | L$_{132}$ | V$_4$ | M$_2$ | | | | | | | | | | | | | 1841 | S$_{13}$ | R$_1$ |
| 338 | L$_{135}$ | I$_1$ | F$_1$ | M$_1$ | | | | | | | | | | | | 1842 | V$_{13}$ | D$_1$ |
| 339 | R$_{138}$ | | | | | | | | | | | | | | | 1843 | G$_{14}$ | |
| 340 | I$_{100}$ | V$_{38}$ | | | | | | | | | | | | | | 1844 | L$_{14}$ | |
| 341 | P$_{138}$ | | | | | | | | | | | | | | | 1845 | G$_{14}$ | |
| 342 | Q$_{137}$ | L$_1$ | | | | | | | | | | | | | | 1846 | K$_{14}$ | |
| 343 | A$_{136}$ | T$_1$ | S$_1$ | | | | | | | | | | | | | 1847 | V$_{14}$ | |
| 344 | I$_{134}$ | V$_3$ | T$_1$ | | | | | | | | | | | | | 1848 | L$_{14}$ | |
| 345 | L$_{104}$ | M$_{26}$ | V$_8$ | | | | | | | | | | | | | 1849 | V$_{13}$ | I$_1$ |
| 346 | D$_{136}$ | N$_2$ | | | | | | | | | | | | | | 1850 | D$_{14}$ | |
| 347 | M$_{138}$ | I$_1$ | | | | | | | | | | | | | | 1851 | I$_{14}$ | |
| 348 | I$_{134}$ | V$_3$ | F$_2$ | | | | | | | | | | | | | 1852 | L$_{14}$ | |
| 349 | A$_{139}$ | | | | | | | | | | | | | | | 1853 | A$_{13}$ | V$_1$ |
| 350 | G$_{138}$ | S$_1$ | | | | | | | | | | | | | | 1854 | G$_{14}$ | |
| 351 | A$_{138}$ | S$_1$ | | | | | | | | | | | | | | 1855 | Y$_{14}$ | |
| 352 | H$_{139}$ | | | | | | | | | | | | | | | 1856 | G$_{14}$ | |
| 353 | W$_{139}$ | | | | | | | | | | | | | | | 1857 | A$_{14}$ | |
| 354 | G$_{139}$ | | | | | | | | | | | | | | | 1858 | G$_{14}$ | |
| 355 | V$_{136}$ | I$_3$ | | | | | | | | | | | | | | 1859 | V$_{14}$ | |
| 356 | L$_{139}$ | | | | | | | | | | | | | | | 1860 | A$_{14}$ | |
| 357 | A$_{139}$ | | | | | | | | | | | | | | | 1861 | G$_{14}$ | |
| 358 | G$_{139}$ | | | | | | | | | | | | | | | 1862 | A$_{14}$ | |
| 359 | I$_{123}$ | V$_7$ | M$_6$ | L$_3$ | | | | | | | | | | | | 1863 | L$_{14}$ | |
| 360 | A$_{134}$ | T$_4$ | G$_1$ | | | | | | | | | | | | | 1864 | V$_{14}$ | |
| 361 | Y$_{139}$ | | | | | | | | | | | | | | | 1865 | A$_{14}$ | |
| 362 | F$_{136}$ | Y$_3$ | | | | | | | | | | | | | | 1866 | F$_{14}$ | |
| 363 | S$_{139}$ | | | | | | | | | | | | | | | 1867 | K$_{14}$ | |
| 364 | M$_{139}$ | | | | | | | | | | | | | | | 1868 | I$_{14}$ | |
| 365 | V$_{133}$ | A$_5$ | L$_1$ | | | | | | | | | | | | | 1869 | M$_{14}$ | |
| 366 | G$_{139}$ | | | | | | | | | | | | | | | 1870 | S$_{14}$ | |
| 367 | N$_{140}$ | | | | | | | | | | | | | | | 1871 | G$_{14}$ | |
| 368 | W$_{140}$ | | | | | | | | | | | | | | | 1872 | E$_{14}$ | |
| 369 | A$_{139}$ | G$_1$ | | | | | | | | | | | | | | 1873 | V$_{13}$ | P$_1$ |
| 370 | K$_{140}$ | | | | | | | | | | | | | | | 1874 | P$_{14}$ | |
| 371 | V$_{139}$ | A$_1$ | | | | | | | | | | | | | | 1875 | S$_{13}$ | T$_1$ |
| 372 | L$_{129}$ | V$_{10}$ | S$_1$ | | | | | | | | | | | | | 1876 | T$_{14}$ | |
| 373 | V$_{127}$ | L$_7$ | I$_3$ | A$_3$ | X$_1$ | | | | | | | | | | | 1877 | E$_{14}$ | |
| 374 | V$_{141}$ | X$_2$ | M$_1$ | | | | | | | | | | | | | 1878 | D$_{14}$ | |
| 375 | L$_{144}$ | M$_1$ | | | | | | | | | | | | | | 1879 | L$_{13}$ | M$_1$ |
| 376 | L$_{145}$ | M$_1$ | | | | | | | | | | | | | | 1880 | V$_{14}$ | |
| 377 | L$_{146}$ | | | | | | | | | | | | | | | 1881 | N$_{14}$ | |
| 378 | F$_{145}$ | V$_1$ | | | | | | | | | | | | | | 1882 | L$_{14}$ | |
| 379 | A$_{142}$ | T$_4$ | | | | | | | | | | | | | | 1883 | L$_{13}$ | X$_1$ |
| 380 | G$_{135}$ | S$_9$ | A$_1$ | X$_1$ | | | | | | | | | | | | 1884 | P$_{14}$ | |
| 381 | V$_{145}$ | I$_1$ | | | | | | | | | | | | | | 1885 | A$_{14}$ | |
| 382 | D$_{146}$ | Q$_1$ | X$_1$ | | | | | | | | | | | | | 1886 | I$_{14}$ | |
| 383 | A$_{145}$ | G$_2$ | R$_1$ | | | | | | | | | | | | | 1887 | L$_{14}$ | |
| 384 | E$_{68}$ | G$_{20}$ | T$_{11}$ | S$_{10}$ | D$_6$ | K$_5$ | N$_5$ | Q$_4$ | A$_3$ | H$_3$ | V$_2$ | R$_2$ | W$_1$ | I$_1$ | | 1888 | S$_{14}$ | |
| 385 | T$_{139}$ | P$_1$ | X$_1$ | | | | | | | | | | | | | 1889 | P$_{14}$ | |
| 386 | H$_{65}$ | Y$_{48}$ | R$_9$ | T$_8$ | V$_2$ | I$_2$ | S$_1$ | M$_1$ | D$_1$ | Q$_1$ | L$_1$ | G$_1$ | X$_1$ | | | 1890 | G$_{14}$ | |
| 387 | V$_{97}$ | T$_{36}$ | I$_4$ | L$_2$ | A$_1$ | R$_1$ | | | | | | | | | | 1891 | A$_{14}$ | |
| 388 | T$_{112}$ | S$_{24}$ | I$_4$ | V$_1$ | | | | | | | | | | | | 1892 | L$_{14}$ | |
| 389 | G$_{141}$ | | | | | | | | | | | | | | | 1893 | V$_{14}$ | |
| 390 | G$_{133}$ | A$_6$ | R$_1$ | D$_1$ | | | | | | | | | | | | 1894 | V$_{14}$ | |
| 391 | S$_{75}$ | A$_{23}$ | T$_{19}$ | N$_9$ | V$_6$ | Q$_5$ | G$_1$ | K$_1$ | H$_1$ | E$_1$ | | | | | | 1895 | G$_{14}$ | |
| 392 | A$_{109}$ | V$_{20}$ | I$_4$ | T$_3$ | P$_2$ | L$_1$ | S$_1$ | X$_1$ | | | | | | | | 1896 | V$_{14}$ | |
| 393 | A$_{88}$ | G$_{49}$ | S$_3$ | V$_1$ | | | | | | | | | | | | 1897 | V$_{14}$ | |
| 394 | R$_{75}$ | H$_{37}$ | Q$_8$ | K$_6$ | Y$_6$ | S$_3$ | F$_2$ | E$_2$ | V$_1$ | N$_1$ | | | | | | 1898 | C$_{13}$ | Y$_1$ |
| 395 | T$_{63}$ | A$_{43}$ | S$_{12}$ | G$_{12}$ | D$_5$ | V$_2$ | N$_2$ | I$_2$ | | | | | | | | 1899 | V$_{14}$ | |
| 396 | T$_{69}$ | A$_{44}$ | V$_{20}$ | M$_4$ | S$_2$ | X$_1$ | I$_1$ | | | | | | | | | 1900 | A$_{13}$ | T$_1$ |
| 397 | S$_{50}$ | A$_{48}$ | L$_{10}$ | Y$_7$ | H$_6$ | Q$_5$ | F$_4$ | R$_3$ | V$_2$ | T$_2$ | N$_2$ | K$_1$ | G$_1$ | | | 1901 | I$_{14}$ | |
| 398 | G$_{97}$ | S$_{11}$ | T$_9$ | R$_9$ | A$_7$ | V$_3$ | I$_3$ | L$_1$ | M$_1$ | | | | | | | 1902 | L$_{13}$ | Q$_1$ |
| 399 | L$_{72}$ | F$_{47}$ | I$_{15}$ | V$_7$ | | | | | | | | | | | | 1903 | G$_{14}$ | |
| 400 | A$_{70}$ | T$_{28}$ | V$_{26}$ | S$_{13}$ | I$_2$ | X$_1$ | N$_1$ | | | | | | | | | 1904 | R$_{14}$ | |
| 401 | G$_{56}$ | S$_{54}$ | R$_{15}$ | N$_6$ | T$_5$ | D$_3$ | A$_1$ | X$_1$ | | | | | | | | 1905 | H$_{14}$ | |
| 402 | L$_{91}$ | F$_{34}$ | I$_{10}$ | M$_3$ | X$_2$ | P$_1$ | | | | | | | | | | 1906 | V$_{14}$ | |
| 403 | F$_{110}$ | L$_{30}$ | S$_1$ | | | | | | | | | | | | | 1907 | G$_{14}$ | |

TABLE 5-continued

HCV 1a Consensus Sequences

| | A | B | C | D | E | F | G | H | I | J | K | L | M | N | O | P | Q | R | S | T | U | V | W |
|---|---|---|---|---|---|---|---|---|---|---|---|---|---|---|---|---|---|---|---|---|---|---|---|
| 404 | $S_{54}$ | $T_{42}$ | $A_{18}$ | $N_{13}$ | $Q_4$ | $D_3$ | $K_3$ | $P_1$ | $E_1$ | $R_1$ | $H_1$ | | | | | 1908 $P_{14}$ | | | | | | | |
| 405 | $P_{84}$ | $Q_{22}$ | $R_{11}$ | $L_7$ | $S_7$ | $T_4$ | $A_3$ | $I_2$ | $V_1$ | | | | | | | 1909 $G_{14}$ | | | | | | | |
| 406 | $G_{141}$ | | | | | | | | | | | | | | | 1910 $E_{14}$ | | | | | | | |
| 407 | $A_{94}$ | $P_{41}$ | $S_6$ | | | | | | | | | | | | | 1911 $G_{14}$ | | | | | | | |
| 408 | $K_{87}$ | $R_{27}$ | $S_{14}$ | $Q_{11}$ | $N_2$ | | | | | | | | | | | 1912 $A_{14}$ | | | | | | | |
| 409 | $Q_{141}$ | | | | | | | | | | | | | | | 1913 $V_{14}$ | | | | | | | |
| 410 | $N_{106}$ | $D_{23}$ | $K_9$ | $H_2$ | $X_1$ | | | | | | | | | | | 1914 $Q_{14}$ | | | | | | | |
| 411 | $I_{107}$ | $V_{32}$ | $L_2$ | | | | | | | | | | | | | 1915 $W_{14}$ | | | | | | | |
| 412 | $Q_{129}$ | $R_8$ | $K_1$ | $H_1$ | | | | | | | | | | | | 1916 $M_{14}$ | | | | | | | |
| 413 | $L_{140}$ | | | | | | | | | | | | | | | 1917 $N_{14}$ | | | | | | | |
| 414 | $I_{107}$ | $V_{29}$ | $T_2$ | $M_2$ | | | | | | | | | | | | 1918 $R_{14}$ | | | | | | | |
| 415 | $N_{136}$ | $K_3$ | $Y_1$ | | | | | | | | | | | | | 1919 $L_{13}$ | $M_1$ | | | | | | |
| 416 | $T_{113}$ | $S_{23}$ | $A_4$ | | | | | | | | | | | | | 1920 $I_{14}$ | | | | | | | |
| 417 | $N_{136}$ | $D_2$ | $E_1$ | $S_1$ | | | | | | | | | | | | 1921 $A_{14}$ | | | | | | | |
| 418 | $G_{140}$ | | | | | | | | | | | | | | | 1922 $F_{14}$ | | | | | | | |
| 419 | $S_{140}$ | | | | | | | | | | | | | | | 1923 $A_{13}$ | $T_1$ | | | | | | |
| 420 | $W_{140}$ | | | | | | | | | | | | | | | 1924 $S_{14}$ | | | | | | | |
| 421 | $H_{140}$ | | | | | | | | | | | | | | | 1925 $R_{14}$ | | | | | | | |
| 422 | $I_{139}$ | $V_1$ | | | | | | | | | | | | | | 1926 $G_{14}$ | | | | | | | |
| 423 | $N_{138}$ | $D_1$ | $X_1$ | | | | | | | | | | | | | 1927 $N_{13}$ | $G_1$ | | | | | | |
| 424 | $R_{81}$ | $S_{59}$ | | | | | | | | | | | | | | 1928 $H_{13}$ | $X_1$ | | | | | | |
| 425 | $T_{138}$ | $A_1$ | $S_1$ | | | | | | | | | | | | | 1929 $V_{14}$ | | | | | | | |
| 426 | $A_{140}$ | | | | | | | | | | | | | | | 1930 $S_{14}$ | | | | | | | |
| 427 | $L_{140}$ | | | | | | | | | | | | | | | 1931 $P_{14}$ | | | | | | | |
| 428 | $N_{140}$ | | | | | | | | | | | | | | | 1932 $T_{14}$ | | | | | | | |
| 429 | $C_{140}$ | | | | | | | | | | | | | | | 1933 $H_{14}$ | | | | | | | |
| 430 | $N_{137}$ | $S_2$ | $D_1$ | | | | | | | | | | | | | 1934 $Y_{14}$ | | | | | | | |
| 431 | $D_{70}$ | $A_{48}$ | $E_{20}$ | $T_1$ | $S_1$ | | | | | | | | | | | 1935 $V_{14}$ | | | | | | | |
| 432 | $S_{137}$ | $N_2$ | $T_1$ | | | | | | | | | | | | | 1936 $P_{14}$ | | | | | | | |
| 433 | $L_{136}$ | $H_2$ | $I_2$ | | | | | | | | | | | | | 1937 $E_{14}$ | | | | | | | |
| 434 | $N_{59}$ | $D_{41}$ | $E_{12}$ | $T_9$ | $H_9$ | $Q_4$ | $S_3$ | $Y_1$ | $K_1$ | $X_1$ | | | | | | 1938 $S_{13}$ | $N_1$ | | | | | | |
| 435 | $T_{135}$ | $A_4$ | $S_1$ | | | | | | | | | | | | | 1939 $D_{14}$ | | | | | | | |
| 436 | $G_{140}$ | | | | | | | | | | | | | | | 1940 $A_{13}$ | $T_1$ | | | | | | |
| 437 | $W_{128}$ | $F_{12}$ | | | | | | | | | | | | | | 1941 $A_{14}$ | | | | | | | |
| 438 | $I_{49}$ | $L_{44}$ | $V_{39}$ | $M_4$ | | | | | | | | | | | | 1942 $A_{13}$ | | | | | | | |
| 439 | $A_{129}$ | $T_4$ | $V_2$ | $G_1$ | | | | | | | | | | | | 1943 $R_{13}$ | | | | | | | |
| 440 | $G_{129}$ | $S_3$ | $R_2$ | $A_2$ | | | | | | | | | | | | 1944 $V_{13}$ | | | | | | | |
| 441 | $L_{135}$ | $P_1$ | | | | | | | | | | | | | | 1945 $T_{13}$ | | | | | | | |
| 442 | $F_{95}$ | $L_{26}$ | $I_{11}$ | $S_1$ | $M_1$ | $X_1$ | $V_1$ | | | | | | | | | 1946 $A_{10}$ | $T_2$ | $V_1$ | | | | | |
| 443 | $Y_{132}$ | $H_4$ | | | | | | | | | | | | | | 1947 $I_{13}$ | | | | | | | |
| 444 | $Y_{70}$ | $H_{40}$ | $R_8$ | $S_4$ | $Q_4$ | $N_3$ | $V_2$ | $F_2$ | $P_1$ | $T_1$ | $A_1$ | | | | | 1948 $L_{13}$ | | | | | | | |
| 445 | $H_{82}$ | $N_{37}$ | $Y_9$ | $D_2$ | $R_2$ | $S_1$ | $K_1$ | $T_1$ | $L_1$ | | | | | | | 1949 $L_{11}$ | $G_2$ | | | | | | |
| 446 | $K_{107}$ | $R_{13}$ | $Q_5$ | $N_3$ | $H_3$ | $S_2$ | $G_2$ | $T_1$ | | | | | | | | 1950 $S_{13}$ | | | | | | | |
| 447 | $F_{136}$ | | | | | | | | | | | | | | | 1951 $L_{13}$ | | | | | | | |
| 448 | $N_{132}$ | $D_3$ | $K_1$ | | | | | | | | | | | | | 1952 $T_{12}$ | | | | | | | |
| 449 | $S_{130}$ | $F_2$ | $D_2$ | $A_2$ | | | | | | | | | | | | 1953 $V_{12}$ | | | | | | | |
| 450 | $S_{125}$ | $T_{11}$ | $X_1$ | | | | | | | | | | | | | 1954 $T_{11}$ | $N_1$ | | | | | | |
| 451 | $G_{137}$ | | | | | | | | | | | | | | | 1955 $Q_9$ | $X_2$ | $K_1$ | | | | | |
| 452 | $C_{137}$ | | | | | | | | | | | | | | | 1956 $L_9$ | $P_2$ | | | | | | |
| 453 | $P_{111}$ | $S_{15}$ | $T_3$ | $A_3$ | $L_2$ | $F_1$ | $R_1$ | $V_1$ | | | | | | | | 1957 $L_{11}$ | | | | | | | |
| 454 | $E_{134}$ | $Q_1$ | $G_1$ | $A_1$ | | | | | | | | | | | | 1958 $R_9$ | $X_2$ | | | | | | |
| 455 | $R_{135}$ | $M_1$ | $G_1$ | | | | | | | | | | | | | 1959 $R_8$ | $X_1$ | $G_1$ | | | | | |
| 456 | $L_{81}$ | $M_{54}$ | $S_1$ | $V_1$ | | | | | | | | | | | | 1960 $L_8$ | | | | | | | |
| 457 | $A_{134}$ | $S_2$ | $T_1$ | | | | | | | | | | | | | 1961 $H_8$ | | | | | | | |
| 458 | $S_{135}$ | $G_1$ | $T_1$ | | | | | | | | | | | | | 1962 $Q_8$ | | | | | | | |
| 459 | $C_{133}$ | $S_1$ | $X_1$ | $R_1$ | $Y_1$ | | | | | | | | | | | 1963 $W_8$ | | | | | | | |
| 460 | $R_{118}$ | $K_{12}$ | $Q_3$ | $X_1$ | $H_1$ | $L_1$ | | | | | | | | | | 1964 $I_6$ | $V_2$ | | | | | | |
| 461 | $P_{96}$ | $R_{28}$ | $S_6$ | $L_2$ | $X_1$ | $N_1$ | | | | | | | | | | 1965 $S_8$ | | | | | | | |
| 462 | $L_{124}$ | $I_4$ | $F_3$ | $V_1$ | | | | | | | | | | | | 1966 $S_8$ | | | | | | | |
| 463 | $T_{79}$ | $A_{49}$ | $S_2$ | $I_1$ | $D_1$ | | | | | | | | | | | 1967 $E_8$ | | | | | | | |
| 464 | $D_{111}$ | $Y_5$ | $N_4$ | $H_4$ | $A_3$ | $S_2$ | $R_1$ | $T_1$ | $G_1$ | | | | | | | 1968 $C_7$ | $S_1$ | | | | | | |
| 465 | $F_{128}$ | $L_2$ | $Y_2$ | | | | | | | | | | | | | 1969 $T_8$ | | | | | | | |
| 466 | $D_{69}$ | $A_{60}$ | $V_1$ | $S_1$ | $G_1$ | | | | | | | | | | | 1970 $S_{10}$ | $T_8$ | | | | | | |
| 467 | $Q_{132}$ | | | | | | | | | | | | | | | 1971 $M_{10}$ | $P_8$ | | | | | | |
| 468 | $G_{132}$ | | | | | | | | | | | | | | | 1972 $G_{10}$ | $C_8$ | $M_3$ | | | | | |
| 469 | $W_{130}$ | $S_1$ | $R_1$ | | | | | | | | | | | | | 1973 $S_{22}$ | $A_3$ | | | | | | |
| 470 | $G_{131}$ | $X_1$ | | | | | | | | | | | | | | 1974 $G_{25}$ | | | | | | | |
| 471 | $P_{131}$ | $L_1$ | | | | | | | | | | | | | | 1975 $S_{25}$ | | | | | | | |
| 472 | $I_{131}$ | $M_1$ | | | | | | | | | | | | | | 1976 $W_{25}$ | | | | | | | |
| 473 | $S_{99}$ | $G_{12}$ | $R_7$ | $T_6$ | $N_2$ | $I_2$ | $X_1$ | $D_1$ | $K_1$ | $E_1$ | | | | | | 1977 $L_{25}$ | $I_1$ | | | | | | |
| 474 | $Y_{84}$ | $H_{47}$ | $F_1$ | | | | | | | | | | | | | 1978 $R_{26}$ | | | | | | | |
| 475 | $A_{99}$ | $T_{21}$ | $V_8$ | $G_2$ | $N_1$ | $I_1$ | | | | | | | | | | 1979 $D_{26}$ | | | | | | | |
| 476 | $N_{110}$ | $D_{17}$ | $T_2$ | $E_2$ | $Y_1$ | | | | | | | | | | | 1980 $I_{26}$ | | | | | | | |
| 477 | $G_{125}$ | $T_2$ | $V_1$ | $R_1$ | $P_1$ | $I_1$ | $Q_1$ | | | | | | | | | 1981 $W_{26}$ | | | | | | | |
| 478 | $S_{111}$ | $G_9$ | $T_7$ | $N_4$ | $D_1$ | | | | | | | | | | | 1982 $D_{26}$ | | | | | | | |
| 479 | $G_{124}$ | $D_3$ | $S_2$ | $N_1$ | $R_1$ | $E_1$ | | | | | | | | | | 1983 $W_{26}$ | | | | | | | |

TABLE 5-continued

HCV 1a Consensus Sequences

| | A | B | C | D | E | F | G | H | I | J | K | L | M | N | O | | P | Q | R | S | T | U | V | W |
|---|---|---|---|---|---|---|---|---|---|---|---|---|---|---|---|---|---|---|---|---|---|---|---|---|
| 480 | $P_{110}$ | $S_{11}$ | $L_8$ | $F_1$ | $R_1$ | $A_1$ | | | | | | | | | | 1984 | $I_{26}$ | | | | | | | |
| 481 | $D_{87}$ | $E_{40}$ | $A_2$ | $G_2$ | $K_1$ | | | | | | | | | | | 1985 | $C_{47}$ | | | | | | | |
| 482 | $Q_{57}$ | $H_{53}$ | $E_{21}$ | $G_1$ | | | | | | | | | | | | 1986 | $E_{47}$ | | | | | | | |
| 483 | $R_{132}$ | | | | | | | | | | | | | | | 1987 | $V_{47}$ | | | | | | | |
| 484 | $P_{132}$ | | | | | | | | | | | | | | | 1988 | $L_{46}$ | $V_1$ | | | | | | |
| 485 | $Y_{131}$ | $H_1$ | | | | | | | | | | | | | | 1989 | $S_{46}$ | $C_1$ | | | | | | |
| 486 | $C_{132}$ | | | | | | | | | | | | | | | 1990 | $D_{47}$ | | | | | | | |
| 487 | $W_{131}$ | | | | | | | | | | | | | | | 1991 | $F_{47}$ | | | | | | | |
| 488 | $H_{132}$ | | | | | | | | | | | | | | | 1992 | $K_{46}$ | $E_1$ | | | | | | |
| 489 | $Y_{130}$ | $C_1$ | $H_1$ | | | | | | | | | | | | | 1993 | $T_{47}$ | | | | | | | |
| 490 | $P_{103}$ | $T_{16}$ | $S_6$ | $A_6$ | $X_1$ | | | | | | | | | | | 1994 | $W_{47}$ | | | | | | | |
| 491 | $P_{111}$ | $X_{20}$ | $T_1$ | | | | | | | | | | | | | 1995 | $L_{26}$ | $X_{21}$ | | | | | | |
| 492 | $K_{77}$ | $R_{35}$ | $L_1$ | | | | | | | | | | | | | 1996 | $K_{47}$ | | | | | | | |
| 493 | $P_{109}$ | $R_1$ | $L_1$ | $S_1$ | | | | | | | | | | | | 1997 | $A_{47}$ | | | | | | | |
| 494 | $C_{110}$ | $W_1$ | $S_1$ | | | | | | | | | | | | | 1998 | $K_{46}$ | $Q_1$ | | | | | | |
| 495 | $G_{111}$ | $D_1$ | | | | | | | | | | | | | | 1999 | $L_{47}$ | | | | | | | |
| 496 | $I_{103}$ | $X_5$ | $V_2$ | $F_1$ | $T_1$ | | | | | | | | | | | 2000 | $M_{46}$ | $V_1$ | | | | | | |
| 497 | $V_{102}$ | $E_2$ | $X_1$ | $G_1$ | | | | | | | | | | | | 2001 | $P_{47}$ | | | | | | | |
| 498 | $P_{100}$ | $S_3$ | $X_1$ | $D_1$ | | | | | | | | | | | | 2002 | $Q_{46}$ | $R_1$ | | | | | | |
| 499 | $A_{100}$ | $X_3$ | $T_1$ | | | | | | | | | | | | | 2003 | $L_{47}$ | | | | | | | |
| 500 | $K_{47}$ | $Q_{26}$ | $R_{14}$ | $E_3$ | $L_3$ | $M_2$ | $X_2$ | $G_2$ | $S_1$ | | | | | | | 2004 | $P_{47}$ | | | | | | | |
| 501 | $S_{51}$ | $T_{20}$ | $N_{19}$ | $Q_2$ | $G_2$ | $X_1$ | $R_1$ | $A_1$ | | | | | | | | 2005 | $G_{47}$ | | | | | | | |
| 502 | $V_{93}$ | $D_1$ | $X_1$ | $I_1$ | | | | | | | | | | | | 2006 | $I_{46}$ | $L_1$ | | | | | | |
| 503 | $C_{72}$ | $W_1$ | $X_1$ | | | | | | | | | | | | | 2007 | $P_{47}$ | | | | | | | |
| 504 | $G_{67}$ | $A_1$ | | | | | | | | | | | | | | 2008 | $F_{42}$ | $L_5$ | | | | | | |
| 505 | $P_{65}$ | $R_2$ | $Q_1$ | | | | | | | | | | | | | 2009 | $V_{46}$ | $M_1$ | | | | | | |
| 506 | $V_{65}$ | $X_3$ | | | | | | | | | | | | | | 2010 | $S_{47}$ | | | | | | | |
| 507 | $Y_{58}$ | $F_1$ | $V_1$ | | | | | | | | | | | | | 2011 | $C_{47}$ | | | | | | | |
| 508 | $C_{57}$ | $Y_1$ | $G_1$ | $X_1$ | | | | | | | | | | | | 2012 | $Q_{47}$ | | | | | | | |
| 509 | $F_{53}$ | $X_7$ | | | | | | | | | | | | | | 2013 | $R_{46}$ | $Q_1$ | | | | | | |
| 510 | $T_{52}$ | $A_1$ | | | | | | | | | | | | | | 2014 | $G_{47}$ | | | | | | | |
| 511 | $P_{52}$ | $L_1$ | | | | | | | | | | | | | | 2015 | $Y_{47}$ | | | | | | | |
| 512 | $S_{53}$ | | | | | | | | | | | | | | | 2016 | $R_{33}$ | $K_{14}$ | | | | | | |
| 513 | $P_{53}$ | | | | | | | | | | | | | | | 2017 | $G_{26}$ | $X_{21}$ | | | | | | |
| 514 | $V_{51}$ | | | | | | | | | | | | | | | 2018 | $V_{45}$ | $A_2$ | | | | | | |
| 515 | $V_{48}$ | $A_3$ | | | | | | | | | | | | | | 2019 | $W_{47}$ | | | | | | | |
| 516 | $V_{51}$ | | | | | | | | | | | | | | | 2020 | $R_{46}$ | $Q_1$ | | | | | | |
| 517 | $G_{51}$ | | | | | | | | | | | | | | | 2021 | $G_{44}$ | $V_2$ | $A_1$ | | | | | |
| 518 | $T_{51}$ | | | | | | | | | | | | | | | 2022 | $D_{46}$ | $E_1$ | | | | | | |
| 519 | $T_{51}$ | | | | | | | | | | | | | | | 2023 | $G_{47}$ | | | | | | | |
| 520 | $D_{47}$ | $N_4$ | | | | | | | | | | | | | | 2024 | $I_{43}$ | $V_4$ | | | | | | |
| 521 | $R_{35}$ | $K_{14}$ | $G_1$ | $H_1$ | | | | | | | | | | | | 2025 | $M_{47}$ | | | | | | | |
| 522 | $S_{33}$ | $L_{11}$ | $A_4$ | $F_1$ | $M_1$ | $T_1$ | | | | | | | | | | 2026 | $H_{46}$ | $Y_1$ | | | | | | |
| 523 | $G_{51}$ | | | | | | | | | | | | | | | 2027 | $T_{47}$ | | | | | | | |
| 524 | $A_{38}$ | $V_{11}$ | $M_1$ | $T_1$ | | | | | | | | | | | | 2028 | $R_{46}$ | $H_1$ | | | | | | |
| 525 | $P_{50}$ | $A_1$ | | | | | | | | | | | | | | 2029 | $C_{47}$ | | | | | | | |
| 526 | $T_{51}$ | | | | | | | | | | | | | | | 2030 | $H_{43}$ | $Y_2$ | $N_1$ | $P_1$ | | | | |
| 527 | $Y_{51}$ | | | | | | | | | | | | | | | 2031 | $C_{46}$ | | | | | | | |
| 528 | $N_{32}$ | $S_{15}$ | $R_3$ | $T_1$ | | | | | | | | | | | | 2032 | $G_{46}$ | $Q_1$ | | | | | | |
| 529 | $W_{51}$ | | | | | | | | | | | | | | | 2033 | $A_{46}$ | $T_1$ | | | | | | |
| 530 | $G_{51}$ | | | | | | | | | | | | | | | 2034 | $E_{45}$ | $A_1$ | $D_1$ | | | | | |
| 531 | $E_{24}$ | $A_{15}$ | $S_{10}$ | $V_1$ | $Q_1$ | | | | | | | | | | | 2035 | $I_{46}$ | $G_1$ | | | | | | |
| 532 | $N_{50}$ | $T_1$ | | | | | | | | | | | | | | 2036 | $T_{44}$ | $A_2$ | $S_1$ | | | | | |
| 533 | $D_{39}$ | $E_{11}$ | $R_1$ | | | | | | | | | | | | | 2037 | $G_{47}$ | | | | | | | |
| 534 | $T_{50}$ | $A_1$ | | | | | | | | | | | | | | 2038 | $H_{47}$ | | | | | | | |
| 535 | $D_{51}$ | | | | | | | | | | | | | | | 2039 | $V_{47}$ | | | | | | | |
| 536 | $V_{49}$ | $I_1$ | $F_1$ | | | | | | | | | | | | | 2040 | $K_{29}$ | $X_{18}$ | | | | | | |
| 537 | $F_{44}$ | $L_7$ | | | | | | | | | | | | | | 2041 | $N_{44}$ | $T_2$ | $M_1$ | | | | | |
| 538 | $V_{45}$ | $I_4$ | $L_1$ | $X_1$ | | | | | | | | | | | | 2042 | $G_{26}$ | $X_{21}$ | | | | | | |
| 539 | $L_{51}$ | | | | | | | | | | | | | | | 2043 | $T_{46}$ | $S_1$ | | | | | | |
| 540 | $N_{50}$ | $T_1$ | | | | | | | | | | | | | | 2044 | $M_{47}$ | | | | | | | |
| 541 | $N_{49}$ | $Y_1$ | $S_1$ | | | | | | | | | | | | | 2045 | $R_{47}$ | | | | | | | |
| 542 | $T_{50}$ | $X_1$ | | | | | | | | | | | | | | 2046 | $I_{45}$ | $T_1$ | $V_1$ | | | | | |
| 543 | $R_{50}$ | | | | | | | | | | | | | | | 2047 | $V_{40}$ | $A_4$ | $I_2$ | $F_1$ | | | | |
| 544 | $P_{50}$ | | | | | | | | | | | | | | | 2048 | $G_{47}$ | | | | | | | |
| 545 | $P_{49}$ | $R_1$ | | | | | | | | | | | | | | 2049 | $P_{47}$ | | | | | | | |
| 546 | $L_{42}$ | $M_3$ | $S_2$ | $Q_1$ | $G_1$ | $W_1$ | | | | | | | | | | 2050 | $R_{24}$ | $K_{23}$ | | | | | | |
| 547 | $G_{49}$ | $A_1$ | | | | | | | | | | | | | | 2051 | $T_{47}$ | | | | | | | |
| 548 | $N_{48}$ | $G_1$ | $L_1$ | | | | | | | | | | | | | 2052 | $C_{47}$ | | | | | | | |
| 549 | $W_{48}$ | $V_1$ | | | | | | | | | | | | | | 2053 | $R_{46}$ | $K_1$ | | | | | | |
| 550 | $F_{46}$ | $S_2$ | $G_1$ | | | | | | | | | | | | | 2054 | $N_{47}$ | | | | | | | |
| 551 | $G_{45}$ | $X_3$ | | | | | | | | | | | | | | 2055 | $M_{44}$ | $T_1$ | $V_1$ | $I_1$ | | | | |
| 552 | $C_{41}$ | $X_2$ | | | | | | | | | | | | | | 2056 | $W_{26}$ | $X_{21}$ | | | | | | |
| 553 | $T_{40}$ | $N_1$ | | | | | | | | | | | | | | 2057 | $S_{39}$ | $N_7$ | $D_1$ | | | | | |
| 554 | $W_{41}$ | | | | | | | | | | | | | | | 2058 | $G_{47}$ | | | | | | | |
| 555 | $M_{41}$ | | | | | | | | | | | | | | | 2059 | $T_{46}$ | $A_1$ | | | | | | |

TABLE 5-continued

HCV 1a Consensus Sequences

| | A | B | C | D | E | F | G | H | I | J | K | L | M | N | O | P | Q | R | S | T | U | V | W |
|---|---|---|---|---|---|---|---|---|---|---|---|---|---|---|---|---|---|---|---|---|---|---|---|
| 556 | $N_{41}$ | | | | | | | | | | | | | | | 2060 $F_{45}$ | $L_2$ | | | | | | |
| 557 | $S_{40}$ | $A_1$ | | | | | | | | | | | | | | 2061 $P_{46}$ | $L_1$ | | | | | | |
| 558 | $T_{27}$ | $S_{13}$ | $C_1$ | | | | | | | | | | | | | 2062 $I_{47}$ | | | | | | | |
| 559 | $G_{41}$ | | | | | | | | | | | | | | | 2063 $N_{47}$ | | | | | | | |
| 560 | $F_{33}$ | $Y_8$ | | | | | | | | | | | | | | 2064 $A_{46}$ | $P_1$ | | | | | | |
| 561 | $T_{41}$ | | | | | | | | | | | | | | | 2065 $Y_{47}$ | | | | | | | |
| 562 | $K_{41}$ | | | | | | | | | | | | | | | 2066 $T_{47}$ | | | | | | | |
| 563 | $V_{36}$ | $T_3$ | $A_2$ | | | | | | | | | | | | | 2067 $T_{47}$ | | | | | | | |
| 564 | $C_{41}$ | | | | | | | | | | | | | | | 2068 $G_{47}$ | | | | | | | |
| 565 | $G_{41}$ | | | | | | | | | | | | | | | 2069 $P_{47}$ | | | | | | | |
| 566 | $A_{40}$ | $G_1$ | | | | | | | | | | | | | | 2070 $C_{47}$ | | | | | | | |
| 567 | $P_{41}$ | | | | | | | | | | | | | | | 2071 $T_{44}$ | $N_2$ | $V_1$ | | | | | |
| 568 | $P_{41}$ | | | | | | | | | | | | | | | 2072 $P_{47}$ | | | | | | | |
| 569 | $C_{41}$ | | | | | | | | | | | | | | | 2073 $L_{26}$ | $X_{18}$ | $S_3$ | | | | | |
| 570 | $V_{23}$ | $A_6$ | $D_5$ | $N_4$ | $T_2$ | $F_1$ | | | | | | | | | | 2074 $P_{44}$ | $X_3$ | | | | | | |
| 571 | $I_{41}$ | | | | | | | | | | | | | | | 2075 $A_{47}$ | | | | | | | |
| 572 | $G_{39}$ | $R_1$ | $K_1$ | | | | | | | | | | | | | 2076 $P_{47}$ | | | | | | | |
| 573 | $G_{41}$ | | | | | | | | | | | | | | | 2077 $N_{45}$ | $S_2$ | | | | | | |
| 574 | $V_{24}$ | $A_7$ | $G_5$ | $M_2$ | $S_1$ | $K_1$ | $I_1$ | | | | | | | | | 2078 $Y_{47}$ | | | | | | | |
| 575 | $G_{38}$ | $S_2$ | $N_1$ | | | | | | | | | | | | | 2079 $T_{30}$ | $K_{13}$ | $S_3$ | | $E_1$ | | | |
| 576 | $N_{41}$ | | | | | | | | | | | | | | | 2080 $F_{47}$ | | | | | | | |
| 577 | $N_{37}$ | $T_2$ | $D_1$ | $H_1$ | | | | | | | | | | | | 2081 $A_{47}$ | | | | | | | |
| 578 | $T_{40}$ | $F_1$ | | | | | | | | | | | | | | 2082 $L_{47}$ | | | | | | | |
| 579 | $L_{40}$ | $W_1$ | | | | | | | | | | | | | | 2083 $W_{47}$ | | | | | | | |
| 580 | $H_{23}$ | $Y_7$ | $R_4$ | $L_3$ | $S_2$ | $Q_1$ | $T_1$ | | | | | | | | | 2084 $R_{26}$ | $X_{21}$ | | | | | | |
| 581 | $C_{41}$ | | | | | | | | | | | | | | | 2085 $V_{47}$ | | | | | | | |
| 582 | $P_{41}$ | | | | | | | | | | | | | | | 2086 $S_{47}$ | | | | | | | |
| 583 | $T_{41}$ | | | | | | | | | | | | | | | 2087 $A_{47}$ | | | | | | | |
| 584 | $D_{41}$ | | | | | | | | | | | | | | | 2088 $E_{47}$ | | | | | | | |
| 585 | $C_{41}$ | | | | | | | | | | | | | | | 2089 $E_{46}$ | $D_1$ | | | | | | |
| 586 | $F_{41}$ | | | | | | | | | | | | | | | 2090 $Y_{47}$ | | | | | | | |
| 587 | $R_{41}$ | | | | | | | | | | | | | | | 2091 $V_{46}$ | $A_1$ | | | | | | |
| 588 | $K_{41}$ | | | | | | | | | | | | | | | 2092 $E_{46}$ | $A_1$ | | | | | | |
| 589 | $H_{41}$ | | | | | | | | | | | | | | | 2093 $I_{44}$ | $V_3$ | | | | | | |
| 590 | $P_{41}$ | | | | | | | | | | | | | | | 2094 $R_{26}$ | $X_{21}$ | | | | | | |
| 591 | $E_{40}$ | $D_1$ | | | | | | | | | | | | | | 2095 $Q_{35}$ | $R_{12}$ | | | | | | |
| 592 | $A_{41}$ | | | | | | | | | | | | | | | 2096 $V_{27}$ | $X_{20}$ | | | | | | |
| 593 | $T_{41}$ | | | | | | | | | | | | | | | 2097 $G_{46}$ | $X_1$ | | | | | | |
| 594 | $Y_{41}$ | | | | | | | | | | | | | | | 2098 $D_{47}$ | | | | | | | |
| 595 | $S_{39}$ | $A_2$ | | | | | | | | | | | | | | 2099 $F_{47}$ | | | | | | | |
| 596 | $R_{40}$ | $K_1$ | | | | | | | | | | | | | | 2100 $H_{47}$ | | | | | | | |
| 597 | $C_{41}$ | | | | | | | | | | | | | | | 2101 $Y_{47}$ | | | | | | | |
| 598 | $G_{41}$ | | | | | | | | | | | | | | | 2102 $V_{47}$ | | | | | | | |
| 599 | $S_{41}$ | | | | | | | | | | | | | | | 2103 $T_{45}$ | $S_1$ | $V_1$ | | | | | |
| 600 | $G_{41}$ | | | | | | | | | | | | | | | 2104 $G_{47}$ | | | | | | | |
| 601 | $P_{40}$ | $A_1$ | | | | | | | | | | | | | | 2105 $M_{46}$ | $V_1$ | | | | | | |
| 602 | $W_{41}$ | | | | | | | | | | | | | | | 2106 $T_{47}$ | | | | | | | |
| 603 | $I_{34}$ | $L_6$ | $V_1$ | | | | | | | | | | | | | 2107 $T_{39}$ | $A_8$ | | | | | | |
| 604 | $T_{41}$ | | | | | | | | | | | | | | | 2108 $D_{47}$ | | | | | | | |
| 605 | $P_{41}$ | | | | | | | | | | | | | | | 2109 $N_{43}$ | $D_4$ | | | | | | |
| 606 | $R_{40}$ | $K_1$ | | | | | | | | | | | | | | 2110 $L_{47}$ | | | | | | | |
| 607 | $C_{41}$ | | | | | | | | | | | | | | | 2111 $K_{44}$ | $R_3$ | | | | | | |
| 608 | $L_{37}$ | $M_3$ | $I_1$ | | | | | | | | | | | | | 2112 $C_{47}$ | | | | | | | |
| 609 | $V_{41}$ | | | | | | | | | | | | | | | 2113 $P_{47}$ | | | | | | | |
| 610 | $H_{16}$ | $D_{14}$ | $N_{11}$ | | | | | | | | | | | | | 2114 $C_{47}$ | | | | | | | |
| 611 | $Y_{41}$ | | | | | | | | | | | | | | | 2115 $Q_{47}$ | | | | | | | |
| 612 | $P_{38}$ | $A_2$ | $S_1$ | | | | | | | | | | | | | 2116 $V_{46}$ | $I_1$ | | | | | | |
| 613 | $Y_{41}$ | | | | | | | | | | | | | | | 2117 $P_{47}$ | | | | | | | |
| 614 | $R_{41}$ | | | | | | | | | | | | | | | 2118 $S_{45}$ | $T_1$ | $A_1$ | | | | | |
| 615 | $L_{41}$ | | | | | | | | | | | | | | | 2119 $P_{47}$ | | | | | | | |
| 616 | $W_{38}$ | | | | | | | | | | | | | | | 2120 $E_{47}$ | | | | | | | |
| 617 | $H_{38}$ | | | | | | | | | | | | | | | 2121 $F_{47}$ | | | | | | | |
| 618 | $X_{25}$ | $Y_{13}$ | | | | | | | | | | | | | | 2122 $F_{47}$ | | | | | | | |
| 619 | $P_{13}$ | | | | | | | | | | | | | | | 2123 $T_{47}$ | | | | | | | |
| 620 | $C_{13}$ | | | | | | | | | | | | | | | 2124 $E_{47}$ | | | | | | | |
| 621 | $T_{13}$ | | | | | | | | | | | | | | | 2125 $L_{46}$ | $V_1$ | | | | | | |
| 622 | $I_8$ | $V_2$ | $L_2$ | $M_1$ | | | | | | | | | | | | 2126 $D_{47}$ | | | | | | | |
| 623 | $N_{13}$ | | | | | | | | | | | | | | | 2127 $G_{47}$ | | | | | | | |
| 624 | $Y_{12}$ | $F_1$ | | | | | | | | | | | | | | 2128 $V_{47}$ | | | | | | | |
| 625 | $T_{12}$ | $S_1$ | | | | | | | | | | | | | | 2129 $R_{47}$ | | | | | | | |
| 626 | $I_8$ | $L_4$ | $T_1$ | | | | | | | | | | | | | 2130 $L_{45}$ | $I_2$ | | | | | | |
| 627 | $F_{13}$ | | | | | | | | | | | | | | | 2131 $H_{47}$ | | | | | | | |
| 628 | $K_{13}$ | | | | | | | | | | | | | | | 2132 $R_{26}$ | $X_{21}$ | | | | | | |
| 629 | $V_9$ | $I_4$ | | | | | | | | | | | | | | 2133 $F_{26}$ | $X_{21}$ | | | | | | |
| 630 | $R_{13}$ | | | | | | | | | | | | | | | 2134 $A_{47}$ | | | | | | | |
| 631 | $M_{13}$ | | | | | | | | | | | | | | | 2135 $P_{47}$ | | | | | | | |

TABLE 5-continued

HCV 1a Consensus Sequences

| | A | B | C | D | E | F | G | H | I | J | K | L | M | N | O | P | Q | R | S | T | U | V | W |
|---|---|---|---|---|---|---|---|---|---|---|---|---|---|---|---|---|---|---|---|---|---|---|---|
| 632 | $Y_{13}$ | | | | | | | | | | | | | | | 2136 | $P_{47}$ | | | | | | |
| 633 | $V_{13}$ | | | | | | | | | | | | | | | 2137 | $C_{47}$ | | | | | | |
| 634 | $G_{13}$ | | | | | | | | | | | | | | | 2138 | $K_{47}$ | | | | | | |
| 635 | $G_{13}$ | | | | | | | | | | | | | | | 2139 | $P_{47}$ | | | | | | |
| 636 | $V_{13}$ | | | | | | | | | | | | | | | 2140 | $L_{47}$ | | | | | | |
| 637 | $E_{13}$ | | | | | | | | | | | | | | | 2141 | $L_{47}$ | | | | | | |
| 638 | $H_{13}$ | | | | | | | | | | | | | | | 2142 | $R_{46}$ | $A_1$ | | | | | |
| 639 | $R_{13}$ | | | | | | | | | | | | | | | 2143 | $E_{31}$ | $D_{16}$ | | | | | |
| 640 | $L_{13}$ | | | | | | | | | | | | | | | 2144 | $E_{47}$ | | | | | | |
| 641 | $E_8$ | $G_1$ | $Q_1$ | $D_1$ | $N_1$ | | | | | | | | | | | 2145 | $V_{28}$ | $X_{19}$ | | | | | |
| 642 | $A_{11}$ | $V_1$ | | | | | | | | | | | | | | 2146 | $S_{24}$ | $T_{15}$ | $A_6$ | $X_2$ | | | |
| 643 | $A_{12}$ | | | | | | | | | | | | | | | 2147 | $F_{27}$ | $X_{20}$ | | | | | |
| 644 | $C_{12}$ | | | | | | | | | | | | | | | 2148 | $R_{46}$ | $S_1$ | | | | | |
| 645 | $N_{12}$ | | | | | | | | | | | | | | | 2149 | $V_{47}$ | | | | | | |
| 646 | $W_{12}$ | | | | | | | | | | | | | | | 2150 | $G_{47}$ | | | | | | |
| 647 | $T_{12}$ | | | | | | | | | | | | | | | 2151 | $L_{47}$ | | | | | | |
| 648 | $R_{12}$ | | | | | | | | | | | | | | | 2152 | $H_{46}$ | $N_1$ | | | | | |
| 649 | $G_{12}$ | | | | | | | | | | | | | | | 2153 | $E_{24}$ | $D_{15}$ | $A_5$ | $S_1$ | $V_1$ | $T_1$ | |
| 650 | $E_{12}$ | | | | | | | | | | | | | | | 2154 | $Y_{47}$ | | | | | | |
| 651 | $R_{12}$ | | | | | | | | | | | | | | | 2155 | $P_{47}$ | | | | | | |
| 652 | $C_{12}$ | | | | | | | | | | | | | | | 2156 | $V_{28}$ | $X_{19}$ | | | | | |
| 653 | $D_{10}$ | $N_2$ | | | | | | | | | | | | | | 2157 | $G_{45}$ | $X_2$ | | | | | |
| 654 | $L_{12}$ | | | | | | | | | | | | | | | 2158 | $S_{47}$ | | | | | | |
| 655 | $E_9$ | $D_3$ | | | | | | | | | | | | | | 2159 | $Q_{47}$ | | | | | | |
| 656 | $D_{12}$ | | | | | | | | | | | | | | | 2160 | $L_{47}$ | | | | | | |
| 657 | $R_{12}$ | | | | | | | | | | | | | | | 2161 | $P_{47}$ | | | | | | |
| 658 | $D_{12}$ | | | | | | | | | | | | | | | 2162 | $C_{47}$ | | | | | | |
| 659 | $R_{12}$ | | | | | | | | | | | | | | | 2163 | $E_{47}$ | | | | | | |
| 660 | $S_{12}$ | | | | | | | | | | | | | | | 2164 | $P_{47}$ | | | | | | |
| 661 | $E_{12}$ | | | | | | | | | | | | | | | 2165 | $E_{47}$ | | | | | | |
| 662 | $L_{12}$ | | | | | | | | | | | | | | | 2166 | $P_{26}$ | $X_{21}$ | | | | | |
| 663 | $S_{12}$ | | | | | | | | | | | | | | | 2167 | $D_{47}$ | | | | | | |
| 664 | $P_{12}$ | | | | | | | | | | | | | | | 2168 | $V_{47}$ | | | | | | |
| 665 | $L_{12}$ | | | | | | | | | | | | | | | 2169 | $A_{45}$ | $T_2$ | | | | | |
| 666 | $L_{12}$ | | | | | | | | | | | | | | | 2170 | $V_{47}$ | | | | | | |
| 667 | $L_{12}$ | | | | | | | | | | | | | | | 2171 | $L_{45}$ | $V_2$ | | | | | |
| 668 | $S_{10}$ | $T_2$ | | | | | | | | | | | | | | 2172 | $T_{47}$ | | | | | | |
| 669 | $T_{12}$ | | | | | | | | | | | | | | | 2173 | $S_{47}$ | | | | | | |
| 670 | $T_{12}$ | | | | | | | | | | | | | | | 2174 | $M_{46}$ | $T_1$ | | | | | |
| 671 | $Q_{11}$ | $E_1$ | | | | | | | | | | | | | | 2175 | $L_{47}$ | | | | | | |
| 672 | $W_{12}$ | | | | | | | | | | | | | | | 2176 | $T_{47}$ | | | | | | |
| 673 | $Q_{12}$ | | | | | | | | | | | | | | | 2177 | $D_{47}$ | | | | | | |
| 674 | $V_9$ | $I_3$ | | | | | | | | | | | | | | 2178 | $P_{46}$ | $S_1$ | | | | | |
| 675 | $L_{12}$ | | | | | | | | | | | | | | | 2179 | $S_{47}$ | | | | | | |
| 676 | $P_{12}$ | | | | | | | | | | | | | | | 2180 | $H_{47}$ | | | | | | |
| 677 | $C_{12}$ | | | | | | | | | | | | | | | 2181 | $I_{44}$ | $V_2$ | $L_1$ | | | | |
| 678 | $S_{12}$ | | | | | | | | | | | | | | | 2182 | $T_{47}$ | | | | | | |
| 679 | $F_{12}$ | | | | | | | | | | | | | | | 2183 | $A_{47}$ | | | | | | |
| 680 | $T_{12}$ | | | | | | | | | | | | | | | 2184 | $E_{47}$ | | | | | | |
| 681 | $T_{12}$ | | | | | | | | | | | | | | | 2185 | $A_{25}$ | $X_{21}$ | $T_1$ | | | | |
| 682 | $L_{12}$ | | | | | | | | | | | | | | | 2186 | $A_{47}$ | | | | | | |
| 683 | $P_{12}$ | | | | | | | | | | | | | | | 2187 | $G_{33}$ | $R_7$ | $K_4$ | $A_3$ | | | |
| 684 | $A_{12}$ | | | | | | | | | | | | | | | 2188 | $R_{47}$ | | | | | | |
| 685 | $L_{12}$ | | | | | | | | | | | | | | | 2189 | $R_{47}$ | | | | | | |
| 686 | $S_9$ | $T_3$ | | | | | | | | | | | | | | 2190 | $L_{47}$ | | | | | | |
| 687 | $T_{12}$ | | | | | | | | | | | | | | | 2191 | $A_{41}$ | $X_4$ | $E_1$ | $T_1$ | | | |
| 688 | $G_{12}$ | | | | | | | | | | | | | | | 2192 | $R_{30}$ | $X_{17}$ | | | | | |
| 689 | $L_{12}$ | | | | | | | | | | | | | | | 2193 | $G_{47}$ | | | | | | |
| 690 | $I_{12}$ | | | | | | | | | | | | | | | 2194 | $S_{47}$ | | | | | | |
| 691 | $H_{12}$ | | | | | | | | | | | | | | | 2195 | $P_{46}$ | $S_1$ | | | | | |
| 692 | $L_{12}$ | | | | | | | | | | | | | | | 2196 | $P_{33}$ | $X_{13}$ | $L_1$ | | | | |
| 693 | $H_{12}$ | | | | | | | | | | | | | | | 2197 | $S_{26}$ | $X_{16}$ | | | | | |
| 694 | $Q_{12}$ | | | | | | | | | | | | | | | 2198 | $V_{24}$ | $E_{11}$ | $M_6$ | $L_3$ | $X_3$ | | |
| 695 | $N_{12}$ | | | | | | | | | | | | | | | 2199 | $A_{47}$ | | | | | | |
| 696 | $I_{12}$ | | | | | | | | | | | | | | | 2200 | $S_{47}$ | | | | | | |
| 697 | $V_{12}$ | | | | | | | | | | | | | | | 2201 | $S_{47}$ | | | | | | |
| 698 | $D_{12}$ | | | | | | | | | | | | | | | 2202 | $S_{47}$ | | | | | | |
| 699 | $V_{12}$ | | | | | | | | | | | | | | | 2203 | $A_{46}$ | $V_1$ | | | | | |
| 700 | $Q_{12}$ | | | | | | | | | | | | | | | 2204 | $S_{47}$ | | | | | | |
| 701 | $Y_{12}$ | | | | | | | | | | | | | | | 2205 | $Q_{47}$ | | | | | | |
| 702 | $L_{12}$ | | | | | | | | | | | | | | | 2206 | $L_{47}$ | | | | | | |
| 703 | $Y_{12}$ | | | | | | | | | | | | | | | 2207 | $S_{47}$ | | | | | | |
| 704 | $G_{12}$ | | | | | | | | | | | | | | | 2208 | $A_{46}$ | $T_1$ | | | | | |
| 705 | $V_{11}$ | $I_1$ | | | | | | | | | | | | | | 2209 | $P_{46}$ | $L_1$ | | | | | |
| 706 | $G_{12}$ | | | | | | | | | | | | | | | 2210 | $S_{46}$ | $P_1$ | | | | | |
| 707 | $S_{12}$ | | | | | | | | | | | | | | | 2211 | $L_{47}$ | | | | | | |

TABLE 5-continued

HCV 1a Consensus Sequences

| | A | B | C | D | E | F | G | H | I | J | K | L | M | N | O | P | Q | R | S | T | U | V | W |
|---|---|---|---|---|---|---|---|---|---|---|---|---|---|---|---|---|---|---|---|---|---|---|---|
| 708 | $S_{11}$ | $A_1$ | | | | | | | | | | | | | | 2212 | $K_{46}$ | $R_1$ | | | | | |
| 709 | $I_8$ | $V_4$ | | | | | | | | | | | | | | 2213 | $A_{47}$ | | | | | | |
| 710 | $A_7$ | $V_4$ | $T_1$ | | | | | | | | | | | | | 2214 | $T_{46}$ | $A_1$ | | | | | |
| 711 | $S_{12}$ | | | | | | | | | | | | | | | 2215 | $C_{47}$ | | | | | | |
| 712 | $W_{11}$ | $Y_1$ | | | | | | | | | | | | | | 2216 | $T_{47}$ | | | | | | |
| 713 | $A_{12}$ | | | | | | | | | | | | | | | 2217 | $A_{24}$ | $T_{17}$ | $V_3$ | $I_2$ | $G_1$ | | |
| 714 | $I_{12}$ | | | | | | | | | | | | | | | 2218 | $N_{44}$ | $H_1$ | $R_1$ | $D_1$ | | | |
| 715 | $K_{12}$ | | | | | | | | | | | | | | | 2219 | $H_{45}$ | $Y_1$ | $R_1$ | | | | |
| 716 | $W_{12}$ | | | | | | | | | | | | | | | 2220 | $D_{44}$ | $V_1$ | $E_1$ | $Y_1$ | | | |
| 717 | $E_8$ | $D_4$ | | | | | | | | | | | | | | 2221 | $S_{47}$ | | | | | | |
| 718 | $Y_{12}$ | | | | | | | | | | | | | | | 2222 | $P_{46}$ | $T_1$ | | | | | |
| 719 | $V_{12}$ | | | | | | | | | | | | | | | 2223 | $D_{47}$ | | | | | | |
| 720 | $V_8$ | $I_3$ | $L_1$ | | | | | | | | | | | | | 2224 | $A_{46}$ | $V_1$ | | | | | |
| 721 | $L_{12}$ | | | | | | | | | | | | | | | 2225 | $E_{45}$ | $D_2$ | | | | | |
| 722 | $L_{12}$ | | | | | | | | | | | | | | | 2226 | $L_{47}$ | | | | | | |
| 723 | $F_{12}$ | | | | | | | | | | | | | | | 2227 | $I_{47}$ | | | | | | |
| 724 | $L_{12}$ | | | | | | | | | | | | | | | 2228 | $E_{42}$ | $A_2$ | $Q_2$ | $T_1$ | | | |
| 725 | $L_{12}$ | | | | | | | | | | | | | | | 2229 | $A_{47}$ | | | | | | |
| 726 | $L_{12}$ | | | | | | | | | | | | | | | 2230 | $N_{47}$ | | | | | | |
| 727 | $A_{12}$ | | | | | | | | | | | | | | | 2231 | $L_{47}$ | | | | | | |
| 728 | $D_{12}$ | | | | | | | | | | | | | | | 2232 | $L_{47}$ | | | | | | |
| 729 | $A_{12}$ | | | | | | | | | | | | | | | 2233 | $W_{47}$ | | | | | | |
| 730 | $R_{12}$ | | | | | | | | | | | | | | | 2234 | $R_{46}$ | $N_1$ | | | | | |
| 731 | $V_7$ | $I_5$ | | | | | | | | | | | | | | 2235 | $Q_{47}$ | | | | | | |
| 732 | $C_{12}$ | | | | | | | | | | | | | | | 2236 | $E_{45}$ | $A_2$ | | | | | |
| 733 | $S_{12}$ | | | | | | | | | | | | | | | 2237 | $M_{47}$ | | | | | | |
| 734 | $C_{12}$ | | | | | | | | | | | | | | | 2238 | $G_{47}$ | | | | | | |
| 735 | $L_{12}$ | | | | | | | | | | | | | | | 2239 | $G_{46}$ | $C_1$ | | | | | |
| 736 | $W_{12}$ | | | | | | | | | | | | | | | 2240 | $N_{47}$ | | | | | | |
| 737 | $M_{12}$ | | | | | | | | | | | | | | | 2241 | $I_{47}$ | | | | | | |
| 738 | $M_{12}$ | | | | | | | | | | | | | | | 2242 | $T_{47}$ | | | | | | |
| 739 | $L_{12}$ | | | | | | | | | | | | | | | 2243 | $R_{47}$ | | | | | | |
| 740 | $L_{12}$ | | | | | | | | | | | | | | | 2244 | $V_{47}$ | | | | | | |
| 741 | $I_{12}$ | | | | | | | | | | | | | | | 2245 | $E_{47}$ | | | | | | |
| 742 | $S_{12}$ | | | | | | | | | | | | | | | 2246 | $S_{47}$ | | | | | | |
| 743 | $Q_{12}$ | | | | | | | | | | | | | | | 2247 | $E_{46}$ | | | | | | |
| 744 | $A_{11}$ | $V_1$ | | | | | | | | | | | | | | 2248 | $N_{46}$ | $S_1$ | | | | | |
| 745 | $E_{12}$ | | | | | | | | | | | | | | | 2249 | $K_{47}$ | | | | | | |
| 746 | $A_{12}$ | | | | | | | | | | | | | | | 2250 | $V_{47}$ | | | | | | |
| 747 | $A_{10}$ | $X_1$ | | | | | | | | | | | | | | 2251 | $V_{45}$ | $A_1$ | $X_1$ | | | | |
| 748 | $L_{10}$ | | | | | | | | | | | | | | | 2252 | $I_{40}$ | $V_6$ | | | | | |
| 749 | $E_{10}$ | | | | | | | | | | | | | | | 2253 | $L_{46}$ | | | | | | |
| 750 | $N_{10}$ | | | | | | | | | | | | | | | 2254 | $D_{46}$ | | | | | | |
| 751 | $L_{10}$ | | | | | | | | | | | | | | | 2255 | $S_{25}$ | $X_{21}$ | | | | | |
| 752 | $V_9$ | $I_1$ | | | | | | | | | | | | | | 2256 | $F_{46}$ | | | | | | |
| 753 | $V_5$ | $I_4$ | $L_1$ | | | | | | | | | | | | | 2257 | $D_{43}$ | $E_2$ | $G_1$ | | | | |
| 754 | $L_{10}$ | | | | | | | | | | | | | | | 2258 | $P_{46}$ | | | | | | |
| 755 | $N_{10}$ | | | | | | | | | | | | | | | 2259 | $L_{28}$ | $X_{18}$ | | | | | |
| 756 | $A_{10}$ | | | | | | | | | | | | | | | 2260 | $V_{24}$ | $X_{18}$ | $C_2$ | $R_1$ | $T_1$ | | |
| 757 | $A_{10}$ | | | | | | | | | | | | | | | 2261 | $A_{41}$ | $X_4$ | $E_1$ | | | | |
| 758 | $S_{10}$ | | | | | | | | | | | | | | | 2262 | $E_{25}$ | $X_{20}$ | | | | | |
| 759 | $L_{10}$ | | | | | | | | | | | | | | | 2263 | $E_{44}$ | $K_1$ | $X_1$ | | | | |
| 760 | $A_{10}$ | | | | | | | | | | | | | | | 2264 | $D_{46}$ | | | | | | |
| 761 | $G_{10}$ | | | | | | | | | | | | | | | 2265 | $E_{46}$ | | | | | | |
| 762 | $T_{10}$ | | | | | | | | | | | | | | | 2266 | $R_{45}$ | $Q_1$ | | | | | |
| 763 | $H_8$ | $R_1$ | $Q_1$ | | | | | | | | | | | | | 2267 | $E_{45}$ | $D_1$ | | | | | |
| 764 | $G_{10}$ | | | | | | | | | | | | | | | 2268 | $X_{21}$ | $I_{14}$ | $V_{11}$ | | | | |
| 765 | $L_{10}$ | | | | | | | | | | | | | | | 2269 | $S_{45}$ | $A_1$ | | | | | |
| 766 | $V_7$ | $A_3$ | | | | | | | | | | | | | | 2270 | $V_{43}$ | $T_1$ | $A_1$ | $I_1$ | | | |
| 767 | $S_9$ | $X_1$ | | | | | | | | | | | | | | 2271 | $P_{42}$ | $A_3$ | $T_1$ | | | | |
| 768 | $F_9$ | | | | | | | | | | | | | | | 2272 | $A_{46}$ | | | | | | |
| 769 | $L_9$ | | | | | | | | | | | | | | | 2273 | $E_{45}$ | $G_1$ | | | | | |
| 770 | $V_8$ | $M_1$ | | | | | | | | | | | | | | 2274 | $I_{45}$ | $M_1$ | | | | | |
| 771 | $F_9$ | | | | | | | | | | | | | | | 2275 | $L_{46}$ | | | | | | |
| 772 | $F_9$ | | | | | | | | | | | | | | | 2276 | $R_{45}$ | $L_1$ | | | | | |
| 773 | $C_9$ | | | | | | | | | | | | | | | 2277 | $K_{43}$ | $R_2$ | $T_1$ | | | | |
| 774 | $F_8$ | $L_1$ | | | | | | | | | | | | | | 2278 | $S_{42}$ | $Y_2$ | $T_1$ | $R_1$ | | | |
| 775 | $A_9$ | | | | | | | | | | | | | | | 2279 | $R_{45}$ | $G_1$ | | | | | |
| 776 | $W_9$ | | | | | | | | | | | | | | | 2280 | $R_{44}$ | $K_2$ | | | | | |
| 777 | $Y_9$ | | | | | | | | | | | | | | | 2281 | $F_{25}$ | $L_{15}$ | $X_6$ | | | | |
| 778 | $L_9$ | | | | | | | | | | | | | | | 2282 | $A_{27}$ | $X_{11}$ | $P_4$ | $T_4$ | | | |
| 779 | $K_9$ | | | | | | | | | | | | | | | 2283 | $P_{13}$ | $Q_{12}$ | $X_{10}$ | $R_7$ | $S_2$ | $A_1$ | $E_1$ |
| 780 | $G_9$ | | | | | | | | | | | | | | | 2284 | $A_{25}$ | $G_{11}$ | $X_{10}$ | | | | |
| 781 | $R_5$ | $K_4$ | | | | | | | | | | | | | | 2285 | $L_{46}$ | | | | | | |
| 782 | $W_9$ | | | | | | | | | | | | | | | 2286 | $P_{45}$ | $A_1$ | | | | | |
| 783 | $V_9$ | | | | | | | | | | | | | | | 2287 | $V_{25}$ | $I_{21}$ | | | | | |

TABLE 5-continued

HCV 1a Consensus Sequences

| | A | B | C | D | E | F | G | H | I | J | K | L | M | N | O | | P | Q | R | S | T | U | V | W |
|---|---|---|---|---|---|---|---|---|---|---|---|---|---|---|---|---|---|---|---|---|---|---|---|---|
| 784 | $P_9$ | | | | | | | | | | | | | | | 2288 | $W_{46}$ | | | | | | | |
| 785 | $G_9$ | | | | | | | | | | | | | | | 2289 | $A_{25}$ | $X_{21}$ | | | | | | |
| 786 | $A_8$ | $M_1$ | | | | | | | | | | | | | | 2290 | $R_{46}$ | | | | | | | |
| 787 | $A_5$ | $V_4$ | | | | | | | | | | | | | | 2291 | $P_{46}$ | | | | | | | |
| 788 | $Y_9$ | | | | | | | | | | | | | | | 2292 | $D_{44}$ | $E_2$ | | | | | | |
| 789 | $A_8$ | $T_1$ | | | | | | | | | | | | | | 2293 | $Y_{46}$ | | | | | | | |
| 790 | $L_4$ | $F_4$ | $I_1$ | | | | | | | | | | | | | 2294 | $N_{46}$ | | | | | | | |
| 791 | $Y_8$ | $F_1$ | | | | | | | | | | | | | | 2295 | $P_{25}$ | $X_{21}$ | | | | | | |
| 792 | $G_9$ | | | | | | | | | | | | | | | 2296 | $P_{46}$ | | | | | | | |
| 793 | $M_9$ | | | | | | | | | | | | | | | 2297 | $L_{46}$ | | | | | | | |
| 794 | $W_9$ | | | | | | | | | | | | | | | 2298 | $L_{23}$ | $V_{12}$ | $I_{10}$ | $M_1$ | | | | |
| 795 | $P_9$ | | | | | | | | | | | | | | | 2299 | $E_{46}$ | | | | | | | |
| 796 | $L_8$ | $F_1$ | | | | | | | | | | | | | | 2300 | $T_{39}$ | $A_4$ | $S_1$ | $L_1$ | $E_1$ | | | |
| 797 | $L_9$ | | | | | | | | | | | | | | | 2301 | $W_{46}$ | | | | | | | |
| 798 | $L_9$ | | | | | | | | | | | | | | | 2302 | $K_{32}$ | $X_{14}$ | | | | | | |
| 799 | $L_9$ | | | | | | | | | | | | | | | 2303 | $K_{38}$ | $X_4$ | $S_3$ | $E_1$ | | | | |
| 800 | $L_9$ | | | | | | | | | | | | | | | 2304 | $P_{43}$ | $X_3$ | | | | | | |
| 801 | $L_9$ | | | | | | | | | | | | | | | 2305 | $D_{44}$ | $G_2$ | | | | | | |
| 802 | $A_9$ | | | | | | | | | | | | | | | 2306 | $Y_{46}$ | | | | | | | |
| 803 | $L_9$ | | | | | | | | | | | | | | | 2307 | $E_{44}$ | $K_2$ | | | | | | |
| 804 | $P_9$ | | | | | | | | | | | | | | | 2308 | $P_{46}$ | | | | | | | |
| 805 | $Q_9$ | | | | | | | | | | | | | | | 2309 | $P_{46}$ | | | | | | | |
| 806 | $R_9$ | | | | | | | | | | | | | | | 2310 | $V_{45}$ | $T_1$ | | | | | | |
| 807 | $A_9$ | | | | | | | | | | | | | | | 2311 | $V_{46}$ | | | | | | | |
| 808 | $Y_9$ | | | | | | | | | | | | | | | 2312 | $H_{45}$ | $Y_1$ | | | | | | |
| 809 | $A_9$ | | | | | | | | | | | | | | | 2313 | $G_{46}$ | | | | | | | |
| 810 | $L_9$ | | | | | | | | | | | | | | | 2314 | $C_{34}$ | $X_{12}$ | | | | | | |
| 811 | $D_9$ | | | | | | | | | | | | | | | 2315 | $P_{37}$ | $X_9$ | | | | | | |
| 812 | $T_9$ | | | | | | | | | | | | | | | 2316 | $L_{46}$ | | | | | | | |
| 813 | $E_9$ | | | | | | | | | | | | | | | 2317 | $P_{46}$ | | | | | | | |
| 814 | $V_7$ | $M_2$ | | | | | | | | | | | | | | 2318 | $P_{45}$ | $S_1$ | | | | | | |
| 815 | $A_8$ | $X_1$ | | | | | | | | | | | | | | 2319 | $P_{44}$ | $S_2$ | | | | | | |
| 816 | $A_8$ | | | | | | | | | | | | | | | 2320 | $Q_{30}$ | $K_8$ | $R_8$ | | | | | |
| 817 | $S_8$ | | | | | | | | | | | | | | | 2321 | $S_{45}$ | $P_1$ | | | | | | |
| 818 | $C_8$ | | | | | | | | | | | | | | | 2322 | $P_{45}$ | $X_1$ | | | | | | |
| 819 | $G_8$ | | | | | | | | | | | | | | | 2323 | $P_{25}$ | $X_{20}$ | $S_1$ | | | | | |
| 820 | $G_8$ | | | | | | | | | | | | | | | 2324 | $V_{46}$ | | | | | | | |
| 821 | $V_8$ | | | | | | | | | | | | | | | 2325 | $P_{46}$ | | | | | | | |
| 822 | $V_8$ | | | | | | | | | | | | | | | 2326 | $P_{45}$ | $S_1$ | | | | | | |
| 823 | $L_8$ | | | | | | | | | | | | | | | 2327 | $P_{46}$ | | | | | | | |
| 824 | $V_8$ | | | | | | | | | | | | | | | 2328 | $R_{25}$ | $X_{21}$ | | | | | | |
| 825 | $G_8$ | | | | | | | | | | | | | | | 2329 | $K_{39}$ | $R_7$ | | | | | | |
| 826 | $L_8$ | | | | | | | | | | | | | | | 2330 | $K_{45}$ | $R_1$ | | | | | | |
| 827 | $M_8$ | | | | | | | | | | | | | | | 2331 | $R_{46}$ | | | | | | | |
| 828 | $A_7$ | $V_1$ | | | | | | | | | | | | | | 2332 | $T_{44}$ | $M_2$ | | | | | | |
| 829 | $L_8$ | | | | | | | | | | | | | | | 2333 | $V_{45}$ | $I_1$ | | | | | | |
| 830 | $T_8$ | | | | | | | | | | | | | | | 2334 | $V_{45}$ | $I_1$ | | | | | | |
| 831 | $L_8$ | | | | | | | | | | | | | | | 2335 | $L_{46}$ | | | | | | | |
| 832 | $S_8$ | | | | | | | | | | | | | | | 2336 | $T_{44}$ | $S_2$ | | | | | | |
| 833 | $P_8$ | | | | | | | | | | | | | | | 2337 | $E_{46}$ | | | | | | | |
| 834 | $Y_7$ | $H_1$ | | | | | | | | | | | | | | 2338 | $S_{46}$ | | | | | | | |
| 835 | $Y_8$ | | | | | | | | | | | | | | | 2339 | $T_{36}$ | $S_4$ | $N_3$ | $P_1$ | $A_1$ | $L_1$ | | |
| 836 | $K_8$ | | | | | | | | | | | | | | | 2340 | $V_{32}$ | $L_{14}$ | | | | | | |
| 837 | $R_7$ | $H_1$ | | | | | | | | | | | | | | 2341 | $S_{43}$ | $P_3$ | | | | | | |
| 838 | $Y_8$ | | | | | | | | | | | | | | | 2342 | $T_{42}$ | $S_2$ | $A_2$ | | | | | |
| 839 | $I_7$ | $V_1$ | | | | | | | | | | | | | | 2343 | $A_{46}$ | | | | | | | |
| 840 | $S_8$ | | | | | | | | | | | | | | | 2344 | $L_{46}$ | | | | | | | |
| 841 | $W_8$ | | | | | | | | | | | | | | | 2345 | $A_{46}$ | | | | | | | |
| 842 | $C_8$ | | | | | | | | | | | | | | | 2346 | $E_{45}$ | | | | | | | |
| 843 | $L_4$ | $F_3$ | $M_1$ | | | | | | | | | | | | | 2347 | $L_{46}$ | | | | | | | |
| 844 | $W_8$ | | | | | | | | | | | | | | | 2348 | $A_{46}$ | | | | | | | |
| 845 | $W_8$ | | | | | | | | | | | | | | | 2349 | $T_{45}$ | $S_1$ | | | | | | |
| 846 | $L_8$ | | | | | | | | | | | | | | | 2350 | $K_{44}$ | $R_1$ | $I_1$ | | | | | |
| 847 | $Q_8$ | | | | | | | | | | | | | | | 2351 | $S_{31}$ | $X_{13}$ | $T_2$ | | | | | |
| 848 | $Y_8$ | | | | | | | | | | | | | | | 2352 | $F_{38}$ | $X_8$ | | | | | | |
| 849 | $F_8$ | | | | | | | | | | | | | | | 2353 | $G_{46}$ | | | | | | | |
| 850 | $L_8$ | | | | | | | | | | | | | | | 2354 | $S_{44}$ | $D_1$ | $G_1$ | | | | | |
| 851 | $T_8$ | | | | | | | | | | | | | | | 2355 | $S_{45}$ | $A_1$ | | | | | | |
| 852 | $R_8$ | | | | | | | | | | | | | | | 2356 | $S_{46}$ | | | | | | | |
| 853 | $V_6$ | $A_2$ | | | | | | | | | | | | | | 2357 | $T_{26}$ | $X_{20}$ | | | | | | |
| 854 | $E_8$ | | | | | | | | | | | | | | | 2358 | $S_{45}$ | $X_1$ | | | | | | |
| 855 | $A_8$ | | | | | | | | | | | | | | | 2359 | $G_{46}$ | | | | | | | |
| 856 | $Q_5$ | $H_2$ | $L_1$ | | | | | | | | | | | | | 2360 | $I_{44}$ | $V_1$ | $T_1$ | | | | | |
| 857 | $L_8$ | | | | | | | | | | | | | | | 2361 | $T_{40}$ | $A_3$ | $S_2$ | $V_1$ | | | | |
| 858 | $H_7$ | $Q_1$ | | | | | | | | | | | | | | 2362 | $G_{38}$ | $S_5$ | $A_3$ | | | | | |
| 859 | $V_8$ | | | | | | | | | | | | | | | 2363 | $D_{42}$ | $G_4$ | | | | | | |

TABLE 5-continued

HCV 1a Consensus Sequences

| | A | B | C | D | E | F | G | H | I | J | K | L | M | N | O | P | Q | R | S | T | U | V | W |
|---|---|---|---|---|---|---|---|---|---|---|---|---|---|---|---|---|---|---|---|---|---|---|---|
| 860 | $W_8$ | | | | | | | | | | | | | | | 2364 | $N_{40}$ | $D_4$ | $S_2$ | | | | |
| 861 | $V_6$ | $I_1$ | $F_1$ | | | | | | | | | | | | | 2365 | $T_{45}$ | $A_1$ | | | | | |
| 862 | $P_8$ | | | | | | | | | | | | | | | 2366 | $T_{41}$ | $A_4$ | $P_1$ | | | | |
| 863 | $P_8$ | | | | | | | | | | | | | | | 2367 | $T_{37}$ | $A_6$ | $S_2$ | $V_1$ | | | |
| 864 | $L_8$ | | | | | | | | | | | | | | | 2368 | $S_{38}$ | $P_8$ | | | | | |
| 865 | $N_8$ | | | | | | | | | | | | | | | 2369 | $S_{43}$ | $T_1$ | $H_1$ | $P_1$ | | | |
| 866 | $V_7$ | $A_1$ | | | | | | | | | | | | | | 2370 | $E_{46}$ | | | | | | |
| 867 | $R_8$ | | | | | | | | | | | | | | | 2371 | $P_{38}$ | $A_5$ | $L_2$ | $S_1$ | | | |
| 868 | $G_8$ | | | | | | | | | | | | | | | 2372 | $A_{37}$ | $T_5$ | $S_3$ | $P_1$ | | | |
| 869 | $G_8$ | | | | | | | | | | | | | | | 2373 | $P_{31}$ | $S_{15}$ | | | | | |
| 870 | $R_8$ | | | | | | | | | | | | | | | 2374 | $S_{39}$ | $P_6$ | $T_1$ | | | | |
| 871 | $D_8$ | | | | | | | | | | | | | | | 2375 | $G_{32}$ | $V_8$ | $D_5$ | $I_1$ | | | |
| 872 | $A_8$ | | | | | | | | | | | | | | | 2376 | $C_{39}$ | $R_4$ | $X_2$ | $H_1$ | | | |
| 873 | $V_7$ | $I_1$ | | | | | | | | | | | | | | 2377 | $P_{23}$ | $X_{14}$ | $S_5$ | $L_3$ | $F_1$ | | |
| 874 | $I_8$ | | | | | | | | | | | | | | | 2378 | $P_{41}$ | $X_5$ | | | | | |
| 875 | $L_8$ | | | | | | | | | | | | | | | 2379 | $D_{46}$ | | | | | | |
| 876 | $L_8$ | | | | | | | | | | | | | | | 2380 | $S_{46}$ | | | | | | |
| 877 | $M_8$ | | | | | | | | | | | | | | | 2381 | $D_{46}$ | | | | | | |
| 878 | $C_8$ | | | | | | | | | | | | | | | 2382 | $A_{36}$ | $V_5$ | $T_3$ | $D_1$ | $N_1$ | | |
| 879 | $A_4$ | $V_4$ | | | | | | | | | | | | | | 2383 | $E_{24}$ | $D_{21}$ | $G_1$ | | | | |
| 880 | $V_6$ | $I_2$ | | | | | | | | | | | | | | 2384 | $S_{25}$ | $X_{21}$ | | | | | |
| 881 | $H_8$ | | | | | | | | | | | | | | | 2385 | $Y_{32}$ | $C_{12}$ | $F_1$ | $N_1$ | | | |
| 882 | $P_8$ | | | | | | | | | | | | | | | 2386 | $S_{46}$ | | | | | | |
| 883 | $T_6$ | $A_1$ | $S_1$ | | | | | | | | | | | | | 2387 | $S_{46}$ | | | | | | |
| 884 | $L_8$ | | | | | | | | | | | | | | | 2388 | $M_{46}$ | | | | | | |
| 885 | $V_8$ | | | | | | | | | | | | | | | 2389 | $P_{27}$ | $X_{19}$ | | | | | |
| 886 | $F_8$ | | | | | | | | | | | | | | | 2390 | $P_{45}$ | $X_1$ | | | | | |
| 887 | $D_8$ | | | | | | | | | | | | | | | 2391 | $L_{45}$ | $X_1$ | | | | | |
| 888 | $I_8$ | | | | | | | | | | | | | | | 2392 | $E_{46}$ | | | | | | |
| 889 | $T_8$ | | | | | | | | | | | | | | | 2393 | $G_{46}$ | | | | | | |
| 890 | $K_8$ | | | | | | | | | | | | | | | 2394 | $E_{46}$ | | | | | | |
| 891 | $L_8$ | | | | | | | | | | | | | | | 2395 | $P_{46}$ | | | | | | |
| 892 | $L_8$ | | | | | | | | | | | | | | | 2396 | $G_{46}$ | | | | | | |
| 893 | $L_8$ | | | | | | | | | | | | | | | 2397 | $D_{45}$ | $G_1$ | | | | | |
| 894 | $A_8$ | | | | | | | | | | | | | | | 2398 | $P_{46}$ | | | | | | |
| 895 | $I_4$ | $V_3$ | $A_1$ | | | | | | | | | | | | | 2399 | $D_{46}$ | | | | | | |
| 896 | $F_7$ | $L_1$ | | | | | | | | | | | | | | 2400 | $L_{46}$ | | | | | | |
| 897 | $G_8$ | | | | | | | | | | | | | | | 2401 | $S_{46}$ | | | | | | |
| 898 | $P_8$ | | | | | | | | | | | | | | | 2402 | $D_{44}$ | $G_1$ | $E_1$ | | | | |
| 899 | $L_8$ | | | | | | | | | | | | | | | 2403 | $G_{45}$ | $A_1$ | | | | | |
| 900 | $W_8$ | | | | | | | | | | | | | | | 2404 | $S_{46}$ | | | | | | |
| 901 | $I_8$ | | | | | | | | | | | | | | | 2405 | $W_{46}$ | | | | | | |
| 902 | $L_8$ | | | | | | | | | | | | | | | 2406 | $S_{46}$ | | | | | | |
| 903 | $Q_8$ | | | | | | | | | | | | | | | 2407 | $T_{46}$ | | | | | | |
| 904 | $A_6$ | $T_2$ | | | | | | | | | | | | | | 2408 | $V_{46}$ | | | | | | |
| 905 | $S_8$ | | | | | | | | | | | | | | | 2409 | $S_{45}$ | $G_1$ | | | | | |
| 906 | $L_8$ | | | | | | | | | | | | | | | 2410 | $S_{45}$ | $N_1$ | | | | | |
| 907 | $L_8$ | | | | | | | | | | | | | | | 2411 | $E_{25}$ | $G_{19}$ | $R_2$ | | | | |
| 908 | $K_8$ | | | | | | | | | | | | | | | 2412 | $A_{41}$ | $T_2$ | $D_1$ | $P_1$ | $S_1$ | | |
| 909 | $V_8$ | | | | | | | | | | | | | | | 2413 | $G_{23}$ | $D_{22}$ | $N_1$ | | | | |
| 910 | $P_8$ | | | | | | | | | | | | | | | 2414 | $T_{37}$ | $A_8$ | $G_1$ | | | | |
| 911 | $Y_8$ | | | | | | | | | | | | | | | 2415 | $E_{46}$ | $X_2$ | | | | | |
| 912 | $F_8$ | | | | | | | | | | | | | | | 2416 | $D_{47}$ | $G_1$ | $X_1$ | | | | |
| 913 | $V_8$ | | | | | | | | | | | | | | | 2417 | $V_{50}$ | | | | | | |
| 914 | $R_8$ | | | | | | | | | | | | | | | 2418 | $V_{49}$ | $L_1$ | | | | | |
| 915 | $V_8$ | | | | | | | | | | | | | | | 2419 | $C_{50}$ | | | | | | |
| 916 | $Q_8$ | | | | | | | | | | | | | | | 2420 | $C_{29}$ | | | | | | |
| 917 | $G_8$ | | | | | | | | | | | | | | | 2421 | $S_{12}$ | | | | | | |
| 918 | $L_8$ | | | | | | | | | | | | | | | 2422 | $M_{12}$ | | | | | | |
| 919 | $L_7$ | $I_1$ | | | | | | | | | | | | | | 2423 | $S_{12}$ | | | | | | |
| 920 | $R_8$ | | | | | | | | | | | | | | | 2424 | $Y_{12}$ | | | | | | |
| 921 | $I_6$ | $F_1$ | $V_1$ | | | | | | | | | | | | | 2425 | $S_{11}$ | $T_1$ | | | | | |
| 922 | $C_8$ | | | | | | | | | | | | | | | 2426 | $W_{12}$ | | | | | | |
| 923 | $A_7$ | $V_1$ | | | | | | | | | | | | | | 2427 | $T_{12}$ | | | | | | |
| 924 | $L_6$ | $A_1$ | $I_1$ | | | | | | | | | | | | | 2428 | $G_{12}$ | | | | | | |
| 925 | $A_7$ | $S_1$ | | | | | | | | | | | | | | 2429 | $A_{12}$ | | | | | | |
| 926 | $R_7$ | $P_1$ | | | | | | | | | | | | | | 2430 | $L_{12}$ | | | | | | |
| 927 | $K_8$ | | | | | | | | | | | | | | | 2431 | $V_7$ | $I_5$ | | | | | |
| 928 | $M_7$ | $I_1$ | | | | | | | | | | | | | | 2432 | $T_{12}$ | | | | | | |
| 929 | $A_5$ | $V_2$ | $I_1$ | | | | | | | | | | | | | 2433 | $P_{12}$ | | | | | | |
| 930 | $G_8$ | | | | | | | | | | | | | | | 2434 | $C_{12}$ | | | | | | |
| 931 | $G_7$ | $L_1$ | | | | | | | | | | | | | | 2435 | $A_{11}$ | $T_1$ | | | | | |
| 932 | $H_7$ | $R_1$ | | | | | | | | | | | | | | 2436 | $A_{12}$ | | | | | | |
| 933 | $Y_8$ | | | | | | | | | | | | | | | 2437 | $E_{12}$ | | | | | | |
| 934 | $V_8$ | | | | | | | | | | | | | | | 2438 | $E_{11}$ | $G_1$ | | | | | |
| 935 | $Q_8$ | | | | | | | | | | | | | | | 2439 | $Q_{12}$ | | | | | | |

TABLE 5-continued

HCV 1a Consensus Sequences

| A | B | C | D | E | F | G | H | I | J | K | L | M | N | O | P | Q | R | S | T | U | V | W |
|---|---|---|---|---|---|---|---|---|---|---|---|---|---|---|---|---|---|---|---|---|---|---|
| 936 $M_8$ | | | | | | | | | | | | | | | 2440 $K_{12}$ | | | | | | | |
| 937 $A_6$ | $V_2$ | | | | | | | | | | | | | | 2441 $L_{12}$ | | | | | | | |
| 938 $I_6$ | $M_1$ | $V_1$ | | | | | | | | | | | | | 2442 $P_{12}$ | | | | | | | |
| 939 $I_8$ | | | | | | | | | | | | | | | 2443 $I_{12}$ | | | | | | | |
| 940 $K_8$ | | | | | | | | | | | | | | | 2444 $N_{12}$ | | | | | | | |
| 941 $L_5$ | $V_1$ | $A_1$ | $I_1$ | | | | | | | | | | | | 2445 $A_{12}$ | | | | | | | |
| 942 $G_8$ | | | | | | | | | | | | | | | 2446 $L_{12}$ | | | | | | | |
| 943 $A_8$ | | | | | | | | | | | | | | | 2447 $S_{12}$ | | | | | | | |
| 944 $L_8$ | | | | | | | | | | | | | | | 2448 $N_{12}$ | | | | | | | |
| 945 $T_8$ | | | | | | | | | | | | | | | 2449 $S_{12}$ | | | | | | | |
| 946 $G_8$ | | | | | | | | | | | | | | | 2450 $L_{12}$ | | | | | | | |
| 947 $T_8$ | | | | | | | | | | | | | | | 2451 $L_{12}$ | | | | | | | |
| 948 $Y_8$ | | | | | | | | | | | | | | | 2452 $R_{12}$ | | | | | | | |
| 949 $V_6$ | $I_2$ | | | | | | | | | | | | | | 2453 $H_{12}$ | | | | | | | |
| 950 $Y_8$ | | | | | | | | | | | | | | | 2454 $H_{12}$ | | | | | | | |
| 951 $N_7$ | $D_1$ | | | | | | | | | | | | | | 2455 $N_{11}$ | | | | | | $X_1$ | |
| 952 $H_8$ | | | | | | | | | | | | | | | 2456 $L_{12}$ | | | | | | | |
| 953 $L_8$ | | | | | | | | | | | | | | | 2457 $V_{12}$ | | | | | | | |
| 954 $T_8$ | | | | | | | | | | | | | | | 2458 $Y_{12}$ | | | | | | | |
| 955 $P_8$ | | | | | | | | | | | | | | | 2459 $S_{12}$ | | | | | | | |
| 956 $L_8$ | | | | | | | | | | | | | | | 2460 $T_{12}$ | | | | | | | |
| 957 $R_8$ | | | | | | | | | | | | | | | 2461 $T_{12}$ | | | | | | | |
| 958 $D_8$ | | | | | | | | | | | | | | | 2462 $S_{12}$ | | | | | | | |
| 959 $W_8$ | | | | | | | | | | | | | | | 2463 $R_{12}$ | | | | | | | |
| 960 $A_8$ | | | | | | | | | | | | | | | 2464 $S_{12}$ | | | | | | | |
| 961 $H_8$ | | | | | | | | | | | | | | | 2465 $A_{12}$ | | | | | | | |
| 962 $N_7$ | $S_1$ | | | | | | | | | | | | | | 2466 $C_{11}$ | | $G_1$ | | | | | |
| 963 $G_7$ | $S_1$ | | | | | | | | | | | | | | 2467 $Q_{11}$ | | $L_1$ | | | | | |
| 964 $L_8$ | | | | | | | | | | | | | | | 2468 $R_{12}$ | | | | | | | |
| 965 $R_8$ | | | | | | | | | | | | | | | 2469 $Q_{12}$ | | | | | | | |
| 966 $D_8$ | | | | | | | | | | | | | | | 2470 $K_{12}$ | | | | | | | |
| 967 $L_8$ | | | | | | | | | | | | | | | 2471 $K_{12}$ | | | | | | | |
| 968 $A_8$ | | | | | | | | | | | | | | | 2472 $V_{12}$ | | | | | | | |
| 969 $V_8$ | | | | | | | | | | | | | | | 2473 $T_{12}$ | | | | | | | |
| 970 $A_8$ | | | | | | | | | | | | | | | 2474 $F_{12}$ | | | | | | | |
| 971 $V_8$ | | | | | | | | | | | | | | | 2475 $D_{12}$ | | | | | | | |
| 972 $E_8$ | | | | | | | | | | | | | | | 2476 $R_{12}$ | | | | | | | |
| 973 $P_8$ | | | | | | | | | | | | | | | 2477 $L_{11}$ | | $V_1$ | | | | | |
| 974 $V_8$ | | | | | | | | | | | | | | | 2478 $Q_{12}$ | | | | | | | |
| 975 $V_8$ | | | | | | | | | | | | | | | 2479 $V_{12}$ | | | | | | | |
| 976 $F_8$ | | | | | | | | | | | | | | | 2480 $L_{12}$ | | | | | | | |
| 977 $S_8$ | | | | | | | | | | | | | | | 2481 $D_{12}$ | | | | | | | |
| 978 $Q_5$ | $R_3$ | | | | | | | | | | | | | | 2482 $S_{10}$ | | $N_2$ | | | | | |
| 979 $M_8$ | | | | | | | | | | | | | | | 2483 $H_{12}$ | | | | | | | |
| 980 $E_8$ | | | | | | | | | | | | | | | 2484 $Y_{12}$ | | | | | | | |
| 981 $T_8$ | | | | | | | | | | | | | | | 2485 $Q_{11}$ | | $R_1$ | | | | | |
| 982 $K_8$ | | | | | | | | | | | | | | | 2486 $D_{12}$ | | | | | | | |
| 983 $L_8$ | | | | | | | | | | | | | | | 2487 $V_{12}$ | | | | | | | |
| 984 $I_8$ | | | | | | | | | | | | | | | 2488 $L_{12}$ | | | | | | | |
| 985 $T_8$ | | | | | | | | | | | | | | | 2489 $K_{12}$ | | | | | | | |
| 986 $W_8$ | | | | | | | | | | | | | | | 2490 $E_{12}$ | | | | | | | |
| 987 $G_8$ | | | | | | | | | | | | | | | 2491 $V_{12}$ | | | | | | | |
| 988 $A_7$ | $G_1$ | | | | | | | | | | | | | | 2492 $K_{12}$ | | | | | | | |
| 989 $D_8$ | | | | | | | | | | | | | | | 2493 $A_{12}$ | | | | | | | |
| 990 $T_8$ | | | | | | | | | | | | | | | 2494 $A_{12}$ | | | | | | | |
| 991 $A_8$ | | | | | | | | | | | | | | | 2495 $A_{12}$ | | | | | | | |
| 992 $A_8$ | | | | | | | | | | | | | | | 2496 $S_{12}$ | | | | | | | |
| 993 $C_8$ | | | | | | | | | | | | | | | 2497 $K_{12}$ | | | | | | | |
| 994 $G_8$ | | | | | | | | | | | | | | | 2498 $V_{12}$ | | | | | | | |
| 995 $D_8$ | | | | | | | | | | | | | | | 2499 $K_{12}$ | | | | | | | |
| 996 $I_8$ | | | | | | | | | | | | | | | 2500 $A_{12}$ | | | | | | | |
| 997 $I_8$ | | | | | | | | | | | | | | | 2501 $N_{12}$ | | | | | | | |
| 998 $N_7$ | $D_1$ | | | | | | | | | | | | | | 2502 $L_{12}$ | | | | | | | |
| 999 $G_7$ | $N_1$ | | | | | | | | | | | | | | 2503 $L_{12}$ | | | | | | | |
| 1000 $L_8$ | | | | | | | | | | | | | | | 2504 $S_{12}$ | | | | | | | |
| 1001 $P_8$ | | | | | | | | | | | | | | | 2505 $V_{12}$ | | | | | | | |
| 1002 $V_8$ | | | | | | | | | | | | | | | 2506 $E_{12}$ | | | | | | | |
| 1003 $S_8$ | | | | | | | | | | | | | | | 2507 $E_{12}$ | | | | | | | |
| 1004 $A_8$ | | | | | | | | | | | | | | | 2508 $A_{12}$ | | | | | | | |
| 1005 $R_8$ | | | | | | | | | | | | | | | 2509 $C_{12}$ | | | | | | | |
| 1006 $R_8$ | | | | | | | | | | | | | | | 2510 $S_{12}$ | | | | | | | |
| 1007 $G_8$ | | | | | | | | | | | | | | | 2511 $L_{12}$ | | | | | | | |
| 1008 $R_6$ | $Q_2$ | | | | | | | | | | | | | | 2512 $T_{12}$ | | | | | | | |
| 1009 $E_8$ | | | | | | | | | | | | | | | 2513 $P_{12}$ | | | | | | | |
| 1010 $I_8$ | | | | | | | | | | | | | | | 2514 $P_{12}$ | | | | | | | |
| 1011 $L_8$ | | | | | | | | | | | | | | | 2515 $H_{12}$ | | | | | | | |

TABLE 5-continued

| HCV 1a Consensus Sequences |
|---|

| A | B | C | D | E | F | G | H | I | J | K | L | M | N | O | P | Q | R | S | T | U | V | W |
|---|---|---|---|---|---|---|---|---|---|---|---|---|---|---|---|---|---|---|---|---|---|---|
| 1012 $L_8$ | | | | | | | | | | | | | | | 2516 $S_{12}$ | | | | | | | |
| 1013 $G_8$ | | | | | | | | | | | | | | | 2517 $A_{12}$ | | | | | | | |
| 1014 $P_8$ | | | | | | | | | | | | | | | 2518 $K_8$ | | $R_4$ | | | | | |
| 1015 $A_8$ | | | | | | | | | | | | | | | 2519 $S_{12}$ | | | | | | | |
| 1016 $D_8$ | | | | | | | | | | | | | | | 2520 $K_{12}$ | | | | | | | |
| 1017 $G_8$ | | | | | | | | | | | | | | | 2521 $F_{12}$ | | | | | | | |
| 1018 $M_8$ | | | | | | | | | | | | | | | 2522 $G_{12}$ | | | | | | | |
| 1019 $V_7$ | $A_1$ | | | | | | | | | | | | | | 2523 $Y_{12}$ | | | | | | | |
| 1020 $S_8$ | | | | | | | | | | | | | | | 2524 $G_{12}$ | | | | | | | |
| 1021 $K_8$ | | | | | | | | | | | | | | | 2525 $A_{12}$ | | | | | | | |
| 1022 $G_8$ | | | | | | | | | | | | | | | 2526 $K_{12}$ | | | | | | | |
| 1023 $W_8$ | | | | | | | | | | | | | | | 2527 $D_{14}$ | | | | | | | |
| 1024 $R_8$ | | | | | | | | | | | | | | | 2528 $V_{14}$ | | | | | | | |
| 1025 $L_8$ | | | | | | | | | | | | | | | 2529 $R_{14}$ | | | | | | | |
| 1026 $L_7$ | $Q_1$ | | | | | | | | | | | | | | 2530 $C_{14}$ | | | | | | | |
| 1027 $A_{122}$ | $X_2$ | | | | | | | | | | | | | | 2531 $H_{14}$ | | | | | | | |
| 1028 $P_{124}$ | | | | | | | | | | | | | | | 2532 $A_{14}$ | | | | | | | |
| 1029 $I_{124}$ | | | | | | | | | | | | | | | 2533 $R_{14}$ | | | | | | | |
| 1030 $T_{124}$ | | | | | | | | | | | | | | | 2534 $K_{14}$ | | | | | | | |
| 1031 $A_{123}$ | $X_1$ | | | | | | | | | | | | | | 2535 $A_{14}$ | | | | | | | |
| 1032 $Y_{124}$ | | | | | | | | | | | | | | | 2536 $V_{14}$ | | | | | | | |
| 1033 $A_{122}$ | $T_2$ | | | | | | | | | | | | | | 2537 $N_8$ | | $A_5$ | | $T_1$ | | | |
| 1034 $Q_{123}$ | $X_1$ | | | | | | | | | | | | | | 2538 $H_{14}$ | | | | | | | |
| 1035 $Q_{124}$ | | | | | | | | | | | | | | | 2539 $I_{14}$ | | | | | | | |
| 1036 $T_{124}$ | | | | | | | | | | | | | | | 2540 $N_{14}$ | | | | | | | |
| 1037 $R_{122}$ | $X_2$ | | | | | | | | | | | | | | 2541 $S_{14}$ | | | | | | | |
| 1038 $G_{124}$ | | | | | | | | | | | | | | | 2542 $V_{14}$ | | | | | | | |
| 1039 $L_{124}$ | | | | | | | | | | | | | | | 2543 $W_{14}$ | | | | | | | |
| 1040 $L_{122}$ | $X_2$ | | | | | | | | | | | | | | 2544 $K_{14}$ | | | | | | | |
| 1041 $G_{123}$ | $R_1$ | | | | | | | | | | | | | | 2545 $D_{14}$ | | | | | | | |
| 1042 $C_{123}$ | $X_1$ | | | | | | | | | | | | | | 2546 $L_{14}$ | | | | | | | |
| 1043 $I_{124}$ | | | | | | | | | | | | | | | 2547 $L_{14}$ | | | | | | | |
| 1044 $I_{108}$ | $V_{14}$ | $X_2$ | | | | | | | | | | | | | 2548 $E_{14}$ | | | | | | | |
| 1045 $T_{124}$ | | | | | | | | | | | | | | | 2549 $D_{13}$ | | $A_1$ | | | | | |
| 1046 $S_{123}$ | $N_1$ | | | | | | | | | | | | | | 2550 $S_{11}$ | | $N_3$ | | | | | |
| 1047 $L_{124}$ | | | | | | | | | | | | | | | 2551 $V_{14}$ | | | | | | | |
| 1048 $T_{124}$ | | | | | | | | | | | | | | | 2552 $T_{14}$ | | | | | | | |
| 1049 $G_{124}$ | | | | | | | | | | | | | | | 2553 $P_{14}$ | | | | | | | |
| 1050 $R_{124}$ | | | | | | | | | | | | | | | 2554 $I_{14}$ | | | | | | | |
| 1051 $D_{124}$ | | | | | | | | | | | | | | | 2555 $D_{14}$ | | | | | | | |
| 1052 $K_{122}$ | $R_1$ | $X_1$ | | | | | | | | | | | | | 2556 $T_{14}$ | | | | | | | |
| 1053 $N_{123}$ | $D_1$ | | | | | | | | | | | | | | 2557 $T_{14}$ | | | | | | | |
| 1054 $Q_{124}$ | | | | | | | | | | | | | | | 2558 $I_{14}$ | | | | | | | |
| 1055 $V_{102}$ | $A_{22}$ | | | | | | | | | | | | | | 2559 $M_{14}$ | | | | | | | |
| 1056 $E_{124}$ | | | | | | | | | | | | | | | 2560 $A_{14}$ | | | | | | | |
| 1057 $G_{124}$ | | | | | | | | | | | | | | | 2561 $K_{14}$ | | | | | | | |
| 1058 $E_{124}$ | | | | | | | | | | | | | | | 2562 $N_{14}$ | | | | | | | |
| 1059 $V_{120}$ | $I_3$ | $A_1$ | | | | | | | | | | | | | 2563 $E_{14}$ | | | | | | | |
| 1060 $Q_{122}$ | $H_1$ | $X_1$ | | | | | | | | | | | | | 2564 $V_{14}$ | | | | | | | |
| 1061 $I_{122}$ | $X_1$ | $V_1$ | | | | | | | | | | | | | 2565 $F_{14}$ | | | | | | | |
| 1062 $V_{124}$ | | | | | | | | | | | | | | | 2566 $C_{14}$ | | | | | | | |
| 1063 $S_{124}$ | | | | | | | | | | | | | | | 2567 $V_{14}$ | | | | | | | |
| 1064 $T_{124}$ | | | | | | | | | | | | | | | 2568 $Q_{14}$ | | | | | | | |
| 1065 $A_{123}$ | $T_1$ | | | | | | | | | | | | | | 2569 $P_{14}$ | | | | | | | |
| 1066 $A_{100}$ | $T_{21}$ | $X_3$ | | | | | | | | | | | | | 2570 $E_{14}$ | | | | | | | |
| 1067 $Q_{124}$ | | | | | | | | | | | | | | | 2571 $K_{14}$ | | | | | | | |
| 1068 $T_{122}$ | $S_1$ | $X_1$ | | | | | | | | | | | | | 2572 $G_{14}$ | | | | | | | |
| 1069 $F_{123}$ | $X_1$ | | | | | | | | | | | | | | 2573 $G_{14}$ | | | | | | | |
| 1070 $L_{124}$ | | | | | | | | | | | | | | | 2574 $R_{13}$ | | $C_1$ | | | | | |
| 1071 $A_{123}$ | $X_1$ | | | | | | | | | | | | | | 2575 $K_{14}$ | | | | | | | |
| 1072 $T_{120}$ | $X_4$ | | | | | | | | | | | | | | 2576 $P_{14}$ | | | | | | | |
| 1073 $C_{123}$ | $S_1$ | | | | | | | | | | | | | | 2577 $A_{14}$ | | | | | | | |
| 1074 $I_{124}$ | | | | | | | | | | | | | | | 2578 $R_{14}$ | | | | | | | |
| 1075 $N_{124}$ | | | | | | | | | | | | | | | 2579 $L_{14}$ | | | | | | | |
| 1076 $G_{124}$ | | | | | | | | | | | | | | | 2580 $I_{14}$ | | | | | | | |
| 1077 $V_{123}$ | $X_1$ | | | | | | | | | | | | | | 2581 $V_{14}$ | | | | | | | |
| 1078 $C_{124}$ | | | | | | | | | | | | | | | 2582 $F_{13}$ | | $Y_1$ | | | | | |
| 1079 $W_{124}$ | | | | | | | | | | | | | | | 2583 $P_{14}$ | | | | | | | |
| 1080 $T_{124}$ | | | | | | | | | | | | | | | 2584 $D_{14}$ | | | | | | | |
| 1081 $V_{124}$ | | | | | | | | | | | | | | | 2585 $L_{14}$ | | | | | | | |
| 1082 $Y_{124}$ | | | | | | | | | | | | | | | 2586 $G_{14}$ | | | | | | | |
| 1083 $H_{124}$ | | | | | | | | | | | | | | | 2587 $V_{14}$ | | | | | | | |
| 1084 $G_{124}$ | | | | | | | | | | | | | | | 2588 $R_{14}$ | | | | | | | |
| 1085 $A_{123}$ | $X_1$ | | | | | | | | | | | | | | 2589 $V_{14}$ | | | | | | | |
| 1086 $G_{123}$ | $R_1$ | | | | | | | | | | | | | | 2590 $C_{13}$ | | $F_1$ | | | | | |
| 1087 $T_{121}$ | $X_1$ | $A_1$ | $S_1$ | | | | | | | | | | | | 2591 $E_{13}$ | | $K_1$ | | | | | |

TABLE 5-continued

HCV 1a Consensus Sequences

| # | A | B | C | D | E | F | G | H | I | J | K | L | M | N | O | # | P | Q | R | S | T | U | V | W |
|---|---|---|---|---|---|---|---|---|---|---|---|---|---|---|---|---|---|---|---|---|---|---|---|---|
| 1088 | $R_{120}$ | $K_4$ | | | | | | | | | | | | | | 2592 | $K_{14}$ | | | | | | | |
| 1089 | $T_{124}$ | | | | | | | | | | | | | | | 2593 | $M_{14}$ | | | | | | | |
| 1090 | $I_{103}$ | $M_{19}$ | $L_2$ | | | | | | | | | | | | | 2594 | $A_{14}$ | | | | | | | |
| 1091 | $A_{124}$ | | | | | | | | | | | | | | | 2595 | $L_{14}$ | | | | | | | |
| 1092 | $S_{122}$ | $T_2$ | | | | | | | | | | | | | | 2596 | $Y_{14}$ | | | | | | | |
| 1093 | $S_{70}$ | $P_{34}$ | $A_{20}$ | | | | | | | | | | | | | 2597 | $D_{12}$ | $E_2$ | | | | | | |
| 1094 | $K_{124}$ | | | | | | | | | | | | | | | 2598 | $V_{13}$ | $L_1$ | | | | | | |
| 1095 | $G_{124}$ | | | | | | | | | | | | | | | 2599 | $V_{14}$ | | | | | | | |
| 1096 | $P_{124}$ | | | | | | | | | | | | | | | 2600 | $S_{11}$ | $T_2$ | $R_1$ | | | | | |
| 1097 | $V_{123}$ | $X_1$ | | | | | | | | | | | | | | 2601 | $K_{14}$ | | | | | | | |
| 1098 | $I_{124}$ | | | | | | | | | | | | | | | 2602 | $L_{14}$ | | | | | | | |
| 1099 | $Q_{124}$ | | | | | | | | | | | | | | | 2603 | $P_{14}$ | | | | | | | |
| 1100 | $M_{123}$ | $T_1$ | | | | | | | | | | | | | | 2604 | $L_{12}$ | $P_1$ | $V_1$ | | | | | |
| 1101 | $Y_{123}$ | $X_1$ | | | | | | | | | | | | | | 2605 | $A_{14}$ | | | | | | | |
| 1102 | $T_{124}$ | | | | | | | | | | | | | | | 2606 | $V_{14}$ | | | | | | | |
| 1103 | $N_{123}$ | $X_1$ | | | | | | | | | | | | | | 2607 | $M_{14}$ | | | | | | | |
| 1104 | $V_{123}$ | $I_1$ | | | | | | | | | | | | | | 2608 | $G_{14}$ | | | | | | | |
| 1105 | $D_{124}$ | $X_1$ | | | | | | | | | | | | | | 2609 | $S_{13}$ | $G_1$ | | | | | | |
| 1106 | $Q_{133}$ | $K_{23}$ | $G_1$ | $R_1$ | | | | | | | | | | | | 2610 | $S_{14}$ | | | | | | | |
| 1107 | $D_{157}$ | $P_1$ | | | | | | | | | | | | | | 2611 | $Y_{14}$ | | | | | | | |
| 1108 | $L_{157}$ | $X_1$ | | | | | | | | | | | | | | 2612 | $G_{14}$ | | | | | | | |
| 1109 | $V_{157}$ | $G_1$ | | | | | | | | | | | | | | 2613 | $F_{14}$ | | | | | | | |
| 1110 | $G_{157}$ | $X_1$ | | | | | | | | | | | | | | 2614 | $Q_{14}$ | | | | | | | |
| 1111 | $W_{156}$ | $R_1$ | $G_1$ | | | | | | | | | | | | | 2615 | $Y_{14}$ | | | | | | | |
| 1112 | $P_{152}$ | $X_2$ | $V_2$ | $A_1$ | $S_1$ | | | | | | | | | | | 2616 | $S_{14}$ | | | | | | | |
| 1113 | $A_{144}$ | $T_{11}$ | $P_1$ | $G_1$ | $X_1$ | | | | | | | | | | | 2617 | $P_{14}$ | | | | | | | |
| 1114 | $P_{128}$ | $L_{21}$ | $X_3$ | $Q_2$ | $A_2$ | $H_1$ | $M_1$ | | | | | | | | | 2618 | $G_{13}$ | $A_1$ | | | | | | |
| 1115 | $Q_{130}$ | $P_{21}$ | $L_3$ | $X_3$ | $E_1$ | | | | | | | | | | | 2619 | $Q_{14}$ | | | | | | | |
| 1116 | $G_{154}$ | $X_1$ | $E_1$ | $N_1$ | $S_1$ | | | | | | | | | | | 2620 | $R_{14}$ | | | | | | | |
| 1117 | $A_{89}$ | $S_{36}$ | $T_{27}$ | $N_1$ | $I_1$ | $C_1$ | $V_1$ | $G_1$ | $R_1$ | | | | | | | 2621 | $V_{14}$ | | | | | | | |
| 1118 | $R_{158}$ | | | | | | | | | | | | | | | 2622 | $E_{14}$ | | | | | | | |
| 1119 | $S_{158}$ | | | | | | | | | | | | | | | 2623 | $F_{14}$ | | | | | | | |
| 1120 | $L_{158}$ | | | | | | | | | | | | | | | 2624 | $L_{14}$ | | | | | | | |
| 1121 | $T_{155}$ | $V_1$ | $A_1$ | $X_1$ | | | | | | | | | | | | 2625 | $V_{14}$ | | | | | | | |
| 1122 | $P_{156}$ | $X_1$ | $A_1$ | | | | | | | | | | | | | 2626 | $Q_{13}$ | $K_1$ | | | | | | |
| 1123 | $C_{158}$ | | | | | | | | | | | | | | | 2627 | $A_{14}$ | | | | | | | |
| 1124 | $T_{152}$ | $A_3$ | $X_2$ | $P_1$ | | | | | | | | | | | | 2628 | $W_{14}$ | | | | | | | |
| 1125 | $C_{157}$ | $G_1$ | | | | | | | | | | | | | | 2629 | $K_{14}$ | | | | | | | |
| 1126 | $G_{157}$ | $X_1$ | | | | | | | | | | | | | | 2630 | $S_{14}$ | | | | | | | |
| 1127 | $S_{155}$ | $X_3$ | | | | | | | | | | | | | | 2631 | $K_{14}$ | | | | | | | |
| 1128 | $S_{156}$ | $X_1$ | $K_1$ | | | | | | | | | | | | | 2632 | $K_{13}$ | $R_1$ | | | | | | |
| 1129 | $D_{156}$ | $N_1$ | $X_1$ | | | | | | | | | | | | | 2633 | $T_{12}$ | $N_2$ | | | | | | |
| 1130 | $L_{158}$ | | | | | | | | | | | | | | | 2634 | $P_{14}$ | | | | | | | |
| 1131 | $Y_{158}$ | | | | | | | | | | | | | | | 2635 | $M_{14}$ | | | | | | | |
| 1132 | $L_{157}$ | $P_1$ | | | | | | | | | | | | | | 2636 | $G_{14}$ | | | | | | | |
| 1133 | $V_{157}$ | $A_1$ | | | | | | | | | | | | | | 2637 | $F_{14}$ | | | | | | | |
| 1134 | $T_{158}$ | | | | | | | | | | | | | | | 2638 | $S_{14}$ | | | | | | | |
| 1135 | $R_{158}$ | | | | | | | | | | | | | | | 2639 | $Y_{14}$ | | | | | | | |
| 1136 | $H_{158}$ | | | | | | | | | | | | | | | 2640 | $D_{14}$ | | | | | | | |
| 1137 | $A_{158}$ | | | | | | | | | | | | | | | 2641 | $T_{14}$ | | | | | | | |
| 1138 | $D_{157}$ | $E_1$ | | | | | | | | | | | | | | 2642 | $R_{14}$ | | | | | | | |
| 1139 | $V_{157}$ | $L_1$ | | | | | | | | | | | | | | 2643 | $C_{14}$ | | | | | | | |
| 1140 | $I_{157}$ | $V_1$ | | | | | | | | | | | | | | 2644 | $F_{14}$ | | | | | | | |
| 1141 | $P_{157}$ | $X_1$ | | | | | | | | | | | | | | 2645 | $D_{14}$ | | | | | | | |
| 1142 | $V_{158}$ | | | | | | | | | | | | | | | 2646 | $S_{14}$ | | | | | | | |
| 1143 | $R_{158}$ | | | | | | | | | | | | | | | 2647 | $T_{14}$ | | | | | | | |
| 1144 | $R_{158}$ | | | | | | | | | | | | | | | 2648 | $V_{14}$ | | | | | | | |
| 1145 | $R_{153}$ | $Q_3$ | $X_2$ | | | | | | | | | | | | | 2649 | $T_{13}$ | $N_1$ | | | | | | |
| 1146 | $G_{157}$ | $D_1$ | | | | | | | | | | | | | | 2650 | $E_{14}$ | | | | | | | |
| 1147 | $D_{157}$ | $X_1$ | | | | | | | | | | | | | | 2651 | $S_{14}$ | | | | | | | |
| 1148 | $S_{154}$ | $G_2$ | $X_2$ | | | | | | | | | | | | | 2652 | $D_{14}$ | | | | | | | |
| 1149 | $R_{157}$ | $T_1$ | | | | | | | | | | | | | | 2653 | $X_{91}$ | $I_{14}$ | | | | | | |
| 1150 | $G_{155}$ | $A_2$ | $X_1$ | | | | | | | | | | | | | 2654 | $R_{106}$ | | | | | | | |
| 1151 | $S_{156}$ | $T_1$ | $G_1$ | | | | | | | | | | | | | 2655 | $T_{105}$ | $X_1$ | | | | | | |
| 1152 | $L_{155}$ | $X_2$ | $Q_1$ | | | | | | | | | | | | | 2656 | $E_{104}$ | $X_2$ | | | | | | |
| 1153 | $L_{155}$ | $X_2$ | $P_1$ | | | | | | | | | | | | | 2657 | $E_{105}$ | $G_1$ | | | | | | |
| 1154 | $S_{158}$ | | | | | | | | | | | | | | | 2658 | $A_{105}$ | $L_1$ | | | | | | |
| 1155 | $P_{157}$ | $H_1$ | | | | | | | | | | | | | | 2659 | $I_{103}$ | $X_2$ | $V_1$ | | | | | |
| 1156 | $R_{157}$ | $X_1$ | | | | | | | | | | | | | | 2660 | $Y_{105}$ | $X_1$ | | | | | | |
| 1157 | $P_{158}$ | | | | | | | | | | | | | | | 2661 | $Q_{105}$ | $L_1$ | | | | | | |
| 1158 | $I_{157}$ | $V_1$ | | | | | | | | | | | | | | 2662 | $C_{106}$ | | | | | | | |
| 1159 | $S_{156}$ | $X_1$ | $P_1$ | | | | | | | | | | | | | 2663 | $C_{105}$ | $X_2$ | | | | | | |
| 1160 | $Y_{158}$ | | | | | | | | | | | | | | | 2664 | $D_{106}$ | $X_1$ | | | | | | |
| 1161 | $L_{157}$ | $X_1$ | | | | | | | | | | | | | | 2665 | $L_{106}$ | $X_2$ | | | | | | |
| 1162 | $K_{156}$ | $X_2$ | | | | | | | | | | | | | | 2666 | $D_{108}$ | | | | | | | |
| 1163 | $G_{158}$ | | | | | | | | | | | | | | | 2667 | $P_{108}$ | | | | | | | |

TABLE 5-continued

HCV 1a Consensus Sequences

| | A | B | C | D | E | F | G | H | I | J | K | L | M | N | O | | P | Q | R | S | T | U | V | W |
|---|---|---|---|---|---|---|---|---|---|---|---|---|---|---|---|---|---|---|---|---|---|---|---|---|
| 1164 | $S_{157}$ | $X_1$ | | | | | | | | | | | | | | 2668 | $Q_{104}$ | $R_2$ | $X_2$ | | | | | |
| 1165 | $S_{158}$ | | | | | | | | | | | | | | | 2669 | $A_{108}$ | | | | | | | |
| 1166 | $G_{158}$ | | | | | | | | | | | | | | | 2670 | $R_{108}$ | | | | | | | |
| 1167 | $G_{158}$ | | | | | | | | | | | | | | | 2671 | $V_{106}$ | $T_1$ | $K_1$ | | | | | |
| 1168 | $P_{157}$ | $X_1$ | | | | | | | | | | | | | | 2672 | $A_{105}$ | $V_1$ | $X_1$ | $P_1$ | | | | |
| 1169 | $L_{157}$ | $X_1$ | | | | | | | | | | | | | | 2673 | $I_{107}$ | $X_1$ | | | | | | |
| 1170 | $L_{156}$ | $X_2$ | | | | | | | | | | | | | | 2674 | $K_{71}$ | $R_{37}$ | | | | | | |
| 1171 | $C_{158}$ | | | | | | | | | | | | | | | 2675 | $S_{108}$ | | | | | | | |
| 1172 | $P_{157}$ | $S_1$ | | | | | | | | | | | | | | 2676 | $L_{108}$ | | | | | | | |
| 1173 | $A_{155}$ | $X_1$ | $P_1$ | $V_1$ | | | | | | | | | | | | 2677 | $T_{107}$ | $I_1$ | | | | | | |
| 1174 | $G_{155}$ | $X_3$ | | | | | | | | | | | | | | 2678 | $E_{106}$ | $Q_1$ | $X_1$ | | | | | |
| 1175 | $H_{157}$ | $N_1$ | | | | | | | | | | | | | | 2679 | $R_{108}$ | | | | | | | |
| 1176 | $A_{157}$ | $X_1$ | | | | | | | | | | | | | | 2680 | $L_{107}$ | $X_1$ | | | | | | |
| 1177 | $V_{157}$ | $X_1$ | | | | | | | | | | | | | | 2681 | $Y_{107}$ | $X_1$ | | | | | | |
| 1178 | $G_{156}$ | $S_2$ | | | | | | | | | | | | | | 2682 | $V_{107}$ | $I_1$ | | | | | | |
| 1179 | $I_{138}$ | $L_{20}$ | | | | | | | | | | | | | | 2683 | $G_{108}$ | | | | | | | |
| 1180 | $F_{157}$ | $X_1$ | | | | | | | | | | | | | | 2684 | $G_{108}$ | | | | | | | |
| 1181 | $R_{156}$ | $X_2$ | | | | | | | | | | | | | | 2685 | $P_{108}$ | | | | | | | |
| 1182 | $A_{155}$ | $P_2$ | $G_1$ | | | | | | | | | | | | | 2686 | $L_{108}$ | | | | | | | |
| 1183 | $A_{157}$ | $X_1$ | | | | | | | | | | | | | | 2687 | $T_{108}$ | | | | | | | |
| 1184 | $V_{158}$ | | | | | | | | | | | | | | | 2688 | $N_{107}$ | $X_1$ | | | | | | |
| 1185 | $C_{154}$ | $X_4$ | | | | | | | | | | | | | | 2689 | $S_{108}$ | | | | | | | |
| 1186 | $T_{158}$ | | | | | | | | | | | | | | | 2690 | $R_{99}$ | $K_8$ | $X_1$ | | | | | |
| 1187 | $R_{157}$ | $P_1$ | | | | | | | | | | | | | | 2691 | $G_{108}$ | | | | | | | |
| 1188 | $G_{157}$ | $X_1$ | | | | | | | | | | | | | | 2692 | $E_{108}$ | | | | | | | |
| 1189 | $V_{158}$ | | | | | | | | | | | | | | | 2693 | $N_{108}$ | | | | | | | |
| 1190 | $A_{158}$ | | | | | | | | | | | | | | | 2694 | $C_{106}$ | $X_2$ | | | | | | |
| 1191 | $K_{157}$ | $X_1$ | | | | | | | | | | | | | | 2695 | $G_{108}$ | | | | | | | |
| 1192 | $A_{156}$ | $X_2$ | | | | | | | | | | | | | | 2696 | $Y_{107}$ | $X_1$ | | | | | | |
| 1193 | $V_{158}$ | | | | | | | | | | | | | | | 2697 | $R_{108}$ | | | | | | | |
| 1194 | $D_{155}$ | $X_2$ | $E_1$ | | | | | | | | | | | | | 2698 | $R_{107}$ | $X_1$ | | | | | | |
| 1195 | $F_{153}$ | $X_5$ | | | | | | | | | | | | | | 2699 | $C_{106}$ | $X_2$ | | | | | | |
| 1196 | $I_{157}$ | $V_1$ | | | | | | | | | | | | | | 2700 | $R_{108}$ | | | | | | | |
| 1197 | $P_{154}$ | $X_4$ | | | | | | | | | | | | | | 2701 | $A_{106}$ | $X_2$ | | | | | | |
| 1198 | $V_{157}$ | $A_1$ | | | | | | | | | | | | | | 2702 | $S_{107}$ | $R_1$ | | | | | | |
| 1199 | $E_{157}$ | $V_1$ | | | | | | | | | | | | | | 2703 | $G_{107}$ | $I_1$ | | | | | | |
| 1200 | $N_{87}$ | $S_{48}$ | $G_{18}$ | $X_3$ | $D_2$ | | | | | | | | | | | 2704 | $V_{108}$ | | | | | | | |
| 1201 | $L_{156}$ | $X_2$ | | | | | | | | | | | | | | 2705 | $L_{107}$ | $X_1$ | | | | | | |
| 1202 | $E_{157}$ | $G_1$ | | | | | | | | | | | | | | 2706 | $T_{108}$ | | | | | | | |
| 1203 | $T_{158}$ | | | | | | | | | | | | | | | 2707 | $T_{108}$ | | | | | | | |
| 1204 | $T_{156}$ | $X_2$ | | | | | | | | | | | | | | 2708 | $S_{108}$ | | | | | | | |
| 1205 | $M_{157}$ | $X_1$ | | | | | | | | | | | | | | 2709 | $C_{108}$ | | | | | | | |
| 1206 | $R_{158}$ | | | | | | | | | | | | | | | 2710 | $G_{108}$ | | | | | | | |
| 1207 | $S_{158}$ | | | | | | | | | | | | | | | 2711 | $N_{107}$ | $X_1$ | | | | | | |
| 1208 | $P_{42}$ | | | | | | | | | | | | | | | 2712 | $T_{108}$ | | | | | | | |
| 1209 | $V_{44}$ | | | | | | | | | | | | | | | 2713 | $L_{108}$ | | | | | | | |
| 1210 | $F_{43}$ | $X_1$ | | | | | | | | | | | | | | 2714 | $T_{108}$ | | | | | | | |
| 1211 | $T_{41}$ | $X_2$ | $S_1$ | | | | | | | | | | | | | 2715 | $C_{108}$ | | | | | | | |
| 1212 | $D_{43}$ | $X_1$ | | | | | | | | | | | | | | 2716 | $Y_{108}$ | | | | | | | |
| 1213 | $N_{43}$ | $X_1$ | | | | | | | | | | | | | | 2717 | $I_{108}$ | | | | | | | |
| 1214 | $S_{44}$ | | | | | | | | | | | | | | | 2718 | $K_{108}$ | | | | | | | |
| 1215 | $S_{41}$ | $A_1$ | $T_1$ | $X_1$ | | | | | | | | | | | | 2719 | $A_{108}$ | | | | | | | |
| 1216 | $P_{44}$ | | | | | | | | | | | | | | | 2720 | $Q_{81}$ | $R_{24}$ | $K_2$ | $L_1$ | | | | |
| 1217 | $P_{44}$ | | | | | | | | | | | | | | | 2721 | $A_{108}$ | | | | | | | |
| 1218 | $A_{38}$ | $X_4$ | $V_2$ | | | | | | | | | | | | | 2722 | $A_{107}$ | $X_1$ | | | | | | |
| 1219 | $V_{43}$ | $X_1$ | | | | | | | | | | | | | | 2723 | $C_{108}$ | | | | | | | |
| 1220 | $P_{44}$ | | | | | | | | | | | | | | | 2724 | $R_{108}$ | | | | | | | |
| 1221 | $Q_{43}$ | $E_1$ | | | | | | | | | | | | | | 2725 | $A_{107}$ | $S_1$ | | | | | | |
| 1222 | $S_{42}$ | $T_2$ | | | | | | | | | | | | | | 2726 | $A_{108}$ | | | | | | | |
| 1223 | $F_{41}$ | $Y_2$ | $X_1$ | | | | | | | | | | | | | 2727 | $G_{100}$ | $R_7$ | $X_1$ | | | | | |
| 1224 | $Q_{44}$ | | | | | | | | | | | | | | | 2728 | $L_{106}$ | $X_1$ | $R_1$ | | | | | |
| 1225 | $V_{44}$ | | | | | | | | | | | | | | | 2729 | $R_{83}$ | $Q_{25}$ | | | | | | |
| 1226 | $A_{43}$ | $X_1$ | | | | | | | | | | | | | | 2730 | $D_{104}$ | $X_2$ | $G_1$ | $E_1$ | | | | |
| 1227 | $H_{44}$ | | | | | | | | | | | | | | | 2731 | $C_{108}$ | | | | | | | |
| 1228 | $L_{44}$ | | | | | | | | | | | | | | | 2732 | $T_{108}$ | | | | | | | |
| 1229 | $H_{43}$ | $X_1$ | | | | | | | | | | | | | | 2733 | $M_{108}$ | | | | | | | |
| 1230 | $A_{44}$ | | | | | | | | | | | | | | | 2734 | $L_{103}$ | $X_3$ | $V_2$ | | | | | |
| 1231 | $P_{44}$ | | | | | | | | | | | | | | | 2735 | $V_{107}$ | $X_1$ | | | | | | |
| 1232 | $T_{43}$ | $X_1$ | | | | | | | | | | | | | | 2736 | $C_{106}$ | $X_2$ | | | | | | |
| 1233 | $G_{44}$ | | | | | | | | | | | | | | | 2737 | $G_{107}$ | $X_1$ | | | | | | |
| 1234 | $S_{44}$ | | | | | | | | | | | | | | | 2738 | $D_{107}$ | $X_1$ | | | | | | |
| 1235 | $G_{44}$ | | | | | | | | | | | | | | | 2739 | $D_{108}$ | | | | | | | |
| 1236 | $K_{41}$ | $X_2$ | $N_1$ | | | | | | | | | | | | | 2740 | $L_{107}$ | $X_1$ | | | | | | |
| 1237 | $S_{43}$ | $X_1$ | | | | | | | | | | | | | | 2741 | $V_{105}$ | $X_2$ | $I_1$ | | | | | |
| 1238 | $T_{44}$ | | | | | | | | | | | | | | | 2742 | $V_{105}$ | $X_2$ | $A_1$ | | | | | |
| 1239 | $K_{43}$ | $X_1$ | | | | | | | | | | | | | | 2743 | $I_{105}$ | $X_1$ | | | | | | |

TABLE 5-continued

HCV 1a Consensus Sequences

| | A | B | C | | | | | | | | | | | | | | A | B | C | D | E |
|---|---|---|---|---|---|---|---|---|---|---|---|---|---|---|---|---|---|---|---|---|---|
| 1240 | $V_{44}$ | | | | | | | | | | | | | | | 2744 | $C_{105}$ | $X_1$ | | | |
| 1241 | $P_{44}$ | | | | | | | | | | | | | | | 2745 | $E_{105}$ | $X_1$ | | | |
| 1242 | $A_{44}$ | | | | | | | | | | | | | | | 2746 | $S_{105}$ | $X_1$ | | | |
| 1243 | $A_{42}$ | $X_2$ | | | | | | | | | | | | | | 2747 | $A_{59}$ | $Q_{44}$ | $V_1$ | $X_1$ | $E_1$ |
| 1244 | $Y_{42}$ | $X_2$ | | | | | | | | | | | | | | 2748 | $G_{106}$ | | | | |
| 1245 | $A_{44}$ | | | | | | | | | | | | | | | 2749 | $V_{104}$ | $I_1$ | $X_1$ | | |
| 1246 | $A_{44}$ | | | | | | | | | | | | | | | 2750 | $Q_{103}$ | $P_3$ | | | |
| 1247 | $Q_{43}$ | $X_1$ | | | | | | | | | | | | | | 2751 | $E_{106}$ | | | | |
| 1248 | $G_{44}$ | | | | | | | | | | | | | | | 2752 | $D_{103}$ | $X_3$ | | | |
| 1249 | $Y_{44}$ | | | | | | | | | | | | | | | 2753 | $A_{106}$ | | | | |
| 1250 | $K_{44}$ | | | | | | | | | | | | | | | 2754 | $A_{102}$ | $X_1$ | $P_1$ | $G_1$ | $M_1$ |
| 1251 | $V_{44}$ | | | | | | | | | | | | | | | 2755 | $S_{102}$ | $N_2$ | $X_1$ | $C_1$ | |
| 1252 | $L_{44}$ | | | | | | | | | | | | | | | 2756 | $L_{106}$ | | | | |
| 1253 | $V_{44}$ | | | | | | | | | | | | | | | 2757 | $R_{105}$ | $X_1$ | | | |
| 1254 | $L_{44}$ | | | | | | | | | | | | | | | 2758 | $A_{106}$ | | | | |
| 1255 | $N_{44}$ | | | | | | | | | | | | | | | 2759 | $F_{105}$ | $X_1$ | | | |
| 1256 | $P_{44}$ | | | | | | | | | | | | | | | 2760 | $T_{105}$ | $X_1$ | | | |
| 1257 | $S_{44}$ | | | | | | | | | | | | | | | 2761 | $E_{106}$ | | | | |
| 1258 | $V_{44}$ | | | | | | | | | | | | | | | 2762 | $A_{106}$ | | | | |
| 1259 | $A_{43}$ | $F_1$ | | | | | | | | | | | | | | 2763 | $M_{106}$ | | | | |
| 1260 | $A_{44}$ | | | | | | | | | | | | | | | 2764 | $T_{105}$ | $I_1$ | | | |
| 1261 | $T_{43}$ | $X_1$ | | | | | | | | | | | | | | 2765 | $R_{106}$ | | | | |
| 1262 | $L_{43}$ | $X_1$ | | | | | | | | | | | | | | 2766 | $Y_{105}$ | $N_1$ | | | |
| 1263 | $G_{43}$ | $S_1$ | | | | | | | | | | | | | | 2767 | $S_{105}$ | $X_1$ | | | |
| 1264 | $F_{44}$ | | | | | | | | | | | | | | | 2768 | $A_{105}$ | $V_1$ | | | |
| 1265 | $G_{44}$ | | | | | | | | | | | | | | | 2769 | $P_{105}$ | | | | |
| 1266 | $A_{41}$ | $V_2$ | $T_1$ | | | | | | | | | | | | | 2770 | $P_{105}$ | | | | |
| 1267 | $Y_{44}$ | | | | | | | | | | | | | | | 2771 | $G_{104}$ | $R_1$ | | | |
| 1268 | $M_{44}$ | | | | | | | | | | | | | | | 2772 | $D_{105}$ | | | | |
| 1269 | $S_{44}$ | | | | | | | | | | | | | | | 2773 | $P_{104}$ | $H_1$ | | | |
| 1270 | $K_{41}$ | $R_2$ | $Q_1$ | | | | | | | | | | | | | 2774 | $P_{105}$ | | | | |
| 1271 | $A_{44}$ | | | | | | | | | | | | | | | 2775 | $Q_{101}$ | $R_3$ | $X_1$ | | |
| 1272 | $H_{43}$ | $Y_1$ | | | | | | | | | | | | | | 2776 | $P_{105}$ | | | | |
| 1273 | $G_{44}$ | | | | | | | | | | | | | | | 2777 | $E_{105}$ | | | | |
| 1274 | $I_{25}$ | $V_{19}$ | | | | | | | | | | | | | | 2778 | $Y_{105}$ | | | | |
| 1275 | $D_{41}$ | $E_2$ | $X_1$ | | | | | | | | | | | | | 2779 | $D_{105}$ | | | | |
| 1276 | $P_{42}$ | $X_2$ | | | | | | | | | | | | | | 2780 | $L_{105}$ | | | | |
| 1277 | $N_{41}$ | $S_2$ | $X_1$ | | | | | | | | | | | | | 2781 | $E_{102}$ | | | | |
| 1278 | $I_{43}$ | $S_1$ | | | | | | | | | | | | | | 2782 | $L_{101}$ | $R_1$ | | | |
| 1279 | $R_{44}$ | | | | | | | | | | | | | | | 2783 | $I_{102}$ | | | | |
| 1280 | $T_{43}$ | $X_1$ | | | | | | | | | | | | | | 2784 | $T_{102}$ | | | | |
| 1281 | $G_{44}$ | | | | | | | | | | | | | | | 2785 | $S_{101}$ | $X_1$ | | | |
| 1282 | $V_{44}$ | | | | | | | | | | | | | | | 2786 | $C_{102}$ | | | | |
| 1283 | $R_{44}$ | | | | | | | | | | | | | | | 2787 | $S_{101}$ | $X_1$ | | | |
| 1284 | $T_{44}$ | | | | | | | | | | | | | | | 2788 | $S_{102}$ | | | | |
| 1285 | $I_{44}$ | | | | | | | | | | | | | | | 2789 | $N_{102}$ | | | | |
| 1286 | $T_{44}$ | | | | | | | | | | | | | | | 2790 | $V_{102}$ | | | | |
| 1287 | $T_{44}$ | | | | | | | | | | | | | | | 2791 | $S_{102}$ | | | | |
| 1288 | $G_{43}$ | $S_1$ | | | | | | | | | | | | | | 2792 | $V_{101}$ | $X_1$ | | | |
| 1289 | $S_{44}$ | | | | | | | | | | | | | | | 2793 | $A_{102}$ | | | | |
| 1290 | $P_{41}$ | $S_2$ | $X_1$ | | | | | | | | | | | | | 2794 | $H_{102}$ | | | | |
| 1291 | $I_{44}$ | | | | | | | | | | | | | | | 2795 | $D_{101}$ | $X_1$ | | | |
| 1292 | $T_{43}$ | $X_1$ | | | | | | | | | | | | | | 2796 | $G_{97}$ | $S_2$ | $X_1$ | $D_1$ | $E_1$ |
| 1293 | $Y_{44}$ | | | | | | | | | | | | | | | 2797 | $A_{92}$ | $T_9$ | $V_1$ | | |
| 1294 | $S_{44}$ | | | | | | | | | | | | | | | 2798 | $G_{102}$ | | | | |
| 1295 | $T_{44}$ | | | | | | | | | | | | | | | 2799 | $K_{101}$ | $R_1$ | | | |
| 1296 | $Y_{44}$ | | | | | | | | | | | | | | | 2800 | $R_{102}$ | | | | |
| 1297 | $G_{44}$ | $X_1$ | | | | | | | | | | | | | | 2801 | $V_{102}$ | | | | |
| 1298 | $K_{45}$ | | | | | | | | | | | | | | | 2802 | $Y_{102}$ | | | | |
| 1299 | $F_{45}$ | | | | | | | | | | | | | | | 2803 | $Y_{102}$ | | | | |
| 1300 | $L_{45}$ | | | | | | | | | | | | | | | 2804 | $L_{101}$ | $X_1$ | | | |
| 1301 | $A_{45}$ | | | | | | | | | | | | | | | 2805 | $T_{102}$ | | | | |
| 1302 | $D_{44}$ | $X_1$ | | | | | | | | | | | | | | 2806 | $R_{102}$ | | | | |
| 1303 | $G_{43}$ | $X_2$ | | | | | | | | | | | | | | 2807 | $D_{102}$ | | | | |
| 1304 | $G_{45}$ | | | | | | | | | | | | | | | 2808 | $P_{101}$ | $X_1$ | | | |
| 1305 | $C_{44}$ | $X_1$ | | | | | | | | | | | | | | 2809 | $T_{101}$ | $A_1$ | | | |
| 1306 | $S_{45}$ | | | | | | | | | | | | | | | 2810 | $T_{102}$ | | | | |
| 1307 | $G_{45}$ | | | | | | | | | | | | | | | 2811 | $P_{102}$ | | | | |
| 1308 | $G_{44}$ | $X_1$ | | | | | | | | | | | | | | 2812 | $L_{97}$ | $F_4$ | $I_1$ | | |
| 1309 | $A_{45}$ | | | | | | | | | | | | | | | 2813 | $A_{100}$ | $V_1$ | $X_1$ | | |
| 1310 | $Y_{45}$ | | | | | | | | | | | | | | | 2814 | $R_{102}$ | | | | |
| 1311 | $D_{45}$ | | | | | | | | | | | | | | | 2815 | $A_{102}$ | | | | |
| 1312 | $I_{45}$ | | | | | | | | | | | | | | | 2816 | $A_{102}$ | | | | |
| 1313 | $I_{45}$ | | | | | | | | | | | | | | | 2817 | $W_{102}$ | | | | |
| 1314 | $I_{44}$ | $X_1$ | | | | | | | | | | | | | | 2818 | $E_{100}$ | $X_2$ | | | |
| 1315 | $C_{44}$ | $X_1$ | | | | | | | | | | | | | | 2819 | $T_{102}$ | | | | |

TABLE 5-continued

HCV 1a Consensus Sequences

| | A | B | C | D | E | F | G | H | I | J | K | L | M | N | O | P | Q | R | S | T | U | V | W |
|---|---|---|---|---|---|---|---|---|---|---|---|---|---|---|---|---|---|---|---|---|---|---|---|
| 1316 | $D_{45}$ | | | | | | | | | | | | | | | 2820 | $A_{102}$ | | | | | | |
| 1317 | $E_{45}$ | | | | | | | | | | | | | | | 2821 | $R_{100}$ | $K_2$ | | | | | |
| 1318 | $C_{45}$ | | | | | | | | | | | | | | | 2822 | $H_{101}$ | $R_1$ | | | | | |
| 1319 | $H_{43}$ | $X_2$ | | | | | | | | | | | | | | 2823 | $T_{102}$ | | | | | | |
| 1320 | $S_{45}$ | | | | | | | | | | | | | | | 2824 | $P_{102}$ | | | | | | |
| 1321 | $T_{44}$ | $P_1$ | | | | | | | | | | | | | | 2825 | $V_{88}$ | $I_{14}$ | | | | | |
| 1322 | $D_{45}$ | | | | | | | | | | | | | | | 2826 | $N_{102}$ | | | | | | |
| 1323 | $A_{43}$ | $X_1$ | | | | | | | | | | | | | | 2827 | $S_{102}$ | | | | | | |
| 1324 | $T_{43}$ | $X_1$ | $P_1$ | | | | | | | | | | | | | 2828 | $W_{102}$ | | | | | | |
| 1325 | $S_{44}$ | $X_1$ | | | | | | | | | | | | | | 2829 | $L_{102}$ | | | | | | |
| 1326 | $I_{39}$ | $V_5$ | $X_1$ | | | | | | | | | | | | | 2830 | $G_{102}$ | | | | | | |
| 1327 | $L_{45}$ | | | | | | | | | | | | | | | 2831 | $N_{101}$ | $X_1$ | | | | | |
| 1328 | $G_{45}$ | | | | | | | | | | | | | | | 2832 | $I_{101}$ | $V_1$ | | | | | |
| 1329 | $I_{45}$ | | | | | | | | | | | | | | | 2833 | $I_{102}$ | | | | | | |
| 1330 | $G_{45}$ | | | | | | | | | | | | | | | 2834 | $M_{102}$ | | | | | | |
| 1331 | $T_{45}$ | | | | | | | | | | | | | | | 2835 | $F_{101}$ | $Y_1$ | | | | | |
| 1332 | $V_{43}$ | $A_2$ | | | | | | | | | | | | | | 2836 | $A_{102}$ | | | | | | |
| 1333 | $L_{42}$ | $X_3$ | | | | | | | | | | | | | | 2837 | $P_{102}$ | | | | | | |
| 1334 | $D_{45}$ | | | | | | | | | | | | | | | 2838 | $T_{102}$ | | | | | | |
| 1335 | $Q_{45}$ | | | | | | | | | | | | | | | 2839 | $L_{102}$ | | | | | | |
| 1336 | $A_{43}$ | $X_2$ | | | | | | | | | | | | | | 2840 | $W_{102}$ | | | | | | |
| 1337 | $E_{43}$ | $D_1$ | $X_1$ | | | | | | | | | | | | | 2841 | $A_{79}$ | $V_{23}$ | | | | | |
| 1338 | $T_{43}$ | $X_2$ | | | | | | | | | | | | | | 2842 | $R_{101}$ | $K_1$ | | | | | |
| 1339 | $A_{44}$ | $X_1$ | | | | | | | | | | | | | | 2843 | $M_{102}$ | | | | | | |
| 1340 | $G_{45}$ | | | | | | | | | | | | | | | 2844 | $I_{97}$ | $V_5$ | | | | | |
| 1341 | $A_{45}$ | | | | | | | | | | | | | | | 2845 | $L_{95}$ | $M_7$ | | | | | |
| 1342 | $R_{43}$ | $T_1$ | $X_1$ | | | | | | | | | | | | | 2846 | $M_{86}$ | $L_{14}$ | $A_1$ | $T_1$ | | | |
| 1343 | $L_{45}$ | | | | | | | | | | | | | | | 2847 | $T_{102}$ | | | | | | |
| 1344 | $V_{44}$ | $L_1$ | | | | | | | | | | | | | | 2848 | $H_{102}$ | | | | | | |
| 1345 | $V_{45}$ | | | | | | | | | | | | | | | 2849 | $F_{102}$ | | | | | | |
| 1346 | $L_{45}$ | | | | | | | | | | | | | | | 2850 | $F_{102}$ | | | | | | |
| 1347 | $A_{45}$ | | | | | | | | | | | | | | | 2851 | $S_{101}$ | $G_1$ | | | | | |
| 1348 | $T_{45}$ | | | | | | | | | | | | | | | 2852 | $V_{68}$ | $I_{33}$ | $X_1$ | | | | |
| 1349 | $A_{44}$ | $P_1$ | | | | | | | | | | | | | | 2853 | $L_{102}$ | | | | | | |
| 1350 | $T_{44}$ | $P_1$ | | | | | | | | | | | | | | 2854 | $I_{81}$ | $M_{19}$ | $L_2$ | | | | |
| 1351 | $P_{45}$ | | | | | | | | | | | | | | | 2855 | $A_{100}$ | $T_1$ | $X_1$ | | | | |
| 1352 | $P_{45}$ | | | | | | | | | | | | | | | 2856 | $R_{102}$ | | | | | | |
| 1353 | $G_{45}$ | | | | | | | | | | | | | | | 2857 | $D_{101}$ | $X_1$ | | | | | |
| 1354 | $S_{44}$ | $X_1$ | | | | | | | | | | | | | | 2858 | $Q_{102}$ | | | | | | |
| 1355 | $V_{36}$ | $I_7$ | $X_2$ | | | | | | | | | | | | | 2859 | $L_{102}$ | | | | | | |
| 1356 | $T_{43}$ | $S_1$ | $X_1$ | | | | | | | | | | | | | 2860 | $E_{102}$ | | | | | | |
| 1357 | $V_{44}$ | $X_1$ | | | | | | | | | | | | | | 2861 | $Q_{102}$ | | | | | | |
| 1358 | $P_{40}$ | $S_5$ | | | | | | | | | | | | | | 2862 | $A_{102}$ | | | | | | |
| 1359 | $H_{44}$ | $X_1$ | | | | | | | | | | | | | | 2863 | $L_{101}$ | $X_1$ | | | | | |
| 1360 | $P_{44}$ | $S_1$ | | | | | | | | | | | | | | 2864 | $D_{98}$ | $N_3$ | $X_1$ | | | | |
| 1361 | $N_{45}$ | | | | | | | | | | | | | | | 2865 | $C_{100}$ | $G_1$ | | | | | |
| 1362 | $I_{45}$ | | | | | | | | | | | | | | | 2866 | $E_{101}$ | | | | | | |
| 1363 | $E_{45}$ | | | | | | | | | | | | | | | 2867 | $I_{101}$ | | | | | | |
| 1364 | $E_{45}$ | | | | | | | | | | | | | | | 2868 | $Y_{100}$ | | | | | | |
| 1365 | $V_{43}$ | $A_1$ | $I_1$ | | | | | | | | | | | | | 2869 | $G_{101}$ | | | | | | |
| 1366 | $A_{45}$ | | | | | | | | | | | | | | | 2870 | $A_{97}$ | $X_2$ | | | | | |
| 1367 | $L_{45}$ | | | | | | | | | | | | | | | 2871 | $C_{92}$ | $X_3$ | | | | | |
| 1368 | $S_{43}$ | $P_2$ | | | | | | | | | | | | | | 2872 | $Y_{92}$ | | | | | | |
| 1369 | $T_{44}$ | $X_1$ | | | | | | | | | | | | | | 2873 | $S_{91}$ | $X_1$ | | | | | |
| 1370 | $T_{45}$ | | | | | | | | | | | | | | | 2874 | $I_{92}$ | | | | | | |
| 1371 | $G_{45}$ | | | | | | | | | | | | | | | 2875 | $E_{91}$ | $X_1$ | | | | | |
| 1372 | $E_{45}$ | | | | | | | | | | | | | | | 2876 | $P_{92}$ | | | | | | |
| 1373 | $I_{43}$ | $V_2$ | | | | | | | | | | | | | | 2877 | $L_{91}$ | $X_1$ | | | | | |
| 1374 | $P_{44}$ | $X_1$ | | | | | | | | | | | | | | 2878 | $D_{88}$ | $X_4$ | | | | | |
| 1375 | $F_{45}$ | | | | | | | | | | | | | | | 2879 | $L_{91}$ | $I_1$ | | | | | |
| 1376 | $Y_{45}$ | | | | | | | | | | | | | | | 2880 | $P_{87}$ | $X_5$ | | | | | |
| 1377 | $G_{45}$ | | | | | | | | | | | | | | | 2881 | $P_{73}$ | $X_6$ | $S_3$ | $Q_3$ | $L_2$ | $A_1$ | |
| 1378 | $K_{45}$ | | | | | | | | | | | | | | | 2882 | $I_{79}$ | $X_3$ | $V_1$ | | | | |
| 1379 | $A_{45}$ | | | | | | | | | | | | | | | 2883 | $I_{80}$ | $X_2$ | | | | | |
| 1380 | $I_{45}$ | | | | | | | | | | | | | | | 2884 | $Q_{80}$ | $X_2$ | | | | | |
| 1381 | $P_{45}$ | | | | | | | | | | | | | | | 2885 | $X_{61}$ | $R_6$ | | | | | |
| 1382 | $L_{45}$ | | | | | | | | | | | | | | | 2886 | $L_6$ | | | | | | |
| 1383 | $E_{44}$ | $G_1$ | | | | | | | | | | | | | | 2887 | $H_5$ | | | | | | |
| 1384 | $V_{32}$ | $A_{11}$ | $X_2$ | | | | | | | | | | | | | 2888 | $G_5$ | | | | | | |
| 1385 | $I_{44}$ | $X_1$ | | | | | | | | | | | | | | 2889 | $L_5$ | | | | | | |
| 1386 | $K_{43}$ | $R_1$ | $X_1$ | | | | | | | | | | | | | 2890 | $S_5$ | | | | | | |
| 1387 | $G_{45}$ | | | | | | | | | | | | | | | 2891 | $A_5$ | | | | | | |
| 1388 | $G_{45}$ | | | | | | | | | | | | | | | 2892 | $F_5$ | | | | | | |
| 1389 | $R_{45}$ | | | | | | | | | | | | | | | 2893 | $S_5$ | | | | | | |
| 1390 | $H_{45}$ | | | | | | | | | | | | | | | 2894 | $L_5$ | | | | | | |
| 1391 | $L_{45}$ | | | | | | | | | | | | | | | 2895 | $H_5$ | | | | | | |

TABLE 5-continued

HCV 1a Consensus Sequences

| A | B | C | D | E | F | G | H | I | J | K | L | M | N | O | P | Q | R | S | T | U | V | W |
|---|---|---|---|---|---|---|---|---|---|---|---|---|---|---|---|---|---|---|---|---|---|---|
| 1392 $I_{45}$ | | | | | | | | | | | | | | | 2896 $S_5$ | | | | | | | |
| 1393 $F_{45}$ | | | | | | | | | | | | | | | 2897 $Y_5$ | | | | | | | |
| 1394 $C_{44}$ | $X_1$ | | | | | | | | | | | | | | 2898 $S_5$ | | | | | | | |
| 1395 $H_{45}$ | | | | | | | | | | | | | | | 2899 $P_5$ | | | | | | | |
| 1396 $S_{45}$ | | | | | | | | | | | | | | | 2900 $G_5$ | | | | | | | |
| 1397 $K_{44}$ | $R_1$ | | | | | | | | | | | | | | 2901 $E_5$ | | | | | | | |
| 1398 $K_{44}$ | $R_1$ | | | | | | | | | | | | | | 2902 $I_5$ | | | | | | | |
| 1399 $K_{45}$ | | | | | | | | | | | | | | | 2903 $N_5$ | | | | | | | |
| 1400 $C_{43}$ | $X_2$ | | | | | | | | | | | | | | 2904 $R_5$ | | | | | | | |
| 1401 $D_{41}$ | $N_2$ | $X_2$ | | | | | | | | | | | | | 2905 $V_5$ | | | | | | | |
| 1402 $E_{43}$ | $D_2$ | | | | | | | | | | | | | | 2906 $A_5$ | | | | | | | |
| 1403 $L_{45}$ | | | | | | | | | | | | | | | 2907 $A_5$ | | | | | | | |
| 1404 $A_{45}$ | | | | | | | | | | | | | | | 2908 $C_5$ | | | | | | | |
| 1405 $A_{42}$ | $T_2$ | $X_1$ | | | | | | | | | | | | | 2909 $L_4$ | | $X_1$ | | | | | |
| 1406 $K_{44}$ | $X_1$ | | | | | | | | | | | | | | 2910 $R_4$ | | | | | | | |
| 1407 $L_{45}$ | | | | | | | | | | | | | | | 2911 $K_4$ | | | | | | | |
| 1408 $V_{42}$ | $X_3$ | | | | | | | | | | | | | | 2912 $L_4$ | | | | | | | |
| 1409 $A_{42}$ | $V_1$ | $G_1$ | $X_1$ | | | | | | | | | | | | 2913 $G_4$ | | | | | | | |
| 1410 $L_{43}$ | $M_2$ | | | | | | | | | | | | | | 2914 $V_4$ | | | | | | | |
| 1411 $G_{44}$ | $X_1$ | | | | | | | | | | | | | | 2915 $P_4$ | | | | | | | |
| 1412 $I_{28}$ | $V_{16}$ | $L_1$ | | | | | | | | | | | | | 2916 $P_3$ | $A_1$ | | | | | | |
| 1413 $N_{45}$ | | | | | | | | | | | | | | | 2917 $L_4$ | | | | | | | |
| 1414 $A_{45}$ | | | | | | | | | | | | | | | 2918 $R_4$ | | | | | | | |
| 1415 $V_{45}$ | | | | | | | | | | | | | | | 2919 $A_4$ | | | | | | | |
| 1416 $A_{44}$ | $X_1$ | | | | | | | | | | | | | | 2920 $W_4$ | | | | | | | |
| 1417 $Y_{43}$ | $X_2$ | | | | | | | | | | | | | | 2921 $R_4$ | | | | | | | |
| 1418 $Y_{45}$ | | | | | | | | | | | | | | | 2922 $H_4$ | | | | | | | |
| 1419 $R_{45}$ | | | | | | | | | | | | | | | 2923 $R_4$ | | | | | | | |
| 1420 $G_{45}$ | | | | | | | | | | | | | | | 2924 $A_4$ | | | | | | | |
| 1421 $L_{45}$ | | | | | | | | | | | | | | | 2925 $R_4$ | | | | | | | |
| 1422 $D_{45}$ | | | | | | | | | | | | | | | 2926 $S_4$ | | | | | | | |
| 1423 $V_{45}$ | | | | | | | | | | | | | | | 2927 $V_4$ | | | | | | | |
| 1424 $S_{45}$ | | | | | | | | | | | | | | | 2928 $R_4$ | | | | | | | |
| 1425 $V_{44}$ | $A_1$ | | | | | | | | | | | | | | 2929 $A_4$ | | | | | | | |
| 1426 $I_{45}$ | | | | | | | | | | | | | | | 2930 $R_3$ | | $K_1$ | | | | | |
| 1427 $P_{45}$ | | | | | | | | | | | | | | | 2931 $L_4$ | | | | | | | |
| 1428 $T_{43}$ | $A_2$ | | | | | | | | | | | | | | 2932 $L_4$ | | | | | | | |
| 1429 $S_{44}$ | $N_1$ | | | | | | | | | | | | | | 2933 $S_4$ | | | | | | | |
| 1430 $G_{44}$ | $X_1$ | | | | | | | | | | | | | | 2934 $R_4$ | | | | | | | |
| 1431 $D_{44}$ | $X_1$ | | | | | | | | | | | | | | 2935 $G_3$ | | $V_1$ | | | | | |
| 1432 $V_{45}$ | | | | | | | | | | | | | | | 2936 $G_4$ | | | | | | | |
| 1433 $V_{45}$ | | | | | | | | | | | | | | | 2937 $R_4$ | | | | | | | |
| 1434 $V_{45}$ | | | | | | | | | | | | | | | 2938 $A_4$ | | | | | | | |
| 1435 $V_{45}$ | | | | | | | | | | | | | | | 2939 $A_4$ | | | | | | | |
| 1436 $A_{39}$ | $S_4$ | $X_2$ | | | | | | | | | | | | | 2940 $I_4$ | | | | | | | |
| 1437 $T_{45}$ | | | | | | | | | | | | | | | 2941 $C_4$ | | | | | | | |
| 1438 $D_{45}$ | | | | | | | | | | | | | | | 2942 $G_4$ | | | | | | | |
| 1439 $A_{44}$ | $X_1$ | | | | | | | | | | | | | | 2943 $K_4$ | | | | | | | |
| 1440 $L_{45}$ | | | | | | | | | | | | | | | 2944 $Y_4$ | | | | | | | |
| 1441 $M_{45}$ | | | | | | | | | | | | | | | 2945 $L_4$ | | | | | | | |
| 1442 $T_{43}$ | $X_2$ | | | | | | | | | | | | | | 2946 $F_4$ | | | | | | | |
| 1443 $G_{45}$ | | | | | | | | | | | | | | | 2947 $N_4$ | | | | | | | |
| 1444 $Y_{26}$ | $F_{19}$ | | | | | | | | | | | | | | 2948 $W_4$ | | | | | | | |
| 1445 $T_{44}$ | $X_1$ | | | | | | | | | | | | | | 2949 $A_4$ | | | | | | | |
| 1446 $G_{45}$ | | | | | | | | | | | | | | | 2950 $V_4$ | | | | | | | |
| 1447 $D_{45}$ | | | | | | | | | | | | | | | 2951 $R_4$ | | | | | | | |
| 1448 $F_{44}$ | $X_1$ | | | | | | | | | | | | | | 2952 $T_4$ | | | | | | | |
| 1449 $D_{45}$ | $X_1$ | | | | | | | | | | | | | | 2953 $K_4$ | | | | | | | |
| 1450 $S_{46}$ | | | | | | | | | | | | | | | 2954 $L_4$ | | | | | | | |
| 1451 $V_{46}$ | | | | | | | | | | | | | | | 2955 $K_4$ | | | | | | | |
| 1452 $I_{46}$ | | | | | | | | | | | | | | | 2956 $L_4$ | | | | | | | |
| 1453 $D_{46}$ | | | | | | | | | | | | | | | 2957 $T_4$ | | | | | | | |
| 1454 $C_{46}$ | $X_2$ | | | | | | | | | | | | | | 2958 $P_4$ | | | | | | | |
| 1455 $N_{47}$ | $X_1$ | | | | | | | | | | | | | | 2959 $I_4$ | | | | | | | |
| 1456 $T_{48}$ | | | | | | | | | | | | | | | 2960 $A_3$ | | $T_1$ | | | | | |
| 1457 $C_{47}$ | $R_1$ | | | | | | | | | | | | | | 2961 $A_4$ | | | | | | | |
| 1458 $V_{48}$ | | | | | | | | | | | | | | | 2962 $A_4$ | | | | | | | |
| 1459 $T_{48}$ | | | | | | | | | | | | | | | 2963 $G_4$ | | | | | | | |
| 1460 $Q_{47}$ | $X_2$ | | | | | | | | | | | | | | 2964 $Q_3$ | | $R_1$ | | | | | |
| 1461 $T_{47}$ | $X_2$ | | | | | | | | | | | | | | 2965 $L_4$ | | | | | | | |
| 1462 $V_{49}$ | | | | | | | | | | | | | | | 2966 $D_4$ | | | | | | | |
| 1463 $D_{49}$ | | | | | | | | | | | | | | | 2967 $L_4$ | | | | | | | |
| 1464 $F_{49}$ | | | | | | | | | | | | | | | 2968 $S_4$ | | | | | | | |
| 1465 $S_{49}$ | | | | | | | | | | | | | | | 2969 $G_4$ | | | | | | | |
| 1466 $L_{48}$ | $F_1$ | | | | | | | | | | | | | | 2970 $W_4$ | | | | | | | |
| 1467 $D_{48}$ | $H_1$ | | | | | | | | | | | | | | 2971 $F_4$ | | | | | | | |

TABLE 5-continued

HCV 1a Consensus Sequences

| | A | B | C | D | E | F | G | H | I | J | K | L | M | N | O | P | Q | R | S | T | U | V | W |
|---|---|---|---|---|---|---|---|---|---|---|---|---|---|---|---|---|---|---|---|---|---|---|---|
| 1468 | $P_{48}$ | $X_1$ | | | | | | | | | | | | | | 2972 $T_4$ | | | | | | | |
| 1469 | $T_{47}$ | $X_1$ | $A_1$ | | | | | | | | | | | | | 2973 $A_4$ | | | | | | | |
| 1470 | $F_{49}$ | | | | | | | | | | | | | | | 2974 $G_4$ | | | | | | | |
| 1471 | $T_{49}$ | | | | | | | | | | | | | | | 2975 $Y_4$ | | | | | | | |
| 1472 | $I_{48}$ | $X_1$ | | | | | | | | | | | | | | 2976 $S_4$ | | | | | | | |
| 1473 | $E_{46}$ | $D_3$ | | | | | | | | | | | | | | 2977 $G_4$ | | | | | | | |
| 1474 | $T_{48}$ | $I_1$ | | | | | | | | | | | | | | 2978 $G_4$ | | | | | | | |
| 1475 | $T_{46}$ | $S_2$ | $I_1$ | | | | | | | | | | | | | 2979 $D_4$ | | | | | | | |
| 1476 | $T_{49}$ | | | | | | | | | | | | | | | 2980 $I_4$ | | | | | | | |
| 1477 | $L_{48}$ | $X_1$ | | | | | | | | | | | | | | 2981 $Y_4$ | | | | | | | |
| 1478 | $P_{49}$ | | | | | | | | | | | | | | | 2982 $H_4$ | | | | | | | |
| 1479 | $Q_{48}$ | $X_1$ | | | | | | | | | | | | | | 2983 $S_4$ | | | | | | | |
| 1480 | $D_{49}$ | | | | | | | | | | | | | | | 2984 $V_4$ | | | | | | | |
| 1481 | $A_{47}$ | $X_2$ | | | | | | | | | | | | | | 2985 $S_4$ | | | | | | | |
| 1482 | $V_{47}$ | $X_2$ | | | | | | | | | | | | | | 2986 $R_3$ | $H_1$ | | | | | | |
| 1483 | $S_{49}$ | | | | | | | | | | | | | | | 2987 $A_4$ | | | | | | | |
| 1484 | $R_{46}$ | $X_3$ | | | | | | | | | | | | | | 2988 $R_4$ | | | | | | | |
| 1485 | $T_{48}$ | $S_1$ | | | | | | | | | | | | | | 2989 $P_4$ | | | | | | | |
| 1486 | $Q_{49}$ | | | | | | | | | | | | | | | 2990 $R_4$ | | | | | | | |
| 1487 | $R_{47}$ | $X_2$ | | | | | | | | | | | | | | 2991 $W_4$ | | | | | | | |
| 1488 | $R_{48}$ | $X_1$ | | | | | | | | | | | | | | 2992 $F_4$ | | | | | | | |
| 1489 | $G_{49}$ | | | | | | | | | | | | | | | 2993 $W_4$ | | | | | | | |
| 1490 | $R_{49}$ | | | | | | | | | | | | | | | 2994 $F_4$ | | | | | | | |
| 1491 | $T_{49}$ | | | | | | | | | | | | | | | 2995 $C_4$ | | | | | | | |
| 1492 | $G_{49}$ | | | | | | | | | | | | | | | 2996 $L_4$ | | | | | | | |
| 1493 | $R_{48}$ | $X_1$ | | | | | | | | | | | | | | 2997 $L_4$ | | | | | | | |
| 1494 | $G_{49}$ | | | | | | | | | | | | | | | 2998 $L_4$ | | | | | | | |
| 1495 | $K_{44}$ | $R_5$ | | | | | | | | | | | | | | 2999 $L_4$ | | | | | | | |
| 1496 | $P_{48}$ | $A_1$ | | | | | | | | | | | | | | 3000 $A_4$ | | | | | | | |
| 1497 | $G_{49}$ | | | | | | | | | | | | | | | 3001 $A_4$ | | | | | | | |
| 1498 | $I_{47}$ | $F_1$ | $X_1$ | | | | | | | | | | | | | 3002 $G_4$ | | | | | | | |
| 1499 | $Y_{49}$ | | | | | | | | | | | | | | | 3003 $V_4$ | | | | | | | |
| 1500 | $R_{49}$ | | | | | | | | | | | | | | | 3004 $G_3$ | $C_1$ | | | | | | |
| 1501 | $F_{49}$ | | | | | | | | | | | | | | | 3005 $I_4$ | | | | | | | |
| 1502 | $V_{49}$ | | | | | | | | | | | | | | | 3006 $Y_4$ | | | | | | | |
| 1503 | $A_{46}$ | $T_3$ | | | | | | | | | | | | | | 3007 $L_4$ | | | | | | | |
| 1504 | $P_{49}$ | | | | | | | | | | | | | | | 3008 $L_4$ | | | | | | | |
| 1505 | | | | | | | | | | | | | | | | 3009 $P_4$ | | | | | | | |
| 1506 | | | | | | | | | | | | | | | | 3010 $N_4$ | | | | | | | |
| 1507 | | | | | | | | | | | | | | | | 3011 $R_4$ | | | | | | | |

TABLE 6

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 1 | $M_{235}$ | $R_1$ | | | | | | | | | | | | | | | | |
| 2 | $S_{235}$ | $Q_1$ | | | | | | | | | | | | | | | | |
| 3 | $T_{235}$ | $E_1$ | | | | | | | | | | | | | | | | |
| 4 | $N_{230}$ | $I_2$ | $T_2$ | $D_1$ | $F_1$ | | | | | | | | | | | | | |
| 5 | $P_{234}$ | $L_1$ | $G_1$ | | | | | | | | | | | | | | | |
| 6 | $K_{236}$ | | | | | | | | | | | | | | | | | |
| 7 | $P_{236}$ | | | | | | | | | | | | | | | | | |
| 8 | $Q_{236}$ | | | | | | | | | | | | | | | | | |
| 9 | $R_{236}$ | | | | | | | | | | | | | | | | | |
| 10 | $K_{227}$ | $Q_8$ | $R_1$ | | | | | | | | | | | | | | | |
| 11 | $T_{232}$ | $I_3$ | $S_1$ | | | | | | | | | | | | | | | |
| 12 | $K_{233}$ | $I_1$ | $N_1$ | $Y_1$ | | | | | | | | | | | | | | |
| 13 | $R_{236}$ | $L_1$ | | | | | | | | | | | | | | | | |
| 14 | $N_{236}$ | | | | | | | | | | | | | | | | | |
| 15 | $T_{236}$ | | | | | | | | | | | | | | | | | |
| 16 | $N_{229}$ | $Y_4$ | $I_1$ | $D_1$ | $S_1$ | | | | | | | | | | | | | |
| 17 | $R_{234}$ | $L_2$ | | | | | | | | | | | | | | | | |
| 18 | $R_{236}$ | | | | | | | | | | | | | | | | | |
| 19 | $P_{236}$ | | | | | | | | | | | | | | | | | |
| 20 | $Q_{236}$ | | | | | | | | | | | | | | | | | |
| 21 | $D_{236}$ | | | | | | | | | | | | | | | | | |
| 22 | $V_{233}$ | $I_2$ | $L_1$ | | | | | | | | | | | | | | | |
| 23 | $K_{236}$ | | | | | | | | | | | | | | | | | |
| 24 | $F_{236}$ | | | | | | | | | | | | | | | | | |
| 25 | $P_{236}$ | | | | | | | | | | | | | | | | | |
| 26 | $G_{235}$ | $A_1$ | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 27 | $G_{236}$ | | | | | | | | | | | | | | | | | |
| 28 | $G_{236}$ | | | | | | | | | | | | | | | | | |
| 29 | $Q_{234}$ | $K_1$ | $R_1$ | | | | | | | | | | | | | | | |
| 30 | $I_{235}$ | $V_1$ | | | | | | | | | | | | | | | | |
| 31 | $V_{236}$ | | | | | | | | | | | | | | | | | |
| 32 | $G_{236}$ | | | | | | | | | | | | | | | | | |
| 33 | $G_{236}$ | | | | | | | | | | | | | | | | | |
| 34 | $V_{236}$ | | | | | | | | | | | | | | | | | |
| 35 | $Y_{236}$ | | | | | | | | | | | | | | | | | |
| 36 | $L_{235}$ | $V_1$ | | | | | | | | | | | | | | | | |
| 37 | $L_{234}$ | $F_1$ | $M_1$ | | | | | | | | | | | | | | | |
| 38 | $P_{234}$ | $T_2$ | | | | | | | | | | | | | | | | |
| 39 | $R_{235}$ | $P_1$ | | | | | | | | | | | | | | | | |
| 40 | $R_{236}$ | | | | | | | | | | | | | | | | | |
| 41 | $G_{235}$ | $C_1$ | | | | | | | | | | | | | | | | |
| 42 | $P_{236}$ | | | | | | | | | | | | | | | | | |
| 43 | $R_{226}$ | $K_5$ | $T_2$ | $A_2$ | $S_1$ | | | | | | | | | | | | | |
| 44 | $L_{236}$ | | | | | | | | | | | | | | | | | |
| 45 | $G_{236}$ | | | | | | | | | | | | | | | | | |
| 46 | $V_{236}$ | | | | | | | | | | | | | | | | | |
| 47 | $R_{236}$ | | | | | | | | | | | | | | | | | |
| 48 | $A_{233}$ | $T_1$ | $P_1$ | $X_1$ | | | | | | | | | | | | | | |
| 49 | $T_{224}$ | $P_8$ | $I_2$ | $R_1$ | $L_1$ | | | | | | | | | | | | | |
| 50 | $R_{236}$ | | | | | | | | | | | | | | | | | |
| 51 | $K_{235}$ | $Q_1$ | | | | | | | | | | | | | | | | |
| 52 | $T_{234}$ | $A_1$ | $I_1$ | | | | | | | | | | | | | | | |
| 53 | $S_{235}$ | $W_1$ | | | | | | | | | | | | | | | | |
| 54 | $E_{236}$ | | | | | | | | | | | | | | | | | |
| 55 | $R_{236}$ | | | | | | | | | | | | | | | | | |
| 56 | $S_{233}$ | $P_3$ | | | | | | | | | | | | | | | | |
| 57 | $Q_{236}$ | | | | | | | | | | | | | | | | | |
| 58 | $P_{234}$ | $A_2$ | | | | | | | | | | | | | | | | |
| 59 | $R_{235}$ | $A_1$ | | | | | | | | | | | | | | | | |
| 60 | $G_{235}$ | $E_1$ | | | | | | | | | | | | | | | | |
| 61 | $R_{235}$ | $S_1$ | | | | | | | | | | | | | | | | |
| 62 | $R_{235}$ | $P_1$ | | | | | | | | | | | | | | | | |
| 63 | $Q_{235}$ | $H_1$ | | | | | | | | | | | | | | | | |
| 64 | $P_{235}$ | $L_1$ | | | | | | | | | | | | | | | | |
| 65 | $I_{235}$ | $V_1$ | | | | | | | | | | | | | | | | |
| 66 | $P_{236}$ | | | | | | | | | | | | | | | | | |
| 67 | $K_{233}$ | $R_1$ | $N_1$ | $E_1$ | | | | | | | | | | | | | | |
| 68 | $A_{228}$ | $V_8$ | | | | | | | | | | | | | | | | |
| 69 | $R_{236}$ | | | | | | | | | | | | | | | | | |
| 70 | $R_{140}$ | $Q_{90}$ | $H_4$ | $K_1$ | $X_1$ | | | | | | | | | | | | | |
| 71 | $P_{229}$ | $L_2$ | $H_2$ | $S_2$ | $R_1$ | | | | | | | | | | | | | |
| 72 | $E_{236}$ | | | | | | | | | | | | | | | | | |
| 73 | $G_{236}$ | | | | | | | | | | | | | | | | | |
| 74 | $R_{235}$ | $W_1$ | | | | | | | | | | | | | | | | |
| 75 | $A_{112}$ | $T_{110}$ | $V_5$ | $S_5$ | $N_4$ | | | | | | | | | | | | | |
| 76 | $W_{234}$ | $C_1$ | $S_1$ | | | | | | | | | | | | | | | |
| 77 | $A_{236}$ | | | | | | | | | | | | | | | | | |
| 78 | $Q_{236}$ | | | | | | | | | | | | | | | | | |
| 79 | $P_{236}$ | | | | | | | | | | | | | | | | | |
| 80 | $G_{235}$ | $W_1$ | | | | | | | | | | | | | | | | |
| 81 | $Y_{235}$ | $H_1$ | | | | | | | | | | | | | | | | |
| 82 | $P_{236}$ | | | | | | | | | | | | | | | | | |
| 83 | $W_{236}$ | | | | | | | | | | | | | | | | | |
| 84 | $P_{236}$ | | | | | | | | | | | | | | | | | |
| 85 | $L_{236}$ | | | | | | | | | | | | | | | | | |
| 86 | $Y_{235}$ | $F_1$ | | | | | | | | | | | | | | | | |
| 87 | $G_{231}$ | $A_5$ | | | | | | | | | | | | | | | | |
| 88 | $N_{234}$ | $D_2$ | | | | | | | | | | | | | | | | |
| 89 | $E_{235}$ | $Q_1$ | | | | | | | | | | | | | | | | |
| 90 | $G_{235}$ | $S_1$ | | | | | | | | | | | | | | | | |
| 91 | $M_{125}$ | $L_{105}$ | $C_3$ | $I_1$ | $X_1$ | $F_1$ | | | | | | | | | | | | |
| 92 | $G_{236}$ | | | | | | | | | | | | | | | | | |
| 93 | $W_{236}$ | | | | | | | | | | | | | | | | | |
| 94 | $A_{233}$ | $T_2$ | $P_1$ | | | | | | | | | | | | | | | |
| 95 | $G_{235}$ | $E_1$ | | | | | | | | | | | | | | | | |
| 96 | $W_{235}$ | $L_1$ | | | | | | | | | | | | | | | | |
| 97 | $L_{235}$ | $F_1$ | | | | | | | | | | | | | | | | |
| 98 | $L_{235}$ | $V_1$ | | | | | | | | | | | | | | | | |
| 99 | $S_{236}$ | | | | | | | | | | | | | | | | | |
| 100 | $P_{236}$ | | | | | | | | | | | | | | | | | |
| 101 | $R_{227}$ | $H_5$ | $Q_2$ | $Y_2$ | | | | | | | | | | | | | | |
| 102 | $G_{235}$ | $S_1$ | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 103 | $S_{236}$ | | | | | | | | | | | | | | | | | |
| 104 | $R_{236}$ | | | | | | | | | | | | | | | | | |
| 105 | $P_{235}$ | $S_1$ | | | | | | | | | | | | | | | | |
| 106 | $S_{216}$ | $N_{18}$ | $R_2$ | | | | | | | | | | | | | | | |
| 107 | $W_{236}$ | | | | | | | | | | | | | | | | | |
| 108 | $G_{236}$ | | | | | | | | | | | | | | | | | |
| 109 | $P_{236}$ | | | | | | | | | | | | | | | | | |
| 110 | $T_{205}$ | $N_{16}$ | $S_{12}$ | $R_1$ | $K_1$ | $I_1$ | | | | | | | | | | | | |
| 111 | $D_{236}$ | | | | | | | | | | | | | | | | | |
| 112 | $P_{236}$ | | | | | | | | | | | | | | | | | |
| 113 | $R_{236}$ | | | | | | | | | | | | | | | | | |
| 114 | $R_{234}$ | $C_2$ | | | | | | | | | | | | | | | | |
| 115 | $R_{230}$ | $K_5$ | $G_1$ | | | | | | | | | | | | | | | |
| 116 | $S_{236}$ | $X_1$ | | | | | | | | | | | | | | | | |
| 117 | $R_{236}$ | $S_1$ | | | | | | | | | | | | | | | | |
| 118 | $N_{236}$ | $I_1$ | | | | | | | | | | | | | | | | |
| 119 | $L_{236}$ | $V_1$ | | | | | | | | | | | | | | | | |
| 120 | $G_{237}$ | | | | | | | | | | | | | | | | | |
| 121 | $K_{237}$ | | | | | | | | | | | | | | | | | |
| 122 | $V_{236}$ | $I_1$ | | | | | | | | | | | | | | | | |
| 123 | $I_{237}$ | | | | | | | | | | | | | | | | | |
| 124 | $D_{237}$ | | | | | | | | | | | | | | | | | |
| 125 | $T_{236}$ | $S_1$ | | | | | | | | | | | | | | | | |
| 126 | $L_{236}$ | $F_1$ | $P_1$ | | | | | | | | | | | | | | | |
| 127 | $T_{238}$ | | | | | | | | | | | | | | | | | |
| 128 | $C_{238}$ | | | | | | | | | | | | | | | | | |
| 129 | $G_{238}$ | | | | | | | | | | | | | | | | | |
| 130 | $F_{227}$ | $L_8$ | $V_3$ | | | | | | | | | | | | | | | |
| 131 | $A_{236}$ | $P_2$ | | | | | | | | | | | | | | | | |
| 132 | $D_{238}$ | | | | | | | | | | | | | | | | | |
| 133 | $L_{236}$ | $P_1$ | $F_1$ | | | | | | | | | | | | | | | |
| 134 | $M_{236}$ | $V_1$ | $L_1$ | | | | | | | | | | | | | | | |
| 135 | $G_{238}$ | $X_{12}$ | | | | | | | | | | | | | | | | |
| 136 | $Y_{249}$ | $H_1$ | | | | | | | | | | | | | | | | |
| 137 | $I_{246}$ | $V_2$ | $L_2$ | | | | | | | | | | | | | | | |
| 138 | $P_{250}$ | | | | | | | | | | | | | | | | | |
| 139 | $L_{242}$ | $R_5$ | $P_1$ | $F_1$ | $V_1$ | | | | | | | | | | | | | |
| 140 | $V_{250}$ | | | | | | | | | | | | | | | | | |
| 141 | $G_{250}$ | | | | | | | | | | | | | | | | | |
| 142 | $A_{242}$ | $P_4$ | $G_4$ | | | | | | | | | | | | | | | |
| 143 | $P_{250}$ | | | | | | | | | | | | | | | | | |
| 144 | $L_{248}$ | $V_1$ | $I_1$ | | | | | | | | | | | | | | | |
| 145 | $G_{247}$ | $R_2$ | $A_1$ | | | | | | | | | | | | | | | |
| 146 | $G_{249}$ | | | | | | | | | | | | | | | | | |
| 147 | $A_{202}$ | $V_{48}$ | | | | | | | | | | | | | | | | |
| 148 | $A_{245}$ | $S_3$ | $V_2$ | | | | | | | | | | | | | | | |
| 149 | $R_{249}$ | $K_1$ | | | | | | | | | | | | | | | | |
| 150 | $A_{241}$ | $V_9$ | | | | | | | | | | | | | | | | |
| 151 | $L_{250}$ | $X_1$ | | | | | | | | | | | | | | | | |
| 152 | $A_{250}$ | $V_1$ | | | | | | | | | | | | | | | | |
| 153 | $H_{251}$ | | | | | | | | | | | | | | | | | |
| 154 | $G_{250}$ | $S_1$ | | | | | | | | | | | | | | | | |
| 155 | $V_{251}$ | $X_1$ | | | | | | | | | | | | | | | | |
| 156 | $R_{252}$ | | | | | | | | | | | | | | | | | |
| 157 | $V_{246}$ | $A_5$ | $X_3$ | $I_2$ | $L_1$ | | | | | | | | | | | | | |
| 158 | $L_{241}$ | $V_{14}$ | $R_2$ | | | | | | | | | | | | | | | |
| 159 | $E_{255}$ | $L_2$ | | | | | | | | | | | | | | | | |
| 160 | $D_{255}$ | $G_1$ | $V_1$ | | | | | | | | | | | | | | | |
| 161 | $G_{233}$ | $S_{24}$ | | | | | | | | | | | | | | | | |
| 162 | $V_{257}$ | | | | | | | | | | | | | | | | | |
| 163 | $N_{257}$ | | | | | | | | | | | | | | | | | |
| 164 | $Y_{257}$ | | | | | | | | | | | | | | | | | |
| 165 | $A_{256}$ | $P_2$ | | | | | | | | | | | | | | | | |
| 166 | $T_{258}$ | $X_1$ | | | | | | | | | | | | | | | | |
| 167 | $G_{259}$ | | | | | | | | | | | | | | | | | |
| 168 | $N_{259}$ | $X_1$ | | | | | | | | | | | | | | | | |
| 169 | $L_{255}$ | $M_3$ | $I_1$ | $F_1$ | | | | | | | | | | | | | | |
| 170 | $P_{259}$ | $A_1$ | | | | | | | | | | | | | | | | |
| 171 | $G_{260}$ | | | | | | | | | | | | | | | | | |
| 172 | $C_{260}$ | | | | | | | | | | | | | | | | | |
| 173 | $S_{253}$ | $P_7$ | $X_1$ | | | | | | | | | | | | | | | |
| 174 | $F_{261}$ | | | | | | | | | | | | | | | | | |
| 175 | $S_{260}$ | $Y_1$ | | | | | | | | | | | | | | | | |
| 176 | $I_{257}$ | $X_8$ | $L_3$ | $V_1$ | | | | | | | | | | | | | | |
| 177 | $F_{272}$ | $S_3$ | | | | | | | | | | | | | | | | |
| 178 | $L_{269}$ | $F_6$ | $X_2$ | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 179 | $L_{268}$ | $W_3$ | $S_2$ | $M_2$ | $G_1$ | $I_1$ | | | | | | | | | | | | |
| 180 | $A_{271}$ | $V_2$ | $P_2$ | $F_1$ | $G_1$ | | | | | | | | | | | | | |
| 181 | $L_{273}$ | $F_3$ | $V_1$ | | | | | | | | | | | | | | | |
| 182 | $L_{270}$ | $V_5$ | $M_2$ | | | | | | | | | | | | | | | |
| 183 | $S_{277}$ | | | | | | | | | | | | | | | | | |
| 184 | $C_{275}$ | $G_2$ | | | | | | | | | | | | | | | | |
| 185 | $L_{275}$ | $V_1$ | $M_1$ | | | | | | | | | | | | | | | |
| 186 | $T_{275}$ | $P1$ | $I_1$ | | | | | | | | | | | | | | | |
| 187 | $I_{216}$ | $T_{40}$ | $V_{16}$ | $A_1$ | $H_1$ | $N_1$ | $X_1$ | $M_1$ | | | | | | | | | | |
| 188 | $P_{275}$ | $Q_1$ | | | | | | | | | | | | | | | | |
| 189 | $A_{246}$ | $V_{21}$ | $T_7$ | $N_1$ | $G_1$ | | | | | | | | | | | | | |
| 190 | $S_{275}$ | $F_1$ | | | | | | | | | | | | | | | | |
| 191 | $A_{274}$ | $T_2$ | $G_1$ | | | | | | | | | | | | | | | |
| 192 | $Y_{182}$ | $I_{31}$ | $H_9$ | $X_6$ | $P_1$ | | | | | | | | | | | | | |
| 193 | $E_{215}$ | $Q_5$ | $D_2$ | $V_1$ | $K_1$ | | | | | | | | | | | | | |
| 194 | $V_{221}$ | $G_1$ | $T_1$ | $M_1$ | | | | | | | | | | | | | | |
| 195 | $R_{208}$ | $H_9$ | $G_4$ | $A_1$ | $N_1$ | $C_1$ | | | | | | | | | | | | |
| 196 | $N_{220}$ | $X_5$ | $H_3$ | $K_1$ | | | | | | | | | | | | | | |
| 197 | $V_{188}$ | $A_{35}$ | $X_1$ | $I_1$ | $L_1$ | $G_1$ | $T_1$ | $S_1$ | | | | | | | | | | |
| 198 | $S_{226}$ | $X_2$ | $F_1$ | $P_1$ | | | | | | | | | | | | | | |
| 199 | $G_{226}$ | $R_2$ | $D_1$ | $E_1$ | | | | | | | | | | | | | | |
| 200 | $V_{144}$ | $I_{43}$ | $A_{17}$ | $M_{15}$ | $L_7$ | $G_3$ | $D_1$ | | | | | | | | | | | |
| 201 | $Y_{229}$ | $V_1$ | | | | | | | | | | | | | | | | |
| 202 | $H_{221}$ | $Q_6$ | $Y_2$ | $L_1$ | | | | | | | | | | | | | | |
| 203 | $V_{229}$ | $G_1$ | | | | | | | | | | | | | | | | |
| 204 | $T_{229}$ | $S_1$ | | | | | | | | | | | | | | | | |
| 205 | $N_{227}$ | $Y_1$ | $H_1$ | $S_1$ | | | | | | | | | | | | | | |
| 206 | $D_{229}$ | $Y_1$ | | | | | | | | | | | | | | | | |
| 207 | $C_{230}$ | | | | | | | | | | | | | | | | | |
| 208 | $S_{228}$ | $P_2$ | | | | | | | | | | | | | | | | |
| 209 | $N_{222}$ | $Y_3$ | $S_2$ | $H_1$ | $K_1$ | $Q_1$ | | | | | | | | | | | | |
| 210 | $S_{179}$ | $A_{44}$ | $T_6$ | $L_1$ | | | | | | | | | | | | | | |
| 211 | $S_{228}$ | $N_1$ | $G_1$ | | | | | | | | | | | | | | | |
| 212 | $I_{229}$ | $V_1$ | | | | | | | | | | | | | | | | |
| 213 | $V_{226}$ | $A_2$ | $G_2$ | | | | | | | | | | | | | | | |
| 214 | $Y_{218}$ | $F_{10}$ | $S_1$ | $Q_1$ | | | | | | | | | | | | | | |
| 215 | $E_{227}$ | $K_1$ | $D_1$ | $G_1$ | | | | | | | | | | | | | | |
| 216 | $A_{193}$ | $T_{33}$ | $V_3$ | $P_1$ | | | | | | | | | | | | | | |
| 217 | $A_{208}$ | $S_6$ | $V_5$ | $E_4$ | $D_3$ | $Q_2$ | $T_1$ | $K_1$ | | | | | | | | | | |
| 218 | $D_{224}$ | $G_4$ | $H_1$ | $N_1$ | | | | | | | | | | | | | | |
| 219 | $M_{161}$ | $V_{35}$ | $L_{19}$ | $I_{12}$ | $T_2$ | $S_1$ | | | | | | | | | | | | |
| 220 | $I_{229}$ | $M_1$ | | | | | | | | | | | | | | | | |
| 221 | $M_{215}$ | $L_{14}$ | $I_1$ | | | | | | | | | | | | | | | |
| 222 | $H_{228}$ | $Q_1$ | $D_1$ | | | | | | | | | | | | | | | |
| 223 | $T_{183}$ | $A_{19}$ | $S_{15}$ | $I_7$ | $L_3$ | $F_1$ | $N_1$ | $V_1$ | | | | | | | | | | |
| 224 | $P_{230}$ | | | | | | | | | | | | | | | | | |
| 225 | $G_{230}$ | | | | | | | | | | | | | | | | | |
| 226 | $C_{229}$ | $F_1$ | | | | | | | | | | | | | | | | |
| 227 | $V_{225}$ | $M_2$ | $A_1$ | $T_1$ | $L_1$ | | | | | | | | | | | | | |
| 228 | $P_{229}$ | $A_1$ | | | | | | | | | | | | | | | | |
| 229 | $C_{228}$ | $F_1$ | $S_1$ | | | | | | | | | | | | | | | |
| 230 | $V_{230}$ | | | | | | | | | | | | | | | | | |
| 231 | $R_{220}$ | $Q_4$ | $L_2$ | $W_2$ | $S_1$ | $G_1$ | | | | | | | | | | | | |
| 232 | $E_{225}$ | $D_4$ | $V_1$ | | | | | | | | | | | | | | | |
| 233 | $N_{106}$ | $G_{49}$ | $D_{40}$ | $S_{16}$ | $A_{11}$ | $K_3$ | $E_2$ | $Q_2$ | $Y_1$ | | | | | | | | | |
| 234 | $N_{224}$ | $D_2$ | $G_2$ | $Y_1$ | $K_1$ | | | | | | | | | | | | | |
| 235 | $S_{183}$ | $F_{12}$ | $A_7$ | $I_6$ | $T_6$ | $H_5$ | $L_5$ | $V_4$ | $Y_1$ | $C_1$ | | | | | | | | |
| 236 | $S_{231}$ | | | | | | | | | | | | | | | | | |
| 237 | $R_{224}$ | $S_3$ | $H_2$ | $K_1$ | $Q_1$ | | | | | | | | | | | | | |
| 238 | $C_{229}$ | $Y_2$ | | | | | | | | | | | | | | | | |
| 239 | $W_{231}$ | | | | | | | | | | | | | | | | | |
| 240 | $V_{223}$ | $A_5$ | $I_2$ | $T_1$ | | | | | | | | | | | | | | |
| 241 | $A_{230}$ | $E_1$ | | | | | | | | | | | | | | | | |
| 242 | $L_{229}$ | $V_1$ | $I_1$ | | | | | | | | | | | | | | | |
| 243 | $T_{225}$ | $A_6$ | | | | | | | | | | | | | | | | |
| 244 | $P_{230}$ | $L_1$ | | | | | | | | | | | | | | | | |
| 245 | $T_{231}$ | | | | | | | | | | | | | | | | | |
| 246 | $L_{228}$ | $V_1$ | $P_1$ | $H_1$ | | | | | | | | | | | | | | |
| 247 | $A_{229}$ | $S_2$ | | | | | | | | | | | | | | | | |
| 248 | $A_{228}$ | $T_1$ | $S_1$ | $G_1$ | | | | | | | | | | | | | | |
| 249 | $R_{228}$ | $K_3$ | | | | | | | | | | | | | | | | |
| 250 | $N_{228}$ | $D_2$ | $S_1$ | | | | | | | | | | | | | | | |
| 251 | $S_{92}$ | $A_{85}$ | $T_{14}$ | $G_9$ | $I_9$ | $N_7$ | $V_5$ | $R_3$ | $F_3$ | $D_1$ | $H_1$ | $L_1$ | $P_1$ | | | | | |
| 252 | $S_{217}$ | $T_{10}$ | $N_3$ | $R_1$ | | | | | | | | | | | | | | |
| 253 | $V_{132}$ | $I_{98}$ | $L_1$ | | | | | | | | | | | | | | | |
| 254 | $P_{229}$ | $S_2$ | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 255 | $T_{228}$ | $V_2$ | $I_1$ | | | | | | | | | | | | | | | |
| 256 | $T_{186}$ | $A_{24}$ | $K_{15}$ | $M_6$ | | | | | | | | | | | | | | |
| 257 | $T_{197}$ | $A_{29}$ | $S_4$ | $Q_1$ | | | | | | | | | | | | | | |
| 258 | $I_{212}$ | $L_{10}$ | $M_5$ | $V_4$ | | | | | | | | | | | | | | |
| 259 | $R_{231}$ | | | | | | | | | | | | | | | | | |
| 260 | $R_{225}$ | $H_4$ | $D_1$ | $C_1$ | | | | | | | | | | | | | | |
| 261 | $H_{231}$ | | | | | | | | | | | | | | | | | |
| 262 | $V_{226}$ | $I_5$ | | | | | | | | | | | | | | | | |
| 263 | $D_{230}$ | $N_1$ | | | | | | | | | | | | | | | | |
| 264 | $L_{230}$ | $V_1$ | | | | | | | | | | | | | | | | |
| 265 | $L_{230}$ | $H_1$ | | | | | | | | | | | | | | | | |
| 266 | $V_{231}$ | | | | | | | | | | | | | | | | | |
| 267 | $G_{242}$ | | | | | | | | | | | | | | | | | |
| 268 | $A_{190}$ | $T_{47}$ | $V_4$ | $G_1$ | | | | | | | | | | | | | | |
| 269 | $A_{242}$ | | | | | | | | | | | | | | | | | |
| 270 | $A_{222}$ | $T_{16}$ | $V_4$ | | | | | | | | | | | | | | | |
| 271 | $F_{211}$ | $L_{31}$ | | | | | | | | | | | | | | | | |
| 272 | $C_{228}$ | $S_7$ | $W_5$ | $L_1$ | $R_1$ | | | | | | | | | | | | | |
| 273 | $S_{241}$ | $A_1$ | | | | | | | | | | | | | | | | |
| 274 | $A_{235}$ | $V_6$ | $S_1$ | | | | | | | | | | | | | | | |
| 275 | $M_{241}$ | $L_1$ | | | | | | | | | | | | | | | | |
| 276 | $Y_{245}$ | | | | | | | | | | | | | | | | | |
| 277 | $V_{243}$ | $G_1$ | $M_1$ | | | | | | | | | | | | | | | |
| 278 | $G_{243}$ | $W_1$ | $E_1$ | | | | | | | | | | | | | | | |
| 279 | $D_{244}$ | $N_1$ | | | | | | | | | | | | | | | | |
| 280 | $L_{236}$ | $F_8$ | $X_1$ | | | | | | | | | | | | | | | |
| 281 | $C_{245}$ | | | | | | | | | | | | | | | | | |
| 282 | $G_{244}$ | $R_1$ | | | | | | | | | | | | | | | | |
| 283 | $S_{245}$ | | | | | | | | | | | | | | | | | |
| 284 | $V_{236}$ | $I_5$ | $A_3$ | $X_1$ | | | | | | | | | | | | | | |
| 285 | $F_{232}$ | $L_{13}$ | | | | | | | | | | | | | | | | |
| 286 | $L_{244}$ | $P_1$ | | | | | | | | | | | | | | | | |
| 287 | $V_{215}$ | $I_{27}$ | $A_2$ | $L_1$ | | | | | | | | | | | | | | |
| 288 | $S_{239}$ | $G_3$ | $A_3$ | | | | | | | | | | | | | | | |
| 289 | $Q_{245}$ | | | | | | | | | | | | | | | | | |
| 290 | $L_{245}$ | | | | | | | | | | | | | | | | | |
| 291 | $F_{243}$ | $I_1$ | $L_1$ | | | | | | | | | | | | | | | |
| 292 | $T_{241}$ | $V_3$ | $A_1$ | | | | | | | | | | | | | | | |
| 293 | $F_{233}$ | $L_9$ | $I_3$ | | | | | | | | | | | | | | | |
| 294 | $S_{244}$ | $L_1$ | | | | | | | | | | | | | | | | |
| 295 | $P_{242}$ | $A_2$ | $T_1$ | | | | | | | | | | | | | | | |
| 296 | $R_{243}$ | $S_1$ | $P_1$ | | | | | | | | | | | | | | | |
| 297 | $R_{220}$ | $Q_{14}$ | $W_3$ | $L_3$ | $H_2$ | $V_2$ | $G_1$ | | | | | | | | | | | |
| 298 | $H_{185}$ | $Y_{60}$ | | | | | | | | | | | | | | | | |
| 299 | $E_{206}$ | $Q_9$ | $M_6$ | $V_6$ | $W_4$ | $T_3$ | $A_3$ | $N_2$ | $G_2$ | $K_2$ | $R_2$ | | | | | | | |
| 300 | $T_{242}$ | $I_2$ | $V_1$ | | | | | | | | | | | | | | | |
| 301 | $V_{216}$ | $I_8$ | $L_7$ | $T_7$ | $A_5$ | $E_2$ | | | | | | | | | | | | |
| 302 | $Q_{243}$ | $H_1$ | $R_1$ | | | | | | | | | | | | | | | |
| 303 | $D_{228}$ | $E_{12}$ | $N_2$ | $Y_1$ | $T_1$ | $S_1$ | | | | | | | | | | | | |
| 304 | $C_{245}$ | | | | | | | | | | | | | | | | | |
| 305 | $N_{243}$ | $K_1$ | $D_1$ | | | | | | | | | | | | | | | |
| 306 | $C_{245}$ | | | | | | | | | | | | | | | | | |
| 307 | $S_{245}$ | | | | | | | | | | | | | | | | | |
| 308 | $I_{202}$ | $L_{42}$ | $H_1$ | | | | | | | | | | | | | | | |
| 309 | $Y_{244}$ | $F_1$ | | | | | | | | | | | | | | | | |
| 310 | $P_{238}$ | $L_3$ | $S_2$ | $A_1$ | $V_1$ | | | | | | | | | | | | | |
| 311 | $G_{245}$ | | | | | | | | | | | | | | | | | |
| 312 | $H_{241}$ | $R_3$ | $K_1$ | | | | | | | | | | | | | | | |
| 313 | $V_{194}$ | $L_{34}$ | $I_{15}$ | $A_2$ | | | | | | | | | | | | | | |
| 314 | $S_{164}$ | $T_{81}$ | | | | | | | | | | | | | | | | |
| 315 | $G_{243}$ | $V_1$ | $S_1$ | | | | | | | | | | | | | | | |
| 316 | $H_{244}$ | $Y_1$ | | | | | | | | | | | | | | | | |
| 317 | $R_{244}$ | $A_1$ | | | | | | | | | | | | | | | | |
| 318 | $M_{249}$ | $I_1$ | | | | | | | | | | | | | | | | |
| 319 | $A_{250}$ | $X_5$ | | | | | | | | | | | | | | | | |
| 320 | $W_{254}$ | $X_{10}$ | $L_1$ | | | | | | | | | | | | | | | |
| 321 | $D_{261}$ | $X_{24}$ | $N_3$ | $E_1$ | | | | | | | | | | | | | | |
| 322 | $M_{288}$ | $V_1$ | $X_1$ | | | | | | | | | | | | | | | |
| 323 | $M_{286}$ | $I_3$ | $R_2$ | $X_1$ | | | | | | | | | | | | | | |
| 324 | $M_{291}$ | $X_3$ | | | | | | | | | | | | | | | | |
| 325 | $N_{290}$ | $T_1$ | | | | | | | | | | | | | | | | |
| 326 | $W_{290}$ | $C_1$ | | | | | | | | | | | | | | | | |
| 327 | $S_{291}$ | | | | | | | | | | | | | | | | | |
| 328 | $P_{313}$ | $L_4$ | $A_1$ | $H_1$ | | | | | | | | | | | | | | |
| 329 | $T_{315}$ | $A_5$ | $K_2$ | $Q_1$ | $S_1$ | | | | | | | | | | | | | |
| 330 | $T_{209}$ | $A_{115}$ | $S_3$ | $X_2$ | $I_1$ | $Q_1$ | $L_1$ | $K_1$ | $V_1$ | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 331 | $A_{329}$ | $G_3$ | $T_3$ | $L_2$ | $D_1$ | $S_1$ | $P_1$ | $V_1$ | | | | | | | | | | |
| 332 | $L_{332}$ | $I_5$ | $P_4$ | $M_2$ | $X_1$ | | | | | | | | | | | | | |
| 333 | $V_{334}$ | $I_4$ | $M_2$ | $G_2$ | $S_1$ | $L_1$ | | | | | | | | | | | | |
| 334 | $V_{328}$ | $M_6$ | $L_5$ | $A_4$ | $P_1$ | $G_1$ | | | | | | | | | | | | |
| 335 | $S_{326}$ | $A_9$ | $V_3$ | $L_2$ | $C_1$ | $X_1$ | $G_1$ | $H_1$ | $D_1$ | | | | | | | | | |
| 336 | $Q_{338}$ | $W_2$ | $H_2$ | $Y_1$ | $E_1$ | $V_1$ | | | | | | | | | | | | |
| 337 | $L_{324}$ | $I_6$ | $X_6$ | $V_5$ | $M_1$ | $Y_1$ | $A_1$ | $F_1$ | | | | | | | | | | |
| 338 | $L_{331}$ | $F_3$ | $P_2$ | $M_1$ | $G_1$ | | | | | | | | | | | | | |
| 339 | $R_{335}$ | $P_1$ | $M_1$ | $Q_1$ | | | | | | | | | | | | | | |
| 340 | $I_{320}$ | $L_8$ | $V_7$ | $N_1$ | $X_1$ | $Y_1$ | | | | | | | | | | | | |
| 341 | $P_{330}$ | $X_7$ | $R_1$ | | | | | | | | | | | | | | | |
| 342 | $Q_{333}$ | $E_1$ | | | | | | | | | | | | | | | | |
| 343 | $A_{325}$ | $T_6$ | $S_2$ | $V_1$ | | | | | | | | | | | | | | |
| 344 | $V_{261}$ | $I_{64}$ | $A_7$ | $T_2$ | | | | | | | | | | | | | | |
| 345 | $V_{231}$ | $M_{76}$ | $L_{24}$ | $I_3$ | $G_1$ | | | | | | | | | | | | | |
| 346 | $D_{332}$ | $X_1$ | $N_1$ | $L_1$ | | | | | | | | | | | | | | |
| 347 | $M_{313}$ | $I_{10}$ | $V_{10}$ | $T_1$ | $E_1$ | | | | | | | | | | | | | |
| 348 | $V_{309}$ | $I_{18}$ | $M_4$ | $L_4$ | | | | | | | | | | | | | | |
| 349 | $A_{301}$ | $V_{14}$ | $T_{13}$ | $G_6$ | $S_1$ | | | | | | | | | | | | | |
| 350 | $G_{335}$ | | | | | | | | | | | | | | | | | |
| 351 | $A_{326}$ | $G_6$ | $S_2$ | $X_1$ | | | | | | | | | | | | | | |
| 352 | $H_{331}$ | $Y_1$ | $Q_1$ | $L_1$ | | | | | | | | | | | | | | |
| 353 | $W_{334}$ | | | | | | | | | | | | | | | | | |
| 354 | $G_{332}$ | $E_1$ | $X_1$ | | | | | | | | | | | | | | | |
| 355 | $V_{316}$ | $I_{17}$ | $A_1$ | | | | | | | | | | | | | | | |
| 356 | $L_{331}$ | $M_1$ | $P_1$ | $X_1$ | | | | | | | | | | | | | | |
| 357 | $A_{329}$ | $V_4$ | $F_1$ | | | | | | | | | | | | | | | |
| 358 | $G_{333}$ | $D_1$ | | | | | | | | | | | | | | | | |
| 359 | $L_{315}$ | $I_{18}$ | $P_1$ | | | | | | | | | | | | | | | |
| 360 | $A_{331}$ | $G_2$ | $V_1$ | | | | | | | | | | | | | | | |
| 361 | $Y_{333}$ | | | | | | | | | | | | | | | | | |
| 362 | $Y_{318}$ | $F_{15}$ | | | | | | | | | | | | | | | | |
| 363 | $S_{322}$ | $A_7$ | $T_2$ | $P_2$ | | | | | | | | | | | | | | |
| 364 | $M_{333}$ | | | | | | | | | | | | | | | | | |
| 365 | $V_{290}$ | $A_{38}$ | $I_6$ | $Q_1$ | | | | | | | | | | | | | | |
| 366 | $G_{330}$ | $A_4$ | $R_1$ | | | | | | | | | | | | | | | |
| 367 | $N_{332}$ | $K_1$ | $S_1$ | $A_1$ | | | | | | | | | | | | | | |
| 368 | $W_{335}$ | | | | | | | | | | | | | | | | | |
| 369 | $A_{334}$ | $X_4$ | | | | | | | | | | | | | | | | |
| 370 | $K_{338}$ | | | | | | | | | | | | | | | | | |
| 371 | $V_{334}$ | $A_2$ | $L_1$ | | | | | | | | | | | | | | | |
| 372 | $L_{331}$ | $V_4$ | $M_1$ | $F_1$ | | | | | | | | | | | | | | |
| 373 | $I_{299}$ | $V_{32}$ | $L_6$ | | | | | | | | | | | | | | | |
| 374 | $V_{329}$ | $X_5$ | $A_2$ | $I_1$ | | | | | | | | | | | | | | |
| 375 | $M_{306}$ | $L_{25}$ | $I_1$ | | | | | | | | | | | | | | | |
| 376 | $L_{332}$ | | | | | | | | | | | | | | | | | |
| 377 | $L_{329}$ | $P_2$ | $R_1$ | | | | | | | | | | | | | | | |
| 378 | $F_{331}$ | $A_1$ | | | | | | | | | | | | | | | | |
| 379 | $A_{324}$ | $S_6$ | $L_1$ | $V_1$ | | | | | | | | | | | | | | |
| 380 | $G_{330}$ | $S_1$ | $R_1$ | | | | | | | | | | | | | | | |
| 381 | $V_{329}$ | $A_3$ | | | | | | | | | | | | | | | | |
| 382 | $D_{329}$ | $N_2$ | $A_1$ | | | | | | | | | | | | | | | |
| 383 | $G_{304}$ | $A_{19}$ | $R_3$ | $E_1$ | $Q_1$ | $T_1$ | $L_1$ | $P_1$ | $X_1$ | | | | | | | | | |
| 384 | $S_{43}$ | $T_{41}$ | $E_{40}$ | $G_{34}$ | $D_{31}$ | $N_{30}$ | $H_{28}$ | $Q_{21}$ | $R_{20}$ | $A_{16}$ | $K_4$ | $V_4$ | $Y_2$ | $M_1$ | $P_1$ | | | |
| 385 | $T_{311}$ | $D_1$ | $S_1$ | $N_1$ | $I_1$ | $A_1$ | | | | | | | | | | | | |
| 386 | $H_{144}$ | $Y_{69}$ | $R_{59}$ | $T_{14}$ | $V_6$ | $S_5$ | $L_5$ | $N_3$ | $Q_3$ | $I_2$ | $M_1$ | $A_1$ | $F_1$ | $K_1$ | $G_1$ | | | |
| 387 | $V_{181}$ | $T_{107}$ | $A_{12}$ | $I_5$ | $L_4$ | $M_3$ | $Q_1$ | $S_1$ | | | | | | | | | | |
| 388 | $T_{183}$ | $S_{56}$ | $V_{26}$ | $I_{21}$ | $M_{14}$ | $L_7$ | $A_5$ | $W_1$ | $X_1$ | | | | | | | | | |
| 389 | $G_{314}$ | $V_1$ | | | | | | | | | | | | | | | | |
| 390 | $G_{278}$ | $A_{27}$ | $E_6$ | $S_2$ | $V_1$ | $K_1$ | | | | | | | | | | | | |
| 391 | $A_{110}$ | $T_{86}$ | $V_{49}$ | $S_{29}$ | $Q_{20}$ | $E_6$ | $K_5$ | $H_4$ | $R_3$ | $X_1$ | $N_1$ | $M_1$ | | | | | | |
| 392 | $A_{110}$ | $Q_{109}$ | $V_{31}$ | $T_{28}$ | $S_{14}$ | $E_6$ | $P_4$ | $L_3$ | $N_2$ | $H_2$ | $M_2$ | $K_1$ | $Y_1$ | $R_1$ | $I_1$ | | | |
| 393 | $A_{143}$ | $G_{130}$ | $S_{40}$ | $T_1$ | $X_1$ | | | | | | | | | | | | | |
| 394 | $R_{144}$ | $H_{88}$ | $Y_{28}$ | $Q_{15}$ | $F_{12}$ | $S_{11}$ | $L_7$ | $K_7$ | $M_1$ | $D_1$ | $A_1$ | | | | | | | |
| 395 | $T_{147}$ | $N_{48}$ | $S_{41}$ | $A_{37}$ | $G_{11}$ | $V_6$ | $D_5$ | $H_4$ | $Q_3$ | $Y_3$ | $L_3$ | $M_1$ | $R_1$ | $I_1$ | $K_1$ | $E_1$ | $C_1$ | $F_1$ |
| 396 | $T_{196}$ | $A_{59}$ | $L_{22}$ | $I_{18}$ | $V_{17}$ | $S_1$ | $G_1$ | $M_1$ | | | | | | | | | | |
| 397 | $R_{89}$ | $S_{85}$ | $Q_{33}$ | $H_{30}$ | $Y_{25}$ | $L_{17}$ | $N_{10}$ | $F_7$ | $A_6$ | $G_4$ | $W_3$ | $V_2$ | $K_1$ | $M_1$ | $T_1$ | $I_1$ | | |
| 398 | $G_{180}$ | $S_{63}$ | $R_{38}$ | $T_{13}$ | $Q_6$ | $K_5$ | $A_3$ | $V_2$ | $I_2$ | $L_1$ | $M_1$ | $E_1$ | | | | | | |
| 399 | $L_{143}$ | $F_{133}$ | $I_{27}$ | $V_{10}$ | $H_1$ | $M_1$ | | | | | | | | | | | | |
| 400 | $T_{180}$ | $A_{94}$ | $V_{34}$ | $M_3$ | $S_3$ | $R_1$ | | | | | | | | | | | | |
| 401 | $S_{245}$ | $G_{29}$ | $T_{16}$ | $N_{10}$ | $A_7$ | $R_5$ | $D_1$ | $H_1$ | $Y_1$ | | | | | | | | | |
| 402 | $L_{235}$ | $F_{44}$ | $I_{24}$ | $M_9$ | $W_2$ | $X_1$ | | | | | | | | | | | | |
| 403 | $F_{293}$ | $L_{21}$ | $Y_1$ | | | | | | | | | | | | | | | |
| 404 | $S_{133}$ | $T_{119}$ | $A_{28}$ | $N_{14}$ | $R_9$ | $Q_3$ | $D_3$ | $M_2$ | $K_1$ | $L_1$ | $I_1$ | $V_1$ | | | | | | |
| 405 | $P_{135}$ | $S_{58}$ | $L_{33}$ | $R_{23}$ | $V_{18}$ | $F_{17}$ | $A_{10}$ | $Q_8$ | $T_7$ | $C_2$ | $I_2$ | $H_1$ | $Y_1$ | | | | | |
| 406 | $G_{314}$ | $E_1$ | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 407 | $P_{173}$ | $A_{103}$ | $S_{36}$ | $Q_1$ | $X_1$ | $R_1$ | | | | | | | | | | | | |
| 408 | $S_{196}$ | $A_{61}$ | $K_{16}$ | $Q_{13}$ | $T_{12}$ | $R_6$ | $H_4$ | $N_3$ | $V_2$ | $E_1$ | $L_1$ | | | | | | | |
| 409 | $Q_{310}$ | $H_4$ | $E_1$ | | | | | | | | | | | | | | | |
| 410 | $K_{193}$ | $N_{85}$ | $R_{26}$ | $T_3$ | $D_3$ | $E_2$ | $H_2$ | $P_1$ | | | | | | | | | | |
| 411 | $I_{274}$ | $V_{20}$ | $L_{20}$ | $N_1$ | | | | | | | | | | | | | | |
| 412 | $Q_{311}$ | $K_2$ | $E_1$ | | | | | | | | | | | | | | | |
| 413 | $L_{312}$ | $I_2$ | | | | | | | | | | | | | | | | |
| 414 | $V_{163}$ | $I_{145}$ | $M_3$ | $X_2$ | | | | | | | | | | | | | | |
| 415 | $N_{303}$ | $K_5$ | $H_2$ | $Y_1$ | | | | | | | | | | | | | | |
| 416 | $T_{291}$ | $S_{15}$ | $N_2$ | $A_1$ | | | | | | | | | | | | | | |
| 417 | $N_{305}$ | $S_1$ | $E_1$ | | | | | | | | | | | | | | | |
| 418 | $G_{305}$ | $D_1$ | $X_1$ | | | | | | | | | | | | | | | |
| 419 | $S_{304}$ | $N_2$ | $I_1$ | | | | | | | | | | | | | | | |
| 420 | $W_{304}$ | $R_1$ | | | | | | | | | | | | | | | | |
| 421 | $H_{305}$ | | | | | | | | | | | | | | | | | |
| 422 | $I_{274}$ | $V_{31}$ | | | | | | | | | | | | | | | | |
| 423 | $N_{305}$ | | | | | | | | | | | | | | | | | |
| 424 | $R_{298}$ | $S_7$ | | | | | | | | | | | | | | | | |
| 425 | $T_{305}$ | | | | | | | | | | | | | | | | | |
| 426 | $A_{303}$ | $S_1$ | $X_1$ | | | | | | | | | | | | | | | |
| 427 | $L_{304}$ | | | | | | | | | | | | | | | | | |
| 428 | $N_{298}$ | $S_5$ | $D_1$ | | | | | | | | | | | | | | | |
| 429 | $C_{303}$ | $W_1$ | | | | | | | | | | | | | | | | |
| 430 | $N_{289}$ | $D_{10}$ | $K_3$ | $Y_1$ | $X_1$ | | | | | | | | | | | | | |
| 431 | $D_{283}$ | $A_{11}$ | $E_8$ | $G_1$ | $X_1$ | | | | | | | | | | | | | |
| 432 | $S_{284}$ | $T_{16}$ | $A_2$ | $P_1$ | | | | | | | | | | | | | | |
| 433 | $L_{292}$ | $I_4$ | $F_3$ | $H_3$ | $Y_1$ | | | | | | | | | | | | | |
| 434 | $Q_{117}$ | $N_{108}$ | $K_{34}$ | $H_{24}$ | $D_7$ | $S_6$ | $E_3$ | $R_3$ | | | | | | | | | | |
| 435 | $T_{295}$ | $S_1$ | $A_1$ | | | | | | | | | | | | | | | |
| 436 | $G_{297}$ | | | | | | | | | | | | | | | | | |
| 437 | $F_{277}$ | $W_{20}$ | | | | | | | | | | | | | | | | |
| 438 | $L_{185}$ | $I_{93}$ | $V_{10}$ | $F_9$ | | | | | | | | | | | | | | |
| 439 | $A_{289}$ | $T_4$ | $S_3$ | $G_1$ | | | | | | | | | | | | | | |
| 440 | $A_{275}$ | $G_{16}$ | $S_5$ | $T_1$ | | | | | | | | | | | | | | |
| 441 | $L_{296}$ | $V_1$ | | | | | | | | | | | | | | | | |
| 442 | $F_{283}$ | $L_6$ | $I_5$ | $S_1$ | $V_1$ | | | | | | | | | | | | | |
| 443 | $Y_{295}$ | $F_1$ | | | | | | | | | | | | | | | | |
| 444 | $T_{159}$ | $A_{83}$ | $V_{25}$ | $Y_8$ | $H_8$ | $K_5$ | $R_4$ | $F_2$ | $Q_1$ | $L_1$ | | | | | | | | |
| 445 | $H_{201}$ | $N_{41}$ | $R_{37}$ | $Y_9$ | $K_6$ | $S_2$ | | | | | | | | | | | | |
| 446 | $K_{149}$ | $R_{105}$ | $S_{19}$ | $N_{16}$ | $Q_3$ | $E_2$ | $M_1$ | $G_1$ | | | | | | | | | | |
| 447 | $F_{283}$ | $I_6$ | $L_6$ | $V_1$ | | | | | | | | | | | | | | |
| 448 | $N_{294}$ | $K_1$ | $D_1$ | | | | | | | | | | | | | | | |
| 449 | $A_{144}$ | $S_{133}$ | $T_7$ | $D_7$ | $G_2$ | $E_1$ | $P_1$ | $M_1$ | | | | | | | | | | |
| 450 | $S_{287}$ | $T_6$ | $C_1$ | $A_1$ | $P_1$ | | | | | | | | | | | | | |
| 451 | $G_{294}$ | $E_1$ | $R_1$ | | | | | | | | | | | | | | | |
| 452 | $C_{293}$ | $X_2$ | $G_1$ | | | | | | | | | | | | | | | |
| 453 | $P_{258}$ | $S_{20}$ | $L_6$ | $T_3$ | $A_2$ | $R_2$ | $I_2$ | $V_1$ | $G_1$ | | | | | | | | | |
| 454 | $E_{270}$ | $Q_{13}$ | $A_6$ | $G_3$ | $K_1$ | $D_1$ | $P_1$ | | | | | | | | | | | |
| 455 | $R_{287}$ | $K_3$ | $H_2$ | $G_2$ | $P_1$ | | | | | | | | | | | | | |
| 456 | $M_{234}$ | $L_{60}$ | $I_1$ | | | | | | | | | | | | | | | |
| 457 | $A_{283}$ | $S_5$ | $X_3$ | $V_2$ | $N_1$ | $T_1$ | | | | | | | | | | | | |
| 458 | $S_{278}$ | $T_4$ | $G_3$ | $Q_2$ | $R_1$ | $H_1$ | $V_1$ | $N_1$ | $X_1$ | | | | | | | | | |
| 459 | $C_{291}$ | | | | | | | | | | | | | | | | | |
| 460 | $R_{272}$ | $S_6$ | $K_6$ | $H_3$ | $Q_2$ | $L_1$ | $C_1$ | | | | | | | | | | | |
| 461 | $P_{206}$ | $S_{75}$ | $T_3$ | $R_2$ | $N_1$ | $A_1$ | $X_1$ | $F_1$ | $H_1$ | | | | | | | | | |
| 462 | $I_{267}$ | $L_{20}$ | $V_3$ | | | | | | | | | | | | | | | |
| 463 | $D_{253}$ | $A_{11}$ | $S_6$ | $T_6$ | $N_5$ | $E_4$ | $G_3$ | $V_1$ | | | | | | | | | | |
| 464 | $K_{150}$ | $E_{51}$ | $T_{32}$ | $Q_{17}$ | $A_{10}$ | $D_9$ | $R_7$ | $G_5$ | $N_3$ | $S_2$ | $Y_1$ | $H_1$ | $W_1$ | | | | | |
| 465 | $F_{288}$ | $Y_1$ | | | | | | | | | | | | | | | | |
| 466 | $A_{149}$ | $D_{87}$ | $S_{25}$ | $N_{10}$ | $V_5$ | $T_5$ | $E_3$ | $H_3$ | $G_1$ | $R_1$ | | | | | | | | |
| 467 | $Q_{288}$ | $I_1$ | | | | | | | | | | | | | | | | |
| 468 | $G_{289}$ | | | | | | | | | | | | | | | | | |
| 469 | $W_{287}$ | $F_1$ | $S_1$ | | | | | | | | | | | | | | | |
| 470 | $G_{288}$ | $X_1$ | | | | | | | | | | | | | | | | |
| 471 | $P_{275}$ | $S_{12}$ | $A_1$ | $L_1$ | | | | | | | | | | | | | | |
| 472 | $I_{284}$ | $V_3$ | $L_2$ | | | | | | | | | | | | | | | |
| 473 | $T_{266}$ | $S_{13}$ | $A_3$ | $N_2$ | $R_2$ | $Q_1$ | $H_1$ | $K_1$ | | | | | | | | | | |
| 474 | $Y_{248}$ | $H_{37}$ | $N_1$ | $F_1$ | $C_1$ | $S_1$ | | | | | | | | | | | | |
| 475 | $A_{165}$ | $V_{38}$ | $T_{36}$ | $D_{28}$ | $G_{11}$ | $N_6$ | $I_2$ | $H_1$ | $S_1$ | $Y_1$ | | | | | | | | |
| 476 | $E_{153}$ | $K_{33}$ | $V_{24}$ | $G_{15}$ | $N_{15}$ | $Q_{12}$ | $R_9$ | $A_9$ | $D_7$ | $T_4$ | $S_4$ | $M_3$ | $P_1$ | | | | | |
| 477 | $P_{175}$ | $S_{48}$ | $G_{26}$ | $A_8$ | $D_6$ | $Q_6$ | $R_6$ | $H_5$ | $Y_3$ | $T_2$ | $N_2$ | $L_1$ | $V_1$ | | | | | |
| 478 | $D_{68}$ | $N_{42}$ | $S_{35}$ | $G_{35}$ | $P_{31}$ | $R_{23}$ | $H_{18}$ | $T_{16}$ | $A_7$ | $E_4$ | $V_4$ | $Q_3$ | $K_2$ | $L_1$ | | | | |
| 479 | $S_{120}$ | $G_{50}$ | $D_{41}$ | $N_{27}$ | $I_{27}$ | $V_8$ | $R_5$ | $T_3$ | $A_2$ | $K_2$ | $P_2$ | $H_1$ | $L_1$ | | | | | |
| 480 | $S_{116}$ | $L_{70}$ | $P_{58}$ | $Q_{26}$ | $V_4$ | $R_4$ | $M_3$ | $T_3$ | $K_2$ | $E_1$ | $X_1$ | $W_1$ | | | | | | |
| 481 | $D_{271}$ | $E_{13}$ | $X_3$ | $G_1$ | | | | | | | | | | | | | | |
| 482 | $Q_{269}$ | $H_{14}$ | $R_1$ | $M_1$ | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 483 | $R_{235}$ | $K_{48}$ | $G_1$ | $S_1$ | | | | | | | | | | | | | | |
| 484 | $P_{284}$ | $L_1$ | | | | | | | | | | | | | | | | |
| 485 | $Y_{285}$ | | | | | | | | | | | | | | | | | |
| 486 | $C_{285}$ | | | | | | | | | | | | | | | | | |
| 487 | $W_{283}$ | $S_1$ | $G_1$ | | | | | | | | | | | | | | | |
| 488 | $H_{283}$ | $S_1$ | $P_1$ | | | | | | | | | | | | | | | |
| 489 | $Y_{271}$ | $X_{13}$ | $N_1$ | | | | | | | | | | | | | | | |
| 490 | $A_{230}$ | $P_{30}$ | $R_1$ | | | | | | | | | | | | | | | |
| 491 | $P_{259}$ | $Q_1$ | $L_1$ | | | | | | | | | | | | | | | |
| 492 | $R_{157}$ | $Q_{62}$ | $K_{36}$ | $P_3$ | $E_2$ | $S_1$ | | | | | | | | | | | | |
| 493 | $P_{193}$ | $Q_{40}$ | $R_{10}$ | $K_9$ | $L_6$ | $A_1$ | $X_1$ | $S_1$ | | | | | | | | | | |
| 494 | $C_{259}$ | | | | | | | | | | | | | | | | | |
| 495 | $G_{249}$ | $S_3$ | $D_2$ | $K_1$ | $V_1$ | $X_1$ | $N_1$ | $T_1$ | | | | | | | | | | |
| 496 | $I_{238}$ | $T_{11}$ | $V_{10}$ | | | | | | | | | | | | | | | |
| 497 | $V_{233}$ | $I_{22}$ | $X_1$ | $A_1$ | $T_1$ | $E_1$ | | | | | | | | | | | | |
| 498 | $P_{249}$ | $S_6$ | $X_2$ | $A_1$ | $H_1$ | | | | | | | | | | | | | |
| 499 | $A_{248}$ | $P_2$ | $X_2$ | $T_2$ | $W_1$ | | | | | | | | | | | | | |
| 500 | $S_{211}$ | $A_{15}$ | $L_{13}$ | $Q_7$ | $R_3$ | $K_2$ | $X_1$ | | | | | | | | | | | |
| 501 | $Q_{133}$ | $E_{74}$ | $K_{20}$ | $T_7$ | $N_7$ | $G_3$ | $D_3$ | $R_1$ | $S_1$ | | | | | | | | | |
| 502 | $V_{243}$ | $A_1$ | $C_1$ | $M_1$ | $X_1$ | | | | | | | | | | | | | |
| 503 | $C_{228}$ | $X_{14}$ | $P_1$ | | | | | | | | | | | | | | | |
| 504 | $G_{227}$ | $V_5$ | $A_1$ | $X_1$ | $S_1$ | | | | | | | | | | | | | |
| 505 | $P_{228}$ | $Q_6$ | $G_1$ | | | | | | | | | | | | | | | |
| 506 | $V_{223}$ | $X_8$ | $M_3$ | | | | | | | | | | | | | | | |
| 507 | $Y_{183}$ | $H_1$ | $X_1$ | | | | | | | | | | | | | | | |
| 508 | $C_{183}$ | $R_1$ | | | | | | | | | | | | | | | | |
| 509 | $F_{179}$ | $L_1$ | $X_1$ | | | | | | | | | | | | | | | |
| 510 | $T_{175}$ | $X_5$ | | | | | | | | | | | | | | | | |
| 511 | $P_{174}$ | | | | | | | | | | | | | | | | | |
| 512 | $S_{171}$ | $T_2$ | $A_1$ | | | | | | | | | | | | | | | |
| 513 | $P_{174}$ | | | | | | | | | | | | | | | | | |
| 514 | $V_{171}$ | $I_2$ | | | | | | | | | | | | | | | | |
| 515 | $V_{171}$ | $A_2$ | | | | | | | | | | | | | | | | |
| 516 | $V_{171}$ | $N_1$ | $X_1$ | | | | | | | | | | | | | | | |
| 517 | $G_{171}$ | $W_1$ | | | | | | | | | | | | | | | | |
| 518 | $T_{168}$ | $S_2$ | $K_1$ | $X_1$ | | | | | | | | | | | | | | |
| 519 | $T_{171}$ | $S_1$ | | | | | | | | | | | | | | | | |
| 520 | $D_{170}$ | $N_1$ | | | | | | | | | | | | | | | | |
| 521 | $R_{161}$ | $H_5$ | $S_2$ | $K_1$ | $G_1$ | $P_1$ | | | | | | | | | | | | |
| 522 | $F_{111}$ | $S_{45}$ | $L_9$ | $Y_2$ | $H_2$ | $A_1$ | $T_1$ | | | | | | | | | | | |
| 523 | $G_{168}$ | $S_2$ | | | | | | | | | | | | | | | | |
| 524 | $V_{112}$ | $A_{55}$ | $N_2$ | $T_1$ | | | | | | | | | | | | | | |
| 525 | $P_{169}$ | $R_1$ | | | | | | | | | | | | | | | | |
| 526 | $T_{170}$ | | | | | | | | | | | | | | | | | |
| 527 | $Y_{158}$ | $X_1$ | $S_1$ | | | | | | | | | | | | | | | |
| 528 | $S_{77}$ | $N_{36}$ | $T_{24}$ | $R_{18}$ | $K_2$ | $D_1$ | $V_1$ | | | | | | | | | | | |
| 529 | $W_{158}$ | $X_{10}$ | $R_1$ | | | | | | | | | | | | | | | |
| 530 | $G_{165}$ | $X_3$ | $R_1$ | | | | | | | | | | | | | | | |
| 531 | $E_{131}$ | $A_{16}$ | $D_6$ | $G_5$ | $V_4$ | $N_3$ | $S_1$ | | | | | | | | | | | |
| 532 | $N_{164}$ | $S_2$ | | | | | | | | | | | | | | | | |
| 533 | $E_{158}$ | $D_3$ | $K_2$ | $G_2$ | $V_1$ | | | | | | | | | | | | | |
| 534 | $T_{163}$ | $S_2$ | $I_1$ | | | | | | | | | | | | | | | |
| 535 | $D_{166}$ | | | | | | | | | | | | | | | | | |
| 536 | $V_{163}$ | $M_1$ | $A_1$ | $I_1$ | | | | | | | | | | | | | | |
| 537 | $L_{165}$ | $F_1$ | | | | | | | | | | | | | | | | |
| 538 | $L_{142}$ | $I_{12}$ | $V_7$ | $F_2$ | $P_2$ | $Y_1$ | | | | | | | | | | | | |
| 539 | $L_{166}$ | | | | | | | | | | | | | | | | | |
| 540 | $N_{164}$ | $T_1$ | $S_1$ | | | | | | | | | | | | | | | |
| 541 | $N_{162}$ | $S_4$ | | | | | | | | | | | | | | | | |
| 542 | $T_{157}$ | $S_4$ | $M_2$ | $A_2$ | $X_1$ | | | | | | | | | | | | | |
| 543 | $R_{163}$ | $G_2$ | $L_1$ | | | | | | | | | | | | | | | |
| 544 | $P_{163}$ | $L_2$ | $A_1$ | | | | | | | | | | | | | | | |
| 545 | $P_{155}$ | $X_{11}$ | | | | | | | | | | | | | | | | |
| 546 | $Q_{112}$ | $R_{28}$ | $H_7$ | $L_7$ | $P_1$ | | | | | | | | | | | | | |
| 547 | $G_{153}$ | $A_1$ | $D_1$ | | | | | | | | | | | | | | | |
| 548 | $N_{151}$ | $T_2$ | $S_2$ | | | | | | | | | | | | | | | |
| 549 | $W_{154}$ | $K_1$ | | | | | | | | | | | | | | | | |
| 550 | $F_{155}$ | | | | | | | | | | | | | | | | | |
| 551 | $G_{155}$ | | | | | | | | | | | | | | | | | |
| 552 | $C_{154}$ | $Y_1$ | | | | | | | | | | | | | | | | |
| 553 | $T_{154}$ | $S_1$ | | | | | | | | | | | | | | | | |
| 554 | $W_{154}$ | $Y_1$ | | | | | | | | | | | | | | | | |
| 555 | $M_{153}$ | $I_1$ | $V_1$ | | | | | | | | | | | | | | | |
| 556 | $N_{154}$ | $S_1$ | | | | | | | | | | | | | | | | |
| 557 | $S_{99}$ | $G_{44}$ | $A_8$ | $T_3$ | $N_1$ | | | | | | | | | | | | | |
| 558 | $T_{153}$ | $S_2$ | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 559 | $G_{154}$ | $R_1$ | | | | | | | | | | | | | | | | |
| 560 | $F_{150}$ | $Y_4$ | $S_1$ | | | | | | | | | | | | | | | |
| 561 | $T_{154}$ | $A_1$ | | | | | | | | | | | | | | | | |
| 562 | $K_{154}$ | $M_1$ | | | | | | | | | | | | | | | | |
| 563 | $T_{153}$ | $V_1$ | $A_1$ | | | | | | | | | | | | | | | |
| 564 | $C_{155}$ | | | | | | | | | | | | | | | | | |
| 565 | $G_{154}$ | $E_1$ | | | | | | | | | | | | | | | | |
| 566 | $G_{142}$ | $A_{10}$ | $R_1$ | $D_1$ | $V_1$ | | | | | | | | | | | | | |
| 567 | $P_{155}$ | | | | | | | | | | | | | | | | | |
| 568 | $P_{151}$ | $S_2$ | $A_1$ | $L_1$ | | | | | | | | | | | | | | |
| 569 | $C_{155}$ | | | | | | | | | | | | | | | | | |
| 570 | $N_{130}$ | $D_9$ | $K_7$ | $G_3$ | $H_2$ | $T_2$ | $V_1$ | $E_1$ | | | | | | | | | | |
| 571 | $I_{155}$ | | | | | | | | | | | | | | | | | |
| 572 | $G_{152}$ | $E_1$ | $S_1$ | $R_1$ | | | | | | | | | | | | | | |
| 573 | $G_{155}$ | | | | | | | | | | | | | | | | | |
| 574 | $V_{105}$ | $A_{33}$ | $I_6$ | $G_5$ | $E_2$ | $L_2$ | $N_1$ | $R_1$ | | | | | | | | | | |
| 575 | $G_{153}$ | $S_1$ | $D_1$ | | | | | | | | | | | | | | | |
| 576 | $N_{153}$ | $S_1$ | | | | | | | | | | | | | | | | |
| 577 | $N_{113}$ | $D_{34}$ | $K_3$ | $T_2$ | $L_1$ | $S_1$ | $E_1$ | | | | | | | | | | | |
| 578 | $T_{150}$ | $S_3$ | $R_1$ | $A_1$ | | | | | | | | | | | | | | |
| 579 | $L_{154}$ | $F_1$ | | | | | | | | | | | | | | | | |
| 580 | $T_{85}$ | $I_{58}$ | $V_{10}$ | $H_1$ | $L_1$ | | | | | | | | | | | | | |
| 581 | $C_{155}$ | | | | | | | | | | | | | | | | | |
| 582 | $P_{153}$ | $S_2$ | | | | | | | | | | | | | | | | |
| 583 | $T_{154}$ | $S_1$ | | | | | | | | | | | | | | | | |
| 584 | $D_{155}$ | | | | | | | | | | | | | | | | | |
| 585 | $C_{155}$ | | | | | | | | | | | | | | | | | |
| 586 | $F_{155}$ | | | | | | | | | | | | | | | | | |
| 587 | $R_{155}$ | | | | | | | | | | | | | | | | | |
| 588 | $K_{153}$ | $X_1$ | $E_1$ | | | | | | | | | | | | | | | |
| 589 | $H_{154}$ | | | | | | | | | | | | | | | | | |
| 590 | $P_{153}$ | $S_1$ | | | | | | | | | | | | | | | | |
| 591 | $E_{145}$ | $G_3$ | $D_3$ | $A_2$ | $Q_1$ | | | | | | | | | | | | | |
| 592 | $A_{153}$ | $S_1$ | | | | | | | | | | | | | | | | |
| 593 | $T_{153}$ | $A_1$ | | | | | | | | | | | | | | | | |
| 594 | $Y_{154}$ | | | | | | | | | | | | | | | | | |
| 595 | $T_{141}$ | $A_9$ | $S_3$ | $X_1$ | | | | | | | | | | | | | | |
| 596 | $K_{144}$ | $R_{10}$ | | | | | | | | | | | | | | | | |
| 597 | $C_{154}$ | | | | | | | | | | | | | | | | | |
| 598 | $G_{153}$ | $X_1$ | | | | | | | | | | | | | | | | |
| 599 | $S_{154}$ | | | | | | | | | | | | | | | | | |
| 600 | $G_{154}$ | | | | | | | | | | | | | | | | | |
| 601 | $P_{154}$ | | | | | | | | | | | | | | | | | |
| 602 | $W_{154}$ | | | | | | | | | | | | | | | | | |
| 603 | $L_{152}$ | $S_1$ | $I_1$ | | | | | | | | | | | | | | | |
| 604 | $T_{149}$ | $R_1$ | $I_1$ | | | | | | | | | | | | | | | |
| 605 | $P_{151}$ | | | | | | | | | | | | | | | | | |
| 606 | $R_{150}$ | $K_1$ | | | | | | | | | | | | | | | | |
| 607 | $C_{151}$ | | | | | | | | | | | | | | | | | |
| 608 | $M_{69}$ | $L_{51}$ | $I_{31}$ | | | | | | | | | | | | | | | |
| 609 | $V_{149}$ | $I_2$ | | | | | | | | | | | | | | | | |
| 610 | $D_{126}$ | $H_{24}$ | $N_1$ | | | | | | | | | | | | | | | |
| 611 | $Y_{151}$ | | | | | | | | | | | | | | | | | |
| 612 | $P_{151}$ | | | | | | | | | | | | | | | | | |
| 613 | $Y_{151}$ | | | | | | | | | | | | | | | | | |
| 614 | $R_{151}$ | | | | | | | | | | | | | | | | | |
| 615 | $L_{150}$ | $P_1$ | | | | | | | | | | | | | | | | |
| 616 | $W_{147}$ | $L_1$ | | | | | | | | | | | | | | | | |
| 617 | $H_{147}$ | $Y_1$ | | | | | | | | | | | | | | | | |
| 618 | $Y_{143}$ | $X_5$ | | | | | | | | | | | | | | | | |
| 619 | $P_{143}$ | | | | | | | | | | | | | | | | | |
| 620 | $C_{142}$ | $S_1$ | | | | | | | | | | | | | | | | |
| 621 | $T_{141}$ | $A_2$ | | | | | | | | | | | | | | | | |
| 622 | $V_{131}$ | $L_5$ | $I_4$ | $A_2$ | $F_1$ | | | | | | | | | | | | | |
| 623 | $N_{142}$ | $H_1$ | | | | | | | | | | | | | | | | |
| 624 | $F_{141}$ | $Y_2$ | | | | | | | | | | | | | | | | |
| 625 | $T_{118}$ | $S_{24}$ | $A_1$ | | | | | | | | | | | | | | | |
| 626 | $I_{126}$ | $V_{12}$ | $T_3$ | $L_2$ | | | | | | | | | | | | | | |
| 627 | $F_{142}$ | $L_1$ | | | | | | | | | | | | | | | | |
| 628 | $K_{139}$ | $T_3$ | $Q_1$ | | | | | | | | | | | | | | | |
| 629 | $V_{131}$ | $I_{12}$ | | | | | | | | | | | | | | | | |
| 630 | $R_{142}$ | $K_1$ | | | | | | | | | | | | | | | | |
| 631 | $M_{143}$ | | | | | | | | | | | | | | | | | |
| 632 | $Y_{142}$ | $N_1$ | | | | | | | | | | | | | | | | |
| 633 | $V_{143}$ | | | | | | | | | | | | | | | | | |
| 634 | $G_{143}$ | | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 635 | $G_{143}$ | | | | | | | | | | | | | | | | | |
| 636 | $V_{134}$ | $I_3$ | $A_2$ | $L_2$ | $M_2$ | | | | | | | | | | | | | |
| 637 | $E_{142}$ | $G_1$ | | | | | | | | | | | | | | | | |
| 638 | $H_{142}$ | $Q_1$ | | | | | | | | | | | | | | | | |
| 639 | $R_{142}$ | $K_1$ | | | | | | | | | | | | | | | | |
| 640 | $L_{140}$ | $F_3$ | | | | | | | | | | | | | | | | |
| 641 | $N_{79}$ | $D_{21}$ | $E_{13}$ | $S_{13}$ | $T_8$ | $K_5$ | $I_2$ | $H_1$ | $V_1$ | | | | | | | | | |
| 642 | $A_{142}$ | $V_1$ | | | | | | | | | | | | | | | | |
| 643 | $A_{141}$ | $G_1$ | $V_1$ | | | | | | | | | | | | | | | |
| 644 | $C_{140}$ | $S_1$ | $G_1$ | $R_1$ | | | | | | | | | | | | | | |
| 645 | $N_{142}$ | $K_1$ | | | | | | | | | | | | | | | | |
| 646 | $W_{143}$ | | | | | | | | | | | | | | | | | |
| 647 | $T_{143}$ | | | | | | | | | | | | | | | | | |
| 648 | $R_{141}$ | $W_1$ | | | | | | | | | | | | | | | | |
| 649 | $G_{142}$ | $R_1$ | | | | | | | | | | | | | | | | |
| 650 | $E_{139}$ | $D_3$ | $A_1$ | | | | | | | | | | | | | | | |
| 651 | $R_{143}$ | | | | | | | | | | | | | | | | | |
| 652 | $C_{142}$ | $R_1$ | | | | | | | | | | | | | | | | |
| 653 | $D_{103}$ | $N_{36}$ | $G_2$ | $A_1$ | $E_1$ | | | | | | | | | | | | | |
| 654 | $L_{140}$ | $V_3$ | | | | | | | | | | | | | | | | |
| 655 | $E_{126}$ | $T_5$ | $D_5$ | $V_2$ | $G_2$ | $S_1$ | $R_1$ | $A_1$ | | | | | | | | | | |
| 656 | $D_{143}$ | | | | | | | | | | | | | | | | | |
| 657 | $R_{143}$ | | | | | | | | | | | | | | | | | |
| 658 | $D_{143}$ | | | | | | | | | | | | | | | | | |
| 659 | $R_{143}$ | | | | | | | | | | | | | | | | | |
| 660 | $S_{134}$ | $A_5$ | $T_2$ | $P_1$ | $L_1$ | | | | | | | | | | | | | |
| 661 | $E_{143}$ | | | | | | | | | | | | | | | | | |
| 662 | $L_{143}$ | | | | | | | | | | | | | | | | | |
| 663 | $S_{143}$ | | | | | | | | | | | | | | | | | |
| 664 | $P_{143}$ | | | | | | | | | | | | | | | | | |
| 665 | $L_{143}$ | | | | | | | | | | | | | | | | | |
| 666 | $L_{142}$ | $I_1$ | | | | | | | | | | | | | | | | |
| 667 | $L_{142}$ | $R_1$ | | | | | | | | | | | | | | | | |
| 668 | $S_{141}$ | $A_1$ | $F_1$ | | | | | | | | | | | | | | | |
| 669 | $T_{142}$ | $I_1$ | | | | | | | | | | | | | | | | |
| 670 | $T_{143}$ | | | | | | | | | | | | | | | | | |
| 671 | $E_{143}$ | | | | | | | | | | | | | | | | | |
| 672 | $W_{142}$ | | | | | | | | | | | | | | | | | |
| 673 | $Q_{143}$ | | | | | | | | | | | | | | | | | |
| 674 | $I_{77}$ | $V_{65}$ | $T_1$ | | | | | | | | | | | | | | | |
| 675 | $L_{142}$ | $M_1$ | | | | | | | | | | | | | | | | |
| 676 | $P_{143}$ | | | | | | | | | | | | | | | | | |
| 677 | $C_{143}$ | | | | | | | | | | | | | | | | | |
| 678 | $S_{138}$ | $A_4$ | $T_1$ | | | | | | | | | | | | | | | |
| 679 | $F_{137}$ | $Y_6$ | | | | | | | | | | | | | | | | |
| 680 | $T_{143}$ | | | | | | | | | | | | | | | | | |
| 681 | $T_{140}$ | $A_1$ | $P_1$ | $G_1$ | | | | | | | | | | | | | | |
| 682 | $L_{143}$ | | | | | | | | | | | | | | | | | |
| 683 | $P_{143}$ | | | | | | | | | | | | | | | | | |
| 684 | $A_{141}$ | $G_1$ | $V_1$ | | | | | | | | | | | | | | | |
| 685 | $L_{141}$ | $V_1$ | $P_1$ | | | | | | | | | | | | | | | |
| 686 | $S_{142}$ | $F_1$ | | | | | | | | | | | | | | | | |
| 687 | $T_{143}$ | | | | | | | | | | | | | | | | | |
| 688 | $G_{143}$ | | | | | | | | | | | | | | | | | |
| 689 | $L_{143}$ | | | | | | | | | | | | | | | | | |
| 690 | $I_{143}$ | | | | | | | | | | | | | | | | | |
| 691 | $H_{143}$ | | | | | | | | | | | | | | | | | |
| 692 | $L_{143}$ | | | | | | | | | | | | | | | | | |
| 693 | $H_{143}$ | | | | | | | | | | | | | | | | | |
| 694 | $Q_{108}$ | $R_{35}$ | | | | | | | | | | | | | | | | |
| 695 | $N_{142}$ | $G_1$ | | | | | | | | | | | | | | | | |
| 696 | $I_{126}$ | $V_{10}$ | $T_6$ | $F_1$ | | | | | | | | | | | | | | |
| 697 | $V_{143}$ | | | | | | | | | | | | | | | | | |
| 698 | $D_{142}$ | $H_1$ | | | | | | | | | | | | | | | | |
| 699 | $V_{132}$ | $I_{10}$ | $A_1$ | | | | | | | | | | | | | | | |
| 700 | $Q_{143}$ | | | | | | | | | | | | | | | | | |
| 701 | $Y_{142}$ | $H_1$ | | | | | | | | | | | | | | | | |
| 702 | $L_{142}$ | $R_1$ | | | | | | | | | | | | | | | | |
| 703 | $Y_{141}$ | $H_1$ | $D_1$ | | | | | | | | | | | | | | | |
| 704 | $G_{142}$ | $C_1$ | | | | | | | | | | | | | | | | |
| 705 | $I_{102}$ | $V_{41}$ | | | | | | | | | | | | | | | | |
| 706 | $G_{143}$ | | | | | | | | | | | | | | | | | |
| 707 | $S_{143}$ | | | | | | | | | | | | | | | | | |
| 708 | $A_{124}$ | $V_{16}$ | $T_2$ | $G_1$ | | | | | | | | | | | | | | |
| 709 | $V_{133}$ | $I_5$ | $A_2$ | $G_1$ | $L_1$ | $F_1$ | | | | | | | | | | | | |
| 710 | $V_{138}$ | $A_4$ | $I_1$ | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 711 | $S_{141}$ | $P_2$ | | | | | | | | | | | | | | | | |
| 712 | $F_{68}$ | $Y_{32}$ | $I_{19}$ | $V_{16}$ | $L_6$ | $A_1$ | | | | | | | | | | | | |
| 713 | $A_{99}$ | $V_{42}$ | $T_1$ | | | | | | | | | | | | | | | |
| 714 | $I_{134}$ | $V_8$ | | | | | | | | | | | | | | | | |
| 715 | $K_{126}$ | $R_{16}$ | | | | | | | | | | | | | | | | |
| 716 | $W_{142}$ | | | | | | | | | | | | | | | | | |
| 717 | $E_{140}$ | $D_2$ | | | | | | | | | | | | | | | | |
| 718 | $Y_{141}$ | | | | | | | | | | | | | | | | | |
| 719 | $V_{113}$ | $I_{28}$ | $F_1$ | | | | | | | | | | | | | | | |
| 720 | $L_{99}$ | $V_{38}$ | $I_4$ | $M_1$ | | | | | | | | | | | | | | |
| 721 | $L_{141}$ | $I_1$ | | | | | | | | | | | | | | | | |
| 722 | $L_{137}$ | $F_4$ | $S_1$ | $X_1$ | | | | | | | | | | | | | | |
| 723 | $F_{141}$ | $S_1$ | $X_1$ | $L_1$ | | | | | | | | | | | | | | |
| 724 | $L_{140}$ | $F_3$ | $N_1$ | | | | | | | | | | | | | | | |
| 725 | $L_{110}$ | $F_{24}$ | $Y_6$ | $P_3$ | $S_1$ | | | | | | | | | | | | | |
| 726 | $L_{143}$ | $A_1$ | | | | | | | | | | | | | | | | |
| 727 | $A_{143}$ | $M_1$ | | | | | | | | | | | | | | | | |
| 728 | $D_{142}$ | $Y_1$ | $A_1$ | | | | | | | | | | | | | | | |
| 729 | $A_{143}$ | $E_1$ | | | | | | | | | | | | | | | | |
| 730 | $R_{143}$ | $S_1$ | | | | | | | | | | | | | | | | |
| 731 | $V_{137}$ | $I_4$ | $F_3$ | | | | | | | | | | | | | | | |
| 732 | $C_{144}$ | | | | | | | | | | | | | | | | | |
| 733 | $A_{141}$ | $P_1$ | $G_1$ | $S_1$ | | | | | | | | | | | | | | |
| 734 | $C_{137}$ | $A_3$ | $W_3$ | $G_1$ | | | | | | | | | | | | | | |
| 735 | $L_{144}$ | | | | | | | | | | | | | | | | | |
| 736 | $W_{144}$ | | | | | | | | | | | | | | | | | |
| 737 | $M_{142}$ | $T_1$ | $R_1$ | | | | | | | | | | | | | | | |
| 738 | $M_{143}$ | $I_1$ | | | | | | | | | | | | | | | | |
| 739 | $L_{140}$ | $M_4$ | | | | | | | | | | | | | | | | |
| 740 | $L_{142}$ | $M_2$ | | | | | | | | | | | | | | | | |
| 741 | $I_{124}$ | $V_{18}$ | $X_1$ | $K_1$ | | | | | | | | | | | | | | |
| 742 | $A_{138}$ | $P_2$ | $V_1$ | $G_1$ | $T_1$ | | | | | | | | | | | | | |
| 743 | $Q_{143}$ | | | | | | | | | | | | | | | | | |
| 744 | $A_{142}$ | $V_1$ | | | | | | | | | | | | | | | | |
| 745 | $E_{140}$ | $D_2$ | $K_1$ | | | | | | | | | | | | | | | |
| 746 | $A_{140}$ | $G_1$ | $P_1$ | | | | | | | | | | | | | | | |
| 747 | $A_{133}$ | $T_5$ | $V_1$ | $L_1$ | $P_1$ | | | | | | | | | | | | | |
| 748 | $L_{140}$ | $M_1$ | | | | | | | | | | | | | | | | |
| 749 | $E_{138}$ | $G_2$ | $K_1$ | | | | | | | | | | | | | | | |
| 750 | $N_{139}$ | $K_1$ | $I_1$ | | | | | | | | | | | | | | | |
| 751 | $L_{141}$ | | | | | | | | | | | | | | | | | |
| 752 | $V_{140}$ | $A_1$ | | | | | | | | | | | | | | | | |
| 753 | $V_{135}$ | $I_4$ | $A_2$ | | | | | | | | | | | | | | | |
| 754 | $L_{140}$ | $F_1$ | | | | | | | | | | | | | | | | |
| 755 | $N_{141}$ | | | | | | | | | | | | | | | | | |
| 756 | $A_{140}$ | $S_1$ | | | | | | | | | | | | | | | | |
| 757 | $A_{138}$ | $S_1$ | $G_1$ | $P_1$ | | | | | | | | | | | | | | |
| 758 | $S_{139}$ | $Y_1$ | $A_1$ | | | | | | | | | | | | | | | |
| 759 | $V_{127}$ | $L_{11}$ | $M_3$ | | | | | | | | | | | | | | | |
| 760 | $A_{139}$ | $T_1$ | $V_1$ | | | | | | | | | | | | | | | |
| 761 | $G_{138}$ | $A_1$ | $D_1$ | $R_1$ | | | | | | | | | | | | | | |
| 762 | $A_{94}$ | $T_{36}$ | $V_4$ | $E_2$ | $M_2$ | $K_1$ | $S_1$ | $R_1$ | | | | | | | | | | |
| 763 | $H_{138}$ | $R_2$ | $D_1$ | | | | | | | | | | | | | | | |
| 764 | $G_{138}$ | $S_2$ | $D_1$ | | | | | | | | | | | | | | | |
| 765 | $I_{114}$ | $V_9$ | $T_8$ | $F_5$ | $L_4$ | $M_1$ | | | | | | | | | | | | |
| 766 | $L_{134}$ | $F_4$ | $P_2$ | $S_1$ | | | | | | | | | | | | | | |
| 767 | $S_{128}$ | $P_{11}$ | $F_1$ | $T_1$ | | | | | | | | | | | | | | |
| 768 | $F_{140}$ | $L_1$ | | | | | | | | | | | | | | | | |
| 769 | $L_{138}$ | $I_2$ | $F_1$ | | | | | | | | | | | | | | | |
| 770 | $V_{139}$ | $M_2$ | | | | | | | | | | | | | | | | |
| 771 | $F_{131}$ | | | | | | | | | | | | | | | | | |
| 772 | $F_{131}$ | | | | | | | | | | | | | | | | | |
| 773 | $C_{131}$ | | | | | | | | | | | | | | | | | |
| 774 | $A_{129}$ | $E_2$ | | | | | | | | | | | | | | | | |
| 775 | $A_{131}$ | | | | | | | | | | | | | | | | | |
| 776 | $W_{129}$ | $E_2$ | | | | | | | | | | | | | | | | |
| 777 | $Y_{127}$ | $F_2$ | $C_2$ | | | | | | | | | | | | | | | |
| 778 | $I_{128}$ | $M_1$ | | | | | | | | | | | | | | | | |
| 779 | $K_{128}$ | $Q_1$ | | | | | | | | | | | | | | | | |
| 780 | $G_{129}$ | | | | | | | | | | | | | | | | | |
| 781 | $R_{99}$ | $K_{29}$ | $E_1$ | | | | | | | | | | | | | | | |
| 782 | $L_{129}$ | | | | | | | | | | | | | | | | | |
| 783 | $V_{121}$ | $X_5$ | $A_2$ | $I_1$ | | | | | | | | | | | | | | |
| 784 | $P_{123}$ | | | | | | | | | | | | | | | | | |
| 785 | $G_{121}$ | $A_2$ | | | | | | | | | | | | | | | | |
| 786 | $A_{120}$ | $V_3$ | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 787 | $A_{118}$ | $T_4$ | $V_1$ | | | | | | | | | | | | | | | |
| 788 | $Y_{123}$ | | | | | | | | | | | | | | | | | |
| 789 | $A_{121}$ | $V_2$ | | | | | | | | | | | | | | | | |
| 790 | $F_{61}$ | $L_{48}$ | $I_8$ | $V_4$ | $Y_1$ | $S_1$ | | | | | | | | | | | | |
| 791 | $Y_{123}$ | | | | | | | | | | | | | | | | | |
| 792 | $G_{118}$ | $S_5$ | | | | | | | | | | | | | | | | |
| 793 | $V_{118}$ | $A_3$ | $M_1$ | $I_1$ | | | | | | | | | | | | | | |
| 794 | $W_{122}$ | $C_1$ | | | | | | | | | | | | | | | | |
| 795 | $P_{123}$ | | | | | | | | | | | | | | | | | |
| 796 | $L_{123}$ | | | | | | | | | | | | | | | | | |
| 797 | $L_{121}$ | $F_2$ | | | | | | | | | | | | | | | | |
| 798 | $L_{122}$ | $M_1$ | | | | | | | | | | | | | | | | |
| 799 | $L_{123}$ | | | | | | | | | | | | | | | | | |
| 800 | $L_{123}$ | | | | | | | | | | | | | | | | | |
| 801 | $L_{120}$ | $M_3$ | | | | | | | | | | | | | | | | |
| 802 | $A_{111}$ | $T_8$ | $S_3$ | $X_1$ | | | | | | | | | | | | | | |
| 803 | $L_{123}$ | | | | | | | | | | | | | | | | | |
| 804 | $P_{123}$ | | | | | | | | | | | | | | | | | |
| 805 | $P_{118}$ | $A_2$ | $Q_1$ | $S_1$ | $H_1$ | | | | | | | | | | | | | |
| 806 | $R_{120}$ | $L_1$ | $Q_1$ | $X_1$ | | | | | | | | | | | | | | |
| 807 | $A_{122}$ | $V_1$ | | | | | | | | | | | | | | | | |
| 808 | $Y_{121}$ | $F_2$ | | | | | | | | | | | | | | | | |
| 809 | $A_{123}$ | | | | | | | | | | | | | | | | | |
| 810 | $M_{122}$ | $L_7$ | $A_2$ | $I_1$ | | | | | | | | | | | | | | |
| 811 | $D_{127}$ | $E_4$ | $A_1$ | | | | | | | | | | | | | | | |
| 812 | $R_{129}$ | $T_1$ | $Q_1$ | $P_1$ | | | | | | | | | | | | | | |
| 813 | $E_{130}$ | $G_2$ | | | | | | | | | | | | | | | | |
| 814 | $M_{124}$ | $V_8$ | | | | | | | | | | | | | | | | |
| 815 | $A_{130}$ | $T_1$ | $V_1$ | | | | | | | | | | | | | | | |
| 816 | $A_{126}$ | $P_3$ | $G_2$ | | | | | | | | | | | | | | | |
| 817 | $S_{130}$ | | | | | | | | | | | | | | | | | |
| 818 | $C_{129}$ | $S_1$ | | | | | | | | | | | | | | | | |
| 819 | $G_{129}$ | $E_1$ | | | | | | | | | | | | | | | | |
| 820 | $G_{130}$ | | | | | | | | | | | | | | | | | |
| 821 | $A_{100}$ | $G_{13}$ | $V_{10}$ | $M_4$ | $T_3$ | | | | | | | | | | | | | |
| 822 | $V_{130}$ | | | | | | | | | | | | | | | | | |
| 823 | $F_{120}$ | $L_{10}$ | | | | | | | | | | | | | | | | |
| 824 | $V_{68}$ | $I_{55}$ | $L_4$ | $A_1$ | $M_1$ | $T_1$ | | | | | | | | | | | | |
| 825 | $G_{130}$ | | | | | | | | | | | | | | | | | |
| 826 | $L_{130}$ | | | | | | | | | | | | | | | | | |
| 827 | $A_{70}$ | $V_{46}$ | $I_7$ | $M_5$ | $T_2$ | | | | | | | | | | | | | |
| 828 | $L_{112}$ | $F_{15}$ | $I_3$ | | | | | | | | | | | | | | | |
| 829 | $L_{130}$ | | | | | | | | | | | | | | | | | |
| 830 | $T_{130}$ | | | | | | | | | | | | | | | | | |
| 831 | $L_{126}$ | $M_4$ | | | | | | | | | | | | | | | | |
| 832 | $S_{130}$ | | | | | | | | | | | | | | | | | |
| 833 | $P_{130}$ | | | | | | | | | | | | | | | | | |
| 834 | $H_{76}$ | $Y_{52}$ | $Q_2$ | | | | | | | | | | | | | | | |
| 835 | $Y_{125}$ | $X_3$ | $C_1$ | | | | | | | | | | | | | | | |
| 836 | $K_{127}$ | $R_3$ | | | | | | | | | | | | | | | | |
| 837 | $V_{106}$ | $A_{14}$ | $L_3$ | $E_3$ | $F_1$ | $M_1$ | $P_1$ | $T_1$ | | | | | | | | | | |
| 838 | $F_{121}$ | $L_6$ | $V_2$ | $I_1$ | | | | | | | | | | | | | | |
| 839 | $L_{130}$ | | | | | | | | | | | | | | | | | |
| 840 | $A_{128}$ | $T_2$ | | | | | | | | | | | | | | | | |
| 841 | $R_{110}$ | $K_{20}$ | | | | | | | | | | | | | | | | |
| 842 | $L_{123}$ | $I_3$ | $F_3$ | $P_1$ | | | | | | | | | | | | | | |
| 843 | $I_{124}$ | $M_3$ | $L_3$ | | | | | | | | | | | | | | | |
| 844 | $W_{128}$ | $R_2$ | | | | | | | | | | | | | | | | |
| 845 | $W_{129}$ | $R_1$ | | | | | | | | | | | | | | | | |
| 846 | $L_{125}$ | $S_4$ | $M_1$ | | | | | | | | | | | | | | | |
| 847 | $Q_{130}$ | | | | | | | | | | | | | | | | | |
| 848 | $Y_{129}$ | $F_1$ | | | | | | | | | | | | | | | | |
| 849 | $F_{103}$ | $L_{26}$ | $Y_1$ | | | | | | | | | | | | | | | |
| 850 | $I_{112}$ | $L_{13}$ | $T_4$ | $S_1$ | | | | | | | | | | | | | | |
| 851 | $T_{127}$ | $A_3$ | | | | | | | | | | | | | | | | |
| 852 | $R_{118}$ | $I_{11}$ | $K_1$ | | | | | | | | | | | | | | | |
| 853 | $A_{123}$ | $T_3$ | $V_2$ | $S_2$ | | | | | | | | | | | | | | |
| 854 | $E_{130}$ | | | | | | | | | | | | | | | | | |
| 855 | $A_{130}$ | | | | | | | | | | | | | | | | | |
| 856 | $H_{104}$ | $L_{16}$ | $Q_4$ | $C_2$ | $Y_2$ | $I_1$ | $D_1$ | | | | | | | | | | | |
| 857 | $L_{128}$ | $V_2$ | | | | | | | | | | | | | | | | |
| 858 | $Q_{114}$ | $H_{14}$ | $C_1$ | $L_1$ | | | | | | | | | | | | | | |
| 859 | $V_{127}$ | $M_2$ | $I_1$ | | | | | | | | | | | | | | | |
| 860 | $W_{129}$ | $S_1$ | | | | | | | | | | | | | | | | |
| 861 | $I_{73}$ | $V_{54}$ | $T_1$ | $A_1$ | $L_1$ | | | | | | | | | | | | | |
| 862 | $P_{128}$ | $S_2$ | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 863 | $P_{130}$ | | | | | | | | | | | | | | | | | |
| 864 | $L_{130}$ | | | | | | | | | | | | | | | | | |
| 865 | $N_{129}$ | $S_1$ | | | | | | | | | | | | | | | | |
| 866 | $V_{109}$ | $I_{18}$ | $A_3$ | | | | | | | | | | | | | | | |
| 867 | $R_{130}$ | | | | | | | | | | | | | | | | | |
| 868 | $G_{128}$ | $X_2$ | | | | | | | | | | | | | | | | |
| 869 | $G_{130}$ | | | | | | | | | | | | | | | | | |
| 870 | $R_{130}$ | | | | | | | | | | | | | | | | | |
| 871 | $D_{128}$ | $N_2$ | | | | | | | | | | | | | | | | |
| 872 | $A_{130}$ | | | | | | | | | | | | | | | | | |
| 873 | $I_{124}$ | $V_6$ | | | | | | | | | | | | | | | | |
| 874 | $I_{130}$ | | | | | | | | | | | | | | | | | |
| 875 | $L_{128}$ | $I_1$ | $F_1$ | | | | | | | | | | | | | | | |
| 876 | $L_{129}$ | $I_1$ | | | | | | | | | | | | | | | | |
| 877 | $T_{81}$ | $M_{36}$ | $A_{10}$ | $V_3$ | | | | | | | | | | | | | | |
| 878 | $C_{130}$ | | | | | | | | | | | | | | | | | |
| 879 | $A_{98}$ | $V_{31}$ | $M_1$ | | | | | | | | | | | | | | | |
| 880 | $V_{77}$ | $I_{38}$ | $A_{12}$ | $F_1$ | $L_1$ | $T_1$ | | | | | | | | | | | | |
| 881 | $H_{127}$ | $Y_2$ | $R_1$ | | | | | | | | | | | | | | | |
| 882 | $P_{122}$ | $S_7$ | $A_1$ | | | | | | | | | | | | | | | |
| 883 | $E_{121}$ | $G_8$ | $D_1$ | | | | | | | | | | | | | | | |
| 884 | $L_{128}$ | $R_1$ | $S_1$ | | | | | | | | | | | | | | | |
| 885 | $I_{121}$ | $V_8$ | $T_1$ | | | | | | | | | | | | | | | |
| 886 | $F_{129}$ | $S_1$ | | | | | | | | | | | | | | | | |
| 887 | $D_{77}$ | $A_{17}$ | $E_{17}$ | $T_{17}$ | $S_2$ | | | | | | | | | | | | | |
| 888 | $I_{129}$ | $V_1$ | | | | | | | | | | | | | | | | |
| 889 | $T_{129}$ | $S_1$ | | | | | | | | | | | | | | | | |
| 890 | $K_{129}$ | $R_1$ | | | | | | | | | | | | | | | | |
| 891 | $I_{62}$ | $L_{58}$ | $N_4$ | $T_2$ | $F_2$ | $Y_2$ | | | | | | | | | | | | |
| 892 | $L_{129}$ | $V_1$ | | | | | | | | | | | | | | | | |
| 893 | $L_{124}$ | $I_4$ | $V_2$ | | | | | | | | | | | | | | | |
| 894 | $A_{125}$ | $S_4$ | $T_1$ | | | | | | | | | | | | | | | |
| 895 | $I_{111}$ | $T_{11}$ | $V_6$ | $M_1$ | $A_1$ | | | | | | | | | | | | | |
| 896 | $L_{108}$ | $F_{21}$ | $V_1$ | | | | | | | | | | | | | | | |
| 897 | $G_{130}$ | | | | | | | | | | | | | | | | | |
| 898 | $P_{130}$ | $K_7$ | | | | | | | | | | | | | | | | |
| 899 | $L_{129}$ | $P_4$ | $I_3$ | $V_1$ | | | | | | | | | | | | | | |
| 900 | $M_{116}$ | $L_{10}$ | $T_8$ | $V_1$ | $Y_1$ | $P_1$ | | | | | | | | | | | | |
| 901 | $V_{130}$ | $M_5$ | $I_2$ | | | | | | | | | | | | | | | |
| 902 | $L_{129}$ | $F_8$ | | | | | | | | | | | | | | | | |
| 903 | $Q_{134}$ | $L_1$ | $R_1$ | $P_1$ | | | | | | | | | | | | | | |
| 904 | $A_{132}$ | $V_3$ | $T_1$ | $G_1$ | | | | | | | | | | | | | | |
| 905 | $G_{114}$ | $S_{12}$ | $A_8$ | $V_2$ | $R_1$ | | | | | | | | | | | | | |
| 906 | $I_{101}$ | $L_{32}$ | $M_4$ | | | | | | | | | | | | | | | |
| 907 | $T_{100}$ | $A_{16}$ | $I_{16}$ | $V_2$ | $S_1$ | $N_1$ | | | | | | | | | | | | |
| 908 | $R_{104}$ | $K_{27}$ | $A_3$ | $Q_2$ | | | | | | | | | | | | | | |
| 909 | $V_{123}$ | $M_9$ | $A_2$ | $L_1$ | $I_1$ | | | | | | | | | | | | | |
| 910 | $P_{136}$ | | | | | | | | | | | | | | | | | |
| 911 | $Y_{135}$ | $D_1$ | | | | | | | | | | | | | | | | |
| 912 | $F_{136}$ | | | | | | | | | | | | | | | | | |
| 913 | $V_{136}$ | | | | | | | | | | | | | | | | | |
| 914 | $R_{134}$ | $P_2$ | | | | | | | | | | | | | | | | |
| 915 | $A_{136}$ | | | | | | | | | | | | | | | | | |
| 916 | $Q_{90}$ | $H_{46}$ | | | | | | | | | | | | | | | | |
| 917 | $G_{136}$ | | | | | | | | | | | | | | | | | |
| 918 | $L_{135}$ | $V_1$ | | | | | | | | | | | | | | | | |
| 919 | $I_{135}$ | $V_1$ | | | | | | | | | | | | | | | | |
| 920 | $R_{134}$ | $H_2$ | | | | | | | | | | | | | | | | |
| 921 | $A_{121}$ | $V_{13}$ | $E_1$ | $M_1$ | | | | | | | | | | | | | | |
| 922 | $C_{136}$ | | | | | | | | | | | | | | | | | |
| 923 | $M_{109}$ | $L_{23}$ | $V_2$ | $A_1$ | $I_1$ | | | | | | | | | | | | | |
| 924 | $L_{136}$ | | | | | | | | | | | | | | | | | |
| 925 | $V_{120}$ | $L_{11}$ | $A_5$ | | | | | | | | | | | | | | | |
| 926 | $R_{134}$ | $W_2$ | | | | | | | | | | | | | | | | |
| 927 | $K_{129}$ | $Q_4$ | $E_3$ | | | | | | | | | | | | | | | |
| 928 | $V_{109}$ | $A_{24}$ | $T_2$ | $I_1$ | | | | | | | | | | | | | | |
| 929 | $A_{128}$ | $V_5$ | $L_1$ | $S_1$ | $G_1$ | | | | | | | | | | | | | |
| 930 | $G_{136}$ | | | | | | | | | | | | | | | | | |
| 931 | $G_{135}$ | $D_1$ | | | | | | | | | | | | | | | | |
| 932 | $H_{131}$ | $Q_4$ | $L_1$ | | | | | | | | | | | | | | | |
| 933 | $Y_{136}$ | | | | | | | | | | | | | | | | | |
| 934 | $V_{116}$ | $I_{13}$ | $A_3$ | $F_3$ | $L_1$ | | | | | | | | | | | | | |
| 935 | $Q_{136}$ | | | | | | | | | | | | | | | | | |
| 936 | $M_{136}$ | | | | | | | | | | | | | | | | | |
| 937 | $A_{130}$ | $V_6$ | | | | | | | | | | | | | | | | |
| 938 | $F_{75}$ | $L_{61}$ | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 939 | $M_{116}$ | $V_{19}$ | $I_1$ | | | | | | | | | | | | | | | |
| 940 | $K_{94}$ | $R_{42}$ | | | | | | | | | | | | | | | | |
| 941 | $L_{136}$ | | | | | | | | | | | | | | | | | |
| 942 | $A_{127}$ | $G_8$ | $T_1$ | | | | | | | | | | | | | | | |
| 943 | $A_{133}$ | $E_1$ | $P_1$ | $G_1$ | | | | | | | | | | | | | | |
| 944 | $L_{131}$ | $M_5$ | | | | | | | | | | | | | | | | |
| 945 | $T_{132}$ | $A_2$ | $S_1$ | $K_1$ | | | | | | | | | | | | | | |
| 946 | $G_{135}$ | $S_1$ | | | | | | | | | | | | | | | | |
| 947 | $T_{136}$ | | | | | | | | | | | | | | | | | |
| 948 | $Y_{135}$ | $S_1$ | | | | | | | | | | | | | | | | |
| 949 | $V_{117}$ | $L_{12}$ | $I_7$ | | | | | | | | | | | | | | | |
| 950 | $Y_{136}$ | $X_1$ | | | | | | | | | | | | | | | | |
| 951 | $D_{110}$ | $N_{25}$ | $T_1$ | $A_1$ | | | | | | | | | | | | | | |
| 952 | $H_{137}$ | | | | | | | | | | | | | | | | | |
| 953 | $L_{137}$ | | | | | | | | | | | | | | | | | |
| 954 | $T_{120}$ | $A_{13}$ | $S_4$ | | | | | | | | | | | | | | | |
| 955 | $P_{137}$ | | | | | | | | | | | | | | | | | |
| 956 | $L_{137}$ | | | | | | | | | | | | | | | | | |
| 957 | $R_{90}$ | $Q_{44}$ | $K_2$ | $G_1$ | | | | | | | | | | | | | | |
| 958 | $D_{111}$ | $H_{11}$ | $Y_9$ | $G_4$ | $N_2$ | | | | | | | | | | | | | |
| 959 | $W_{136}$ | $C_1$ | | | | | | | | | | | | | | | | |
| 960 | $A_{133}$ | $P_3$ | $R_1$ | | | | | | | | | | | | | | | |
| 961 | $H_{134}$ | $R_3$ | | | | | | | | | | | | | | | | |
| 962 | $A_{76}$ | $E_{28}$ | $T_{16}$ | $V_{11}$ | $S_3$ | $G_3$ | | | | | | | | | | | | |
| 963 | $G_{131}$ | $S_5$ | $A_1$ | | | | | | | | | | | | | | | |
| 964 | $L_{137}$ | | | | | | | | | | | | | | | | | |
| 965 | $R_{135}$ | $Q_2$ | | | | | | | | | | | | | | | | |
| 966 | $D_{135}$ | $G_1$ | $E_1$ | | | | | | | | | | | | | | | |
| 967 | $L_{137}$ | | | | | | | | | | | | | | | | | |
| 968 | $A_{133}$ | $V_3$ | $T_1$ | | | | | | | | | | | | | | | |
| 969 | $V_{135}$ | $A_2$ | | | | | | | | | | | | | | | | |
| 970 | $A_{137}$ | | | | | | | | | | | | | | | | | |
| 971 | $V_{137}$ | | | | | | | | | | | | | | | | | |
| 972 | $E_{137}$ | | | | | | | | | | | | | | | | | |
| 973 | $P_{137}$ | | | | | | | | | | | | | | | | | |
| 974 | $V_{136}$ | $I_1$ | | | | | | | | | | | | | | | | |
| 975 | $V_{112}$ | $I_{23}$ | $L_1$ | $T_1$ | | | | | | | | | | | | | | |
| 976 | $F_{137}$ | | | | | | | | | | | | | | | | | |
| 977 | $S_{137}$ | | | | | | | | | | | | | | | | | |
| 978 | $D_{131}$ | $A_5$ | $N_1$ | | | | | | | | | | | | | | | |
| 979 | $M_{136}$ | $T_1$ | | | | | | | | | | | | | | | | |
| 980 | $E_{137}$ | | | | | | | | | | | | | | | | | |
| 981 | $T_{125}$ | $I_{12}$ | | | | | | | | | | | | | | | | |
| 982 | $K_{137}$ | | | | | | | | | | | | | | | | | |
| 983 | $I_{122}$ | $V_{14}$ | $L_1$ | | | | | | | | | | | | | | | |
| 984 | $I_{135}$ | $V_1$ | $T_1$ | | | | | | | | | | | | | | | |
| 985 | $T_{137}$ | | | | | | | | | | | | | | | | | |
| 986 | $W_{136}$ | $G_1$ | | | | | | | | | | | | | | | | |
| 987 | $G_{136}$ | $R_1$ | | | | | | | | | | | | | | | | |
| 988 | $A_{135}$ | $G_1$ | $P_1$ | | | | | | | | | | | | | | | |
| 989 | $D_{136}$ | $E_1$ | | | | | | | | | | | | | | | | |
| 990 | $T_{137}$ | $X_1$ | | | | | | | | | | | | | | | | |
| 991 | $A_{138}$ | $X_1$ | | | | | | | | | | | | | | | | |
| 992 | $A_{137}$ | $T_1$ | $E_1$ | | | | | | | | | | | | | | | |
| 993 | $C_{139}$ | | | | | | | | | | | | | | | | | |
| 994 | $G_{138}$ | $V_1$ | | | | | | | | | | | | | | | | |
| 995 | $D_{138}$ | $N_1$ | | | | | | | | | | | | | | | | |
| 996 | $I_{138}$ | $F_1$ | | | | | | | | | | | | | | | | |
| 997 | $I_{138}$ | $L_1$ | | | | | | | | | | | | | | | | |
| 998 | $L_{69}$ | $S_{55}$ | $Q_{10}$ | $A_2$ | $X_1$ | $M_1$ | $W_1$ | | | | | | | | | | | |
| 999 | $G_{135}$ | $A_2$ | $C_1$ | $S_1$ | | | | | | | | | | | | | | |
| 1000 | $L_{137}$ | $C_1$ | $Y_1$ | | | | | | | | | | | | | | | |
| 1001 | $P_{135}$ | $A_2$ | $R_1$ | $L_1$ | | | | | | | | | | | | | | |
| 1002 | $V_{136}$ | $A_2$ | $S_1$ | | | | | | | | | | | | | | | |
| 1003 | $S_{139}$ | | | | | | | | | | | | | | | | | |
| 1004 | $A_{135}$ | $G_4$ | | | | | | | | | | | | | | | | |
| 1005 | $R_{139}$ | | | | | | | | | | | | | | | | | |
| 1006 | $R_{138}$ | $K_1$ | | | | | | | | | | | | | | | | |
| 1007 | $G_{138}$ | $R_1$ | | | | | | | | | | | | | | | | |
| 1008 | $R_{106}$ | $K_{32}$ | $N_1$ | | | | | | | | | | | | | | | |
| 1009 | $E_{138}$ | | | | | | | | | | | | | | | | | |
| 1010 | $I_{128}$ | $V_9$ | $L_1$ | | | | | | | | | | | | | | | |
| 1011 | $L_{124}$ | $F_9$ | $H_5$ | | | | | | | | | | | | | | | |
| 1012 | $L_{138}$ | $X_1$ | | | | | | | | | | | | | | | | |
| 1013 | $G_{139}$ | | | | | | | | | | | | | | | | | |
| 1014 | $P_{139}$ | | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 1015 | $A_{139}$ | | | | | | | | | | | | | | | | | |
| 1016 | $D_{139}$ | | | | | | | | | | | | | | | | | |
| 1017 | $S_{128}$ | $G_5$ | $N_3$ | $R_2$ | $K_1$ | | | | | | | | | | | | | |
| 1018 | $L_{82}$ | $F_{53}$ | $H_2$ | $I_1$ | $Y_1$ | | | | | | | | | | | | | |
| 1019 | $E_{100}$ | $G_{24}$ | $D_7$ | $K_5$ | $V_2$ | $R_1$ | | | | | | | | | | | | |
| 1020 | $G_{106}$ | $E_{30}$ | $H_2$ | $W_1$ | | | | | | | | | | | | | | |
| 1021 | $Q_{127}$ | $R_6$ | $H_4$ | $K_1$ | $S_1$ | | | | | | | | | | | | | |
| 1022 | $G_{139}$ | | | | | | | | | | | | | | | | | |
| 1023 | $W_{138}$ | $L_1$ | | | | | | | | | | | | | | | | |
| 1024 | $R_{139}$ | | | | | | | | | | | | | | | | | |
| 1025 | $L_{139}$ | $K_2$ | | | | | | | | | | | | | | | | |
| 1026 | $L_{141}$ | | | | | | | | | | | | | | | | | |
| 1027 | $A_{517}$ | $G_1$ | $S_1$ | $X_1$ | | | | | | | | | | | | | | |
| 1028 | $P_{517}$ | $X_1$ | $A_1$ | $H_1$ | | | | | | | | | | | | | | |
| 1029 | $I_{519}$ | $X_1$ | | | | | | | | | | | | | | | | |
| 1030 | $T_{515}$ | $A_2$ | $R_2$ | $S_1$ | | | | | | | | | | | | | | |
| 1031 | $A_{520}$ | | | | | | | | | | | | | | | | | |
| 1032 | $Y_{520}$ | | | | | | | | | | | | | | | | | |
| 1033 | $S_{303}$ | $A_{211}$ | $C_3$ | $X_1$ | $T_1$ | $I_1$ | | | | | | | | | | | | |
| 1034 | $Q_{517}$ | $H_2$ | $R_1$ | | | | | | | | | | | | | | | |
| 1035 | $Q_{518}$ | $H_1$ | $R_1$ | | | | | | | | | | | | | | | |
| 1036 | $T_{520}$ | | | | | | | | | | | | | | | | | |
| 1037 | $R_{519}$ | $L_1$ | | | | | | | | | | | | | | | | |
| 1038 | $G_{516}$ | $X_2$ | $C_1$ | $A_1$ | | | | | | | | | | | | | | |
| 1039 | $L_{515}$ | $M_2$ | $P_1$ | $I_1$ | $V_1$ | | | | | | | | | | | | | |
| 1040 | $L_{476}$ | $F_{40}$ | $V_3$ | $I_1$ | | | | | | | | | | | | | | |
| 1041 | $G_{517}$ | $A_1$ | $R_1$ | $C_1$ | | | | | | | | | | | | | | |
| 1042 | $C_{519}$ | $S_1$ | | | | | | | | | | | | | | | | |
| 1043 | $I_{518}$ | $V_2$ | $X_1$ | | | | | | | | | | | | | | | |
| 1044 | $I_{451}$ | $V_{70}$ | | | | | | | | | | | | | | | | |
| 1045 | $T_{521}$ | | | | | | | | | | | | | | | | | |
| 1046 | $S_{521}$ | | | | | | | | | | | | | | | | | |
| 1047 | $L_{521}$ | | | | | | | | | | | | | | | | | |
| 1048 | $T_{521}$ | | | | | | | | | | | | | | | | | |
| 1049 | $G_{520}$ | $R_1$ | | | | | | | | | | | | | | | | |
| 1050 | $R_{519}$ | $P_1$ | $Q_1$ | | | | | | | | | | | | | | | |
| 1051 | $D_{521}$ | | | | | | | | | | | | | | | | | |
| 1052 | $K_{508}$ | $R_{12}$ | $Q_1$ | | | | | | | | | | | | | | | |
| 1053 | $N_{518}$ | $X_2$ | $K_1$ | | | | | | | | | | | | | | | |
| 1054 | $Q_{516}$ | $X_3$ | $P_1$ | $R_1$ | | | | | | | | | | | | | | |
| 1055 | $V_{517}$ | $X_1$ | $T_1$ | $F_1$ | $A_1$ | | | | | | | | | | | | | |
| 1056 | $E_{505}$ | $D_{15}$ | $G_1$ | | | | | | | | | | | | | | | |
| 1057 | $G_{521}$ | | | | | | | | | | | | | | | | | |
| 1058 | $E_{518}$ | $X_1$ | $K_1$ | $G_1$ | | | | | | | | | | | | | | |
| 1059 | $V_{519}$ | $I_2$ | | | | | | | | | | | | | | | | |
| 1060 | $Q_{520}$ | $X_1$ | | | | | | | | | | | | | | | | |
| 1061 | $V_{506}$ | $I_{11}$ | $M_3$ | $E_1$ | | | | | | | | | | | | | | |
| 1062 | $V_{506}$ | $L_{15}$ | | | | | | | | | | | | | | | | |
| 1063 | $S_{519}$ | $X_2$ | | | | | | | | | | | | | | | | |
| 1064 | $T_{519}$ | $I_1$ | $P_1$ | | | | | | | | | | | | | | | |
| 1065 | $A_{520}$ | $X_1$ | | | | | | | | | | | | | | | | |
| 1066 | $T_{515}$ | $A_5$ | $K_1$ | | | | | | | | | | | | | | | |
| 1067 | $Q_{517}$ | $H_3$ | $K_1$ | | | | | | | | | | | | | | | |
| 1068 | $S_{513}$ | $T_8$ | | | | | | | | | | | | | | | | |
| 1069 | $F_{521}$ | | | | | | | | | | | | | | | | | |
| 1070 | $L_{521}$ | | | | | | | | | | | | | | | | | |
| 1071 | $A_{516}$ | $S_4$ | $G_1$ | | | | | | | | | | | | | | | |
| 1072 | $T_{516}$ | $S_4$ | $N_1$ | | | | | | | | | | | | | | | |
| 1073 | $C_{519}$ | $X_1$ | $R_1$ | | | | | | | | | | | | | | | |
| 1074 | $V_{368}$ | $I_{115}$ | $L_{35}$ | $A_2$ | $T_1$ | | | | | | | | | | | | | |
| 1075 | $N_{515}$ | $S_3$ | $G_2$ | $I_1$ | | | | | | | | | | | | | | |
| 1076 | $G_{521}$ | | | | | | | | | | | | | | | | | |
| 1077 | $V_{485}$ | $A_{35}$ | $T_1$ | | | | | | | | | | | | | | | |
| 1078 | $C_{519}$ | $F_1$ | $X_1$ | | | | | | | | | | | | | | | |
| 1079 | $W_{520}$ | $R_1$ | | | | | | | | | | | | | | | | |
| 1080 | $T_{515}$ | $S_6$ | | | | | | | | | | | | | | | | |
| 1081 | $V_{517}$ | $I_2$ | $X_2$ | | | | | | | | | | | | | | | |
| 1082 | $Y_{380}$ | $F_{141}$ | | | | | | | | | | | | | | | | |
| 1083 | $H_{520}$ | $X_1$ | | | | | | | | | | | | | | | | |
| 1084 | $G_{521}$ | | | | | | | | | | | | | | | | | |
| 1085 | $A_{520}$ | $X_1$ | | | | | | | | | | | | | | | | |
| 1086 | $G_{520}$ | $C_1$ | | | | | | | | | | | | | | | | |
| 1087 | $S_{442}$ | $T_{46}$ | $A_{28}$ | $P_4$ | $C_1$ | | | | | | | | | | | | | |
| 1088 | $K_{513}$ | $R_8$ | | | | | | | | | | | | | | | | |
| 1089 | $T_{511}$ | $A_8$ | $D_1$ | $I_1$ | | | | | | | | | | | | | | |
| 1090 | $L_{517}$ | $I_4$ | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 1091 | $A_{516}$ | $T_1$ | $D_1$ | $X_1$ | $V_1$ | $G_1$ | | | | | | | | | | | | |
| 1092 | $G_{512}$ | $S_6$ | $A_2$ | $P_1$ | | | | | | | | | | | | | | |
| 1093 | $P_{461}$ | $Q_{33}$ | $I_{13}$ | $S_6$ | $A_4$ | $R_1$ | $L_1$ | $G_1$ | $K_1$ | | | | | | | | | |
| 1094 | $K_{476}$ | $G_{38}$ | $X_2$ | $Q_2$ | $R_1$ | $M_1$ | $N_1$ | | | | | | | | | | | |
| 1095 | $G_{520}$ | $X_1$ | | | | | | | | | | | | | | | | |
| 1096 | $P_{520}$ | $Q_1$ | | | | | | | | | | | | | | | | |
| 1097 | $I_{467}$ | $V_{53}$ | $T_1$ | | | | | | | | | | | | | | | |
| 1098 | $T_{391}$ | $I_{102}$ | $V_{18}$ | $A_7$ | $S_1$ | $X_1$ | $N_1$ | | | | | | | | | | | |
| 1099 | $Q_{521}$ | | | | | | | | | | | | | | | | | |
| 1100 | $M_{519}$ | $K_1$ | $I_1$ | | | | | | | | | | | | | | | |
| 1101 | $Y_{521}$ | | | | | | | | | | | | | | | | | |
| 1102 | $T_{520}$ | $X_1$ | | | | | | | | | | | | | | | | |
| 1103 | $N_{520}$ | $X_1$ | $S_1$ | | | | | | | | | | | | | | | |
| 1104 | $V_{522}$ | | | | | | | | | | | | | | | | | |
| 1105 | $D_{521}$ | $N_1$ | | | | | | | | | | | | | | | | |
| 1106 | $Q_{498}$ | $L_{24}$ | $X_1$ | | | | | | | | | | | | | | | |
| 1107 | $D_{522}$ | $G_1$ | | | | | | | | | | | | | | | | |
| 1108 | $L_{523}$ | | | | | | | | | | | | | | | | | |
| 1109 | $V_{521}$ | $D_1$ | $L_1$ | | | | | | | | | | | | | | | |
| 1110 | $G_{520}$ | $D_2$ | $X_1$ | | | | | | | | | | | | | | | |
| 1111 | $W_{523}$ | | | | | | | | | | | | | | | | | |
| 1112 | $Q_{320}$ | $P_{156}$ | $H_{25}$ | $L_{12}$ | $A_5$ | $M_1$ | $W_1$ | $S_1$ | $X_1$ | $R_1$ | | | | | | | | |
| 1113 | $A_{517}$ | $R_2$ | $S_1$ | $E_1$ | $K_1$ | $V_1$ | | | | | | | | | | | | |
| 1114 | $P_{517}$ | $A_3$ | $T_1$ | $L_1$ | $R_1$ | | | | | | | | | | | | | |
| 1115 | $P_{410}$ | $S_{103}$ | $Q_6$ | $A_2$ | $H_1$ | $X_1$ | | | | | | | | | | | | |
| 1116 | $G_{522}$ | $R_1$ | | | | | | | | | | | | | | | | |
| 1117 | $A_{483}$ | $S_{36}$ | $X_2$ | $T_1$ | $M_1$ | | | | | | | | | | | | | |
| 1118 | $R_{519}$ | $X_2$ | $H_1$ | | | | | | | | | | | | | | | |
| 1119 | $S_{522}$ | | | | | | | | | | | | | | | | | |
| 1120 | $L_{438}$ | $M_{82}$ | $I_2$ | | | | | | | | | | | | | | | |
| 1121 | $T_{497}$ | $S_{20}$ | $I_3$ | $A_2$ | | | | | | | | | | | | | | |
| 1122 | $P_{519}$ | $X_1$ | $A_1$ | $S_1$ | | | | | | | | | | | | | | |
| 1123 | $C_{511}$ | $R_7$ | $X_1$ | $W_1$ | $Y_1$ | $G_1$ | | | | | | | | | | | | |
| 1124 | $T_{519}$ | $X_1$ | $N_1$ | $A_1$ | | | | | | | | | | | | | | |
| 1125 | $C_{522}$ | | | | | | | | | | | | | | | | | |
| 1126 | $G_{521}$ | $V_1$ | | | | | | | | | | | | | | | | |
| 1127 | $S_{515}$ | $G_4$ | $X_1$ | $I_1$ | $A_1$ | | | | | | | | | | | | | |
| 1128 | $S_{521}$ | $X_1$ | | | | | | | | | | | | | | | | |
| 1129 | $D_{521}$ | $V_1$ | | | | | | | | | | | | | | | | |
| 1130 | $L_{521}$ | $P_1$ | | | | | | | | | | | | | | | | |
| 1131 | $Y_{519}$ | $F_2$ | $H_1$ | | | | | | | | | | | | | | | |
| 1132 | $L_{521}$ | $X_1$ | | | | | | | | | | | | | | | | |
| 1133 | $V_{520}$ | $I_1$ | $G_1$ | | | | | | | | | | | | | | | |
| 1134 | $T_{520}$ | $S_1$ | $P_1$ | | | | | | | | | | | | | | | |
| 1135 | $R_{520}$ | $X_1$ | $W_1$ | | | | | | | | | | | | | | | |
| 1136 | $H_{516}$ | $Q_2$ | $Y_2$ | $X_1$ | $N_1$ | | | | | | | | | | | | | |
| 1137 | $A_{521}$ | $T_1$ | | | | | | | | | | | | | | | | |
| 1138 | $D_{522}$ | | | | | | | | | | | | | | | | | |
| 1139 | $V_{520}$ | $I_2$ | | | | | | | | | | | | | | | | |
| 1140 | $I_{513}$ | $V_9$ | | | | | | | | | | | | | | | | |
| 1141 | $P_{522}$ | | | | | | | | | | | | | | | | | |
| 1142 | $V_{521}$ | $A_1$ | | | | | | | | | | | | | | | | |
| 1143 | $R_{495}$ | $H_{23}$ | $C_4$ | | | | | | | | | | | | | | | |
| 1144 | $R_{521}$ | $X_1$ | | | | | | | | | | | | | | | | |
| 1145 | $R_{521}$ | $G_1$ | | | | | | | | | | | | | | | | |
| 1146 | $G_{517}$ | $S_5$ | | | | | | | | | | | | | | | | |
| 1147 | $D_{522}$ | | | | | | | | | | | | | | | | | |
| 1148 | $S_{441}$ | $G_{39}$ | $N_{23}$ | $T_{16}$ | $X_1$ | $V_1$ | $C_1$ | | | | | | | | | | | |
| 1149 | $R_{520}$ | $Q_1$ | $K_1$ | | | | | | | | | | | | | | | |
| 1150 | $G_{521}$ | $X_1$ | | | | | | | | | | | | | | | | |
| 1151 | $S_{492}$ | $A_{28}$ | $G_1$ | $P_1$ | | | | | | | | | | | | | | |
| 1152 | $L_{520}$ | $X_2$ | | | | | | | | | | | | | | | | |
| 1153 | $L_{522}$ | | | | | | | | | | | | | | | | | |
| 1154 | $S_{520}$ | $P_2$ | | | | | | | | | | | | | | | | |
| 1155 | $P_{520}$ | $X_2$ | | | | | | | | | | | | | | | | |
| 1156 | $R_{516}$ | $K_4$ | $X_1$ | $G_1$ | | | | | | | | | | | | | | |
| 1157 | $P_{520}$ | $H_2$ | | | | | | | | | | | | | | | | |
| 1158 | $V_{343}$ | $I_{178}$ | $L_1$ | | | | | | | | | | | | | | | |
| 1159 | $S_{521}$ | $X_1$ | | | | | | | | | | | | | | | | |
| 1160 | $Y_{521}$ | $R_1$ | | | | | | | | | | | | | | | | |
| 1161 | $L_{522}$ | | | | | | | | | | | | | | | | | |
| 1162 | $K_{521}$ | $X_1$ | | | | | | | | | | | | | | | | |
| 1163 | $G_{522}$ | | | | | | | | | | | | | | | | | |
| 1164 | $S_{522}$ | | | | | | | | | | | | | | | | | |
| 1165 | $S_{521}$ | $P_1$ | | | | | | | | | | | | | | | | |
| 1166 | $G_{522}$ | | | | | | | | | | | | | | | | | |

TABLE 6-continued

| | HCV 1b Consensus Sequences | | | | | | | | | | | | | | | | |
|---|---|---|---|---|---|---|---|---|---|---|---|---|---|---|---|---|---|
| A | B | C | D | E | F | G | H | I | J | K | L | M | N | O | P | Q | R |
| 1167 $G_{522}$ | | | | | | | | | | | | | | | | | |
| 1168 $P_{521}$ | $T_1$ | | | | | | | | | | | | | | | | |
| 1169 $L_{522}$ | | | | | | | | | | | | | | | | | |
| 1170 $L_{519}$ | $P_2$ | $X_1$ | | | | | | | | | | | | | | | |
| 1171 $C_{521}$ | $W_1$ | | | | | | | | | | | | | | | | |
| 1172 $P_{520}$ | $X_1$ | $S_1$ | | | | | | | | | | | | | | | |
| 1173 $S_{415}$ | $L_{96}$ | $A_9$ | $F_2$ | | | | | | | | | | | | | | |
| 1174 $G_{520}$ | $V_1$ | $R_1$ | | | | | | | | | | | | | | | |
| 1175 $H_{519}$ | $X_1$ | $R_1$ | $L_1$ | | | | | | | | | | | | | | |
| 1176 $A_{346}$ | $V_{162}$ | $L_8$ | $I_4$ | $T_2$ | | | | | | | | | | | | | |
| 1177 $V_{513}$ | $A_8$ | $X_1$ | | | | | | | | | | | | | | | |
| 1178 $G_{520}$ | $S_1$ | $X_1$ | | | | | | | | | | | | | | | |
| 1179 $I_{508}$ | $V_8$ | $L_5$ | $N_1$ | | | | | | | | | | | | | | |
| 1180 $F_{520}$ | $L_2$ | | | | | | | | | | | | | | | | |
| 1181 $R_{520}$ | $P_2$ | | | | | | | | | | | | | | | | |
| 1182 $A_{521}$ | $T_1$ | | | | | | | | | | | | | | | | |
| 1183 $A_{518}$ | $P_4$ | | | | | | | | | | | | | | | | |
| 1184 $V_{519}$ | $L_1$ | $X_1$ | $A_1$ | | | | | | | | | | | | | | |
| 1185 $C_{521}$ | $R_1$ | | | | | | | | | | | | | | | | |
| 1186 $T_{521}$ | $N_1$ | | | | | | | | | | | | | | | | |
| 1187 $R_{514}$ | $T_4$ | $P_3$ | $G_1$ | $X_1$ | | | | | | | | | | | | | |
| 1188 $G_{521}$ | $R_1$ | $M_1$ | | | | | | | | | | | | | | | |
| 1189 $V_{523}$ | $X_1$ | | | | | | | | | | | | | | | | |
| 1190 $A_{520}$ | $T_2$ | $X_1$ | $S_1$ | | | | | | | | | | | | | | |
| 1191 $K_{520}$ | $M_2$ | $Q_1$ | $N_1$ | | | | | | | | | | | | | | |
| 1192 $A_{520}$ | $T_2$ | $S_1$ | $X_1$ | | | | | | | | | | | | | | |
| 1193 $V_{518}$ | $L_4$ | $M_1$ | $X_1$ | | | | | | | | | | | | | | |
| 1194 $D_{515}$ | $E_9$ | | | | | | | | | | | | | | | | |
| 1195 $F_{523}$ | $L_1$ | | | | | | | | | | | | | | | | |
| 1196 $V_{347}$ | $I_{173}$ | $X_1$ | $G_1$ | $A_1$ | $L_1$ | | | | | | | | | | | | |
| 1197 $P_{522}$ | $X_1$ | $S_1$ | | | | | | | | | | | | | | | |
| 1198 $V_{521}$ | $A_3$ | | | | | | | | | | | | | | | | |
| 1199 $E_{523}$ | $D_1$ | | | | | | | | | | | | | | | | |
| 1200 $S_{501}$ | $A_8$ | $C_4$ | $G_3$ | $F_2$ | $N_1$ | $X_1$ | $P_1$ | $Y_1$ | $T_1$ | $H_1$ | | | | | | | |
| 1201 $M_{517}$ | $L_7$ | | | | | | | | | | | | | | | | |
| 1202 $E_{521}$ | $A_1$ | $X_1$ | $D_1$ | | | | | | | | | | | | | | |
| 1203 $T_{524}$ | | | | | | | | | | | | | | | | | |
| 1204 $T_{521}$ | $X_1$ | $I_1$ | $S_1$ | | | | | | | | | | | | | | |
| 1205 $M_{494}$ | $A_{18}$ | $T_7$ | $I_4$ | $L_1$ | | | | | | | | | | | | | |
| 1206 $R_{523}$ | $W_1$ | | | | | | | | | | | | | | | | |
| 1207 $S_{362}$ | $P_1$ | $A_1$ | | | | | | | | | | | | | | | |
| 1208 $P_{134}$ | $T_1$ | $L_1$ | | | | | | | | | | | | | | | |
| 1209 $V_{138}$ | $I_2$ | | | | | | | | | | | | | | | | |
| 1210 $F_{136}$ | $Y_4$ | | | | | | | | | | | | | | | | |
| 1211 $T_{140}$ | | | | | | | | | | | | | | | | | |
| 1212 $D_{140}$ | | | | | | | | | | | | | | | | | |
| 1213 $N_{139}$ | $T_1$ | | | | | | | | | | | | | | | | |
| 1214 $S_{138}$ | $P_2$ | | | | | | | | | | | | | | | | |
| 1215 $S_{135}$ | $T_5$ | | | | | | | | | | | | | | | | |
| 1216 $P_{140}$ | | | | | | | | | | | | | | | | | |
| 1217 $P_{140}$ | | | | | | | | | | | | | | | | | |
| 1218 $A_{139}$ | $G_1$ | | | | | | | | | | | | | | | | |
| 1219 $V_{140}$ | | | | | | | | | | | | | | | | | |
| 1220 $P_{140}$ | $X_2$ | | | | | | | | | | | | | | | | |
| 1221 $Q_{141}$ | $E_1$ | | | | | | | | | | | | | | | | |
| 1222 $T_{124}$ | $A_{10}$ | $S_8$ | | | | | | | | | | | | | | | |
| 1223 $F_{139}$ | $Y_3$ | | | | | | | | | | | | | | | | |
| 1224 $Q_{142}$ | | | | | | | | | | | | | | | | | |
| 1225 $V_{142}$ | | | | | | | | | | | | | | | | | |
| 1226 $A_{141}$ | $G_1$ | | | | | | | | | | | | | | | | |
| 1227 $H_{142}$ | | | | | | | | | | | | | | | | | |
| 1228 $L_{141}$ | $I_1$ | | | | | | | | | | | | | | | | |
| 1229 $H_{142}$ | | | | | | | | | | | | | | | | | |
| 1230 $A_{142}$ | | | | | | | | | | | | | | | | | |
| 1231 $P_{142}$ | | | | | | | | | | | | | | | | | |
| 1232 $T_{142}$ | | | | | | | | | | | | | | | | | |
| 1233 $G_{142}$ | | | | | | | | | | | | | | | | | |
| 1234 $S_{142}$ | | | | | | | | | | | | | | | | | |
| 1235 $G_{142}$ | | | | | | | | | | | | | | | | | |
| 1236 $K_{142}$ | | | | | | | | | | | | | | | | | |
| 1237 $S_{141}$ | $T_1$ | | | | | | | | | | | | | | | | |
| 1238 $T_{140}$ | $A_1$ | $N_1$ | | | | | | | | | | | | | | | |
| 1239 $K_{133}$ | $R_9$ | | | | | | | | | | | | | | | | |
| 1240 $V_{141}$ | $X_1$ | | | | | | | | | | | | | | | | |
| 1241 $P_{141}$ | $X_1$ | | | | | | | | | | | | | | | | |
| 1242 $A_{141}$ | $V_1$ | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 1243 | $A_{141}$ | $E_1$ | | | | | | | | | | | | | | | | |
| 1244 | $Y_{141}$ | $X_1$ | | | | | | | | | | | | | | | | |
| 1245 | $A_{142}$ | | | | | | | | | | | | | | | | | |
| 1246 | $A_{137}$ | $T_3$ | $S_2$ | | | | | | | | | | | | | | | |
| 1247 | $Q_{142}$ | | | | | | | | | | | | | | | | | |
| 1248 | $G_{142}$ | | | | | | | | | | | | | | | | | |
| 1249 | $Y_{142}$ | | | | | | | | | | | | | | | | | |
| 1250 | $K_{141}$ | $M_1$ | | | | | | | | | | | | | | | | |
| 1251 | $V_{142}$ | | | | | | | | | | | | | | | | | |
| 1252 | $L_{140}$ | $R_2$ | | | | | | | | | | | | | | | | |
| 1253 | $V_{142}$ | | | | | | | | | | | | | | | | | |
| 1254 | $L_{142}$ | | | | | | | | | | | | | | | | | |
| 1255 | $N_{142}$ | | | | | | | | | | | | | | | | | |
| 1256 | $P_{142}$ | | | | | | | | | | | | | | | | | |
| 1257 | $S_{142}$ | | | | | | | | | | | | | | | | | |
| 1258 | $V_{142}$ | | | | | | | | | | | | | | | | | |
| 1259 | $A_{141}$ | $T_1$ | | | | | | | | | | | | | | | | |
| 1260 | $A_{142}$ | | | | | | | | | | | | | | | | | |
| 1261 | $T_{133}$ | | | | | | | | | | | | | | | | | |
| 1262 | $L_{133}$ | | | | | | | | | | | | | | | | | |
| 1263 | $G_{122}$ | $S_{10}$ | $A_1$ | | | | | | | | | | | | | | | |
| 1264 | $F_{133}$ | | | | | | | | | | | | | | | | | |
| 1265 | $G_{133}$ | | | | | | | | | | | | | | | | | |
| 1266 | $A_{131}$ | $T_2$ | | | | | | | | | | | | | | | | |
| 1267 | $Y_{133}$ | | | | | | | | | | | | | | | | | |
| 1268 | $M_{131}$ | $T_1$ | $V_1$ | | | | | | | | | | | | | | | |
| 1269 | $S_{133}$ | | | | | | | | | | | | | | | | | |
| 1270 | $K_{133}$ | | | | | | | | | | | | | | | | | |
| 1271 | $A_{133}$ | | | | | | | | | | | | | | | | | |
| 1272 | $H_{111}$ | $Y_{22}$ | | | | | | | | | | | | | | | | |
| 1273 | $G_{133}$ | | | | | | | | | | | | | | | | | |
| 1274 | $V_{72}$ | $I_{32}$ | $T_{28}$ | $M_1$ | | | | | | | | | | | | | | |
| 1275 | $D_{122}$ | $E_{10}$ | | | | | | | | | | | | | | | | |
| 1276 | $P_{132}$ | | | | | | | | | | | | | | | | | |
| 1277 | $N_{120}$ | $S_{12}$ | | | | | | | | | | | | | | | | |
| 1278 | $I_{122}$ | $V_5$ | $L_4$ | $T_1$ | | | | | | | | | | | | | | |
| 1279 | $R_{131}$ | $S_1$ | | | | | | | | | | | | | | | | |
| 1280 | $T_{132}$ | | | | | | | | | | | | | | | | | |
| 1281 | $G_{132}$ | | | | | | | | | | | | | | | | | |
| 1282 | $V_{116}$ | $I_8$ | $A_6$ | $T_2$ | | | | | | | | | | | | | | |
| 1283 | $R_{132}$ | | | | | | | | | | | | | | | | | |
| 1284 | $T_{129}$ | $A_3$ | | | | | | | | | | | | | | | | |
| 1285 | $I_{126}$ | $V_5$ | $T_1$ | | | | | | | | | | | | | | | |
| 1286 | $T_{132}$ | $X_1$ | | | | | | | | | | | | | | | | |
| 1287 | $T_{132}$ | $X_1$ | | | | | | | | | | | | | | | | |
| 1288 | $G_{133}$ | | | | | | | | | | | | | | | | | |
| 1289 | $A_{121}$ | $S_6$ | $G_6$ | | | | | | | | | | | | | | | |
| 1290 | $P_{126}$ | $S_6$ | $G_1$ | | | | | | | | | | | | | | | |
| 1291 | $I_{131}$ | $M_1$ | $V_1$ | | | | | | | | | | | | | | | |
| 1292 | $T_{133}$ | | | | | | | | | | | | | | | | | |
| 1293 | $Y_{133}$ | | | | | | | | | | | | | | | | | |
| 1294 | $S_{133}$ | | | | | | | | | | | | | | | | | |
| 1295 | $T_{133}$ | $X_1$ | | | | | | | | | | | | | | | | |
| 1296 | $Y_{134}$ | | | | | | | | | | | | | | | | | |
| 1297 | $G_{132}$ | $C_2$ | | | | | | | | | | | | | | | | |
| 1298 | $K_{134}$ | | | | | | | | | | | | | | | | | |
| 1299 | $F_{134}$ | | | | | | | | | | | | | | | | | |
| 1300 | $L_{133}$ | $F_1$ | | | | | | | | | | | | | | | | |
| 1301 | $A_{134}$ | | | | | | | | | | | | | | | | | |
| 1302 | $D_{133}$ | $X_1$ | | | | | | | | | | | | | | | | |
| 1303 | $G_{134}$ | | | | | | | | | | | | | | | | | |
| 1304 | $G_{134}$ | | | | | | | | | | | | | | | | | |
| 1305 | $C_{132}$ | $G_2$ | | | | | | | | | | | | | | | | |
| 1306 | $S_{134}$ | | | | | | | | | | | | | | | | | |
| 1307 | $G_{134}$ | | | | | | | | | | | | | | | | | |
| 1308 | $G_{134}$ | | | | | | | | | | | | | | | | | |
| 1309 | $A_{134}$ | | | | | | | | | | | | | | | | | |
| 1310 | $Y_{134}$ | | | | | | | | | | | | | | | | | |
| 1311 | $D_{133}$ | $G_1$ | | | | | | | | | | | | | | | | |
| 1312 | $I_{134}$ | | | | | | | | | | | | | | | | | |
| 1313 | $I_{133}$ | $V_1$ | | | | | | | | | | | | | | | | |
| 1314 | $I_{111}$ | $M_{23}$ | | | | | | | | | | | | | | | | |
| 1315 | $C_{133}$ | $X_1$ | | | | | | | | | | | | | | | | |
| 1316 | $D_{133}$ | | | | | | | | | | | | | | | | | |
| 1317 | $E_{133}$ | | | | | | | | | | | | | | | | | |
| 1318 | $C_{133}$ | | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 1319 | $H_{132}$ | $X_1$ | | | | | | | | | | | | | | | | |
| 1320 | $S_{132}$ | | | | | | | | | | | | | | | | | |
| 1321 | $T_{131}$ | $I_1$ | | | | | | | | | | | | | | | | |
| 1322 | $D_{132}$ | | | | | | | | | | | | | | | | | |
| 1323 | $S_{128}$ | $A_2$ | $W_2$ | | | | | | | | | | | | | | | |
| 1324 | $T_{132}$ | | | | | | | | | | | | | | | | | |
| 1325 | $T_{86}$ | $S_{46}$ | | | | | | | | | | | | | | | | |
| 1326 | $I_{128}$ | $V_4$ | | | | | | | | | | | | | | | | |
| 1327 | $L_{128}$ | $Y_2$ | $M_2$ | | | | | | | | | | | | | | | |
| 1328 | $G_{131}$ | $S_1$ | | | | | | | | | | | | | | | | |
| 1329 | $I_{130}$ | $V_2$ | | | | | | | | | | | | | | | | |
| 1330 | $G_{132}$ | | | | | | | | | | | | | | | | | |
| 1331 | $T_{131}$ | $A_1$ | | | | | | | | | | | | | | | | |
| 1332 | $V_{131}$ | $A_1$ | | | | | | | | | | | | | | | | |
| 1333 | $L_{132}$ | | | | | | | | | | | | | | | | | |
| 1334 | $D_{132}$ | | | | | | | | | | | | | | | | | |
| 1335 | $Q_{131}$ | $R_1$ | | | | | | | | | | | | | | | | |
| 1336 | $A_{132}$ | | | | | | | | | | | | | | | | | |
| 1337 | $E_{131}$ | $K_1$ | | | | | | | | | | | | | | | | |
| 1338 | $T_{132}$ | | | | | | | | | | | | | | | | | |
| 1339 | $A_{130}$ | $V_2$ | | | | | | | | | | | | | | | | |
| 1340 | $G_{132}$ | | | | | | | | | | | | | | | | | |
| 1341 | $A_{132}$ | | | | | | | | | | | | | | | | | |
| 1342 | $R_{132}$ | | | | | | | | | | | | | | | | | |
| 1343 | $L_{131}$ | $F_1$ | | | | | | | | | | | | | | | | |
| 1344 | $V_{132}$ | | | | | | | | | | | | | | | | | |
| 1345 | $V_{131}$ | $L_1$ | | | | | | | | | | | | | | | | |
| 1346 | $L_{132}$ | | | | | | | | | | | | | | | | | |
| 1347 | $A_{130}$ | $S_2$ | | | | | | | | | | | | | | | | |
| 1348 | $T_{131}$ | $N_1$ | | | | | | | | | | | | | | | | |
| 1349 | $A_{131}$ | $R_1$ | | | | | | | | | | | | | | | | |
| 1350 | $T_{132}$ | | | | | | | | | | | | | | | | | |
| 1351 | $P_{132}$ | | | | | | | | | | | | | | | | | |
| 1352 | $P_{132}$ | | | | | | | | | | | | | | | | | |
| 1353 | $G_{132}$ | | | | | | | | | | | | | | | | | |
| 1354 | $S_{132}$ | | | | | | | | | | | | | | | | | |
| 1355 | $V_{121}$ | $I_{10}$ | $T_1$ | | | | | | | | | | | | | | | |
| 1356 | $T_{132}$ | | | | | | | | | | | | | | | | | |
| 1357 | $V_{131}$ | $F_1$ | | | | | | | | | | | | | | | | |
| 1358 | $P_{132}$ | | | | | | | | | | | | | | | | | |
| 1359 | $H_{132}$ | | | | | | | | | | | | | | | | | |
| 1360 | $P_{127}$ | $S_3$ | $L_2$ | | | | | | | | | | | | | | | |
| 1361 | $N_{130}$ | $S_2$ | | | | | | | | | | | | | | | | |
| 1362 | $I_{132}$ | | | | | | | | | | | | | | | | | |
| 1363 | $E_{127}$ | $Q_5$ | | | | | | | | | | | | | | | | |
| 1364 | $E_{132}$ | | | | | | | | | | | | | | | | | |
| 1365 | $V_{123}$ | $I_5$ | $A_3$ | $S_1$ | | | | | | | | | | | | | | |
| 1366 | $A_{126}$ | $G_5$ | $P_1$ | | | | | | | | | | | | | | | |
| 1367 | $L_{131}$ | $Q_1$ | | | | | | | | | | | | | | | | |
| 1368 | $S_{129}$ | $P_1$ | $T_1$ | $A_1$ | | | | | | | | | | | | | | |
| 1369 | $N_{125}$ | $T_4$ | $S_3$ | | | | | | | | | | | | | | | |
| 1370 | $T_{108}$ | $I_{17}$ | $V_3$ | $A_2$ | $S_2$ | | | | | | | | | | | | | |
| 1371 | $G_{132}$ | | | | | | | | | | | | | | | | | |
| 1372 | $E_{132}$ | | | | | | | | | | | | | | | | | |
| 1373 | $I_{127}$ | $V_5$ | | | | | | | | | | | | | | | | |
| 1374 | $P_{133}$ | | | | | | | | | | | | | | | | | |
| 1375 | $F_{133}$ | | | | | | | | | | | | | | | | | |
| 1376 | $Y_{133}$ | | | | | | | | | | | | | | | | | |
| 1377 | $G_{132}$ | $A_1$ | | | | | | | | | | | | | | | | |
| 1378 | $K_{131}$ | $R_2$ | | | | | | | | | | | | | | | | |
| 1379 | $A_{131}$ | $G_1$ | $T_1$ | | | | | | | | | | | | | | | |
| 1380 | $I_{132}$ | $F_1$ | | | | | | | | | | | | | | | | |
| 1381 | $P_{133}$ | | | | | | | | | | | | | | | | | |
| 1382 | $I_{112}$ | $L_{20}$ | $V_1$ | | | | | | | | | | | | | | | |
| 1383 | $E_{124}$ | $D_6$ | $A_2$ | $G_1$ | | | | | | | | | | | | | | |
| 1384 | $T_{64}$ | $A_{34}$ | $V_{28}$ | $N_3$ | $I_2$ | $F_1$ | $L_1$ | | | | | | | | | | | |
| 1385 | $I_{132}$ | $V_1$ | | | | | | | | | | | | | | | | |
| 1386 | $K_{127}$ | $R_6$ | | | | | | | | | | | | | | | | |
| 1387 | $G_{130}$ | $E_3$ | | | | | | | | | | | | | | | | |
| 1388 | $G_{133}$ | | | | | | | | | | | | | | | | | |
| 1389 | $R_{133}$ | | | | | | | | | | | | | | | | | |
| 1390 | $H_{133}$ | | | | | | | | | | | | | | | | | |
| 1391 | $L_{133}$ | | | | | | | | | | | | | | | | | |
| 1392 | $I_{133}$ | | | | | | | | | | | | | | | | | |
| 1393 | $F_{133}$ | | | | | | | | | | | | | | | | | |
| 1394 | $C_{132}$ | $W_1$ | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 1395 | $H_{131}$ | $R_1$ | $P_1$ | | | | | | | | | | | | | | | |
| 1396 | $S_{133}$ | | | | | | | | | | | | | | | | | |
| 1397 | $K_{113}$ | $R_{20}$ | | | | | | | | | | | | | | | | |
| 1398 | $K_{132}$ | $E_1$ | | | | | | | | | | | | | | | | |
| 1399 | $K_{132}$ | $E_1$ | | | | | | | | | | | | | | | | |
| 1400 | $C_{132}$ | $Y_1$ | | | | | | | | | | | | | | | | |
| 1401 | $D_{133}$ | | | | | | | | | | | | | | | | | |
| 1402 | $E_{132}$ | $D_1$ | | | | | | | | | | | | | | | | |
| 1403 | $L_{131}$ | $P_1$ | $V_1$ | | | | | | | | | | | | | | | |
| 1404 | $A_{132}$ | $P_1$ | | | | | | | | | | | | | | | | |
| 1405 | $A_{117}$ | $T_{10}$ | $G_3$ | $S_1$ | $V_1$ | $E_1$ | | | | | | | | | | | | |
| 1406 | $K_{130}$ | $Q_2$ | $R_1$ | | | | | | | | | | | | | | | |
| 1407 | $L_{133}$ | | | | | | | | | | | | | | | | | |
| 1408 | $S_{120}$ | $T_6$ | $V_4$ | $L_3$ | | | | | | | | | | | | | | |
| 1409 | $G_{60}$ | $A_{47}$ | $S_{21}$ | $T_3$ | $D_1$ | $N_1$ | | | | | | | | | | | | |
| 1410 | $L_{133}$ | | | | | | | | | | | | | | | | | |
| 1411 | $G_{133}$ | | | | | | | | | | | | | | | | | |
| 1412 | $L_{83}$ | $I_{30}$ | $V_{19}$ | $M_1$ | | | | | | | | | | | | | | |
| 1413 | $N_{132}$ | $H_1$ | | | | | | | | | | | | | | | | |
| 1414 | $A_{133}$ | | | | | | | | | | | | | | | | | |
| 1415 | $V_{132}$ | $I_1$ | | | | | | | | | | | | | | | | |
| 1416 | $A_{131}$ | $V_1$ | $S_1$ | | | | | | | | | | | | | | | |
| 1417 | $Y_{133}$ | | | | | | | | | | | | | | | | | |
| 1418 | $Y_{133}$ | | | | | | | | | | | | | | | | | |
| 1419 | $R_{133}$ | | | | | | | | | | | | | | | | | |
| 1420 | $G_{133}$ | | | | | | | | | | | | | | | | | |
| 1421 | $L_{131}$ | $F_2$ | | | | | | | | | | | | | | | | |
| 1422 | $D_{133}$ | | | | | | | | | | | | | | | | | |
| 1423 | $V_{133}$ | | | | | | | | | | | | | | | | | |
| 1424 | $S_{133}$ | | | | | | | | | | | | | | | | | |
| 1425 | $V_{127}$ | $I_5$ | $D_1$ | | | | | | | | | | | | | | | |
| 1426 | $I_{133}$ | | | | | | | | | | | | | | | | | |
| 1427 | $P_{133}$ | | | | | | | | | | | | | | | | | |
| 1428 | $T_{115}$ | $A_{10}$ | $S_6$ | $V_1$ | $P_1$ | | | | | | | | | | | | | |
| 1429 | $S_{128}$ | $N_4$ | $I_1$ | | | | | | | | | | | | | | | |
| 1430 | $G_{133}$ | | | | | | | | | | | | | | | | | |
| 1431 | $D_{120}$ | $N_{13}$ | | | | | | | | | | | | | | | | |
| 1432 | $V_{130}$ | $X_1$ | $D_1$ | $A_1$ | | | | | | | | | | | | | | |
| 1433 | $V_{130}$ | $I_3$ | | | | | | | | | | | | | | | | |
| 1434 | $V_{131}$ | $A_1$ | $I_1$ | | | | | | | | | | | | | | | |
| 1435 | $V_{133}$ | | | | | | | | | | | | | | | | | |
| 1436 | $A_{132}$ | $T_1$ | | | | | | | | | | | | | | | | |
| 1437 | $T_{132}$ | $S_1$ | | | | | | | | | | | | | | | | |
| 1438 | $D_{133}$ | | | | | | | | | | | | | | | | | |
| 1439 | $A_{133}$ | | | | | | | | | | | | | | | | | |
| 1440 | $L_{133}$ | | | | | | | | | | | | | | | | | |
| 1441 | $M_{133}$ | | | | | | | | | | | | | | | | | |
| 1442 | $T_{133}$ | | | | | | | | | | | | | | | | | |
| 1443 | $G_{134}$ | | | | | | | | | | | | | | | | | |
| 1444 | $F_{78}$ | $Y_{56}$ | | | | | | | | | | | | | | | | |
| 1445 | $T_{134}$ | | | | | | | | | | | | | | | | | |
| 1446 | $G_{134}$ | | | | | | | | | | | | | | | | | |
| 1447 | $D_{132}$ | $N_2$ | | | | | | | | | | | | | | | | |
| 1448 | $F_{132}$ | $L_1$ | $S_1$ | | | | | | | | | | | | | | | |
| 1449 | $D_{133}$ | $X_1$ | $V_1$ | | | | | | | | | | | | | | | |
| 1450 | $S_{135}$ | | | | | | | | | | | | | | | | | |
| 1451 | $V_{133}$ | $W_1$ | $X_1$ | | | | | | | | | | | | | | | |
| 1452 | $I_{134}$ | $T_1$ | | | | | | | | | | | | | | | | |
| 1453 | $D_{135}$ | | | | | | | | | | | | | | | | | |
| 1454 | $C_{134}$ | $R_1$ | | | | | | | | | | | | | | | | |
| 1455 | $N_{135}$ | | | | | | | | | | | | | | | | | |
| 1456 | $T_{131}$ | $V_3$ | $X_1$ | | | | | | | | | | | | | | | |
| 1457 | $C_{134}$ | $X_1$ | | | | | | | | | | | | | | | | |
| 1458 | $V_{135}$ | | | | | | | | | | | | | | | | | |
| 1459 | $T_{130}$ | $I_3$ | $N_1$ | $A_1$ | | | | | | | | | | | | | | |
| 1460 | $Q_{135}$ | | | | | | | | | | | | | | | | | |
| 1461 | $T_{135}$ | | | | | | | | | | | | | | | | | |
| 1462 | $V_{135}$ | | | | | | | | | | | | | | | | | |
| 1463 | $D_{135}$ | | | | | | | | | | | | | | | | | |
| 1464 | $F_{134}$ | $L_1$ | | | | | | | | | | | | | | | | |
| 1465 | $S_{135}$ | | | | | | | | | | | | | | | | | |
| 1466 | $L_{134}$ | | | | | | | | | | | | | | | | | |
| 1467 | $D_{134}$ | | | | | | | | | | | | | | | | | |
| 1468 | $P_{134}$ | | | | | | | | | | | | | | | | | |
| 1469 | $T_{134}$ | | | | | | | | | | | | | | | | | |
| 1470 | $F_{134}$ | | | | | | | | | | | | | | | | | |

TABLE 6-continued

| | HCV 1b Consensus Sequences | | | | | | | | | | | | | | | | | |
|---|---|---|---|---|---|---|---|---|---|---|---|---|---|---|---|---|---|---|
| | A | B | C | D | E | F | G | H | I | J | K | L | M | N | O | P | Q | R |
| 1471 | $T_{134}$ | | | | | | | | | | | | | | | | | |
| 1472 | $I_{133}$ | $M_1$ | | | | | | | | | | | | | | | | |
| 1473 | $E_{131}$ | $D_3$ | | | | | | | | | | | | | | | | |
| 1474 | $T_{133}$ | $X_1$ | | | | | | | | | | | | | | | | |
| 1475 | $T_{131}$ | $M_1$ | $A_1$ | | | | | | | | | | | | | | | |
| 1476 | $T_{133}$ | | | | | | | | | | | | | | | | | |
| 1477 | $V_{128}$ | $L_3$ | $M_2$ | | | | | | | | | | | | | | | |
| 1478 | $P_{133}$ | | | | | | | | | | | | | | | | | |
| 1479 | $Q_{132}$ | $H_1$ | | | | | | | | | | | | | | | | |
| 1480 | $D_{132}$ | $Y_1$ | | | | | | | | | | | | | | | | |
| 1481 | $A_{131}$ | $S_2$ | | | | | | | | | | | | | | | | |
| 1482 | $V_{133}$ | | | | | | | | | | | | | | | | | |
| 1483 | $S_{132}$ | $A_1$ | | | | | | | | | | | | | | | | |
| 1484 | $R_{131}$ | $S_1$ | $A_1$ | | | | | | | | | | | | | | | |
| 1485 | $S_{123}$ | $T_8$ | $A_2$ | | | | | | | | | | | | | | | |
| 1486 | $Q_{133}$ | | | | | | | | | | | | | | | | | |
| 1487 | $R_{131}$ | $L_1$ | $X_1$ | | | | | | | | | | | | | | | |
| 1488 | $R_{133}$ | | | | | | | | | | | | | | | | | |
| 1489 | $G_{133}$ | | | | | | | | | | | | | | | | | |
| 1490 | $R_{132}$ | $K_1$ | | | | | | | | | | | | | | | | |
| 1491 | $T_{133}$ | | | | | | | | | | | | | | | | | |
| 1492 | $G_{132}$ | $S_1$ | | | | | | | | | | | | | | | | |
| 1493 | $R_{132}$ | $S_1$ | | | | | | | | | | | | | | | | |
| 1494 | $G_{133}$ | | | | | | | | | | | | | | | | | |
| 1495 | $R_{132}$ | $T_1$ | | | | | | | | | | | | | | | | |
| 1496 | $R_{41}$ | $G_{30}$ | $T_{25}$ | $A_{12}$ | $M_9$ | $P_4$ | $S_4$ | $Q_3$ | $I_2$ | $E_2$ | $X_1$ | | | | | | | |
| 1497 | $G_{133}$ | | | | | | | | | | | | | | | | | |
| 1498 | $I_{126}$ | $T_5$ | $M_1$ | $V_1$ | | | | | | | | | | | | | | |
| 1499 | $Y_{133}$ | | | | | | | | | | | | | | | | | |
| 1500 | $R_{133}$ | | | | | | | | | | | | | | | | | |
| 1501 | $F_{132}$ | $Y_1$ | | | | | | | | | | | | | | | | |
| 1502 | $V_{133}$ | | | | | | | | | | | | | | | | | |
| 1503 | $T_{126}$ | $A_4$ | $I_2$ | $X_1$ | | | | | | | | | | | | | | |
| 1504 | $P_{132}$ | | | | | | | | | | | | | | | | | |
| 1505 | $G_{131}$ | $X_1$ | | | | | | | | | | | | | | | | |
| 1506 | $E_{131}$ | | | | | | | | | | | | | | | | | |
| 1507 | $R_{131}$ | | | | | | | | | | | | | | | | | |
| 1508 | $P_{129}$ | $T_2$ | | | | | | | | | | | | | | | | |
| 1509 | $S_{129}$ | $L_2$ | | | | | | | | | | | | | | | | |
| 1510 | $G_{129}$ | $A_2$ | | | | | | | | | | | | | | | | |
| 1511 | $M_{131}$ | | | | | | | | | | | | | | | | | |
| 1512 | $F_{130}$ | $L_1$ | | | | | | | | | | | | | | | | |
| 1513 | $D_{131}$ | | | | | | | | | | | | | | | | | |
| 1514 | $S_{131}$ | | | | | | | | | | | | | | | | | |
| 1515 | $S_{131}$ | | | | | | | | | | | | | | | | | |
| 1516 | $V_{131}$ | | | | | | | | | | | | | | | | | |
| 1517 | $L_{131}$ | | | | | | | | | | | | | | | | | |
| 1518 | $C_{131}$ | | | | | | | | | | | | | | | | | |
| 1519 | $E_{130}$ | $D_1$ | | | | | | | | | | | | | | | | |
| 1520 | $C_{129}$ | $Y_1$ | $S_1$ | | | | | | | | | | | | | | | |
| 1521 | $Y_{131}$ | | | | | | | | | | | | | | | | | |
| 1522 | $D_{131}$ | | | | | | | | | | | | | | | | | |
| 1523 | $A_{130}$ | $S_1$ | | | | | | | | | | | | | | | | |
| 1524 | $G_{131}$ | | | | | | | | | | | | | | | | | |
| 1525 | $C_{131}$ | | | | | | | | | | | | | | | | | |
| 1526 | $A_{129}$ | $T_1$ | | | | | | | | | | | | | | | | |
| 1527 | $W_{130}$ | | | | | | | | | | | | | | | | | |
| 1528 | $Y_{130}$ | $D_1$ | | | | | | | | | | | | | | | | |
| 1529 | $E_{130}$ | $D_1$ | | | | | | | | | | | | | | | | |
| 1530 | $L_{130}$ | $V_1$ | | | | | | | | | | | | | | | | |
| 1531 | $T_{130}$ | $A_1$ | | | | | | | | | | | | | | | | |
| 1532 | $P_{131}$ | | | | | | | | | | | | | | | | | |
| 1533 | $A_{130}$ | $S_1$ | | | | | | | | | | | | | | | | |
| 1534 | $E_{131}$ | | | | | | | | | | | | | | | | | |
| 1535 | $T_{130}$ | $A_1$ | | | | | | | | | | | | | | | | |
| 1536 | $S_{101}$ | $T_{30}$ | | | | | | | | | | | | | | | | |
| 1537 | $V_{129}$ | $I_2$ | | | | | | | | | | | | | | | | |
| 1538 | $R_{131}$ | | | | | | | | | | | | | | | | | |
| 1539 | $L_{129}$ | $V_2$ | | | | | | | | | | | | | | | | |
| 1540 | $R_{131}$ | | | | | | | | | | | | | | | | | |
| 1541 | $A_{131}$ | | | | | | | | | | | | | | | | | |
| 1542 | $Y_{131}$ | | | | | | | | | | | | | | | | | |
| 1543 | $L_{130}$ | $M_1$ | | | | | | | | | | | | | | | | |
| 1544 | $N_{130}$ | $X_1$ | | | | | | | | | | | | | | | | |
| 1545 | $T_{129}$ | $A_1$ | | | | | | | | | | | | | | | | |
| 1546 | $P_{130}$ | | | | | | | | | | | | | | | | | |

TABLE 6-continued

| | HCV 1b Consensus Sequences | | | | | | | | | | | | | | | | | |
|---|---|---|---|---|---|---|---|---|---|---|---|---|---|---|---|---|---|---|
| | A | B | C | D | E | F | G | H | I | J | K | L | M | N | O | P | Q | R |
| 1547 | $G_{130}$ | | | | | | | | | | | | | | | | | |
| 1548 | $L_{129}$ | $F_1$ | | | | | | | | | | | | | | | | |
| 1549 | $P_{129}$ | $A_1$ | | | | | | | | | | | | | | | | |
| 1550 | $V_{129}$ | $F_1$ | | | | | | | | | | | | | | | | |
| 1551 | $C_{129}$ | $W_1$ | | | | | | | | | | | | | | | | |
| 1552 | $Q_{130}$ | | | | | | | | | | | | | | | | | |
| 1553 | $D_{130}$ | | | | | | | | | | | | | | | | | |
| 1554 | $H_{129}$ | $Y_1$ | | | | | | | | | | | | | | | | |
| 1555 | $L_{130}$ | | | | | | | | | | | | | | | | | |
| 1556 | $E_{130}$ | | | | | | | | | | | | | | | | | |
| 1557 | $F_{130}$ | | | | | | | | | | | | | | | | | |
| 1558 | $W_{128}$ | $S_2$ | | | | | | | | | | | | | | | | |
| 1559 | $E_{130}$ | | | | | | | | | | | | | | | | | |
| 1560 | $S_{73}$ | $G_{56}$ | $D_1$ | | | | | | | | | | | | | | | |
| 1561 | $V_{130}$ | | | | | | | | | | | | | | | | | |
| 1562 | $F_{129}$ | $S_1$ | | | | | | | | | | | | | | | | |
| 1563 | $T_{130}$ | | | | | | | | | | | | | | | | | |
| 1564 | $G_{130}$ | | | | | | | | | | | | | | | | | |
| 1565 | $L_{130}$ | | | | | | | | | | | | | | | | | |
| 1566 | $T_{129}$ | $N_1$ | | | | | | | | | | | | | | | | |
| 1567 | $H_{128}$ | $K_1$ | $R_1$ | | | | | | | | | | | | | | | |
| 1568 | $I_{130}$ | | | | | | | | | | | | | | | | | |
| 1569 | $D_{129}$ | $E_1$ | | | | | | | | | | | | | | | | |
| 1570 | $A_{129}$ | $S_1$ | | | | | | | | | | | | | | | | |
| 1571 | $H_{130}$ | $X_8$ | | | | | | | | | | | | | | | | |
| 1572 | $F_{138}$ | | | | | | | | | | | | | | | | | |
| 1573 | $L_{137}$ | $M_1$ | | | | | | | | | | | | | | | | |
| 1574 | $S_{138}$ | | | | | | | | | | | | | | | | | |
| 1575 | $Q_{138}$ | | | | | | | | | | | | | | | | | |
| 1576 | $T_{138}$ | | | | | | | | | | | | | | | | | |
| 1577 | $K_{138}$ | | | | | | | | | | | | | | | | | |
| 1578 | $Q_{138}$ | | | | | | | | | | | | | | | | | |
| 1579 | $A_{138}$ | | | | | | | | | | | | | | | | | |
| 1580 | $G_{137}$ | $R_1$ | | | | | | | | | | | | | | | | |
| 1581 | $D_{129}$ | $E_9$ | | | | | | | | | | | | | | | | |
| 1582 | $N_{135}$ | $D_1$ | $H_1$ | $S_1$ | | | | | | | | | | | | | | |
| 1583 | $F_{134}$ | $L_4$ | | | | | | | | | | | | | | | | |
| 1584 | $P_{138}$ | | | | | | | | | | | | | | | | | |
| 1585 | $Y_{138}$ | | | | | | | | | | | | | | | | | |
| 1586 | $L_{137}$ | $M_1$ | | | | | | | | | | | | | | | | |
| 1587 | $V_{133}$ | $I_2$ | $T_2$ | $A_1$ | | | | | | | | | | | | | | |
| 1588 | $A_{138}$ | | | | | | | | | | | | | | | | | |
| 1589 | $Y_{138}$ | | | | | | | | | | | | | | | | | |
| 1590 | $Q_{138}$ | | | | | | | | | | | | | | | | | |
| 1591 | $A_{138}$ | | | | | | | | | | | | | | | | | |
| 1592 | $T_{138}$ | | | | | | | | | | | | | | | | | |
| 1593 | $V_{138}$ | | | | | | | | | | | | | | | | | |
| 1594 | $C_{137}$ | $R_1$ | | | | | | | | | | | | | | | | |
| 1595 | $A_{138}$ | | | | | | | | | | | | | | | | | |
| 1596 | $R_{137}$ | $K_1$ | | | | | | | | | | | | | | | | |
| 1597 | $A_{135}$ | $S_2$ | $X_1$ | | | | | | | | | | | | | | | |
| 1598 | $Q_{133}$ | $K_5$ | | | | | | | | | | | | | | | | |
| 1599 | $A_{138}$ | | | | | | | | | | | | | | | | | |
| 1600 | $P_{133}$ | $L_3$ | $R_1$ | $S_1$ | | | | | | | | | | | | | | |
| 1601 | $P_{138}$ | | | | | | | | | | | | | | | | | |
| 1602 | $P_{138}$ | | | | | | | | | | | | | | | | | |
| 1603 | $S_{138}$ | | | | | | | | | | | | | | | | | |
| 1604 | $W_{138}$ | | | | | | | | | | | | | | | | | |
| 1605 | $D_{138}$ | | | | | | | | | | | | | | | | | |
| 1606 | $Q_{134}$ | $L_2$ | $E_2$ | | | | | | | | | | | | | | | |
| 1607 | $M_{139}$ | | | | | | | | | | | | | | | | | |
| 1608 | $W_{139}$ | | | | | | | | | | | | | | | | | |
| 1609 | $K_{137}$ | $R_2$ | | | | | | | | | | | | | | | | |
| 1610 | $C_{138}$ | $S_1$ | | | | | | | | | | | | | | | | |
| 1611 | $L_{139}$ | | | | | | | | | | | | | | | | | |
| 1612 | $I_{117}$ | $T_{20}$ | $V_1$ | $L_1$ | | | | | | | | | | | | | | |
| 1613 | $R_{138}$ | $W_1$ | | | | | | | | | | | | | | | | |
| 1614 | $L_{138}$ | $X_1$ | | | | | | | | | | | | | | | | |
| 1615 | $K_{138}$ | $R_1$ | | | | | | | | | | | | | | | | |
| 1616 | $P_{138}$ | $A_1$ | | | | | | | | | | | | | | | | |
| 1617 | $T_{135}$ | $V_4$ | | | | | | | | | | | | | | | | |
| 1618 | $L_{139}$ | | | | | | | | | | | | | | | | | |
| 1619 | $H_{137}$ | $Q_2$ | | | | | | | | | | | | | | | | |
| 1620 | $G_{138}$ | $X_1$ | | | | | | | | | | | | | | | | |
| 1621 | $P_{137}$ | $X_1$ | | | | | | | | | | | | | | | | |
| 1622 | $T_{137}$ | | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 1623 | $P_{137}$ | | | | | | | | | | | | | | | | | |
| 1624 | $L_{137}$ | | | | | | | | | | | | | | | | | |
| 1625 | $L_{137}$ | | | | | | | | | | | | | | | | | |
| 1626 | $Y_{136}$ | $C_1$ | | | | | | | | | | | | | | | | |
| 1627 | $R_{137}$ | | | | | | | | | | | | | | | | | |
| 1628 | $L_{136}$ | $M_1$ | | | | | | | | | | | | | | | | |
| 1629 | $G_{137}$ | | | | | | | | | | | | | | | | | |
| 1630 | $A_{131}$ | $G_3$ | $S_1$ | $T_1$ | $P_1$ | | | | | | | | | | | | | |
| 1631 | $V_{135}$ | $A_1$ | $L_1$ | | | | | | | | | | | | | | | |
| 1632 | $Q_{136}$ | $H_1$ | | | | | | | | | | | | | | | | |
| 1633 | $N_{135}$ | $H_1$ | $S_1$ | | | | | | | | | | | | | | | |
| 1634 | $E_{129}$ | $D_8$ | | | | | | | | | | | | | | | | |
| 1635 | $V_{119}$ | $I_{17}$ | $T_1$ | | | | | | | | | | | | | | | |
| 1636 | $T_{116}$ | $I_{13}$ | $V_4$ | $N_2$ | $X_1$ | $S_1$ | | | | | | | | | | | | |
| 1637 | $L_{130}$ | $T_3$ | $F_2$ | $P_1$ | | | | | | | | | | | | | | |
| 1638 | $T_{136}$ | | | | | | | | | | | | | | | | | |
| 1639 | $H_{136}$ | | | | | | | | | | | | | | | | | |
| 1640 | $P_{136}$ | | | | | | | | | | | | | | | | | |
| 1641 | $I_{115}$ | $V_{19}$ | $M_2$ | | | | | | | | | | | | | | | |
| 1642 | $T_{135}$ | $A_1$ | | | | | | | | | | | | | | | | |
| 1643 | $K_{136}$ | | | | | | | | | | | | | | | | | |
| 1644 | $Y_{71}$ | $F_{61}$ | $L_3$ | | | | | | | | | | | | | | | |
| 1645 | $I_{132}$ | $V_3$ | | | | | | | | | | | | | | | | |
| 1646 | $M_{132}$ | $T_3$ | | | | | | | | | | | | | | | | |
| 1647 | $A_{105}$ | $T_{30}$ | | | | | | | | | | | | | | | | |
| 1648 | $C_{134}$ | $S_1$ | | | | | | | | | | | | | | | | |
| 1649 | $M_{135}$ | | | | | | | | | | | | | | | | | |
| 1650 | $S_{125}$ | $A_9$ | $X_1$ | | | | | | | | | | | | | | | |
| 1651 | $A_{134}$ | | | | | | | | | | | | | | | | | |
| 1652 | $D_{134}$ | | | | | | | | | | | | | | | | | |
| 1653 | $L_{134}$ | | | | | | | | | | | | | | | | | |
| 1654 | $E_{134}$ | | | | | | | | | | | | | | | | | |
| 1655 | $V_{132}$ | $I_2$ | | | | | | | | | | | | | | | | |
| 1656 | $V_{102}$ | $A_{32}$ | | | | | | | | | | | | | | | | |
| 1657 | $T_{134}$ | | | | | | | | | | | | | | | | | |
| 1658 | $S_{129}$ | $G_1$ | | | | | | | | | | | | | | | | |
| 1659 | $T_{130}$ | | | | | | | | | | | | | | | | | |
| 1660 | $W_{130}$ | | | | | | | | | | | | | | | | | |
| 1661 | $V_{129}$ | $X_1$ | | | | | | | | | | | | | | | | |
| 1662 | $L_{130}$ | | | | | | | | | | | | | | | | | |
| 1663 | $V_{130}$ | | | | | | | | | | | | | | | | | |
| 1664 | $G_{129}$ | $S_1$ | | | | | | | | | | | | | | | | |
| 1665 | $G_{130}$ | | | | | | | | | | | | | | | | | |
| 1666 | $V_{130}$ | | | | | | | | | | | | | | | | | |
| 1667 | $L_{129}$ | $P_1$ | | | | | | | | | | | | | | | | |
| 1668 | $A_{130}$ | | | | | | | | | | | | | | | | | |
| 1669 | $A_{130}$ | | | | | | | | | | | | | | | | | |
| 1670 | $L_{130}$ | | | | | | | | | | | | | | | | | |
| 1671 | $A_{129}$ | $T_1$ | | | | | | | | | | | | | | | | |
| 1672 | $A_{130}$ | | | | | | | | | | | | | | | | | |
| 1673 | $Y_{130}$ | | | | | | | | | | | | | | | | | |
| 1674 | $C_{130}$ | | | | | | | | | | | | | | | | | |
| 1675 | $L_{130}$ | | | | | | | | | | | | | | | | | |
| 1676 | $T_{129}$ | $P_1$ | | | | | | | | | | | | | | | | |
| 1677 | $T_{128}$ | $A_2$ | | | | | | | | | | | | | | | | |
| 1678 | $G_{130}$ | | | | | | | | | | | | | | | | | |
| 1679 | $S_{127}$ | $C_3$ | | | | | | | | | | | | | | | | |
| 1680 | $V_{130}$ | | | | | | | | | | | | | | | | | |
| 1681 | $V_{130}$ | | | | | | | | | | | | | | | | | |
| 1682 | $I_{130}$ | | | | | | | | | | | | | | | | | |
| 1683 | $V_{130}$ | | | | | | | | | | | | | | | | | |
| 1684 | $G_{130}$ | | | | | | | | | | | | | | | | | |
| 1685 | $R_{130}$ | | | | | | | | | | | | | | | | | |
| 1686 | $I_{124}$ | $V_4$ | $T_1$ | $L_1$ | | | | | | | | | | | | | | |
| 1687 | $I_{123}$ | $V_5$ | $T_1$ | $N_1$ | | | | | | | | | | | | | | |
| 1688 | $L_{130}$ | | | | | | | | | | | | | | | | | |
| 1689 | $S_{130}$ | | | | | | | | | | | | | | | | | |
| 1690 | $G_{130}$ | | | | | | | | | | | | | | | | | |
| 1691 | $K_{68}$ | $R_{61}$ | $S_1$ | | | | | | | | | | | | | | | |
| 1692 | $P_{130}$ | | | | | | | | | | | | | | | | | |
| 1693 | $A_{129}$ | $V_1$ | | | | | | | | | | | | | | | | |
| 1694 | $V_{68}$ | $I_{62}$ | | | | | | | | | | | | | | | | |
| 1695 | $I_{79}$ | $V_{47}$ | $L_4$ | | | | | | | | | | | | | | | |
| 1696 | $P_{130}$ | | | | | | | | | | | | | | | | | |
| 1697 | $D_{129}$ | $H_1$ | | | | | | | | | | | | | | | | |
| 1698 | $R_{130}$ | | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 1699 | $E_{128}$ | $D_1$ | $G_1$ | | | | | | | | | | | | | | | |
| 1700 | $V_{123}$ | $A_5$ | $L_1$ | $I_1$ | | | | | | | | | | | | | | |
| 1701 | $L_{130}$ | | | | | | | | | | | | | | | | | |
| 1702 | $Y_{125}$ | $H_5$ | | | | | | | | | | | | | | | | |
| 1703 | $Q_{73}$ | $R_{57}$ | | | | | | | | | | | | | | | | |
| 1704 | $E_{101}$ | $Q_{27}$ | $A_1$ | $D_1$ | | | | | | | | | | | | | | |
| 1705 | $F_{130}$ | | | | | | | | | | | | | | | | | |
| 1706 | $D_{130}$ | | | | | | | | | | | | | | | | | |
| 1707 | $E_{130}$ | | | | | | | | | | | | | | | | | |
| 1708 | $M_{130}$ | | | | | | | | | | | | | | | | | |
| 1709 | $E_{130}$ | | | | | | | | | | | | | | | | | |
| 1710 | $E_{128}$ | $A_1$ | $D_1$ | | | | | | | | | | | | | | | |
| 1711 | $C_{129}$ | $G_1$ | | | | | | | | | | | | | | | | |
| 1712 | $A_{128}$ | $G_1$ | $S_1$ | | | | | | | | | | | | | | | |
| 1713 | $S_{94}$ | $T_{34}$ | $A_1$ | $P_1$ | | | | | | | | | | | | | | |
| 1714 | $H_{127}$ | $Q_3$ | | | | | | | | | | | | | | | | |
| 1715 | $L_{130}$ | | | | | | | | | | | | | | | | | |
| 1716 | $P_{130}$ | | | | | | | | | | | | | | | | | |
| 1717 | $Y_{130}$ | | | | | | | | | | | | | | | | | |
| 1718 | $I_{128}$ | $F_2$ | | | | | | | | | | | | | | | | |
| 1719 | $E_{130}$ | | | | | | | | | | | | | | | | | |
| 1720 | $Q_{130}$ | | | | | | | | | | | | | | | | | |
| 1721 | $G_{130}$ | | | | | | | | | | | | | | | | | |
| 1722 | $M_{126}$ | $I_3$ | $V_1$ | | | | | | | | | | | | | | | |
| 1723 | $Q_{124}$ | $H_5$ | $L_1$ | | | | | | | | | | | | | | | |
| 1724 | $L_{130}$ | | | | | | | | | | | | | | | | | |
| 1725 | $A_{130}$ | | | | | | | | | | | | | | | | | |
| 1726 | $E_{128}$ | $A_1$ | | | | | | | | | | | | | | | | |
| 1727 | $Q_{129}$ | $E_1$ | | | | | | | | | | | | | | | | |
| 1728 | $F_{130}$ | | | | | | | | | | | | | | | | | |
| 1729 | $K_{128}$ | $R_2$ | | | | | | | | | | | | | | | | |
| 1730 | $Q_{130}$ | | | | | | | | | | | | | | | | | |
| 1731 | $K_{129}$ | $R_1$ | | | | | | | | | | | | | | | | |
| 1732 | $A_{130}$ | | | | | | | | | | | | | | | | | |
| 1733 | $L_{125}$ | $I_4$ | $F_1$ | | | | | | | | | | | | | | | |
| 1734 | $G_{130}$ | | | | | | | | | | | | | | | | | |
| 1735 | $L_{130}$ | | | | | | | | | | | | | | | | | |
| 1736 | $L_{128}$ | $P_1$ | $X_1$ | | | | | | | | | | | | | | | |
| 1737 | $Q_{130}$ | | | | | | | | | | | | | | | | | |
| 1738 | $T_{122}$ | $I_4$ | $V_2$ | $M_1$ | $A_1$ | | | | | | | | | | | | | |
| 1739 | $A_{130}$ | | | | | | | | | | | | | | | | | |
| 1740 | $T_{128}$ | $S_2$ | | | | | | | | | | | | | | | | |
| 1741 | $K_{128}$ | $T_1$ | $N_1$ | | | | | | | | | | | | | | | |
| 1742 | $Q_{130}$ | | | | | | | | | | | | | | | | | |
| 1743 | $A_{130}$ | | | | | | | | | | | | | | | | | |
| 1744 | $E_{122}$ | $X_8$ | | | | | | | | | | | | | | | | |
| 1745 | $A_{118}$ | $V_4$ | | | | | | | | | | | | | | | | |
| 1746 | $A_{121}$ | $V_1$ | | | | | | | | | | | | | | | | |
| 1747 | $A_{118}$ | $V_3$ | $X_1$ | | | | | | | | | | | | | | | |
| 1748 | $P_{122}$ | | | | | | | | | | | | | | | | | |
| 1749 | $V_{117}$ | $A_3$ | $I_1$ | $M_1$ | | | | | | | | | | | | | | |
| 1750 | $V_{121}$ | $M_1$ | | | | | | | | | | | | | | | | |
| 1751 | $E_{122}$ | | | | | | | | | | | | | | | | | |
| 1752 | $S_{121}$ | $T_1$ | | | | | | | | | | | | | | | | |
| 1753 | $K_{118}$ | $R_4$ | | | | | | | | | | | | | | | | |
| 1754 | $W_{122}$ | | | | | | | | | | | | | | | | | |
| 1755 | $R_{112}$ | $Q_8$ | $K_2$ | | | | | | | | | | | | | | | |
| 1756 | $A_{104}$ | $T_{16}$ | $G_2$ | | | | | | | | | | | | | | | |
| 1757 | $L_{122}$ | | | | | | | | | | | | | | | | | |
| 1758 | $E_{122}$ | | | | | | | | | | | | | | | | | |
| 1759 | $T_{44}$ | $A_{41}$ | $S_{31}$ | $V_4$ | $G_2$ | | | | | | | | | | | | | |
| 1760 | $F_{122}$ | | | | | | | | | | | | | | | | | |
| 1761 | $W_{122}$ | | | | | | | | | | | | | | | | | |
| 1762 | $A_{120}$ | $E_1$ | $G_1$ | | | | | | | | | | | | | | | |
| 1763 | $K_{120}$ | $N_2$ | | | | | | | | | | | | | | | | |
| 1764 | $H_{120}$ | $D_2$ | | | | | | | | | | | | | | | | |
| 1765 | $M_{120}$ | $X_2$ | | | | | | | | | | | | | | | | |
| 1766 | $W_{119}$ | $R_1$ | | | | | | | | | | | | | | | | |
| 1767 | $N_{119}$ | $S_1$ | | | | | | | | | | | | | | | | |
| 1768 | $F_{120}$ | | | | | | | | | | | | | | | | | |
| 1769 | $I_{120}$ | | | | | | | | | | | | | | | | | |
| 1770 | $S_{120}$ | | | | | | | | | | | | | | | | | |
| 1771 | $G_{120}$ | | | | | | | | | | | | | | | | | |
| 1772 | $I_{114}$ | $V_6$ | | | | | | | | | | | | | | | | |
| 1773 | $Q_{120}$ | | | | | | | | | | | | | | | | | |
| 1774 | $Y_{120}$ | | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 1775 | $L_{120}$ | | | | | | | | | | | | | | | | | |
| 1776 | $A_{120}$ | | | | | | | | | | | | | | | | | |
| 1777 | $G_{119}$ | $A_1$ | | | | | | | | | | | | | | | | |
| 1778 | $L_{120}$ | | | | | | | | | | | | | | | | | |
| 1779 | $S_{120}$ | | | | | | | | | | | | | | | | | |
| 1780 | $T_{120}$ | | | | | | | | | | | | | | | | | |
| 1781 | $L_{120}$ | | | | | | | | | | | | | | | | | |
| 1782 | $P_{119}$ | $H_1$ | | | | | | | | | | | | | | | | |
| 1783 | $G_{120}$ | | | | | | | | | | | | | | | | | |
| 1784 | $N_{120}$ | | | | | | | | | | | | | | | | | |
| 1785 | $P_{119}$ | $L_1$ | | | | | | | | | | | | | | | | |
| 1786 | $A_{120}$ | | | | | | | | | | | | | | | | | |
| 1787 | $I_{119}$ | $M_1$ | | | | | | | | | | | | | | | | |
| 1788 | $A_{118}$ | $R_2$ | | | | | | | | | | | | | | | | |
| 1789 | $S_{120}$ | | | | | | | | | | | | | | | | | |
| 1790 | $L_{118}$ | $P_2$ | | | | | | | | | | | | | | | | |
| 1791 | $M_{120}$ | | | | | | | | | | | | | | | | | |
| 1792 | $A_{118}$ | $E_1$ | $V_1$ | | | | | | | | | | | | | | | |
| 1793 | $F_{120}$ | | | | | | | | | | | | | | | | | |
| 1794 | $T_{120}$ | | | | | | | | | | | | | | | | | |
| 1795 | $A_{119}$ | $S_1$ | | | | | | | | | | | | | | | | |
| 1796 | $S_{119}$ | $A_1$ | | | | | | | | | | | | | | | | |
| 1797 | $I_{108}$ | $V_{12}$ | | | | | | | | | | | | | | | | |
| 1798 | $T_{120}$ | | | | | | | | | | | | | | | | | |
| 1799 | $S_{119}$ | $X_1$ | | | | | | | | | | | | | | | | |
| 1800 | $P_{119}$ | | | | | | | | | | | | | | | | | |
| 1801 | $L_{116}$ | $F_3$ | | | | | | | | | | | | | | | | |
| 1802 | $T_{117}$ | $S_1$ | $A_1$ | | | | | | | | | | | | | | | |
| 1803 | $T_{118}$ | $I_1$ | | | | | | | | | | | | | | | | |
| 1804 | $Q_{117}$ | $N_2$ | | | | | | | | | | | | | | | | |
| 1805 | $H_{57}$ | $S_{30}$ | $N_{22}$ | $Y_7$ | $Q_2$ | $T_1$ | | | | | | | | | | | | |
| 1806 | $T_{119}$ | | | | | | | | | | | | | | | | | |
| 1807 | $L_{118}$ | $F_1$ | | | | | | | | | | | | | | | | |
| 1808 | $L_{117}$ | $M_2$ | | | | | | | | | | | | | | | | |
| 1809 | $F_{118}$ | $L_1$ | | | | | | | | | | | | | | | | |
| 1810 | $N_{118}$ | $D_1$ | | | | | | | | | | | | | | | | |
| 1811 | $I_{119}$ | | | | | | | | | | | | | | | | | |
| 1812 | $L_{118}$ | $W_1$ | | | | | | | | | | | | | | | | |
| 1813 | $G_{119}$ | | | | | | | | | | | | | | | | | |
| 1814 | $G_{119}$ | | | | | | | | | | | | | | | | | |
| 1815 | $W_{119}$ | | | | | | | | | | | | | | | | | |
| 1816 | $V_{118}$ | $L_1$ | | | | | | | | | | | | | | | | |
| 1817 | $A_{119}$ | | | | | | | | | | | | | | | | | |
| 1818 | $A_{119}$ | | | | | | | | | | | | | | | | | |
| 1819 | $Q_{118}$ | $X_1$ | | | | | | | | | | | | | | | | |
| 1820 | $L_{117}$ | $I_1$ | $P_1$ | | | | | | | | | | | | | | | |
| 1821 | $A_{118}$ | $P_1$ | | | | | | | | | | | | | | | | |
| 1822 | $P_{119}$ | | | | | | | | | | | | | | | | | |
| 1823 | $P_{118}$ | $A_1$ | | | | | | | | | | | | | | | | |
| 1824 | $S_{111}$ | $G_4$ | $R_3$ | $N_1$ | | | | | | | | | | | | | | |
| 1825 | $A_{119}$ | | | | | | | | | | | | | | | | | |
| 1826 | $A_{117}$ | $S_1$ | $V_1$ | | | | | | | | | | | | | | | |
| 1827 | $S_{118}$ | $T_1$ | | | | | | | | | | | | | | | | |
| 1828 | $A_{119}$ | | | | | | | | | | | | | | | | | |
| 1829 | $F_{119}$ | | | | | | | | | | | | | | | | | |
| 1830 | $V_{119}$ | | | | | | | | | | | | | | | | | |
| 1831 | $G_{119}$ | | | | | | | | | | | | | | | | | |
| 1832 | $A_{119}$ | | | | | | | | | | | | | | | | | |
| 1833 | $G_{119}$ | | | | | | | | | | | | | | | | | |
| 1834 | $I_{117}$ | $S_1$ | $V_1$ | | | | | | | | | | | | | | | |
| 1835 | $A_{112}$ | $V_5$ | $T_2$ | | | | | | | | | | | | | | | |
| 1836 | $G_{117}$ | $X_1$ | $R_1$ | | | | | | | | | | | | | | | |
| 1837 | $A_{118}$ | $X_1$ | | | | | | | | | | | | | | | | |
| 1838 | $A_{119}$ | | | | | | | | | | | | | | | | | |
| 1839 | $V_{109}$ | $I_{10}$ | | | | | | | | | | | | | | | | |
| 1840 | $G_{119}$ | | | | | | | | | | | | | | | | | |
| 1841 | $S_{116}$ | $T_3$ | | | | | | | | | | | | | | | | |
| 1842 | $I_{116}$ | $V_3$ | | | | | | | | | | | | | | | | |
| 1843 | $G_{119}$ | | | | | | | | | | | | | | | | | |
| 1844 | $L_{117}$ | $V_1$ | $F_1$ | | | | | | | | | | | | | | | |
| 1845 | $G_{119}$ | | | | | | | | | | | | | | | | | |
| 1846 | $K_{116}$ | $R_3$ | | | | | | | | | | | | | | | | |
| 1847 | $V_{119}$ | | | | | | | | | | | | | | | | | |
| 1848 | $L_{117}$ | $I_2$ | | | | | | | | | | | | | | | | |
| 1849 | $V_{119}$ | | | | | | | | | | | | | | | | | |
| 1850 | $D_{118}$ | $E_1$ | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 1851 | $I_{115}$ | $V_3$ | $M_1$ | | | | | | | | | | | | | | | |
| 1852 | $L_{118}$ | $V_1$ | | | | | | | | | | | | | | | | |
| 1853 | $A_{119}$ | | | | | | | | | | | | | | | | | |
| 1854 | $G_{119}$ | | | | | | | | | | | | | | | | | |
| 1855 | $Y_{119}$ | | | | | | | | | | | | | | | | | |
| 1856 | $G_{119}$ | | | | | | | | | | | | | | | | | |
| 1857 | $A_{119}$ | | | | | | | | | | | | | | | | | |
| 1858 | $G_{119}$ | | | | | | | | | | | | | | | | | |
| 1859 | $V_{118}$ | $X_1$ | | | | | | | | | | | | | | | | |
| 1860 | $A_{119}$ | | | | | | | | | | | | | | | | | |
| 1861 | $G_{119}$ | | | | | | | | | | | | | | | | | |
| 1862 | $A_{119}$ | | | | | | | | | | | | | | | | | |
| 1863 | $L_{119}$ | | | | | | | | | | | | | | | | | |
| 1864 | $V_{119}$ | | | | | | | | | | | | | | | | | |
| 1865 | $A_{118}$ | $D_1$ | | | | | | | | | | | | | | | | |
| 1866 | $F_{119}$ | | | | | | | | | | | | | | | | | |
| 1867 | $K_{119}$ | | | | | | | | | | | | | | | | | |
| 1868 | $V_{95}$ | $I_{24}$ | | | | | | | | | | | | | | | | |
| 1869 | $M_{119}$ | | | | | | | | | | | | | | | | | |
| 1870 | $S_{119}$ | | | | | | | | | | | | | | | | | |
| 1871 | $G_{119}$ | | | | | | | | | | | | | | | | | |
| 1872 | $E_{104}$ | $D_{15}$ | | | | | | | | | | | | | | | | |
| 1873 | $M_{82}$ | $A_{17}$ | $V_{12}$ | $T_4$ | $L_2$ | $R_1$ | $I_1$ | | | | | | | | | | | |
| 1874 | $P_{119}$ | | | | | | | | | | | | | | | | | |
| 1875 | $S_{118}$ | $A_1$ | | | | | | | | | | | | | | | | |
| 1876 | $T_{103}$ | $A_{14}$ | $P_1$ | $S_1$ | | | | | | | | | | | | | | |
| 1877 | $E_{119}$ | | | | | | | | | | | | | | | | | |
| 1878 | $D_{118}$ | $E_1$ | | | | | | | | | | | | | | | | |
| 1879 | $L_{109}$ | $M_8$ | $R_1$ | $I_1$ | | | | | | | | | | | | | | |
| 1880 | $V_{113}$ | $I_5$ | $D_1$ | | | | | | | | | | | | | | | |
| 1881 | $N_{119}$ | | | | | | | | | | | | | | | | | |
| 1882 | $L_{118}$ | $M_1$ | | | | | | | | | | | | | | | | |
| 1883 | $L_{118}$ | $I_1$ | | | | | | | | | | | | | | | | |
| 1884 | $P_{117}$ | $H_1$ | $L_1$ | | | | | | | | | | | | | | | |
| 1885 | $A_{119}$ | | | | | | | | | | | | | | | | | |
| 1886 | $I_{118}$ | $V_1$ | | | | | | | | | | | | | | | | |
| 1887 | $L_{118}$ | $F_1$ | | | | | | | | | | | | | | | | |
| 1888 | $S_{119}$ | | | | | | | | | | | | | | | | | |
| 1889 | $P_{119}$ | | | | | | | | | | | | | | | | | |
| 1890 | $G_{119}$ | | | | | | | | | | | | | | | | | |
| 1891 | $A_{119}$ | | | | | | | | | | | | | | | | | |
| 1892 | $L_{119}$ | | | | | | | | | | | | | | | | | |
| 1893 | $V_{119}$ | | | | | | | | | | | | | | | | | |
| 1894 | $V_{119}$ | | | | | | | | | | | | | | | | | |
| 1895 | $G_{119}$ | | | | | | | | | | | | | | | | | |
| 1896 | $V_{114}$ | $I_5$ | | | | | | | | | | | | | | | | |
| 1897 | $V_{119}$ | | | | | | | | | | | | | | | | | |
| 1898 | $C_{119}$ | | | | | | | | | | | | | | | | | |
| 1899 | $A_{119}$ | | | | | | | | | | | | | | | | | |
| 1900 | $A_{119}$ | | | | | | | | | | | | | | | | | |
| 1901 | $I_{118}$ | $V_1$ | | | | | | | | | | | | | | | | |
| 1902 | $L_{118}$ | $Q_1$ | | | | | | | | | | | | | | | | |
| 1903 | $R_{119}$ | | | | | | | | | | | | | | | | | |
| 1904 | $R_{118}$ | $G_1$ | | | | | | | | | | | | | | | | |
| 1905 | $H_{119}$ | | | | | | | | | | | | | | | | | |
| 1906 | $V_{119}$ | | | | | | | | | | | | | | | | | |
| 1907 | $G_{118}$ | $D_1$ | | | | | | | | | | | | | | | | |
| 1908 | $P_{118}$ | $X_1$ | | | | | | | | | | | | | | | | |
| 1909 | $G_{118}$ | | | | | | | | | | | | | | | | | |
| 1910 | $E_{118}$ | | | | | | | | | | | | | | | | | |
| 1911 | $G_{118}$ | | | | | | | | | | | | | | | | | |
| 1912 | $A_{118}$ | | | | | | | | | | | | | | | | | |
| 1913 | $V_{118}$ | | | | | | | | | | | | | | | | | |
| 1914 | $Q_{117}$ | $H_1$ | | | | | | | | | | | | | | | | |
| 1915 | $W_{118}$ | | | | | | | | | | | | | | | | | |
| 1916 | $M_{117}$ | $V_1$ | | | | | | | | | | | | | | | | |
| 1917 | $N_{118}$ | | | | | | | | | | | | | | | | | |
| 1918 | $R_{118}$ | | | | | | | | | | | | | | | | | |
| 1919 | $L_{118}$ | | | | | | | | | | | | | | | | | |
| 1920 | $I_{118}$ | | | | | | | | | | | | | | | | | |
| 1921 | $A_{118}$ | | | | | | | | | | | | | | | | | |
| 1922 | $F_{119}$ | | | | | | | | | | | | | | | | | |
| 1923 | $A_{119}$ | | | | | | | | | | | | | | | | | |
| 1924 | $S_{118}$ | $F_1$ | | | | | | | | | | | | | | | | |
| 1925 | $R_{118}$ | $A_1$ | | | | | | | | | | | | | | | | |
| 1926 | $G_{119}$ | | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 1927 | $N_{119}$ | | | | | | | | | | | | | | | | | |
| 1928 | $H_{119}$ | | | | | | | | | | | | | | | | | |
| 1929 | $V_{118}$ | $D_1$ | | | | | | | | | | | | | | | | |
| 1930 | $S_{119}$ | | | | | | | | | | | | | | | | | |
| 1931 | $P_{119}$ | | | | | | | | | | | | | | | | | |
| 1932 | $T_{116}$ | $R_2$ | $A_1$ | | | | | | | | | | | | | | | |
| 1933 | $H_{119}$ | | | | | | | | | | | | | | | | | |
| 1934 | $Y_{119}$ | | | | | | | | | | | | | | | | | |
| 1935 | $V_{119}$ | | | | | | | | | | | | | | | | | |
| 1936 | $P_{119}$ | | | | | | | | | | | | | | | | | |
| 1937 | $E_{119}$ | | | | | | | | | | | | | | | | | |
| 1938 | $S_{118}$ | $N_1$ | | | | | | | | | | | | | | | | |
| 1939 | $D_{117}$ | $E_2$ | | | | | | | | | | | | | | | | |
| 1940 | $A_{117}$ | $P_2$ | | | | | | | | | | | | | | | | |
| 1941 | $A_{119}$ | | | | | | | | | | | | | | | | | |
| 1942 | $A_{105}$ | $V_{11}$ | $S_1$ | $G_1$ | $Q_1$ | | | | | | | | | | | | | |
| 1943 | $R_{118}$ | $P_1$ | | | | | | | | | | | | | | | | |
| 1944 | $V_{119}$ | | | | | | | | | | | | | | | | | |
| 1945 | $T_{119}$ | | | | | | | | | | | | | | | | | |
| 1946 | $Q_{119}$ | | | | | | | | | | | | | | | | | |
| 1947 | $I_{115}$ | $V_4$ | | | | | | | | | | | | | | | | |
| 1948 | $L_{119}$ | | | | | | | | | | | | | | | | | |
| 1949 | $S_{119}$ | | | | | | | | | | | | | | | | | |
| 1950 | $S_{104}$ | $N_{11}$ | $G_4$ | | | | | | | | | | | | | | | |
| 1951 | $L_{119}$ | | | | | | | | | | | | | | | | | |
| 1952 | $T_{119}$ | | | | | | | | | | | | | | | | | |
| 1953 | $I_{117}$ | $V_2$ | | | | | | | | | | | | | | | | |
| 1954 | $T_{119}$ | | | | | | | | | | | | | | | | | |
| 1955 | $Q_{119}$ | | | | | | | | | | | | | | | | | |
| 1956 | $L_{119}$ | | | | | | | | | | | | | | | | | |
| 1957 | $L_{119}$ | | | | | | | | | | | | | | | | | |
| 1958 | $K_{111}$ | $R_8$ | | | | | | | | | | | | | | | | |
| 1959 | $R_{118}$ | $K_1$ | | | | | | | | | | | | | | | | |
| 1960 | $L_{119}$ | | | | | | | | | | | | | | | | | |
| 1961 | $H_{119}$ | | | | | | | | | | | | | | | | | |
| 1962 | $Q_{117}$ | $R_1$ | $H_1$ | | | | | | | | | | | | | | | |
| 1963 | $W_{119}$ | | | | | | | | | | | | | | | | | |
| 1964 | $I_{119}$ | | | | | | | | | | | | | | | | | |
| 1965 | $N_{118}$ | $S_1$ | | | | | | | | | | | | | | | | |
| 1966 | $E_{119}$ | | | | | | | | | | | | | | | | | |
| 1967 | $D_{119}$ | | | | | | | | | | | | | | | | | |
| 1968 | $C_{119}$ | | | | | | | | | | | | | | | | | |
| 1969 | $S_{119}$ | | | | | | | | | | | | | | | | | |
| 1970 | $T_{119}$ | $X_1$ | | | | | | | | | | | | | | | | |
| 1971 | $P_{119}$ | $M_4$ | | | | | | | | | | | | | | | | |
| 1972 | $C_{119}$ | $G_4$ | $M_1$ | | | | | | | | | | | | | | | |
| 1973 | $S_{236}$ | $A_1$ | | | | | | | | | | | | | | | | |
| 1974 | $G_{233}$ | $S_3$ | $D_1$ | | | | | | | | | | | | | | | |
| 1975 | $S_{236}$ | $T_1$ | | | | | | | | | | | | | | | | |
| 1976 | $W_{237}$ | | | | | | | | | | | | | | | | | |
| 1977 | $L_{237}$ | | | | | | | | | | | | | | | | | |
| 1978 | $R_{228}$ | $K_9$ | | | | | | | | | | | | | | | | |
| 1979 | $D_{234}$ | $E_3$ | | | | | | | | | | | | | | | | |
| 1980 | $V_{222}$ | $I_{15}$ | | | | | | | | | | | | | | | | |
| 1981 | $W_{237}$ | | | | | | | | | | | | | | | | | |
| 1982 | $D_{235}$ | $E_2$ | | | | | | | | | | | | | | | | |
| 1983 | $W_{237}$ | | | | | | | | | | | | | | | | | |
| 1984 | $I_{234}$ | $V_3$ | | | | | | | | | | | | | | | | |
| 1985 | $D_{237}$ | | | | | | | | | | | | | | | | | |
| 1986 | $T_{229}$ | $S_2$ | $A_2$ | $M_2$ | $I_1$ | $X_1$ | | | | | | | | | | | | |
| 1987 | $V_{235}$ | $A_1$ | $M_1$ | | | | | | | | | | | | | | | |
| 1988 | $L_{236}$ | $V_1$ | | | | | | | | | | | | | | | | |
| 1989 | $T_{171}$ | $S_{33}$ | $A_{28}$ | $V_2$ | $I_2$ | $N_1$ | | | | | | | | | | | | |
| 1990 | $D_{237}$ | | | | | | | | | | | | | | | | | |
| 1991 | $F_{235}$ | $L_2$ | | | | | | | | | | | | | | | | |
| 1992 | $K_{236}$ | $R_1$ | | | | | | | | | | | | | | | | |
| 1993 | $T_{234}$ | $N_1$ | $S_1$ | $A_1$ | | | | | | | | | | | | | | |
| 1994 | $W_{236}$ | $R_1$ | | | | | | | | | | | | | | | | |
| 1995 | $L_{236}$ | $I_1$ | | | | | | | | | | | | | | | | |
| 1996 | $Q_{230}$ | $K_5$ | $R_2$ | | | | | | | | | | | | | | | |
| 1997 | $S_{231}$ | $T_6$ | | | | | | | | | | | | | | | | |
| 1998 | $K_{234}$ | $R_3$ | | | | | | | | | | | | | | | | |
| 1999 | $L_{233}$ | $V_3$ | $I_1$ | | | | | | | | | | | | | | | |
| 2000 | $L_{227}$ | $M_9$ | $V_1$ | | | | | | | | | | | | | | | |
| 2001 | $P_{236}$ | $X_1$ | | | | | | | | | | | | | | | | |
| 2002 | $R_{222}$ | $Q_{10}$ | $K_4$ | $L_1$ | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 2003 | $L_{228}$ | $M_6$ | $X_1$ | $I_1$ | $F_1$ | | | | | | | | | | | | | |
| 2004 | $P_{237}$ | | | | | | | | | | | | | | | | | |
| 2005 | $G_{237}$ | | | | | | | | | | | | | | | | | |
| 2006 | $V_{215}$ | $I_{15}$ | $L_5$ | $A_2$ | | | | | | | | | | | | | | |
| 2007 | $P_{237}$ | | | | | | | | | | | | | | | | | |
| 2008 | $F_{236}$ | $X_1$ | | | | | | | | | | | | | | | | |
| 2009 | $F_{115}$ | $L_{109}$ | $I_8$ | $Y_4$ | $M_1$ | | | | | | | | | | | | | |
| 2010 | $S_{235}$ | $X_2$ | | | | | | | | | | | | | | | | |
| 2011 | $C_{236}$ | $W_1$ | | | | | | | | | | | | | | | | |
| 2012 | $Q_{237}$ | | | | | | | | | | | | | | | | | |
| 2013 | $R_{237}$ | | | | | | | | | | | | | | | | | |
| 2014 | $G_{237}$ | | | | | | | | | | | | | | | | | |
| 2015 | $Y_{236}$ | $F_1$ | | | | | | | | | | | | | | | | |
| 2016 | $K_{190}$ | $R_{47}$ | | | | | | | | | | | | | | | | |
| 2017 | $G_{237}$ | | | | | | | | | | | | | | | | | |
| 2018 | $V_{200}$ | $I_{36}$ | $A_1$ | | | | | | | | | | | | | | | |
| 2019 | $W_{237}$ | | | | | | | | | | | | | | | | | |
| 2020 | $R_{233}$ | $Q_3$ | $L_1$ | | | | | | | | | | | | | | | |
| 2021 | $G_{234}$ | $E_2$ | $S_1$ | | | | | | | | | | | | | | | |
| 2022 | $D_{235}$ | $E_2$ | | | | | | | | | | | | | | | | |
| 2023 | $G_{237}$ | | | | | | | | | | | | | | | | | |
| 2024 | $I_{214}$ | $V_{23}$ | | | | | | | | | | | | | | | | |
| 2025 | $M_{236}$ | $V_1$ | | | | | | | | | | | | | | | | |
| 2026 | $Q_{154}$ | $H_{70}$ | $Y_8$ | $L_2$ | $N_1$ | $X_1$ | $C_1$ | | | | | | | | | | | |
| 2027 | $T_{235}$ | $A_2$ | | | | | | | | | | | | | | | | |
| 2028 | $T_{226}$ | $I_8$ | $V_1$ | $A_1$ | $N_1$ | | | | | | | | | | | | | |
| 2029 | $C_{237}$ | | | | | | | | | | | | | | | | | |
| 2030 | $P_{225}$ | $S_5$ | $Q_3$ | $L_3$ | $A_1$ | | | | | | | | | | | | | |
| 2031 | $C_{237}$ | | | | | | | | | | | | | | | | | |
| 2032 | $G_{234}$ | $X_2$ | $A_1$ | | | | | | | | | | | | | | | |
| 2033 | $A_{233}$ | $G_3$ | | | | | | | | | | | | | | | | |
| 2034 | $Q_{231}$ | $R_2$ | $H_1$ | $D_1$ | $E_1$ | | | | | | | | | | | | | |
| 2035 | $I_{233}$ | $L_2$ | $M_1$ | | | | | | | | | | | | | | | |
| 2036 | $T_{192}$ | $A_{32}$ | $S_{12}$ | | | | | | | | | | | | | | | |
| 2037 | $G_{236}$ | | | | | | | | | | | | | | | | | |
| 2038 | $H_{236}$ | | | | | | | | | | | | | | | | | |
| 2039 | $V_{235}$ | $F_1$ | | | | | | | | | | | | | | | | |
| 2040 | $K_{234}$ | $R_1$ | $T_1$ | | | | | | | | | | | | | | | |
| 2041 | $N_{234}$ | $T_2$ | | | | | | | | | | | | | | | | |
| 2042 | $G_{236}$ | | | | | | | | | | | | | | | | | |
| 2043 | $S_{236}$ | | | | | | | | | | | | | | | | | |
| 2044 | $M_{236}$ | | | | | | | | | | | | | | | | | |
| 2045 | $R_{226}$ | $K_{10}$ | | | | | | | | | | | | | | | | |
| 2046 | $I_{231}$ | $X_3$ | $L_1$ | $V_1$ | | | | | | | | | | | | | | |
| 2047 | $V_{215}$ | $A_8$ | $T_6$ | $F_2$ | $I_2$ | $X_1$ | $Y_1$ | $W_1$ | | | | | | | | | | |
| 2048 | $G_{236}$ | | | | | | | | | | | | | | | | | |
| 2049 | $P_{233}$ | $S_2$ | $X_1$ | | | | | | | | | | | | | | | |
| 2050 | $K_{147}$ | $R_{89}$ | | | | | | | | | | | | | | | | |
| 2051 | $T_{227}$ | $A_8$ | $S_1$ | | | | | | | | | | | | | | | |
| 2052 | $C_{236}$ | | | | | | | | | | | | | | | | | |
| 2053 | $S_{236}$ | | | | | | | | | | | | | | | | | |
| 2054 | $N_{235}$ | $S_1$ | | | | | | | | | | | | | | | | |
| 2055 | $T_{216}$ | $M_{17}$ | $X_1$ | $V_1$ | $A_1$ | | | | | | | | | | | | | |
| 2056 | $W_{233}$ | $C_3$ | | | | | | | | | | | | | | | | |
| 2057 | $H_{215}$ | $Y_8$ | $L_3$ | $C_3$ | $R_2$ | $Q_2$ | $S_1$ | $N_1$ | $D_1$ | | | | | | | | | |
| 2058 | $G_{236}$ | | | | | | | | | | | | | | | | | |
| 2059 | $T_{231}$ | $A_3$ | $X_1$ | $S_1$ | | | | | | | | | | | | | | |
| 2060 | $F_{236}$ | | | | | | | | | | | | | | | | | |
| 2061 | $P_{234}$ | $S_2$ | | | | | | | | | | | | | | | | |
| 2062 | $I_{231}$ | $V_4$ | $T_1$ | | | | | | | | | | | | | | | |
| 2063 | $N_{236}$ | | | | | | | | | | | | | | | | | |
| 2064 | $A_{229}$ | $T_5$ | $V_1$ | $G_1$ | | | | | | | | | | | | | | |
| 2065 | $Y_{224}$ | $H_{11}$ | $C_1$ | | | | | | | | | | | | | | | |
| 2066 | $T_{236}$ | | | | | | | | | | | | | | | | | |
| 2067 | $T_{236}$ | | | | | | | | | | | | | | | | | |
| 2068 | $G_{235}$ | $D_1$ | | | | | | | | | | | | | | | | |
| 2069 | $P_{226}$ | $S_8$ | $R_1$ | $H_1$ | | | | | | | | | | | | | | |
| 2070 | $C_{228}$ | $S_7$ | $W_1$ | | | | | | | | | | | | | | | | |
| 2071 | $T_{227}$ | $S_4$ | $V_3$ | $M_1$ | $A_1$ | | | | | | | | | | | | | |
| 2072 | $P_{234}$ | $X_1$ | $A_1$ | | | | | | | | | | | | | | | |
| 2073 | $S_{220}$ | $T_{13}$ | $A_3$ | | | | | | | | | | | | | | | |
| 2074 | $P_{236}$ | | | | | | | | | | | | | | | | | |
| 2075 | $A_{235}$ | $T_1$ | | | | | | | | | | | | | | | | |
| 2076 | $P_{232}$ | $X_3$ | $S_1$ | | | | | | | | | | | | | | | |
| 2077 | $N_{232}$ | $S_2$ | $X_1$ | $D_1$ | | | | | | | | | | | | | | |
| 2078 | $Y_{236}$ | | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 2079 | $S_{229}$ | $T_5$ | $F_2$ | | | | | | | | | | | | | | | |
| 2080 | $R_{201}$ | $K_{33}$ | $N_1$ | $T_1$ | | | | | | | | | | | | | | |
| 2081 | $A_{234}$ | $G_2$ | | | | | | | | | | | | | | | | |
| 2082 | $L_{236}$ | | | | | | | | | | | | | | | | | |
| 2083 | $W_{235}$ | $L_1$ | | | | | | | | | | | | | | | | |
| 2084 | $R_{235}$ | $W_1$ | | | | | | | | | | | | | | | | |
| 2085 | $V_{234}$ | $M_1$ | $R_1$ | | | | | | | | | | | | | | | |
| 2086 | $A_{224}$ | $T_7$ | $S_3$ | $V_2$ | | | | | | | | | | | | | | |
| 2087 | $A_{233}$ | $S_1$ | $P_1$ | $F_1$ | | | | | | | | | | | | | | |
| 2088 | $E_{235}$ | $D_1$ | | | | | | | | | | | | | | | | |
| 2089 | $E_{234}$ | $G_1$ | $D_1$ | | | | | | | | | | | | | | | |
| 2090 | $Y_{236}$ | | | | | | | | | | | | | | | | | |
| 2091 | $V_{233}$ | $L_3$ | | | | | | | | | | | | | | | | |
| 2092 | $E_{236}$ | | | | | | | | | | | | | | | | | |
| 2093 | $V_{226}$ | $I_{10}$ | | | | | | | | | | | | | | | | |
| 2094 | $T_{229}$ | $R_3$ | $K_2$ | $A_1$ | $V_1$ | | | | | | | | | | | | | |
| 2095 | $R_{230}$ | $Q_6$ | | | | | | | | | | | | | | | | |
| 2096 | $V_{231}$ | $M_3$ | $L_2$ | | | | | | | | | | | | | | | |
| 2097 | $G_{236}$ | | | | | | | | | | | | | | | | | |
| 2098 | $D_{232}$ | $E_4$ | | | | | | | | | | | | | | | | |
| 2099 | $F_{231}$ | $S_3$ | $C_1$ | $Y_1$ | | | | | | | | | | | | | | |
| 2100 | $H_{236}$ | | | | | | | | | | | | | | | | | |
| 2101 | $Y_{235}$ | $H_1$ | | | | | | | | | | | | | | | | |
| 2102 | $V_{231}$ | $I_5$ | | | | | | | | | | | | | | | | |
| 2103 | $T_{236}$ | | | | | | | | | | | | | | | | | |
| 2104 | $G_{233}$ | $D_2$ | $S_1$ | | | | | | | | | | | | | | | |
| 2105 | $M_{224}$ | $V_7$ | $I_4$ | $L_1$ | | | | | | | | | | | | | | |
| 2106 | $T_{236}$ | | | | | | | | | | | | | | | | | |
| 2107 | $T_{224}$ | $A_7$ | $N_2$ | $V_1$ | $I_1$ | $S_1$ | | | | | | | | | | | | |
| 2108 | $D_{236}$ | | | | | | | | | | | | | | | | | |
| 2109 | $N_{235}$ | $D_1$ | | | | | | | | | | | | | | | | |
| 2110 | $V_{182}$ | $I_{44}$ | $L_{10}$ | | | | | | | | | | | | | | | |
| 2111 | $K_{230}$ | $R_3$ | $X_2$ | $E_1$ | | | | | | | | | | | | | | |
| 2112 | $C_{236}$ | | | | | | | | | | | | | | | | | |
| 2113 | $P_{236}$ | | | | | | | | | | | | | | | | | |
| 2114 | $C_{235}$ | $X_1$ | | | | | | | | | | | | | | | | |
| 2115 | $Q_{236}$ | | | | | | | | | | | | | | | | | |
| 2116 | $V_{235}$ | $E_1$ | | | | | | | | | | | | | | | | |
| 2117 | $P_{236}$ | | | | | | | | | | | | | | | | | |
| 2118 | $A_{230}$ | $T_2$ | $P_2$ | $S_2$ | | | | | | | | | | | | | | |
| 2119 | $P_{234}$ | $X_1$ | $L_1$ | | | | | | | | | | | | | | | |
| 2120 | $E_{236}$ | $D_1$ | | | | | | | | | | | | | | | | |
| 2121 | $F_{236}$ | $X_1$ | | | | | | | | | | | | | | | | |
| 2122 | $F_{236}$ | | | | | | | | | | | | | | | | | |
| 2123 | $T_{234}$ | $K_1$ | $S_1$ | | | | | | | | | | | | | | | |
| 2124 | $E_{234}$ | $X_1$ | $A_1$ | | | | | | | | | | | | | | | |
| 2125 | $V_{187}$ | $L_{49}$ | | | | | | | | | | | | | | | | |
| 2126 | $D_{236}$ | | | | | | | | | | | | | | | | | |
| 2127 | $G_{236}$ | | | | | | | | | | | | | | | | | |
| 2128 | $V_{234}$ | $G_1$ | $I_1$ | | | | | | | | | | | | | | | |
| 2129 | $R_{232}$ | $Q_4$ | | | | | | | | | | | | | | | | |
| 2130 | $L_{236}$ | | | | | | | | | | | | | | | | | |
| 2131 | $H_{236}$ | | | | | | | | | | | | | | | | | |
| 2132 | $R_{235}$ | $X_1$ | $T_1$ | | | | | | | | | | | | | | | |
| 2133 | $Y_{234}$ | $F_2$ | $N_1$ | | | | | | | | | | | | | | | |
| 2134 | $A_{237}$ | | | | | | | | | | | | | | | | | |
| 2135 | $P_{237}$ | | | | | | | | | | | | | | | | | |
| 2136 | $A_{189}$ | $P_{29}$ | $V_{16}$ | $E_1$ | $X_1$ | $T_1$ | | | | | | | | | | | | |
| 2137 | $C_{234}$ | $S_2$ | $G_1$ | | | | | | | | | | | | | | | |
| 2138 | $K_{209}$ | $R_{26}$ | $X_1$ | $G_1$ | | | | | | | | | | | | | | |
| 2139 | $P_{233}$ | $X_2$ | $A_1$ | $T_1$ | | | | | | | | | | | | | | |
| 2140 | $L_{235}$ | $X_1$ | $V_1$ | | | | | | | | | | | | | | | |
| 2141 | $L_{238}$ | $P_1$ | $X_1$ | $I_1$ | | | | | | | | | | | | | | |
| 2142 | $R_{239}$ | $P_1$ | $H_1$ | | | | | | | | | | | | | | | |
| 2143 | $E_{147}$ | $D_{86}$ | $V_3$ | $X_2$ | $Q_1$ | $K_1$ | $T_1$ | | | | | | | | | | | |
| 2144 | $E_{231}$ | $D_9$ | $G_1$ | | | | | | | | | | | | | | | |
| 2145 | $V_{239}$ | $T_1$ | $A_1$ | | | | | | | | | | | | | | | |
| 2146 | $T_{198}$ | $V_{19}$ | $S_{15}$ | $D_4$ | $A_3$ | $M_1$ | $K_1$ | | | | | | | | | | | |
| 2147 | $F_{238}$ | $Y_2$ | $L_1$ | | | | | | | | | | | | | | | |
| 2148 | $Q_{213}$ | $L_{17}$ | $M_9$ | $R_1$ | $T_1$ | | | | | | | | | | | | | |
| 2149 | $V_{298}$ | | | | | | | | | | | | | | | | | |
| 2150 | $G_{297}$ | $R_1$ | | | | | | | | | | | | | | | | |
| 2151 | $L_{294}$ | $C_4$ | | | | | | | | | | | | | | | | |
| 2152 | $N_{278}$ | $H_{20}$ | | | | | | | | | | | | | | | | |
| 2153 | $Q_{292}$ | $R_2$ | $X_1$ | $E_1$ | $K_1$ | $H_1$ | | | | | | | | | | | | |
| 2154 | $Y_{288}$ | $F_8$ | $X_2$ | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 2155 | $L_{201}$ | $P_{56}$ | $V_{29}$ | $A_5$ | $T_5$ | $C_1$ | $I_1$ | | | | | | | | | | | |
| 2156 | $V_{295}$ | $I_2$ | $X_1$ | | | | | | | | | | | | | | | |
| 2157 | $G_{296}$ | $X_1$ | $E_1$ | | | | | | | | | | | | | | | |
| 2158 | $S_{297}$ | $A_1$ | | | | | | | | | | | | | | | | |
| 2159 | $Q_{297}$ | $P_1$ | | | | | | | | | | | | | | | | |
| 2160 | $L_{298}$ | | | | | | | | | | | | | | | | | |
| 2161 | $P_{298}$ | | | | | | | | | | | | | | | | | |
| 2162 | $C_{297}$ | $X_1$ | | | | | | | | | | | | | | | | |
| 2163 | $E_{298}$ | | | | | | | | | | | | | | | | | |
| 2164 | $P_{298}$ | | | | | | | | | | | | | | | | | |
| 2165 | $E_{298}$ | | | | | | | | | | | | | | | | | |
| 2166 | $P_{296}$ | $L_2$ | | | | | | | | | | | | | | | | |
| 2167 | $D_{294}$ | $N_2$ | $X_1$ | $G_1$ | | | | | | | | | | | | | | |
| 2168 | $V_{294}$ | $A_2$ | $X_1$ | $T_1$ | | | | | | | | | | | | | | |
| 2169 | $A_{156}$ | $T_{134}$ | $V_4$ | $S_2$ | $X_1$ | $E_1$ | | | | | | | | | | | | |
| 2170 | $V_{297}$ | $T_1$ | | | | | | | | | | | | | | | | |
| 2171 | $L_{274}$ | $V_{16}$ | $I_4$ | $X_2$ | $F_2$ | | | | | | | | | | | | | |
| 2172 | $T_{293}$ | $A_4$ | $X_1$ | | | | | | | | | | | | | | | |
| 2173 | $S_{297}$ | $A_1$ | | | | | | | | | | | | | | | | |
| 2174 | $M_{296}$ | $L_2$ | | | | | | | | | | | | | | | | |
| 2175 | $L_{293}$ | $F_3$ | $R_1$ | $H_1$ | | | | | | | | | | | | | | |
| 2176 | $T_{294}$ | $S_2$ | $A_1$ | $I_1$ | | | | | | | | | | | | | | |
| 2177 | $D_{298}$ | | | | | | | | | | | | | | | | | |
| 2178 | $P_{298}$ | | | | | | | | | | | | | | | | | |
| 2179 | $S_{292}$ | $P_4$ | $A_1$ | $T_1$ | | | | | | | | | | | | | | |
| 2180 | $H_{298}$ | | | | | | | | | | | | | | | | | |
| 2181 | $I_{298}$ | | | | | | | | | | | | | | | | | |
| 2182 | $T_{298}$ | | | | | | | | | | | | | | | | | |
| 2183 | $A_{296}$ | $X_1$ | $G_1$ | | | | | | | | | | | | | | | |
| 2184 | $E_{298}$ | | | | | | | | | | | | | | | | | |
| 2185 | $T_{238}$ | $A_{57}$ | $M_1$ | $X_1$ | $V_1$ | | | | | | | | | | | | | |
| 2186 | $A_{298}$ | | | | | | | | | | | | | | | | | |
| 2187 | $K_{249}$ | $R_{31}$ | $G_{17}$ | $A_1$ | | | | | | | | | | | | | | |
| 2188 | $R_{297}$ | $X_1$ | | | | | | | | | | | | | | | | |
| 2189 | $R_{295}$ | $K_2$ | $M_1$ | | | | | | | | | | | | | | | |
| 2190 | $L_{294}$ | $P_3$ | $V_1$ | | | | | | | | | | | | | | | |
| 2191 | $A_{286}$ | $D_9$ | $P_1$ | $E_1$ | $X_1$ | | | | | | | | | | | | | |
| 2192 | $R_{297}$ | $K_1$ | | | | | | | | | | | | | | | | |
| 2193 | $G_{298}$ | | | | | | | | | | | | | | | | | |
| 2194 | $S_{294}$ | $X_2$ | $C_1$ | $P_1$ | | | | | | | | | | | | | | |
| 2195 | $P_{295}$ | $S_2$ | $G_1$ | | | | | | | | | | | | | | | |
| 2196 | $P_{297}$ | $G_1$ | | | | | | | | | | | | | | | | |
| 2197 | $S_{297}$ | $X_1$ | | | | | | | | | | | | | | | | |
| 2198 | $L_{295}$ | $M_2$ | $X_1$ | | | | | | | | | | | | | | | |
| 2199 | $A_{297}$ | $G_1$ | | | | | | | | | | | | | | | | |
| 2200 | $S_{296}$ | $R_1$ | $G_1$ | | | | | | | | | | | | | | | |
| 2201 | $S_{297}$ | $X_1$ | | | | | | | | | | | | | | | | |
| 2202 | $S_{297}$ | $X_1$ | | | | | | | | | | | | | | | | |
| 2203 | $A_{298}$ | | | | | | | | | | | | | | | | | |
| 2204 | $S_{296}$ | $X_1$ | $T_1$ | | | | | | | | | | | | | | | |
| 2205 | $Q_{296}$ | $X_2$ | | | | | | | | | | | | | | | | |
| 2206 | $L_{296}$ | $X_1$ | $P_1$ | | | | | | | | | | | | | | | |
| 2207 | $S_{297}$ | $X_1$ | | | | | | | | | | | | | | | | |
| 2208 | $A_{298}$ | | | | | | | | | | | | | | | | | |
| 2209 | $P_{283}$ | $L_{12}$ | $V_1$ | $A_1$ | $F_1$ | | | | | | | | | | | | | |
| 2210 | $S_{296}$ | $X_1$ | $P_1$ | | | | | | | | | | | | | | | |
| 2211 | $L_{296}$ | $X_1$ | $S_1$ | | | | | | | | | | | | | | | |
| 2212 | $K_{288}$ | $R_9$ | $W_1$ | | | | | | | | | | | | | | | |
| 2213 | $A_{295}$ | $V_3$ | | | | | | | | | | | | | | | | |
| 2214 | $T_{288}$ | $A_7$ | $K_2$ | $S_1$ | | | | | | | | | | | | | | |
| 2215 | $C_{297}$ | $X_1$ | | | | | | | | | | | | | | | | |
| 2216 | $T_{295}$ | $P_2$ | $I_1$ | | | | | | | | | | | | | | | |
| 2217 | $T_{279}$ | $A_{11}$ | $I_4$ | $Y_2$ | $S_1$ | $X_1$ | | | | | | | | | | | | |
| 2218 | $R_{146}$ | $H_{128}$ | $C_{11}$ | $Q_4$ | $L_3$ | $N_3$ | $X_1$ | $Y_1$ | $G_1$ | | | | | | | | | |
| 2219 | $H_{283}$ | $N_5$ | $R_5$ | $L_2$ | $X_1$ | $P_1$ | $Q_1$ | | | | | | | | | | | |
| 2220 | $D_{283}$ | $G_8$ | $N_2$ | $V_2$ | $X_1$ | $H_1$ | $T_1$ | | | | | | | | | | | |
| 2221 | $S_{285}$ | $A_6$ | $P_3$ | $C_1$ | $H_1$ | $T_1$ | $F_1$ | | | | | | | | | | | |
| 2222 | $P_{296}$ | $X_1$ | $T_1$ | | | | | | | | | | | | | | | |
| 2223 | $D_{296}$ | $N_1$ | $E_1$ | | | | | | | | | | | | | | | |
| 2224 | $A_{270}$ | $V_{17}$ | $T_6$ | $L_2$ | $X_1$ | $I_1$ | $P_1$ | | | | | | | | | | | |
| 2225 | $D_{295}$ | $E_2$ | $G_1$ | | | | | | | | | | | | | | | |
| 2226 | $L_{297}$ | $X_1$ | | | | | | | | | | | | | | | | |
| 2227 | $I_{287}$ | $V_8$ | $L_2$ | $X_1$ | | | | | | | | | | | | | | |
| 2228 | $E_{293}$ | $D_5$ | | | | | | | | | | | | | | | | |
| 2229 | $A_{298}$ | | | | | | | | | | | | | | | | | |
| 2230 | $N_{293}$ | $X_2$ | $S_2$ | $H_1$ | | | | | | | | | | | | | | |

TABLE 6-continued

| | HCV 1b Consensus Sequences | | | | | | | | | | | | | | | | | |
|---|---|---|---|---|---|---|---|---|---|---|---|---|---|---|---|---|---|---|
| | A | B | C | D | E | F | G | H | I | J | K | L | M | N | O | P | Q | R |
| 2231 | $L_{295}$ | $X_2$ | $F_1$ | | | | | | | | | | | | | | | |
| 2232 | $L_{294}$ | $M_4$ | | | | | | | | | | | | | | | | |
| 2233 | $W_{298}$ | | | | | | | | | | | | | | | | | |
| 2234 | $R_{291}$ | $W_4$ | $K_1$ | $L_1$ | $H_1$ | | | | | | | | | | | | | |
| 2235 | $Q_{296}$ | $R_1$ | $H_1$ | | | | | | | | | | | | | | | |
| 2236 | $E_{293}$ | $X_2$ | $A_1$ | $G_1$ | $V_1$ | | | | | | | | | | | | | |
| 2237 | $M_{295}$ | $L_2$ | $K_1$ | | | | | | | | | | | | | | | |
| 2238 | $G_{296}$ | $X_2$ | | | | | | | | | | | | | | | | |
| 2239 | $G_{292}$ | $S_3$ | $D_2$ | $X_1$ | | | | | | | | | | | | | | |
| 2240 | $N_{287}$ | $E_3$ | $D_3$ | $S_3$ | $K_1$ | $I_1$ | | | | | | | | | | | | |
| 2241 | $I_{296}$ | $V_1$ | $H_1$ | | | | | | | | | | | | | | | |
| 2242 | $T_{295}$ | $S_2$ | $N_1$ | | | | | | | | | | | | | | | |
| 2243 | $R_{298}$ | | | | | | | | | | | | | | | | | |
| 2244 | $V_{298}$ | | | | | | | | | | | | | | | | | |
| 2245 | $E_{298}$ | | | | | | | | | | | | | | | | | |
| 2246 | $S_{297}$ | $P_1$ | | | | | | | | | | | | | | | | |
| 2247 | $E_{294}$ | $X_3$ | $D_1$ | | | | | | | | | | | | | | | |
| 2248 | $N_{293}$ | $T_2$ | $X_2$ | $S_1$ | | | | | | | | | | | | | | |
| 2249 | $K_{296}$ | $E_1$ | $R_1$ | | | | | | | | | | | | | | | |
| 2250 | $V_{288}$ | $I_9$ | $T_1$ | | | | | | | | | | | | | | | |
| 2251 | $V_{284}$ | $I_{13}$ | $X_1$ | | | | | | | | | | | | | | | |
| 2252 | $I_{281}$ | $V_{17}$ | | | | | | | | | | | | | | | | |
| 2253 | $L_{295}$ | $M_2$ | $X_1$ | | | | | | | | | | | | | | | |
| 2254 | $D_{298}$ | | | | | | | | | | | | | | | | | |
| 2255 | $S_{297}$ | $X_1$ | | | | | | | | | | | | | | | | |
| 2256 | $F_{295}$ | $X_2$ | $L_1$ | | | | | | | | | | | | | | | |
| 2257 | $D_{218}$ | $E_{74}$ | $V_4$ | $G_1$ | $C_1$ | | | | | | | | | | | | | |
| 2258 | $P_{296}$ | $Q_1$ | $S_1$ | | | | | | | | | | | | | | | |
| 2259 | $L_{291}$ | $I_4$ | $V_1$ | $P_1$ | $C_1$ | | | | | | | | | | | | | |
| 2260 | $R_{275}$ | $Q_{13}$ | $H_6$ | $V_2$ | $G_1$ | $Y_1$ | | | | | | | | | | | | |
| 2261 | $A_{292}$ | $V_4$ | $T_2$ | | | | | | | | | | | | | | | |
| 2262 | $E_{294}$ | $A_1$ | $D_1$ | $G_1$ | $V_1$ | | | | | | | | | | | | | |
| 2263 | $E_{290}$ | $K_2$ | $X_2$ | $G_2$ | $D_2$ | $R_1$ | | | | | | | | | | | | |
| 2264 | $D_{284}$ | $E_8$ | $G_5$ | $S_1$ | $N_1$ | | | | | | | | | | | | | |
| 2265 | $E_{279}$ | $D_9$ | $V_5$ | $G_4$ | $Q_2$ | | | | | | | | | | | | | |
| 2266 | $R_{271}$ | $G_{19}$ | $K_6$ | $W_2$ | $N_1$ | | | | | | | | | | | | | |
| 2267 | $E_{299}$ | | | | | | | | | | | | | | | | | |
| 2268 | $V_{218}$ | $I_{62}$ | $M_8$ | $P_8$ | $E_1$ | $R_1$ | $L_1$ | | | | | | | | | | | |
| 2269 | $S_{299}$ | | | | | | | | | | | | | | | | | |
| 2270 | $V_{282}$ | $I_{13}$ | $L_2$ | $X_1$ | $A_1$ | | | | | | | | | | | | | |
| 2271 | $P_{218}$ | $A_{64}$ | $E_{16}$ | $T_1$ | | | | | | | | | | | | | | |
| 2272 | $A_{296}$ | $S_2$ | $E_1$ | | | | | | | | | | | | | | | |
| 2273 | $E_{296}$ | $X_2$ | $D_1$ | | | | | | | | | | | | | | | |
| 2274 | $I_{295}$ | $V_3$ | $X_1$ | | | | | | | | | | | | | | | |
| 2275 | $L_{298}$ | $P_1$ | | | | | | | | | | | | | | | | |
| 2276 | $R_{288}$ | $L_7$ | $Q_2$ | $W_2$ | | | | | | | | | | | | | | |
| 2277 | $K_{230}$ | $R_{68}$ | $T_1$ | | | | | | | | | | | | | | | |
| 2278 | $S_{230}$ | $T_{60}$ | $P_8$ | $N_1$ | | | | | | | | | | | | | | |
| 2279 | $R_{244}$ | $K_{53}$ | $G_2$ | | | | | | | | | | | | | | | |
| 2280 | $K_{262}$ | $R_{25}$ | $N_3$ | $E_3$ | $X_1$ | $D_1$ | $A_1$ | $V_1$ | $S_1$ | $G_1$ | | | | | | | | |
| 2281 | $F_{298}$ | $Y_1$ | | | | | | | | | | | | | | | | |
| 2282 | $P_{296}$ | $X_2$ | $T_1$ | | | | | | | | | | | | | | | |
| 2283 | $P_{169}$ | $R_{70}$ | $S_{27}$ | $A_{16}$ | $L_8$ | $Q_6$ | $T_2$ | $M_1$ | | | | | | | | | | |
| 2284 | $A_{298}$ | $X_1$ | | | | | | | | | | | | | | | | |
| 2285 | $M_{186}$ | $L_{92}$ | $I_{18}$ | $V_3$ | | | | | | | | | | | | | | |
| 2286 | $P_{298}$ | $L_1$ | | | | | | | | | | | | | | | | |
| 2287 | $I_{228}$ | $V_{70}$ | $E_1$ | | | | | | | | | | | | | | | |
| 2288 | $W_{299}$ | | | | | | | | | | | | | | | | | |
| 2289 | $A_{297}$ | $T_1$ | $X_1$ | | | | | | | | | | | | | | | |
| 2290 | $R_{295}$ | $P_2$ | $H_1$ | $Q_1$ | | | | | | | | | | | | | | |
| 2291 | $P_{298}$ | $A_1$ | | | | | | | | | | | | | | | | |
| 2292 | $D_{294}$ | $E_3$ | $G_1$ | $N_1$ | | | | | | | | | | | | | | |
| 2293 | $Y_{298}$ | $H_1$ | | | | | | | | | | | | | | | | |
| 2294 | $N_{298}$ | $Y_1$ | | | | | | | | | | | | | | | | |
| 2295 | $P_{299}$ | | | | | | | | | | | | | | | | | |
| 2296 | $P_{299}$ | | | | | | | | | | | | | | | | | |
| 2297 | $L_{297.}$ | $I_1$ | $V_1$ | | | | | | | | | | | | | | | |
| 2298 | $L_{224}$ | $I_{40}$ | $V_{34}$ | $M_1$ | | | | | | | | | | | | | | |
| 2299 | $E_{295}$ | $Q_4$ | | | | | | | | | | | | | | | | |
| 2300 | $S_{263}$ | $P_{28}$ | $T_4$ | $A_3$ | $X_1$ | | | | | | | | | | | | | |
| 2301 | $W_{299}$ | | | | | | | | | | | | | | | | | |
| 2302 | $K_{286}$ | $R_{12}$ | $E_1$ | | | | | | | | | | | | | | | |
| 2303 | $D_{255}$ | $N_{24}$ | $A_6$ | $K_5$ | $S_5$ | $R_2$ | $G_2$ | | | | | | | | | | | |
| 2304 | $P_{299}$ | | | | | | | | | | | | | | | | | |
| 2305 | $D_{285}$ | $A_5$ | $E_4$ | $N_4$ | $G_1$ | | | | | | | | | | | | | |
| 2306 | $Y_{298}$ | $S_1$ | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 2307 | $V_{276}$ | $I_8$ | $A_5$ | $T_4$ | $D_2$ | $E_1$ | $S_1$ | $N_1$ | $P_1$ | | | | | | | | | |
| 2308 | $P_{298}$ | $L_1$ | | | | | | | | | | | | | | | | |
| 2309 | $P_{297}$ | $X_2$ | | | | | | | | | | | | | | | | |
| 2310 | $V_{292}$ | $A_5$ | $G_1$ | $L_1$ | | | | | | | | | | | | | | |
| 2311 | $V_{298}$ | $X_1$ | | | | | | | | | | | | | | | | |
| 2312 | $H_{296}$ | $R_1$ | $Y_1$ | $L_1$ | | | | | | | | | | | | | | |
| 2313 | $G_{298}$ | | | | | | | | | | | | | | | | | |
| 2314 | $C_{298}$ | | | | | | | | | | | | | | | | | |
| 2315 | $P_{297}$ | $A_1$ | | | | | | | | | | | | | | | | |
| 2316 | $L_{297}$ | $F_1$ | | | | | | | | | | | | | | | | |
| 2317 | $P_{297}$ | $S_1$ | | | | | | | | | | | | | | | | |
| 2318 | $P_{291}$ | $S_7$ | | | | | | | | | | | | | | | | |
| 2319 | $T_{209}$ | $A_{63}$ | $V_{13}$ | $I_8$ | $P_2$ | $N_1$ | $S_1$ | $D_1$ | | | | | | | | | | |
| 2320 | $K_{265}$ | $R_{18}$ | $T_8$ | $E_3$ | $G_3$ | | | | | | | | | | | | | |
| 2321 | $A_{255}$ | $T_{20}$ | $G_{10}$ | $V_7$ | $N_1$ | $I_1$ | $E_1$ | $S_1$ | $D_1$ | | | | | | | | | |
| 2322 | $P_{292}$ | $A_3$ | $H_1$ | $L_1$ | | | | | | | | | | | | | | |
| 2323 | $P_{297}$ | | | | | | | | | | | | | | | | | |
| 2324 | $I_{266}$ | $V_{28}$ | $L_2$ | $T_1$ | | | | | | | | | | | | | | |
| 2325 | $P_{295}$ | $L_1$ | $S_1$ | | | | | | | | | | | | | | | |
| 2326 | $P_{297}$ | | | | | | | | | | | | | | | | | |
| 2327 | $P_{296}$ | $Q_1$ | | | | | | | | | | | | | | | | |
| 2328 | $R_{296}$ | $X_1$ | | | | | | | | | | | | | | | | |
| 2329 | $R_{274}$ | $K_{23}$ | | | | | | | | | | | | | | | | |
| 2330 | $K_{294}$ | $R_3$ | | | | | | | | | | | | | | | | |
| 2331 | $R_{283}$ | $K_{14}$ | | | | | | | | | | | | | | | | |
| 2332 | $T_{293}$ | $A_2$ | $V_1$ | | | | | | | | | | | | | | | |
| 2333 | $V_{283}$ | $I_9$ | $X_1$ | $F_1$ | | | | | | | | | | | | | | |
| 2334 | $V_{282}$ | $I_{10}$ | $A_1$ | | | | | | | | | | | | | | | |
| 2335 | $L_{293}$ | | | | | | | | | | | | | | | | | |
| 2336 | $T_{282}$ | $S_{11}$ | | | | | | | | | | | | | | | | |
| 2337 | $E_{288}$ | $D_4$ | $G_1$ | | | | | | | | | | | | | | | |
| 2338 | $S_{293}$ | | | | | | | | | | | | | | | | | |
| 2339 | $T_{278}$ | $N_8$ | $S_6$ | $A_1$ | | | | | | | | | | | | | | |
| 2340 | $V_{288}$ | $L_3$ | $M_2$ | | | | | | | | | | | | | | | |
| 2341 | $S_{291}$ | $P_1$ | $A_1$ | | | | | | | | | | | | | | | |
| 2342 | $S_{291}$ | $T_1$ | $A_1$ | | | | | | | | | | | | | | | |
| 2343 | $A_{288}$ | $V_4$ | $S_1$ | | | | | | | | | | | | | | | |
| 2344 | $L_{293}$ | | | | | | | | | | | | | | | | | |
| 2345 | $A_{293}$ | | | | | | | | | | | | | | | | | |
| 2346 | $E_{291}$ | $G_1$ | $D_1$ | | | | | | | | | | | | | | | |
| 2347 | $L_{291}$ | $F_2$ | | | | | | | | | | | | | | | | |
| 2348 | $A_{290}$ | $X_1$ | $P_1$ | $G_1$ | | | | | | | | | | | | | | |
| 2349 | $T_{272}$ | $A_{10}$ | $V_5$ | $K_3$ | $I_3$ | | | | | | | | | | | | | |
| 2350 | $K_{287}$ | $R_2$ | $E_1$ | $T_1$ | $S_1$ | $Q_1$ | | | | | | | | | | | | |
| 2351 | $T_{287}$ | $A_5$ | $S_1$ | | | | | | | | | | | | | | | |
| 2352 | $F_{293}$ | | | | | | | | | | | | | | | | | |
| 2353 | $G_{259}$ | $S_{31}$ | $D_2$ | $C_1$ | | | | | | | | | | | | | | |
| 2354 | $S_{264}$ | $G_{20}$ | $N_7$ | $D_2$ | | | | | | | | | | | | | | |
| 2355 | $S_{290}$ | $P_2$ | $F_1$ | | | | | | | | | | | | | | | |
| 2356 | $E_{152}$ | $G_{128}$ | $K_5$ | $D_3$ | $T_1$ | $R_1$ | $X_1$ | $M_1$ | $V_1$ | | | | | | | | | |
| 2357 | $S_{282}$ | $P_4$ | $T_3$ | $L_3$ | $A_1$ | | | | | | | | | | | | | |
| 2358 | $S_{278}$ | $P_6$ | $A_3$ | $T_2$ | $L_2$ | $R_1$ | $E_1$ | | | | | | | | | | | |
| 2359 | $A_{270}$ | $G_9$ | $I_5$ | $S_3$ | $T_3$ | $V_2$ | $C_1$ | | | | | | | | | | | |
| 2360 | $V_{222}$ | $A_{52}$ | $I_{10}$ | $G_4$ | $X_1$ | $D_1$ | $S_1$ | $P_1$ | $T_1$ | | | | | | | | | |
| 2361 | $D_{287}$ | $G_3$ | $A_2$ | $N_1$ | | | | | | | | | | | | | | |
| 2362 | $S_{285}$ | $G_4$ | $N_3$ | $R_1$ | | | | | | | | | | | | | | |
| 2363 | $G_{287}$ | $S_5$ | $R_1$ | | | | | | | | | | | | | | | |
| 2364 | $T_{275}$ | $A_6$ | $V_6$ | $M_5$ | $I_1$ | | | | | | | | | | | | | |
| 2365 | $A_{283}$ | $V_5$ | $S_2$ | $E_1$ | $T_1$ | $M_1$ | | | | | | | | | | | | |
| 2366 | $T_{264}$ | $S_{20}$ | $A_4$ | $I_4$ | $P_1$ | | | | | | | | | | | | | |
| 2367 | $A_{274}$ | $G_{14}$ | $T_3$ | $D_1$ | $I_1$ | | | | | | | | | | | | | |
| 2368 | $P_{273}$ | $S_{13}$ | $L_5$ | $Y_1$ | $C_1$ | | | | | | | | | | | | | |
| 2369 | $P_{284}$ | $H_4$ | $L_4$ | $S_1$ | | | | | | | | | | | | | | |
| 2370 | $D_{265}$ | $G_{20}$ | $N_3$ | $E_3$ | $T_2$ | | | | | | | | | | | | | |
| 2371 | $Q_{282}$ | $L_4$ | $R_2$ | $E_2$ | $H_2$ | $G_1$ | | | | | | | | | | | | |
| 2372 | $P_{162}$ | $A_{73}$ | $S_{23}$ | $T_{19}$ | $L_{12}$ | $V_3$ | $I_1$ | | | | | | | | | | | |
| 2373 | $S_{257}$ | $P_{19}$ | $L_8$ | $F_6$ | $A_1$ | $Y_1$ | $T_1$ | | | | | | | | | | | |
| 2374 | $D_{242}$ | $N_{19}$ | $G_{14}$ | $E_6$ | $S_5$ | $A_5$ | $K_2$ | | | | | | | | | | | |
| 2375 | $D_{210}$ | $N_{48}$ | $G_{10}$ | $E_9$ | $S_6$ | $A_5$ | $C_3$ | $V_1$ | $Y_1$ | | | | | | | | | |
| 2376 | $G_{278}$ | $D_{12}$ | $E_1$ | $S_1$ | $V_1$ | | | | | | | | | | | | | |
| 2377 | $D_{245}$ | $G_{43}$ | $N_2$ | $A_1$ | $H_1$ | $E_1$ | | | | | | | | | | | | |
| 2378 | $A_{124}$ | $T_{109}$ | $K_{44}$ | $R_5$ | $S_4$ | $P_1$ | $M_1$ | $G_1$ | $V_1$ | $L_1$ | $N_1$ | $Q_1$ | | | | | | |
| 2379 | $G_{255}$ | $E_{28}$ | $R_4$ | $S_2$ | $C_1$ | $D_1$ | $A_1$ | $K_1$ | | | | | | | | | | |
| 2380 | $S_{290}$ | $T_3$ | | | | | | | | | | | | | | | | |
| 2381 | $D_{293}$ | | | | | | | | | | | | | | | | | |
| 2382 | $V_{229}$ | $A_{58}$ | $I_4$ | $G_1$ | $T_1$ | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 2383 | $E_{245}$ | $G_{48}$ | | | | | | | | | | | | | | | | |
| 2384 | $S_{291}$ | $A_1$ | $E_1$ | | | | | | | | | | | | | | | |
| 2385 | $Y_{276}$ | $C_8$ | $H_6$ | $F_2$ | $A_1$ | | | | | | | | | | | | | |
| 2386 | $S_{292}$ | $P_1$ | | | | | | | | | | | | | | | | |
| 2387 | $S_{293}$ | | | | | | | | | | | | | | | | | |
| 2388 | $M_{291}$ | $T_2$ | | | | | | | | | | | | | | | | |
| 2389 | $P_{293}$ | | | | | | | | | | | | | | | | | |
| 2390 | $P_{293}$ | | | | | | | | | | | | | | | | | |
| 2391 | $L_{293}$ | | | | | | | | | | | | | | | | | |
| 2392 | $E_{293}$ | | | | | | | | | | | | | | | | | |
| 2393 | $G_{293}$ | | | | | | | | | | | | | | | | | |
| 2394 | $E_{293}$ | | | | | | | | | | | | | | | | | |
| 2395 | $P_{292}$ | $Q_1$ | | | | | | | | | | | | | | | | |
| 2396 | $G_{293}$ | | | | | | | | | | | | | | | | | |
| 2397 | $D_{292}$ | $T_1$ | | | | | | | | | | | | | | | | |
| 2398 | $P_{292}$ | $L_1$ | | | | | | | | | | | | | | | | |
| 2399 | $D_{293}$ | | | | | | | | | | | | | | | | | |
| 2400 | $L_{289}$ | $F_4$ | | | | | | | | | | | | | | | | |
| 2401 | $S_{291}$ | $N_2$ | | | | | | | | | | | | | | | | |
| 2402 | $D_{292}$ | $E_1$ | | | | | | | | | | | | | | | | |
| 2403 | $G_{236}$ | | | | | | | | | | | | | | | | | |
| 2404 | $S_{236}$ | | | | | | | | | | | | | | | | | |
| 2405 | $W_{234}$ | $G_2$ | | | | | | | | | | | | | | | | |
| 2406 | $S_{236}$ | $X_1$ | | | | | | | | | | | | | | | | |
| 2407 | $T_{236}$ | $S_1$ | | | | | | | | | | | | | | | | |
| 2408 | $V_{229}$ | $M_8$ | | | | | | | | | | | | | | | | |
| 2409 | $S_{235}$ | $G_1$ | $N_1$ | | | | | | | | | | | | | | | |
| 2410 | $E_{226}$ | $G_{10}$ | $D_1$ | | | | | | | | | | | | | | | |
| 2411 | $E_{234}$ | $X_{10}$ | $G_1$ | $Q_1$ | | | | | | | | | | | | | | |
| 2412 | $A_{232}$ | $D_5$ | $V_4$ | $G_3$ | $P_2$ | | | | | | | | | | | | | |
| 2413 | $S_{168}$ | $G_{70}$ | $T_2$ | $N_2$ | $E_1$ | $D_1$ | $A_1$ | $R_1$ | | | | | | | | | | |
| 2414 | $E_{236}$ | $D_5$ | $Q_4$ | $G_1$ | | | | | | | | | | | | | | |
| 2415 | $D_{238}$ | $S_2$ | $V_2$ | $N_2$ | $G_2$ | | | | | | | | | | | | | |
| 2416 | $V_{241}$ | $I_5$ | $A_1$ | $X_1$ | | | | | | | | | | | | | | |
| 2417 | $V_{245}$ | $I_3$ | | | | | | | | | | | | | | | | |
| 2418 | $C_{248}$ | | | | | | | | | | | | | | | | | |
| 2419 | $C_{244}$ | $W_3$ | $X_1$ | | | | | | | | | | | | | | | |
| 2420 | $S_{170}$ | $P_2$ | $X_1$ | | | | | | | | | | | | | | | |
| 2421 | $M_{171}$ | $L_1$ | | | | | | | | | | | | | | | | |
| 2422 | $S_{172}$ | | | | | | | | | | | | | | | | | |
| 2423 | $Y_{166}$ | $H_1$ | $S_1$ | | | | | | | | | | | | | | | |
| 2424 | $T_{155}$ | $S_{10}$ | $A_1$ | $P_1$ | | | | | | | | | | | | | | |
| 2425 | $W_{167}$ | | | | | | | | | | | | | | | | | |
| 2426 | $T_{166}$ | $A_1$ | | | | | | | | | | | | | | | | |
| 2427 | $G_{167}$ | | | | | | | | | | | | | | | | | |
| 2428 | $A_{167}$ | | | | | | | | | | | | | | | | | |
| 2429 | $L_{166}$ | $M_1$ | | | | | | | | | | | | | | | | |
| 2430 | $I_{164}$ | $V_2$ | $N_1$ | | | | | | | | | | | | | | | |
| 2431 | $T_{166}$ | $P_1$ | | | | | | | | | | | | | | | | |
| 2432 | $P_{167}$ | | | | | | | | | | | | | | | | | |
| 2433 | $C_{167}$ | | | | | | | | | | | | | | | | | |
| 2434 | $A_{135}$ | $S_{31}$ | $G_1$ | | | | | | | | | | | | | | | |
| 2435 | $A_{167}$ | | | | | | | | | | | | | | | | | |
| 2436 | $E_{167}$ | | | | | | | | | | | | | | | | | |
| 2437 | $E_{165}$ | $G_2$ | | | | | | | | | | | | | | | | |
| 2438 | $S_{159}$ | $T_5$ | $N_3$ | | | | | | | | | | | | | | | |
| 2439 | $K_{165}$ | $Q_1$ | $E_1$ | | | | | | | | | | | | | | | |
| 2440 | $L_{167}$ | | | | | | | | | | | | | | | | | |
| 2441 | $P_{167}$ | | | | | | | | | | | | | | | | | |
| 2442 | $I_{167}$ | | | | | | | | | | | | | | | | | |
| 2443 | $N_{166}$ | $I_1$ | | | | | | | | | | | | | | | | |
| 2444 | $A_{128}$ | $P_{38}$ | $S_1$ | | | | | | | | | | | | | | | |
| 2445 | $L_{167}$ | | | | | | | | | | | | | | | | | |
| 2446 | $S_{165}$ | $I_1$ | $N_1$ | | | | | | | | | | | | | | | |
| 2447 | $N_{166}$ | $Y_1$ | | | | | | | | | | | | | | | | |
| 2448 | $S_{162}$ | $P_4$ | $T_1$ | | | | | | | | | | | | | | | |
| 2449 | $L_{166}$ | $Q_1$ | | | | | | | | | | | | | | | | |
| 2450 | $L_{167}$ | | | | | | | | | | | | | | | | | |
| 2451 | $R_{167}$ | | | | | | | | | | | | | | | | | |
| 2452 | $H_{163}$ | $N_3$ | $R_1$ | | | | | | | | | | | | | | | |
| 2453 | $H_{166}$ | $R_1$ | | | | | | | | | | | | | | | | |
| 2454 | $N_{164}$ | $S_3$ | | | | | | | | | | | | | | | | |
| 2455 | $M_{159}$ | $L_8$ | | | | | | | | | | | | | | | | |
| 2456 | $V_{162}$ | $I_5$ | | | | | | | | | | | | | | | | |
| 2457 | $Y_{167}$ | | | | | | | | | | | | | | | | | |
| 2458 | $A_{157}$ | $S_8$ | $T_1$ | $V_1$ | | | | | | | | | | | | | | |

TABLE 6-continued

| | HCV 1b Consensus Sequences | | | | | | | | | | | | | | | | |
|---|---|---|---|---|---|---|---|---|---|---|---|---|---|---|---|---|---|
| | A | B | C | D | E | F | G | H | I | J | K | L | M | N | O | P | Q | R |
| 2459 | $T_{166}$ | $A_1$ | | | | | | | | | | | | | | | | |
| 2460 | $T_{167}$ | | | | | | | | | | | | | | | | | |
| 2461 | $S_{167}$ | | | | | | | | | | | | | | | | | |
| 2462 | $R_{167}$ | | | | | | | | | | | | | | | | | |
| 2463 | $S_{166}$ | $I_1$ | | | | | | | | | | | | | | | | |
| 2464 | $A_{167}$ | | | | | | | | | | | | | | | | | |
| 2465 | $S_{136}$ | $G_{26}$ | $C_4$ | $V_1$ | | | | | | | | | | | | | | |
| 2466 | $Q_{107}$ | $L_{60}$ | | | | | | | | | | | | | | | | |
| 2467 | $R_{167}$ | | | | | | | | | | | | | | | | | |
| 2468 | $Q_{167}$ | | | | | | | | | | | | | | | | | |
| 2469 | $K_{162}$ | $R_5$ | | | | | | | | | | | | | | | | |
| 2470 | $K_{167}$ | | | | | | | | | | | | | | | | | |
| 2471 | $V_{167}$ | | | | | | | | | | | | | | | | | |
| 2472 | $T_{166}$ | $A_1$ | | | | | | | | | | | | | | | | |
| 2473 | $F_{165}$ | $I_2$ | | | | | | | | | | | | | | | | |
| 2474 | $D_{167}$ | | | | | | | | | | | | | | | | | |
| 2475 | $R_{167}$ | | | | | | | | | | | | | | | | | |
| 2476 | $L_{153}$ | $M_9$ | $Q_5$ | | | | | | | | | | | | | | | |
| 2477 | $Q_{167}$ | | | | | | | | | | | | | | | | | |
| 2478 | $V_{167}$ | | | | | | | | | | | | | | | | | |
| 2479 | $L_{166}$ | $Q_1$ | | | | | | | | | | | | | | | | |
| 2480 | $D_{166}$ | $E_1$ | | | | | | | | | | | | | | | | |
| 2481 | $D_{162}$ | $N_3$ | $S_1$ | $K_1$ | | | | | | | | | | | | | | |
| 2482 | $H_{167}$ | | | | | | | | | | | | | | | | | |
| 2483 | $Y_{167}$ | | | | | | | | | | | | | | | | | |
| 2484 | $R_{159}$ | $Q_7$ | $W_1$ | | | | | | | | | | | | | | | |
| 2485 | $D_{166}$ | $G_1$ | | | | | | | | | | | | | | | | |
| 2486 | $V_{167}$ | | | | | | | | | | | | | | | | | |
| 2487 | $L_{167}$ | | | | | | | | | | | | | | | | | |
| 2488 | $K_{167}$ | | | | | | | | | | | | | | | | | |
| 2489 | $E_{164}$ | $D_2$ | $G_1$ | | | | | | | | | | | | | | | |
| 2490 | $M_{163}$ | $V_3$ | $I_1$ | | | | | | | | | | | | | | | |
| 2491 | $K_{166}$ | $N_1$ | | | | | | | | | | | | | | | | |
| 2492 | $A_{164}$ | $V_3$ | | | | | | | | | | | | | | | | |
| 2493 | $K_{166}$ | $E_1$ | | | | | | | | | | | | | | | | |
| 2494 | $A_{167}$ | | | | | | | | | | | | | | | | | |
| 2495 | $S_{167}$ | | | | | | | | | | | | | | | | | |
| 2496 | $T_{166}$ | $K_1$ | | | | | | | | | | | | | | | | |
| 2497 | $V_{167}$ | | | | | | | | | | | | | | | | | |
| 2498 | $K_{163}$ | $R_2$ | $N_1$ | | | | | | | | | | | | | | | |
| 2499 | $A_{166}$ | | | | | | | | | | | | | | | | | |
| 2500 | $K_{144}$ | $R_{22}$ | | | | | | | | | | | | | | | | |
| 2501 | $L_{165}$ | $F_1$ | | | | | | | | | | | | | | | | |
| 2502 | $L_{166}$ | | | | | | | | | | | | | | | | | |
| 2503 | $S_{163}$ | $P_2$ | $T_1$ | | | | | | | | | | | | | | | |
| 2504 | $V_{124}$ | $I_{41}$ | $L_1$ | | | | | | | | | | | | | | | |
| 2505 | $E_{166}$ | | | | | | | | | | | | | | | | | |
| 2506 | $E_{165}$ | $X_1$ | | | | | | | | | | | | | | | | |
| 2507 | $A_{165}$ | $P_1$ | | | | | | | | | | | | | | | | |
| 2508 | $C_{166}$ | | | | | | | | | | | | | | | | | |
| 2509 | $K_{136}$ | $M_{22}$ | $R_6$ | $Q_1$ | $N_1$ | | | | | | | | | | | | | |
| 2510 | $L_{165}$ | $W_1$ | | | | | | | | | | | | | | | | |
| 2511 | $T_{166}$ | | | | | | | | | | | | | | | | | |
| 2512 | $P_{166}$ | | | | | | | | | | | | | | | | | |
| 2513 | $P_{166}$ | | | | | | | | | | | | | | | | | |
| 2514 | $H_{164}$ | $Q_1$ | $L_1$ | | | | | | | | | | | | | | | |
| 2515 | $S_{166}$ | | | | | | | | | | | | | | | | | |
| 2516 | $A_{166}$ | | | | | | | | | | | | | | | | | |
| 2517 | $K_{108}$ | $R_{57}$ | $S_1$ | | | | | | | | | | | | | | | |
| 2518 | $S_{165}$ | $L_1$ | | | | | | | | | | | | | | | | |
| 2519 | $K_{163}$ | $Q_3$ | | | | | | | | | | | | | | | | |
| 2520 | $F_{156}$ | $Y_8$ | $V_1$ | $S_1$ | | | | | | | | | | | | | | |
| 2521 | $G_{166}$ | | | | | | | | | | | | | | | | | |
| 2522 | $Y_{166}$ | $X_1$ | | | | | | | | | | | | | | | | |
| 2523 | $G_{167}$ | | | | | | | | | | | | | | | | | |
| 2524 | $A_{166}$ | $G_1$ | | | | | | | | | | | | | | | | |
| 2525 | $K_{166}$ | $S_1$ | | | | | | | | | | | | | | | | |
| 2526 | $D_{167}$ | | | | | | | | | | | | | | | | | |
| 2527 | $V_{167}$ | | | | | | | | | | | | | | | | | |
| 2528 | $R_{167}$ | | | | | | | | | | | | | | | | | |
| 2529 | $N_{136}$ | $S_{31}$ | | | | | | | | | | | | | | | | |
| 2530 | $L_{167}$ | | | | | | | | | | | | | | | | | |
| 2531 | $S_{164}$ | $T_3$ | | | | | | | | | | | | | | | | |
| 2532 | $S_{148}$ | $G_{13}$ | $N_3$ | $R_3$ | | | | | | | | | | | | | | |
| 2533 | $K_{132}$ | $R_{34}$ | $G_1$ | | | | | | | | | | | | | | | |
| 2534 | $A_{167}$ | | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 2535 | $V_{121}$ | $I_{37}$ | $T_8$ | $L_1$ | | | | | | | | | | | | | | |
| 2536 | $N_{152}$ | $D_5$ | $K_3$ | $S_3$ | $R_2$ | $T_2$ | | | | | | | | | | | | |
| 2537 | $H_{167}$ | | | | | | | | | | | | | | | | | |
| 2538 | $I_{167}$ | | | | | | | | | | | | | | | | | |
| 2539 | $R_{117}$ | $H_{39}$ | $N_6$ | $S_2$ | $L_2$ | $T_1$ | | | | | | | | | | | | |
| 2540 | $S_{167}$ | | | | | | | | | | | | | | | | | |
| 2541 | $V_{167}$ | | | | | | | | | | | | | | | | | |
| 2542 | $W_{167}$ | | | | | | | | | | | | | | | | | |
| 2543 | $K_{134}$ | $E_{33}$ | | | | | | | | | | | | | | | | |
| 2544 | $D_{167}$ | | | | | | | | | | | | | | | | | |
| 2545 | $L_{166}$ | $S_1$ | | | | | | | | | | | | | | | | |
| 2546 | $L_{165}$ | $Q_2$ | | | | | | | | | | | | | | | | |
| 2547 | $E_{166}$ | $D_1$ | | | | | | | | | | | | | | | | |
| 2548 | $D_{167}$ | | | | | | | | | | | | | | | | | |
| 2549 | $T_{147}$ | $S_9$ | $N_8$ | $P_2$ | $D_1$ | | | | | | | | | | | | | |
| 2550 | $E_{133}$ | $V_{12}$ | $D_{12}$ | $Q_6$ | $A_2$ | $K_1$ | $I_1$ | | | | | | | | | | | |
| 2551 | $T_{167}$ | | | | | | | | | | | | | | | | | |
| 2552 | $P_{167}$ | | | | | | | | | | | | | | | | | |
| 2553 | $I_{161}$ | $L_5$ | $F_1$ | | | | | | | | | | | | | | | |
| 2554 | $D_{138}$ | $N_{17}$ | $Q_4$ | $S_3$ | $E_2$ | $T_1$ | $I_1$ | $P_1$ | | | | | | | | | | |
| 2555 | $T_{167}$ | | | | | | | | | | | | | | | | | |
| 2556 | $T_{166}$ | $V_1$ | | | | | | | | | | | | | | | | |
| 2557 | $I_{151}$ | $V_{16}$ | | | | | | | | | | | | | | | | |
| 2558 | $M_{167}$ | | | | | | | | | | | | | | | | | |
| 2559 | $A_{167}$ | | | | | | | | | | | | | | | | | |
| 2560 | $K_{167}$ | | | | | | | | | | | | | | | | | |
| 2561 | $N_{144}$ | $S_{23}$ | | | | | | | | | | | | | | | | |
| 2562 | $E_{167}$ | | | | | | | | | | | | | | | | | |
| 2563 | $V_{162}$ | $I_5$ | | | | | | | | | | | | | | | | |
| 2564 | $F_{166}$ | $I_1$ | | | | | | | | | | | | | | | | |
| 2565 | $C_{164}$ | $V_2$ | $D_1$ | | | | | | | | | | | | | | | |
| 2566 | $V_{161}$ | $I_5$ | $L_1$ | | | | | | | | | | | | | | | |
| 2567 | $Q_{164}$ | $D_1$ | $K_1$ | $E_1$ | | | | | | | | | | | | | | |
| 2568 | $P_{167}$ | | | | | | | | | | | | | | | | | |
| 2569 | $E_{165}$ | $T_1$ | $X_1$ | | | | | | | | | | | | | | | |
| 2570 | $K_{165}$ | $M_1$ | $R_1$ | | | | | | | | | | | | | | | |
| 2571 | $G_{167}$ | | | | | | | | | | | | | | | | | |
| 2572 | $G_{167}$ | | | | | | | | | | | | | | | | | |
| 2573 | $R_{167}$ | | | | | | | | | | | | | | | | | |
| 2574 | $K_{167}$ | | | | | | | | | | | | | | | | | |
| 2575 | $P_{160}$ | $A_5$ | $S_2$ | | | | | | | | | | | | | | | |
| 2576 | $A_{167}$ | | | | | | | | | | | | | | | | | |
| 2577 | $R_{167}$ | | | | | | | | | | | | | | | | | |
| 2578 | $L_{163}$ | $F_4$ | | | | | | | | | | | | | | | | |
| 2579 | $I_{167}$ | | | | | | | | | | | | | | | | | |
| 2580 | $V_{167}$ | | | | | | | | | | | | | | | | | |
| 2581 | $F_{164}$ | $Y_3$ | | | | | | | | | | | | | | | | |
| 2582 | $P_{167}$ | | | | | | | | | | | | | | | | | |
| 2583 | $D_{167}$ | | | | | | | | | | | | | | | | | |
| 2584 | $L_{167}$ | | | | | | | | | | | | | | | | | |
| 2585 | $G_{167}$ | | | | | | | | | | | | | | | | | |
| 2586 | $V_{167}$ | | | | | | | | | | | | | | | | | |
| 2587 | $R_{167}$ | | | | | | | | | | | | | | | | | |
| 2588 | $V_{166}$ | $I_1$ | | | | | | | | | | | | | | | | |
| 2589 | $C_{167}$ | | | | | | | | | | | | | | | | | |
| 2590 | $E_{167}$ | | | | | | | | | | | | | | | | | |
| 2591 | $K_{167}$ | | | | | | | | | | | | | | | | | |
| 2592 | $M_{167}$ | | | | | | | | | | | | | | | | | |
| 2593 | $A_{167}$ | | | | | | | | | | | | | | | | | |
| 2594 | $L_{167}$ | | | | | | | | | | | | | | | | | |
| 2595 | $Y_{167}$ | | | | | | | | | | | | | | | | | |
| 2596 | $D_{166}$ | $N_1$ | | | | | | | | | | | | | | | | |
| 2597 | $V_{166}$ | $X_1$ | | | | | | | | | | | | | | | | |
| 2598 | $V_{167}$ | | | | | | | | | | | | | | | | | |
| 2599 | $S_{167}$ | | | | | | | | | | | | | | | | | |
| 2600 | $T_{163}$ | $N_3$ | $I_1$ | | | | | | | | | | | | | | | |
| 2601 | $L_{167}$ | | | | | | | | | | | | | | | | | |
| 2602 | $P_{167}$ | | | | | | | | | | | | | | | | | |
| 2603 | $Q_{159}$ | $H_6$ | $K_1$ | $R_1$ | | | | | | | | | | | | | | |
| 2604 | $A_{163}$ | $V_2$ | $P_1$ | $T_1$ | | | | | | | | | | | | | | |
| 2605 | $V_{167}$ | | | | | | | | | | | | | | | | | |
| 2606 | $M_{167}$ | | | | | | | | | | | | | | | | | |
| 2607 | $G_{167}$ | | | | | | | | | | | | | | | | | |
| 2608 | $S_{150}$ | $P_{13}$ | $A_4$ | | | | | | | | | | | | | | | |
| 2609 | $S_{161}$ | $A_5$ | $L_1$ | | | | | | | | | | | | | | | |
| 2610 | $Y_{166}$ | $F_1$ | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 2611 | $G_{167}$ | | | | | | | | | | | | | | | | | |
| 2612 | $F_{166}$ | $C_1$ | | | | | | | | | | | | | | | | |
| 2613 | $Q_{167}$ | | | | | | | | | | | | | | | | | |
| 2614 | $Y_{167}$ | | | | | | | | | | | | | | | | | |
| 2615 | $S_{167}$ | | | | | | | | | | | | | | | | | |
| 2616 | $P_{165}$ | $L_1$ | $S_1$ | | | | | | | | | | | | | | | |
| 2617 | $G_{143}$ | $K_{21}$ | $A_2$ | $S_1$ | | | | | | | | | | | | | | |
| 2618 | $Q_{166}$ | $H_1$ | | | | | | | | | | | | | | | | |
| 2619 | $R_{167}$ | | | | | | | | | | | | | | | | | |
| 2620 | $V_{167}$ | | | | | | | | | | | | | | | | | |
| 2621 | $E_{163}$ | $D_3$ | $Q_1$ | | | | | | | | | | | | | | | |
| 2622 | $F_{167}$ | | | | | | | | | | | | | | | | | |
| 2623 | $L_{167}$ | | | | | | | | | | | | | | | | | |
| 2624 | $V_{166}$ | $L_1$ | | | | | | | | | | | | | | | | |
| 2625 | $N_{155}$ | $K_{11}$ | $D_1$ | | | | | | | | | | | | | | | |
| 2626 | $A_{129}$ | $T_{38}$ | | | | | | | | | | | | | | | | |
| 2627 | $W_{167}$ | | | | | | | | | | | | | | | | | |
| 2628 | $K_{166}$ | $S_1$ | | | | | | | | | | | | | | | | |
| 2629 | $S_{131}$ | $K_{29}$ | $A_5$ | $Q_2$ | | | | | | | | | | | | | | |
| 2630 | $K_{167}$ | | | | | | | | | | | | | | | | | |
| 2631 | $K_{158}$ | $R_7$ | $N_1$ | $E_1$ | | | | | | | | | | | | | | |
| 2632 | $N_{66}$ | $C_{57}$ | $S_{34}$ | $T_6$ | $V_2$ | $A_1$ | $K_1$ | | | | | | | | | | | |
| 2633 | $P_{166}$ | $A_1$ | | | | | | | | | | | | | | | | |
| 2634 | $M_{167}$ | | | | | | | | | | | | | | | | | |
| 2635 | $G_{165}$ | $A_1$ | $X_1$ | | | | | | | | | | | | | | | |
| 2636 | $F_{165}$ | $X_1$ | $S_1$ | | | | | | | | | | | | | | | |
| 2637 | $A_{96}$ | $S_{71}$ | | | | | | | | | | | | | | | | |
| 2638 | $Y_{167}$ | | | | | | | | | | | | | | | | | |
| 2639 | $D_{167}$ | | | | | | | | | | | | | | | | | |
| 2640 | $T_{166}$ | $A_1$ | | | | | | | | | | | | | | | | |
| 2641 | $R_{167}$ | | | | | | | | | | | | | | | | | |
| 2642 | $C_{166}$ | $R_1$ | | | | | | | | | | | | | | | | |
| 2643 | $F_{167}$ | | | | | | | | | | | | | | | | | |
| 2644 | $D_{166}$ | $E_1$ | | | | | | | | | | | | | | | | |
| 2645 | $S_{167}$ | $X_1$ | | | | | | | | | | | | | | | | |
| 2646 | $T_{168}$ | | | | | | | | | | | | | | | | | |
| 2647 | $V_{168}$ | | | | | | | | | | | | | | | | | |
| 2648 | $T_{168}$ | $X_2$ | | | | | | | | | | | | | | | | |
| 2649 | $E_{169}$ | $Q_1$ | | | | | | | | | | | | | | | | |
| 2650 | $N_{89}$ | $S_{80}$ | $H_1$ | | | | | | | | | | | | | | | |
| 2651 | $D_{170}$ | | | | | | | | | | | | | | | | | |
| 2652 | $I_{170}$ | | | | | | | | | | | | | | | | | |
| 2653 | $R_{170}$ | | | | | | | | | | | | | | | | | |
| 2654 | $V_{140}$ | $T_{24}$ | $I_5$ | $F_1$ | | | | | | | | | | | | | | |
| 2655 | $E_{169}$ | $G_1$ | | | | | | | | | | | | | | | | |
| 2656 | $E_{170}$ | | | | | | | | | | | | | | | | | |
| 2657 | $S_{169}$ | $P_1$ | | | | | | | | | | | | | | | | |
| 2658 | $I_{170}$ | | | | | | | | | | | | | | | | | |
| 2659 | $Y_{170}$ | | | | | | | | | | | | | | | | | |
| 2660 | $Q_{170}$ | | | | | | | | | | | | | | | | | |
| 2661 | $C_{156}$ | $S_{14}$ | | | | | | | | | | | | | | | | |
| 2662 | $C_{170}$ | $X_{13}$ | | | | | | | | | | | | | | | | |
| 2663 | $D_{182}$ | $E_1$ | | | | | | | | | | | | | | | | |
| 2664 | $L_{183}$ | | | | | | | | | | | | | | | | | |
| 2665 | $A_{174}$ | $V_3$ | $D_3$ | $T_1$ | $S_1$ | $G_1$ | | | | | | | | | | | | |
| 2666 | $P_{183}$ | | | | | | | | | | | | | | | | | |
| 2667 | $E_{180}$ | $D_3$ | $X_1$ | | | | | | | | | | | | | | | |
| 2668 | $A_{184}$ | | | | | | | | | | | | | | | | | |
| 2669 | $R_{164}$ | $K_{19}$ | $S_1$ | | | | | | | | | | | | | | | |
| 2670 | $Q_{168}$ | $L_{10}$ | $R_3$ | $K_2$ | $T_1$ | | | | | | | | | | | | | |
| 2671 | $A_{165}$ | $V_{19}$ | | | | | | | | | | | | | | | | |
| 2672 | $I_{184}$ | | | | | | | | | | | | | | | | | |
| 2673 | $R_{139}$ | $K_{45}$ | | | | | | | | | | | | | | | | |
| 2674 | $S_{184}$ | | | | | | | | | | | | | | | | | |
| 2675 | $L_{184}$ | | | | | | | | | | | | | | | | | |
| 2676 | $T_{184}$ | | | | | | | | | | | | | | | | | |
| 2677 | $E_{184}$ | | | | | | | | | | | | | | | | | |
| 2678 | $R_{184}$ | | | | | | | | | | | | | | | | | |
| 2679 | $L_{184}$ | | | | | | | | | | | | | | | | | |
| 2680 | $Y_{184}$ | | | | | | | | | | | | | | | | | |
| 2681 | $I_{162}$ | $V_{22}$ | | | | | | | | | | | | | | | | |
| 2682 | $G_{184}$ | | | | | | | | | | | | | | | | | |
| 2683 | $G_{184}$ | | | | | | | | | | | | | | | | | |
| 2684 | $P_{184}$ | | | | | | | | | | | | | | | | | |
| 2685 | $L_{177}$ | $M_7$ | | | | | | | | | | | | | | | | |
| 2686 | $T_{183}$ | $I_1$ | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 2687 | $N_{184}$ | | | | | | | | | | | | | | | | | |
| 2688 | $S_{184}$ | | | | | | | | | | | | | | | | | |
| 2689 | $K_{184}$ | | | | | | | | | | | | | | | | | |
| 2690 | $G_{184}$ | | | | | | | | | | | | | | | | | |
| 2691 | $Q_{184}$ | | | | | | | | | | | | | | | | | |
| 2692 | $N_{173}$ | $S_8$ | $D_2$ | $H_1$ | | | | | | | | | | | | | | |
| 2693 | $C_{184}$ | | | | | | | | | | | | | | | | | |
| 2694 | $G_{184}$ | | | | | | | | | | | | | | | | | |
| 2695 | $Y_{184}$ | | | | | | | | | | | | | | | | | |
| 2696 | $R_{184}$ | | | | | | | | | | | | | | | | | |
| 2697 | $R_{184}$ | | | | | | | | | | | | | | | | | |
| 2698 | $C_{184}$ | | | | | | | | | | | | | | | | | |
| 2699 | $R_{184}$ | | | | | | | | | | | | | | | | | |
| 2700 | $A_{181}$ | $V_2$ | $X_1$ | | | | | | | | | | | | | | | |
| 2701 | $S_{183}$ | $T_1$ | | | | | | | | | | | | | | | | |
| 2702 | $G_{183}$ | $V_1$ | | | | | | | | | | | | | | | | |
| 2703 | $V_{184}$ | | | | | | | | | | | | | | | | | |
| 2704 | $L_{184}$ | | | | | | | | | | | | | | | | | |
| 2705 | $T_{184}$ | $R_1$ | | | | | | | | | | | | | | | | |
| 2706 | $T_{184}$ | $R_1$ | | | | | | | | | | | | | | | | |
| 2707 | $S_{184}$ | $R_1$ | | | | | | | | | | | | | | | | |
| 2708 | $C_{184}$ | $X_1$ | | | | | | | | | | | | | | | | |
| 2709 | $G_{183}$ | $S_1$ | $A_1$ | | | | | | | | | | | | | | | |
| 2710 | $N_{184}$ | $X_1$ | | | | | | | | | | | | | | | | |
| 2711 | $T_{184}$ | $X_1$ | | | | | | | | | | | | | | | | |
| 2712 | $L_{182}$ | $I_2$ | $X_1$ | | | | | | | | | | | | | | | |
| 2713 | $T_{185}$ | | | | | | | | | | | | | | | | | |
| 2714 | $C_{185}$ | | | | | | | | | | | | | | | | | |
| 2715 | $Y_{182}$ | $F_2$ | $H_1$ | | | | | | | | | | | | | | | |
| 2716 | $L_{185}$ | | | | | | | | | | | | | | | | | |
| 2717 | $K_{185}$ | | | | | | | | | | | | | | | | | |
| 2718 | $A_{185}$ | | | | | | | | | | | | | | | | | |
| 2719 | $S_{149}$ | $T_{30}$ | $A_6$ | | | | | | | | | | | | | | | |
| 2720 | $A_{185}$ | | | | | | | | | | | | | | | | | |
| 2721 | $A_{185}$ | | | | | | | | | | | | | | | | | |
| 2722 | $C_{185}$ | | | | | | | | | | | | | | | | | |
| 2723 | $R_{185}$ | | | | | | | | | | | | | | | | | |
| 2724 | $A_{183}$ | $D_1$ | $V_1$ | | | | | | | | | | | | | | | |
| 2725 | $A_{184}$ | $G_1$ | | | | | | | | | | | | | | | | |
| 2726 | $K_{183}$ | $G_1$ | $X_1$ | | | | | | | | | | | | | | | |
| 2727 | $L_{184}$ | $X_1$ | | | | | | | | | | | | | | | | |
| 2728 | $Q_{165}$ | $R_{20}$ | | | | | | | | | | | | | | | | |
| 2729 | $D_{183}$ | $G_1$ | $S_1$ | | | | | | | | | | | | | | | |
| 2730 | $C_{184}$ | $Y_1$ | | | | | | | | | | | | | | | | |
| 2731 | $T_{185}$ | | | | | | | | | | | | | | | | | |
| 2732 | $M_{182}$ | $L_2$ | $T_1$ | | | | | | | | | | | | | | | |
| 2733 | $L_{185}$ | | | | | | | | | | | | | | | | | |
| 2734 | $V_{185}$ | | | | | | | | | | | | | | | | | |
| 2735 | $C_{119}$ | $N_{65}$ | $H_1$ | | | | | | | | | | | | | | | |
| 2736 | $G_{185}$ | | | | | | | | | | | | | | | | | |
| 2737 | $D_{185}$ | | | | | | | | | | | | | | | | | |
| 2738 | $D_{185}$ | | | | | | | | | | | | | | | | | |
| 2739 | $L_{184}$ | $X_1$ | | | | | | | | | | | | | | | | |
| 2740 | $V_{182}$ | $I_2$ | $X_1$ | | | | | | | | | | | | | | | |
| 2741 | $V_{183}$ | $X_1$ | $I_1$ | | | | | | | | | | | | | | | |
| 2742 | $I_{184}$ | $X_1$ | | | | | | | | | | | | | | | | |
| 2743 | $C_{184}$ | $X_1$ | | | | | | | | | | | | | | | | |
| 2744 | $E_{179}$ | $D_5$ | $X_1$ | | | | | | | | | | | | | | | |
| 2745 | $S_{183}$ | $X_1$ | $C_1$ | | | | | | | | | | | | | | | |
| 2746 | $A_{181}$ | $E_2$ | $T_1$ | $X_1$ | | | | | | | | | | | | | | |
| 2747 | $G_{184}$ | | | | | | | | | | | | | | | | | |
| 2748 | $T_{181}$ | $A_1$ | $V_1$ | $I_1$ | | | | | | | | | | | | | | |
| 2749 | $Q_{181}$ | $E_2$ | $X_1$ | | | | | | | | | | | | | | | |
| 2750 | $E_{184}$ | | | | | | | | | | | | | | | | | |
| 2751 | $D_{184}$ | | | | | | | | | | | | | | | | | |
| 2752 | $A_{169}$ | $E_{14}$ | $P_1$ | | | | | | | | | | | | | | | |
| 2753 | $A_{183}$ | $E_1$ | | | | | | | | | | | | | | | | |
| 2754 | $S_{151}$ | $N_{26}$ | $A_4$ | $R_2$ | $C_1$ | | | | | | | | | | | | | |
| 2755 | $L_{184}$ | | | | | | | | | | | | | | | | | |
| 2756 | $R_{184}$ | | | | | | | | | | | | | | | | | |
| 2757 | $V_{163}$ | $A_{20}$ | $F_1$ | | | | | | | | | | | | | | | |
| 2758 | $F_{184}$ | | | | | | | | | | | | | | | | | |
| 2759 | $T_{183}$ | $A_1$ | | | | | | | | | | | | | | | | |
| 2760 | $E_{184}$ | | | | | | | | | | | | | | | | | |
| 2761 | $A_{184}$ | | | | | | | | | | | | | | | | | |
| 2762 | $M_{184}$ | | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 2763 | $T_{184}$ | | | | | | | | | | | | | | | | | |
| 2764 | $R_{184}$ | | | | | | | | | | | | | | | | | |
| 2765 | $Y_{176}$ | $N_7$ | $X_1$ | | | | | | | | | | | | | | | |
| 2766 | $S_{182}$ | $X_1$ | | | | | | | | | | | | | | | | |
| 2767 | $A_{182}$ | $G_1$ | | | | | | | | | | | | | | | | |
| 2768 | $P_{176}$ | $H_7$ | | | | | | | | | | | | | | | | |
| 2769 | $P_{175}$ | $G_5$ | $A_2$ | $X_1$ | | | | | | | | | | | | | | |
| 2770 | $G_{174}$ | $X_4$ | $H_3$ | $A_1$ | $S_1$ | | | | | | | | | | | | | |
| 2771 | $D_{174}$ | $X_5$ | $G_1$ | $K_1$ | $E_1$ | $S_1$ | | | | | | | | | | | | |
| 2772 | $P_{162}$ | $L_{18}$ | $C_2$ | $S_1$ | | | | | | | | | | | | | | |
| 2773 | $P_{179}$ | $V_1$ | $L_1$ | | | | | | | | | | | | | | | |
| 2774 | $Q_{117}$ | $K_{47}$ | $R_{16}$ | $X_2$ | | | | | | | | | | | | | | |
| 2775 | $P_{181}$ | | | | | | | | | | | | | | | | | |
| 2776 | $E_{176}$ | $A_3$ | $V_1$ | $T_1$ | | | | | | | | | | | | | | |
| 2777 | $Y_{181}$ | | | | | | | | | | | | | | | | | |
| 2778 | $D_{181}$ | | | | | | | | | | | | | | | | | |
| 2779 | $L_{179}$ | $Q_1$ | $K_1$ | | | | | | | | | | | | | | | |
| 2780 | $E_{181}$ | | | | | | | | | | | | | | | | | |
| 2781 | $L_{176}$ | $S_2$ | $X_1$ | $R_1$ | $M_1$ | | | | | | | | | | | | | |
| 2782 | $I_{181}$ | | | | | | | | | | | | | | | | | |
| 2783 | $T_{179}$ | $I_1$ | $S_1$ | | | | | | | | | | | | | | | |
| 2784 | $S_{180}$ | $A_1$ | | | | | | | | | | | | | | | | |
| 2785 | $C_{180}$ | $R_1$ | | | | | | | | | | | | | | | | |
| 2786 | $S_{173}$ | $X_8$ | | | | | | | | | | | | | | | | |
| 2787 | $S_{172}$ | $P_1$ | | | | | | | | | | | | | | | | |
| 2788 | $N_{173}$ | | | | | | | | | | | | | | | | | |
| 2789 | $V_{173}$ | | | | | | | | | | | | | | | | | |
| 2790 | $S_{173}$ | | | | | | | | | | | | | | | | | |
| 2791 | $V_{173}$ | | | | | | | | | | | | | | | | | |
| 2792 | $A_{171}$ | $X_2$ | | | | | | | | | | | | | | | | |
| 2793 | $H_{172}$ | $Y_1$ | | | | | | | | | | | | | | | | |
| 2794 | $D_{173}$ | | | | | | | | | | | | | | | | | |
| 2795 | $A_{171}$ | $V_2$ | | | | | | | | | | | | | | | | |
| 2796 | $S_{166}$ | $A_3$ | $L_2$ | $T_1$ | $N_1$ | | | | | | | | | | | | | |
| 2797 | $G_{171}$ | $N_2$ | | | | | | | | | | | | | | | | |
| 2798 | $K_{171}$ | $R_2$ | | | | | | | | | | | | | | | | |
| 2799 | $R_{172}$ | $X_1$ | | | | | | | | | | | | | | | | |
| 2800 | $V_{173}$ | | | | | | | | | | | | | | | | | |
| 2801 | $Y_{173}$ | | | | | | | | | | | | | | | | | |
| 2802 | $Y_{173}$ | | | | | | | | | | | | | | | | | |
| 2803 | $L_{173}$ | | | | | | | | | | | | | | | | | |
| 2804 | $T_{173}$ | | | | | | | | | | | | | | | | | |
| 2805 | $R_{173}$ | | | | | | | | | | | | | | | | | |
| 2806 | $D_{171}$ | $N_2$ | | | | | | | | | | | | | | | | |
| 2807 | $P_{173}$ | | | | | | | | | | | | | | | | | |
| 2808 | $T_{161}$ | $A_5$ | $I_4$ | $S_2$ | $X_1$ | | | | | | | | | | | | | |
| 2809 | $T_{166}$ | $I_5$ | $N_1$ | $S_1$ | | | | | | | | | | | | | | |
| 2810 | $P_{172}$ | $X_1$ | | | | | | | | | | | | | | | | |
| 2811 | $L_{155}$ | $I_{14}$ | $F_4$ | | | | | | | | | | | | | | | |
| 2812 | $A_{169}$ | $S_2$ | $G_2$ | | | | | | | | | | | | | | | |
| 2813 | $R_{173}$ | | | | | | | | | | | | | | | | | |
| 2814 | $A_{171}$ | $X_1$ | $T_1$ | | | | | | | | | | | | | | | |
| 2815 | $A_{173}$ | | | | | | | | | | | | | | | | | |
| 2816 | $W_{173}$ | | | | | | | | | | | | | | | | | |
| 2817 | $E_{172}$ | $A_1$ | | | | | | | | | | | | | | | | |
| 2818 | $T_{172}$ | $A_1$ | | | | | | | | | | | | | | | | |
| 2819 | $A_{167}$ | $V_4$ | $S_1$ | $X_1$ | | | | | | | | | | | | | | |
| 2820 | $R_{167}$ | $K_6$ | | | | | | | | | | | | | | | | |
| 2821 | $H_{168}$ | $S_5$ | | | | | | | | | | | | | | | | |
| 2822 | $T_{172}$ | $I_1$ | | | | | | | | | | | | | | | | |
| 2823 | $P_{171}$ | $L_1$ | $S_1$ | | | | | | | | | | | | | | | |
| 2824 | $V_{167}$ | $I_4$ | $T_2$ | | | | | | | | | | | | | | | |
| 2825 | $N_{173}$ | | | | | | | | | | | | | | | | | |
| 2826 | $S_{172}$ | $T_1$ | | | | | | | | | | | | | | | | |
| 2827 | $W_{173}$ | | | | | | | | | | | | | | | | | |
| 2828 | $L_{173}$ | | | | | | | | | | | | | | | | | |
| 2829 | $G_{173}$ | | | | | | | | | | | | | | | | | |
| 2830 | $N_{173}$ | | | | | | | | | | | | | | | | | |
| 2831 | $I_{172}$ | $V_1$ | | | | | | | | | | | | | | | | |
| 2832 | $I_{172}$ | $M_1$ | | | | | | | | | | | | | | | | |
| 2833 | $M_{173}$ | | | | | | | | | | | | | | | | | |
| 2834 | $Y_{172}$ | $F_1$ | | | | | | | | | | | | | | | | |
| 2835 | $A_{172}$ | $G_1$ | | | | | | | | | | | | | | | | |
| 2836 | $P_{173}$ | | | | | | | | | | | | | | | | | |
| 2837 | $T_{172}$ | $A_1$ | | | | | | | | | | | | | | | | |
| 2838 | $L_{172}$ | $I_1$ | | | | | | | | | | | | | | | | |

TABLE 6-continued

| | HCV 1b Consensus Sequences | | | | | | | | | | | | | | | | | |
|---|---|---|---|---|---|---|---|---|---|---|---|---|---|---|---|---|---|---|
| | A | B | C | D | E | F | G | H | I | J | K | L | M | N | O | P | Q | R |
| 2839 | $W_{173}$ | | | | | | | | | | | | | | | | | |
| 2840 | $A_{162}$ | $V_{11}$ | | | | | | | | | | | | | | | | |
| 2841 | $R_{173}$ | | | | | | | | | | | | | | | | | |
| 2842 | $M_{173}$ | | | | | | | | | | | | | | | | | |
| 2843 | $I_{156}$ | $V_{17}$ | | | | | | | | | | | | | | | | |
| 2844 | $L_{168}$ | $M_3$ | $I_2$ | | | | | | | | | | | | | | | |
| 2845 | $M_{171}$ | $L_2$ | | | | | | | | | | | | | | | | |
| 2846 | $T_{170}$ | $P_2$ | $I_1$ | | | | | | | | | | | | | | | |
| 2847 | $H_{173}$ | | | | | | | | | | | | | | | | | |
| 2848 | $F_{171}$ | $I_2$ | | | | | | | | | | | | | | | | |
| 2849 | $F_{172}$ | $S_1$ | | | | | | | | | | | | | | | | |
| 2850 | $S_{173}$ | | | | | | | | | | | | | | | | | |
| 2851 | $I_{171}$ | $V_1$ | $N_1$ | | | | | | | | | | | | | | | |
| 2852 | $L_{172}$ | $X_1$ | | | | | | | | | | | | | | | | |
| 2853 | $L_{171}$ | $M_1$ | $I_1$ | | | | | | | | | | | | | | | |
| 2854 | $A_{167}$ | $V_3$ | $X_1$ | $P_1$ | $F_1$ | | | | | | | | | | | | | |
| 2855 | $Q_{172}$ | $R_1$ | | | | | | | | | | | | | | | | |
| 2856 | $E_{173}$ | | | | | | | | | | | | | | | | | |
| 2857 | $Q_{172}$ | $Y_1$ | | | | | | | | | | | | | | | | |
| 2858 | $L_{173}$ | | | | | | | | | | | | | | | | | |
| 2859 | $E_{161}$ | $G_8$ | $D_4$ | | | | | | | | | | | | | | | |
| 2860 | $K_{170}$ | $R_2$ | $Q_1$ | | | | | | | | | | | | | | | |
| 2861 | $A_{165}$ | $T_6$ | $V_2$ | | | | | | | | | | | | | | | |
| 2862 | $L_{170}$ | $X_2$ | $Q_1$ | | | | | | | | | | | | | | | |
| 2863 | $D_{166}$ | $E_5$ | $X_2$ | | | | | | | | | | | | | | | |
| 2864 | $C_{172}$ | $F_1$ | | | | | | | | | | | | | | | | |
| 2865 | $Q_{172}$ | $H_1$ | | | | | | | | | | | | | | | | |
| 2866 | $I_{173}$ | | | | | | | | | | | | | | | | | |
| 2867 | $Y_{173}$ | | | | | | | | | | | | | | | | | |
| 2868 | $G_{171}$ | $R_1$ | $E_1$ | | | | | | | | | | | | | | | |
| 2869 | $A_{172}$ | $T_1$ | | | | | | | | | | | | | | | | |
| 2870 | $C_{116}$ | $T_{38}$ | $Y_8$ | $I_5$ | $X_2$ | $S_2$ | $H_1$ | $V_1$ | | | | | | | | | | |
| 2871 | $Y_{170}$ | $H_2$ | | | | | | | | | | | | | | | | |
| 2872 | $S_{172}$ | | | | | | | | | | | | | | | | | |
| 2873 | $I_{170}$ | $V_1$ | | | | | | | | | | | | | | | | |
| 2874 | $E_{155}$ | $Q_3$ | $G_1$ | | | | | | | | | | | | | | | |
| 2875 | $P_{159}$ | | | | | | | | | | | | | | | | | |
| 2876 | $L_{159}$ | | | | | | | | | | | | | | | | | |
| 2877 | $D_{159}$ | | | | | | | | | | | | | | | | | |
| 2878 | $L_{158}$ | $I_1$ | | | | | | | | | | | | | | | | |
| 2879 | $P_{159}$ | | | | | | | | | | | | | | | | | |
| 2880 | $Q_{156}$ | $P_2$ | $L_1$ | | | | | | | | | | | | | | | |
| 2881 | $I_{158}$ | $V_1$ | | | | | | | | | | | | | | | | |
| 2882 | $I_{159}$ | | | | | | | | | | | | | | | | | |
| 2883 | $Q_{99}$ | $E_{59}$ | $G_1$ | | | | | | | | | | | | | | | |
| 2884 | $R_{159}$ | | | | | | | | | | | | | | | | | |
| 2885 | $L_{159}$ | | | | | | | | | | | | | | | | | |
| 2886 | $H_{159}$ | | | | | | | | | | | | | | | | | |
| 2887 | $G_{158}$ | $S_1$ | | | | | | | | | | | | | | | | |
| 2888 | $L_{159}$ | | | | | | | | | | | | | | | | | |
| 2889 | $S_{158}$ | $G_1$ | | | | | | | | | | | | | | | | |
| 2890 | $A_{159}$ | | | | | | | | | | | | | | | | | |
| 2891 | $F_{159}$ | | | | | | | | | | | | | | | | | |
| 2892 | $S_{159}$ | | | | | | | | | | | | | | | | | |
| 2893 | $L_{159}$ | | | | | | | | | | | | | | | | | |
| 2894 | $H_{159}$ | | | | | | | | | | | | | | | | | |
| 2895 | $S_{156}$ | $N_1$ | $I_1$ | $T_1$ | | | | | | | | | | | | | | |
| 2896 | $Y_{159}$ | | | | | | | | | | | | | | | | | |
| 2897 | $S_{158}$ | $P_1$ | | | | | | | | | | | | | | | | |
| 2898 | $P_{159}$ | | | | | | | | | | | | | | | | | |
| 2899 | $G_{158}$ | $R_1$ | | | | | | | | | | | | | | | | |
| 2900 | $E_{159}$ | | | | | | | | | | | | | | | | | |
| 2901 | $I_{159}$ | | | | | | | | | | | | | | | | | |
| 2902 | $N_{159}$ | | | | | | | | | | | | | | | | | |
| 2903 | $R_{159}$ | | | | | | | | | | | | | | | | | |
| 2904 | $V_{159}$ | | | | | | | | | | | | | | | | | |
| 2905 | $A_{159}$ | | | | | | | | | | | | | | | | | |
| 2906 | $S_{121}$ | $A_{35}$ | $T_2$ | $X_1$ | | | | | | | | | | | | | | |
| 2907 | $C_{158}$ | $S_1$ | | | | | | | | | | | | | | | | |
| 2908 | $L_{159}$ | | | | | | | | | | | | | | | | | |
| 2909 | $R_{159}$ | | | | | | | | | | | | | | | | | |
| 2910 | $K_{158}$ | $Q_1$ | | | | | | | | | | | | | | | | |
| 2911 | $L_{159}$ | | | | | | | | | | | | | | | | | |
| 2912 | $G_{159}$ | | | | | | | | | | | | | | | | | |
| 2913 | $V_{159}$ | | | | | | | | | | | | | | | | | |
| 2914 | $P_{159}$ | | | | | | | | | | | | | | | | | |

TABLE 6-continued

| | A | B | C | D | E | F | G | H | I | J | K | L | M | N | O | P | Q | R |
|---|---|---|---|---|---|---|---|---|---|---|---|---|---|---|---|---|---|---|
| 2915 | $P_{159}$ | | | | | | | | | | | | | | | | | |
| 2916 | $L_{159}$ | | | | | | | | | | | | | | | | | |
| 2917 | $R_{159}$ | | | | | | | | | | | | | | | | | |
| 2918 | $V_{146}$ | $A_{10}$ | $T_2$ | $I_1$ | | | | | | | | | | | | | | |
| 2919 | $W_{159}$ | | | | | | | | | | | | | | | | | |
| 2920 | $R_{158}$ | $I_1$ | | | | | | | | | | | | | | | | |
| 2921 | $H_{158}$ | $L_1$ | | | | | | | | | | | | | | | | |
| 2922 | $R_{159}$ | | | | | | | | | | | | | | | | | |
| 2923 | $A_{159}$ | | | | | | | | | | | | | | | | | |
| 2924 | $R_{158}$ | $K_1$ | | | | | | | | | | | | | | | | |
| 2925 | $S_{156}$ | $N_1$ | $G_1$ | $R_1$ | | | | | | | | | | | | | | |
| 2926 | $V_{159}$ | | | | | | | | | | | | | | | | | |
| 2927 | $R_{159}$ | | | | | | | | | | | | | | | | | |
| 2928 | $A_{159}$ | | | | | | | | | | | | | | | | | |
| 2929 | $K_{148}$ | $R_{11}$ | | | | | | | | | | | | | | | | |
| 2930 | $L_{159}$ | | | | | | | | | | | | | | | | | |
| 2931 | $L_{159}$ | | | | | | | | | | | | | | | | | |
| 2932 | $S_{159}$ | | | | | | | | | | | | | | | | | |
| 2933 | $Q_{152}$ | $R_6$ | $P_1$ | | | | | | | | | | | | | | | |
| 2934 | $G_{158}$ | $R_1$ | | | | | | | | | | | | | | | | |
| 2935 | $G_{159}$ | | | | | | | | | | | | | | | | | |
| 2936 | $R_{157}$ | $K_1$ | $E_1$ | | | | | | | | | | | | | | | |
| 2937 | $A_{157}$ | $Y_1$ | $G_1$ | | | | | | | | | | | | | | | |
| 2938 | $A_{158}$ | $S_1$ | | | | | | | | | | | | | | | | |
| 2939 | $T_{124}$ | $N_{26}$ | $I_9$ | | | | | | | | | | | | | | | |
| 2940 | $C_{159}$ | | | | | | | | | | | | | | | | | |
| 2941 | $G_{158}$ | $X_1$ | | | | | | | | | | | | | | | | |
| 2942 | $K_{138}$ | $R_{19}$ | $X_1$ | $T_1$ | | | | | | | | | | | | | | |
| 2943 | $Y_{159}$ | | | | | | | | | | | | | | | | | |
| 2944 | $L_{159}$ | | | | | | | | | | | | | | | | | |
| 2945 | $F_{159}$ | | | | | | | | | | | | | | | | | |
| 2946 | $N_{159}$ | | | | | | | | | | | | | | | | | |
| 2947 | $W_{159}$ | | | | | | | | | | | | | | | | | |
| 2948 | $A_{159}$ | | | | | | | | | | | | | | | | | |
| 2949 | $V_{159}$ | | | | | | | | | | | | | | | | | |
| 2950 | $R_{117}$ | $K_{42}$ | | | | | | | | | | | | | | | | |
| 2951 | $T_{159}$ | | | | | | | | | | | | | | | | | |
| 2952 | $K_{159}$ | | | | | | | | | | | | | | | | | |
| 2953 | $L_{159}$ | | | | | | | | | | | | | | | | | |
| 2954 | $K_{159}$ | | | | | | | | | | | | | | | | | |
| 2955 | $L_{159}$ | | | | | | | | | | | | | | | | | |
| 2956 | $T_{159}$ | | | | | | | | | | | | | | | | | |
| 2957 | $P_{159}$ | | | | | | | | | | | | | | | | | |
| 2958 | $I_{156}$ | $N_3$ | | | | | | | | | | | | | | | | |
| 2959 | $P_{159}$ | | | | | | | | | | | | | | | | | |
| 2960 | $A_{153}$ | $E_4$ | $G_2$ | | | | | | | | | | | | | | | |
| 2961 | $A_{159}$ | | | | | | | | | | | | | | | | | |
| 2962 | $S_{157}$ | $Y_1$ | $F_1$ | | | | | | | | | | | | | | | |
| 2963 | $Q_{110}$ | $R_{45}$ | $H_2$ | $K_2$ | | | | | | | | | | | | | | |
| 2964 | $L_{159}$ | | | | | | | | | | | | | | | | | |
| 2965 | $D_{159}$ | | | | | | | | | | | | | | | | | |
| 2966 | $L_{159}$ | | | | | | | | | | | | | | | | | |
| 2967 | $S_{159}$ | | | | | | | | | | | | | | | | | |
| 2968 | $G_{93}$ | $S_{51}$ | $N_{13}$ | $D_1$ | $K_1$ | | | | | | | | | | | | | |
| 2969 | $W_{159}$ | | | | | | | | | | | | | | | | | |
| 2970 | $F_{159}$ | | | | | | | | | | | | | | | | | |
| 2971 | $V_{149}$ | $I_6$ | $T_4$ | | | | | | | | | | | | | | | |
| 2972 | $A_{159}$ | | | | | | | | | | | | | | | | | |
| 2973 | $G_{159}$ | | | | | | | | | | | | | | | | | |
| 2974 | $Y_{159}$ | | | | | | | | | | | | | | | | | |
| 2975 | $S_{143}$ | $G_{10}$ | $N_6$ | | | | | | | | | | | | | | | |
| 2976 | $G_{159}$ | | | | | | | | | | | | | | | | | |
| 2977 | $G_{159}$ | | | | | | | | | | | | | | | | | |
| 2978 | $D_{159}$ | | | | | | | | | | | | | | | | | |
| 2979 | $I_{155}$ | $V_3$ | $T_1$ | | | | | | | | | | | | | | | |
| 2980 | $Y_{159}$ | | | | | | | | | | | | | | | | | |
| 2981 | $H_{158}$ | $R_1$ | | | | | | | | | | | | | | | | |
| 2982 | $S_{159}$ | | | | | | | | | | | | | | | | | |
| 2983 | $L_{133}$ | $V_{24}$ | $P_2$ | | | | | | | | | | | | | | | |
| 2984 | $S_{157}$ | $P_2$ | | | | | | | | | | | | | | | | |
| 2985 | $R_{147}$ | $H_{10}$ | $P_1$ | $C_1$ | | | | | | | | | | | | | | |
| 2986 | $A_{155}$ | $X_2$ | $T_2$ | | | | | | | | | | | | | | | |
| 2987 | $R_{157}$ | | | | | | | | | | | | | | | | | |
| 2988 | $P_{157}$ | | | | | | | | | | | | | | | | | |
| 2989 | $R_{157}$ | | | | | | | | | | | | | | | | | |
| 2990 | $W_{157}$ | | | | | | | | | | | | | | | | | |

TABLE 6-continued

HCV 1b Consensus Sequences

| | A | B | C | D | E | F | G | H | I | J | K | L | M | N | O | P | Q | R |
|---|---|---|---|---|---|---|---|---|---|---|---|---|---|---|---|---|---|---|
| 2991 | $F_{149}$ | $L_7$ | $P_1$ | | | | | | | | | | | | | | | |
| 2992 | $M_{153}$ | $L_4$ | | | | | | | | | | | | | | | | |
| 2993 | $L_{84}$ | $W_{71}$ | $F_2$ | | | | | | | | | | | | | | | |
| 2994 | $C_{157}$ | | | | | | | | | | | | | | | | | |
| 2995 | $L_{157}$ | | | | | | | | | | | | | | | | | |
| 2996 | $L_{155}$ | $F_1$ | $P_1$ | | | | | | | | | | | | | | | |
| 2997 | $L_{157}$ | | | | | | | | | | | | | | | | | |
| 2998 | $L_{157}$ | | | | | | | | | | | | | | | | | |
| 2999 | $S_{154}$ | $T_1$ | $F_1$ | $X_1$ | | | | | | | | | | | | | | |
| 3000 | $V_{157}$ | | | | | | | | | | | | | | | | | |
| 3001 | $G_{157}$ | | | | | | | | | | | | | | | | | |
| 3002 | $V_{157}$ | | | | | | | | | | | | | | | | | |
| 3003 | $G_{157}$ | | | | | | | | | | | | | | | | | |
| 3004 | $I_{152}$ | $V_5$ | | | | | | | | | | | | | | | | |
| 3005 | $Y_{156}$ | $N_1$ | | | | | | | | | | | | | | | | |
| 3006 | $L_{156}$ | $C_1$ | | | | | | | | | | | | | | | | |
| 3007 | $L_{156}$ | $X_1$ | | | | | | | | | | | | | | | | |
| 3008 | $P_{156}$ | | | | | | | | | | | | | | | | | |
| 3009 | $N_{154}$ | $A_1$ | $K_1$ | | | | | | | | | | | | | | | |
| 3010 | $R_{156}$ | | | | | | | | | | | | | | | | | |

What is claimed as new and desired to be protected by Letters Patent of the United States is:

1. A composition comprising at least one nucleic acid sequence which codes for an HCV 1a E2 protein, said protein comprising the consensus sequence at residues 384-746 of SEQ ID NO: 1.

2. A composition comprising at least one nucleic acid sequence which codes for an immunogenic fragment of an HCV 1a E2 protein, said fragment comprising at least 45 contiguous residues of the consensus sequence at residues 384-746 of SEQ ID NO: 1, and further wherein the immunogenic fragment comprises residues 518-531 of SEQ ID NO: 1.

* * * * *

UNITED STATES PATENT AND TRADEMARK OFFICE
CERTIFICATE OF CORRECTION

PATENT NO. : 8,168,771 B2
APPLICATION NO. : 11/815203
DATED : May 1, 2012
INVENTOR(S) : Stuart C. Ray et al.

Page 1 of 1

It is certified that error appears in the above-identified patent and that said Letters Patent is hereby corrected as shown below:

On the Title page; under Inventors:
        Please delete "Andrew L. Cox" and replace with --Andrea L. Cox--

Signed and Sealed this
Thirtieth Day of July, 2013

Teresa Stanek Rea
*Acting Director of the United States Patent and Trademark Office*